United States Patent
Pan et al.

(10) Patent No.: US 11,234,990 B2
(45) Date of Patent: *Feb. 1, 2022

(54) METHODS AND COMPOSITIONS RELATED TO GLUCOCORTICOID RECEPTOR ANTAGONISTS AND BREAST CANCER

(71) Applicant: The University of Chicago, Chicago, IL (US)

(72) Inventors: Deng Pan, Chicago, IL (US); Masha Kocherginsky, Chicago, IL (US); Suzanne D. Conzen, Park Ridge, IL (US)

(73) Assignee: The University of Chicago, Chicago, IL (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/596,342

(22) Filed: Oct. 8, 2019

(65) Prior Publication Data

US 2020/0030344 A1 Jan. 30, 2020

Related U.S. Application Data

(63) Continuation of application No. 15/448,827, filed on Mar. 3, 2017, now Pat. No. 10,441,596, which is a continuation of application No. 14/296,127, filed on Jun. 4, 2014, now Pat. No. 9,623,032, which is a continuation of application No. 14/172,051, filed on Feb. 4, 2014, now Pat. No. 9,149,485, which is a continuation of application No. 13/071,363, filed on Mar. 24, 2011, now Pat. No. 8,710,035.

(60) Provisional application No. 61/317,182, filed on Mar. 24, 2010.

(51) Int. Cl.

| | | |
|---|---|---|
| *A61K 31/575* | (2006.01) | |
| *A61K 45/06* | (2006.01) | |
| *A61K 33/243* | (2019.01) | |
| *A61K 31/282* | (2006.01) | |
| *A61K 31/337* | (2006.01) | |
| *A61K 31/357* | (2006.01) | |
| *A61K 31/4745* | (2006.01) | |
| *A61K 31/7068* | (2006.01) | |
| *A61K 39/395* | (2006.01) | |
| *A61N 5/00* | (2006.01) | |
| *A61J 1/00* | (2006.01) | |
| *A61K 31/567* | (2006.01) | |
| *A61K 31/58* | (2006.01) | |

(52) U.S. Cl.
CPC .............. *A61K 31/575* (2013.01); *A61J 1/00* (2013.01); *A61K 31/282* (2013.01); *A61K 31/337* (2013.01); *A61K 31/357* (2013.01); *A61K 31/4745* (2013.01); *A61K 31/567* (2013.01); *A61K 31/58* (2013.01); *A61K 31/7068* (2013.01); *A61K 33/243* (2019.01); *A61K 39/3955* (2013.01); *A61K 45/06* (2013.01); *A61N 5/00* (2013.01)

(58) Field of Classification Search
CPC .... A61K 31/575; A61K 45/06; A61K 33/243; A61K 31/282; A61K 31/337; A61K 31/357; A61K 31/4745; A61K 31/7068; A61K 39/395; A61K 31/567; A61K 31/56; A61N 5/00; A61J 1/00
See application file for complete search history.

(56) References Cited

U.S. PATENT DOCUMENTS

| | | |
|---|---|---|
| 8,003,689 B2 | 8/2011 | Veverka |
| 8,658,128 B2 | 2/2014 | Altschul et al. |
| 8,710,035 B2 | 4/2014 | Pan et al. |
| 9,114,147 B2 | 8/2015 | Altschul et al. |
| 9,149,485 B2 | 10/2015 | Pan et al. |
| 9,623,032 B2 | 4/2017 | Pan et al. |
| 2002/0115613 A1 | 8/2002 | Kumar |
| 2005/0124533 A1 | 6/2005 | Schatzberg et al. |
| 2006/0063748 A1 | 3/2006 | Belanoff |
| 2008/0287419 A1 | 11/2008 | Bruncko et al. |
| 2010/0135956 A1 | 6/2010 | Gant et al. |
| 2014/0186367 A1 | 7/2014 | Pan et al. |
| 2014/0315866 A1 | 10/2014 | Pan et al. |
| 2017/0182066 A1 | 6/2017 | Pan et al. |

FOREIGN PATENT DOCUMENTS

WO    2009064738 A2    5/2009

OTHER PUBLICATIONS

Neckers et al. Expert Opin Emerg Drugs Oct. 2002;7(2):277-88. (abstract).*

"Data Sheet: Glucocorticoid Receptor mouse monoclonal antibody NCL-GCR", Novocastra Laboratories Ltd., available at http://www.ebiotrade.com/buyf/Novocastra/data/hrerp/gcr.pdf, accessed on Jun. 7, 2011.

"Identification of Glucocorticoid Receptor (GR) Signatures in Primary Human Breast Cancer: Association With Relapse-Free Survival Time", poster presented by S.D. Conzen as a short talk, presented at Nuclear Receptors: Signaling, Gene Regulation and Cancer, Keystone Symposia on Molecular and Cellular Biology, Keystone Resort, Keystone, Colorado, Mar. 25, 2010.

(Continued)

*Primary Examiner* — Shirley V Gembeh
(74) *Attorney, Agent, or Firm* — Kilpatrick Townsend & Stockton LLP

(57) ABSTRACT

Embodiments of the invention are directed to methods of determining the prognosis of a breast cancer patient by evaluating the activity of the glucocorticoid receptor in tumor cells. Other embodiment include methods of treating breast cancer cells, particularly, chemo-resistant cells, with a glucocorticoid receptor antagonist and an anticancer agent or compound.

20 Claims, 12 Drawing Sheets

Specification includes a Sequence Listing.

(56) References Cited

OTHER PUBLICATIONS

U.S. Appl. No. 14/451,207 , "Non-Final Office Action", dated Feb. 24, 2016, 11 pages.
Belanoff et al., "Selective Glucocorticoid Receptor (Type II) Antagonists Prevent Weight Gain Caused by Olanzapine in Rats", Eur J Pharmacol., vol. 655, Issue 1-3, Mar. 25, 2011, pp. 117-120.
Belova et al., "Glucocorticoid Receptor Expression in Breast Cancer Associates with Older Patient Age", Breast Cancer Res Treat, vol. 116, Issue 3, Aug. 2009, pp. 441-447.
Cho et al., "Role of Activation Function Domain-1, DNA Binding, and Coactivator GRIP1 in the Expression of Partial Agonist Activity of Glucocorticoid Receptor-Antagonist Complexes", Biochemistry, vol. 44, Issue 9, 2005, pp. 3547-3561.
Clark, "Glucocorticoid Receptor Antagonists", Current Topics in Medicinal Chemistry, vol. 8, Issue 9, Jun. 1, 2008, pp. 813-838.
Colleoni et al., "Response to Primary Chemotherapy in Breast Cancer Patients with Tumors Not Expressing Estrogen and Progesterone Receptors", Annals of Oncology, vol. 11, Issue 8, Aug. 1, 2000, pp. 1057-1059.
Dennis, "Off by a Whisker", Nature, vol. 442, Aug. 7, 2006, pp. 739-741.
Desmedt et al., "Strong Time Dependence of the 76-Gene Prognostic Signature for Node-Negative Breast Cancer Patients in the TRANSBIG Multicenter Independent Validation Series", Clin Cancer Res., vol. 13, Issue 11, Jun. 2007, pp. 3207-3214.
Gaddy et al., "Mifepristone Induces Growth Arrest, Caspase Activation, and Apoptosis of Estrogen Receptor-Expressing, Antiestrogen-Resistant Breast Cancer Cells", Clin Cancer Res., vol. 10, Issue 15, Aug. 1, 2004, pp. 5215-5225.
Grover et al., "The Initiation of Breast and Prostate Cancer", Carcinogenesis, vol. 23, Issue 7, Jul. 1, 2002, pp. 1095-1102.
Gura , "Systems for Identifying New Drugs are Often Faulty", Science, vol. 278, No. 5340, Cancer Models, Nov. 7, 1997, pp. 1041-1042.
Hein et al., "Click Chemistry, a Powerful Tool for Pharmaceutical Sciences", Pharmaceutical Research, vol. 25, Issue 10, Oct. 2008, pp. 2216-2230.
Henderson et al., "Estrogens as a Cause of Human Cancer: the Richard and Hinda Rosenthal Foundation Award Lecture", Cancer Res., vol. 48, Issue 2, Jan. 15, 1988, pp. 246-253.
Huang et al., "Reversal Effect of Mifepristone on Adriamycin Resistance in Human Breast Cancer Cell Abstract Only Line MCF-7/ADM in Vitro and in Vivo", J Cent South Univ (Med Sci), vol. 35, Issue 6, Jun. 2010, pp. 576-583.
Keen et al., "The Biology of Breast Carcinoma", Cancer, vol. 97, Issue S3, Feb. 1, 2003, pp. 825-833.
Kriaucionis et al., "The Nuclear DNA Base 5-Hydroxymethylcytosine is Present in Purkinje Neurons and the Brain", Science, vol. 324, Issue 5929, May 15, 2009, pp. 929-930.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated with Tamoxifen", BMC Genomics, vol. 9, No. 239, May 22, 2008, pp. 1-12.
Lucci et al., "Modification of Ceramide Metabolism Increases Cancer Cell Sensitivity to Cytotoxics", Int J. Onco., vol. 15 Issue 3, Sep. 1999, pp. 541-546.
Ma et al., "IL-21 Activates Both Innate and Adaptive Immunity to Generate Potent Antitumor Responses that Require Perforin but are Independent of IFN-Gamma", J. Jmmunol, vol. 171, Issue 2, Jul. 15, 2003, pp. 608-615.
Melhem et al., "Administration of Glucocorticoids to Ovarian Cancer Patients is Associated with Expression of the Anti-apoptotic Genes SGK1 and MKP1/DUSP1 in Ovarian Tissues", Clin. Cancer Res., vol. 15, Issue 9, May 2009, pp. 3196-3204.

Mikosz et al., "Glucocorticoid Receptor-Mediated Protection from Apoptosis Is Associated with Induction of the Serine/Threonine Survival Kinase Gene, sgk-1", J. Biol. Chem., vol. 276, No. 20, Feb. 13, 2001, pp. 16649-16654.
Minn et al., "Genes that Mediate Breast Cancer Metastasis to Lung", Nature. vol. 436, No. 7050, Jul. 28, 2005, pp. 518-524.
Moran et al., "The Glucocorticoid Receptor Mediates a Survival Signal in Human Mammary Epithelial Cells", Cancer Res., vol. 60, Issue 4, Feb. 2000, pp. 867-872.
Moses et al., "The Growing Applications of Click Chemistry", Chem Soc Rev., vol. 36, Issue 8, May 2007, pp. 1249-1262.
Pan et al., "Activation of the Glucocorticoid Receptor is Associated with Poor Prognosis in Estrogen Receptor-Negative Breast Cancer", Cancer Research, vol. 71, Issue 20, Oct. 15, 2011, pp. 6360-6370.
Pang et al., "Dexamethasone Decreases Xenograft Response to Paclitaxel through Inhibition of Tumor Cell Apoptosis", Cancer Biology & Therapy, vol. 5, Issue 8, Aug. 2006, pp. 933-940.
Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Ann. NY Acad. Sci., vol. 1148, Issue 1, Dec. 2008, pp. 536-541.
Pike et al., "Estrogens, Progestogens, Normal Breast Cell Proliferation, and Breast Cancer Risk", Epidemiologic Rev., vol. 15, Issue 1, Jan. 1, 1993, pp. 17-35.
Reagan-Shaw et al., "Dose Translation from Animal to Human Studies Revisited", The Faseb Journal, vol. 22, Mar. 2007, pp. 659-661.
Robinson et al., "Octahydrophenanthrene-2,7-diol Analogues as Dissociated Glucocorticoid Receptor Agonists: Discovery and Lead Exploration", J. Med. Chem., vol. 52, No. 6, 2009, pp. 1731-1743.
Sims et al., "The Removal of Multiplicative, Systematic Bias Allows Integration of Breast Cancer Gene Expression Datasets—Improving Meta-Analysis and Prediction of Prognosis", BMC Medical Genomics, vol. 1, No. 42, Sep. 21, 2008, pp. 1-14.
Smith et al., "Expression of Glucocorticoid and Progesterone Nuclear Receptor Genes in Archival Breast Cancer Tissue", Breast Cancer Res., vol. 5, Issue 1, 2003, pp. R9-R12.
Smith et al., "Progesterone, Glucocorticoid, but not Estrogen Receptor mRNA is Altered in Breast Cancer Stroma", Cancer Letters, vol. 255, Issue 1, Sep. 18, 2007, pp. 77-84.
Sorlie et al., "Gene Expression Patterns of Breast Carcinomas Distinguish Tumor Subclasses With Clinical Implications", Proc. Nat!. Acad. Sci., vol. 98, No. 19, Sep. 11, 2001, pp. 10869-10874.
Sotiriou et al., "Gene Expression Profiling in Breast Cancer: Understanding the Molecular Basis of Histologic Grade to Improve Prognosis", J. Nat/. Cancer Inst, vol. 98, Issue 4, Feb. 15, 2006, pp. 262-272.
Srinivas et al., "Proteomics for Cancer Biomarker Discovery", Clin. Chem., vol. 48, Issue 8, Aug. 2002, pp. 1160-1169.
Sui et al., "Estrogen Receptor α Mediates Breast Cancer Cell Resistance to Paclitaxel through Inhibition of Apoptotic Cell Death", Cancer Res., vol. 67, Issue 11, Jun. 1, 2007, pp. 5337-5344.
Wang et al., "Gene-Expression Profiles to Predict Distant Metastasis of Lymph-Node-Negative Primary Breast Cancer", The Lancet, vol. 365, Issue 9460, Feb. 19-25, 2005, pp. 671-679.
Wu et al., "Glucocorticoid Receptor Activation Signals through Forkhead Transcription Factor 3a in Breast Cancer Cells", Mol. Endocrinol, vol. 20, Issue 10, Oct. 1, 2006, pp. 2304-2314.
Wu et al., "Microarray Analysis Reveals Glucocorticoid-Regulated Survival Genes that are Associated with Inhibition of Apoptosis in Breast Epithelial Cells", Cancer Research, vol. 64, Issue 5, Mar. 1, 2004, pp. 1757-1764.
Wu et al., "Prevalent Expression of the Immunostimulatory MHC Class I Chain-Related Molecule is Counteracted by Shedding in Prostate Cancer", J. Clin. Invest., vol. 114, Issue 4, Aug. 16, 2004, pp. 560-568.
U.S. Appl. No. 61/317,182, filed Mar. 24, 2010.
Notice of Withdrawal from Issue under 37 CFR 1.313(b) dated Feb. 4, 2016.

\* cited by examiner

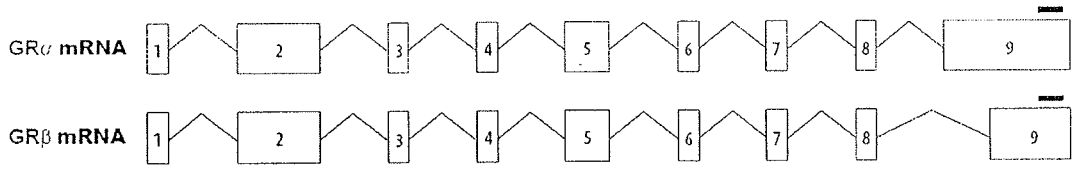

```
Query = GR alpha
Length=6784

18665 = GR beta

ALIGNMENTS

Query   1     GGCGCCGCCTCCACCCGCTCCCCGCTCGGTCCCGCTCGCTCGCCCAGGCCGGGCTGCCCT    60
18665   1     GGCGCCGCCTCCACCCGCTCCCCGCTCGGTCCCGCTCGCTCGCCCAGGCCGGGCTGCCCT    60

Query   61    TTCGCGTGTCCGCGCTCTCTTCCCTCCGCCGCCGCCTCCTCCATTTTGCGAGCTCGTGTC   120
18665   61    TTCGCGTGTCCGCGCTCTCTTCCCTCCGCCGCCGCCTCCTCCATTTTGCGAGCTCGTGTC   120

Query   121   TGTGACGGGAGCCCGAGTCACCGCCTGCCCGTCGGGGACGGATTCTGTGGGTGGAAGGAG   180
18665   121   TGTGACGGGAGCCCGAGTCACCGCCTGCCCGTCGGGGACGGATTCTGTGGGTGGAAGGAG   180

Query   181   ACGCCGCAGCCGGAGCGGCCGAAGCAGCTGGGACCGGGACGGGGCACGCGCGCCCGGAAC   240
18665   181   ACGCCGCAGCCGGAGCGGCCGAAGCAGCTGGGACCGGGACGGGGCACGCGCGCCCGGAAC   240

Query   241   CTCGACCCGCGGAGCCCGGCGCGGGGCGGAGGGCTGGCTTGTCAGCTGGGCAATGGGAGA   300
18665   241   CTCGACCCGCGGAGCCCGGCGCGGGGCGGAGGGCTGGCTTGTCAGCTGGGCAATGGGAGA   300

Query   301   CTTTCTTAAATAGGGGCTCTCCCCCCACCCATGGAGAAAGGGGCGGCTGTTTACTTCCtt   360
18665   301   CTTTCTTAAATAGGGGCTCTCCCCCCACCCATGGAGAAAGGGGCGGCTGTTTACTTCCTT   360

Query   361   ttttttAGaaaaaaaaaaaTATATTTCCCTCCTGCTCCTTCTGCGTTCACAAGCTAAGTTGT   420
18665   361   TTTTTAGAAAAAAAAAAATATATTTCCCTCCTGCTCCTTCTGCGTTCACAAGCTAAGTTGT   420

Query   421   TTATCTCGGCTGCGGCGGGAACTGCGGACGGTGGCGGGCGAGCGGCTCCTCTGCCAGAGT   480
18665   421   TTATCTCGGCTGCGGCGGGAACTGCGGACGGTGGCGGGCGAGCGGCTCCTCTGCCAGAGT   480

Query   481   TGATATTCACTGATGGACTCCAAAGAATCATTAACTCCTGGTAGAGAAGAAAACCCCAGC   540
18665   481   TGATATTCACTGATGGACTCCAAAGAATCATTAACTCCTGGTAGAGAAGAAAACCCCAGC   540

Query   541   AGTGTGCTTGCTCAGGAGAGGGGAGATGTGATGGACTTCTATAAACCCTAAGAGGAGGA   600
18665   541   AGTGTGCTTGCTCAGGAGAGGGGAGATGTGATGGACTTCTATAAACCCTAAGAGGAGGA   600

Query   601   GCTACTGTGAAGGTTTCTGCGTCTTCACCCTCACTGGCTGTCGCTTCTCAATCAGACTCC   660
18665   601   GCTACTGTGAAGGTTTCTGCGTCTTCACCCTCACTGGCTGTCGCTTCTCAATCAGACTCC   660

Query   661   AAGCAGCGAAGACTTTTGGTTGATTTTCCAAAAGGCTCAGTAAGCAATGCGCAGCAGCCA   720
18665   661   AAGCAGCGAAGACTTTTGGTTGATTTTCCAAAAGGCTCAGTAAGCAATGCGCAGCAGCCA   720

Query   721   GATCTGTCCAAAGCAGTTTCACTCTCAATGGGACTGTATATGGGAGAGACAGAAACAAAA   780
18665   721   GATCTGTCCAAAGCAGTTTCACTCTCAATGGGACTGTATATGGGAGAGACAGAAACAAAA   780

Query   781   GTGATGGGAAATGACCTGGATTCCCACAGCAGGGCCAAATCAGCCTTTCCTCGGGGGAA   840
18665   781   GTGATGGGAAATGACCTGGATTCCCACAGCAGGGCCAAATCAGCCTTTCCTCGGGGGAA   840

Query   841   ACAGACTTAAAGCTTTTGGAAGAAAGCATTGCAAACCTCAATAGGTCGACCAGTGTTCCA   900
18665   841   ACAGACTTAAAGCTTTTGGAAGAAAGCATTGCAAACCTCAATAGGTCGACCAGTGTTCCA   900
```

FIG. 7A

```
Query   901   GAGAACCCCAAGAGTTCAGCATCCACTGCTGTGTCTGCTGCCCCCACAGAGAAGGAGTTT   960
18665   901   GAGAACCCCAAGAGTTCAGCATCCACTGCTGTGTCTGCTGCCCCCACAGAGAAGGAGTTT   960

Query   961   CCAAAAACTCACTCTGATGTATCTTCAGAACAGCAACATTTGAAGGGCCAGACTGGCACC   1020
18665   961   CCAAAAACTCACTCTGATGTATCTTCAGAACAGCAACATTTGAAGGGCCAGACTGGCACC   1020

Query   1021  AACGGTGGCAATGTGAAATTGTATACCACAGACCAAAGCACCTTTGACATTTTGCAGGAT   1080
18665   1021  AACGGTGGCAATGTGAAATTGTATACCACAGACCAAAGCACCTTTGACATTTTGCAGGAT   1080

Query   1081  TTGGAGTTTTCTTCTGGGTCCCCAGGTAAAGAGACGAATGAGAGTCCTTGGAGATCAGAC   1140
18665   1081  TTGGAGTTTTCTTCTGGGTCCCCAGGTAAAGAGACGAATGAGAGTCCTTGGAGATCAGAC   1140

Query   1141  CTGTTGATAGATGAAAACTGTTTGCTTTCTCCTCTGGCGGGAGAAGACGATTCATTCCTT   1200
18665   1141  CTGTTGATAGATGAAAACTGTTTGCTTTCTCCTCTGGCGGGAGAAGACGATTCATTCCTT   1200

Query   1201  TTGGAAGGAAACTCGAATGAGGACTGCAAGCCTCTCATTTTACCGGACACTAAACCCAAA   1260
18665   1201  TTGGAAGGAAACTCGAATGAGGACTGCAAGCCTCTCATTTTACCGGACACTAAACCCAAA   1260

Query   1261  ATTAAGGATAATGGAGATCTGGTTTTGTCAAGCCCCAGTAATGTAACACTGCCCCAAGTG   1320
18665   1261  ATTAAGGATAATGGAGATCTGGTTTTGTCAAGCCCCAGTAATGTAACACTGCCCCAAGTG   1320

Query   1321  AAAACAGAAAAGAAGATTTCATCGAACTCTGCACCCCTGGGGTAATTAAGCAAGAGAAA   1380
18665   1321  AAAACAGAAAAGAAGATTTCATCGAACTCTGCACCCCTGGGGTAATTAAGCAAGAGAAA   1380

Query   1381  CTGGGCACAGTTTACTGTCAGGCAAGCTTTCCTGGAGCAAATATAATTGGTAATAAAATG   1440
18665   1381  CTGGGCACAGTTTACTGTCAGGCAAGCTTTCCTGGAGCAAATATAATTGGTAATAAAATG   1440

Query   1441  TCTGCCATTTCTGTTCATGGTGTGAGTACCTCTGGAGGACAGATGTACCACTATGACATG   1500
18665   1441  TCTGCCATTTCTGTTCATGGTGTGAGTACCTCTGGAGGACAGATGTACCACTATGACATG   1500

Query   1501  AATACAGCATCCCTTTCTCAACAGCAGGATCAGAAGCCTATTTTTAATGTCATTCCACCA   1560
18665   1501  AATACAGCATCCCTTTCTCAACAGCAGGATCAGAAGCCTATTTTTAATGTCATTCCACCA   1560

Query   1561  ATTCCCGTTGGTTCCGAAAATTGGAATAGGTGCCAAGGATCTGGAGATGACAACTTGACT   1620
18665   1561  ATTCCCGTTGGTTCCGAAAATTGGAATAGGTGCCAAGGATCTGGAGATGACAACTTGACT   1620

Query   1621  TCTCTGGGGACTCTGAACTTCCCTGGTCGAACAGTTTTTTCTAATGGCTATTCAAGCCCC   1680
18665   1621  TCTCTGGGGACTCTGAACTTCCCTGGTCGAACAGTTTTTTCTAATGGCTATTCAAGCCCC   1680

Query   1681  AGCATGAGACCAGATGTAAGCTCTCCTCCATCCAGCTCCTCAACAGCAACAACAGGACCA   1740
18665   1681  AGCATGAGACCAGATGTAAGCTCTCCTCCATCCAGCTCCTCAACAGCAACAACAGGACCA   1740

Query   1741  CCTCCCAAACTCTGCCTGGTGTGCTCTGATGAAGCTTCAGGATGTCATTATGGAGTCTTA   1800
18665   1741  CCTCCCAAACTCTGCCTGGTGTGCTCTGATGAAGCTTCAGGATGTCATTATGGAGTCTTA   1800

Query   1801  ACTTGTGGAAGCTGTAAAGTTTTCTTCAAAAGAGCAGTGGAAGGACAGCACAATTACCTA   1860
18665   1801  ACTTGTGGAAGCTGTAAAGTTTTCTTCAAAAGAGCAGTGGAAGGACAGCACAATTACCTA   1860

Query   1861  TGTGCTGGAAGGAATGATTGCATCATCGATAAAATTCGAAGAAAAACTGCCCAGCATGC   1920
18665   1861  TGTGCTGGAAGGAATGATTGCATCATCGATAAAATTCGAAGAAAAACTGCCCAGCATGC   1920

Query   1921  CGCTATCGAAAATGTCTTCAGGCTGGAATGAACCTGGAAGCTCGaaaaacaaagaaaaaa   1980
18665   1921  CGCTATCGAAAATGTCTTCAGGCTGGAATGAACCTGGAAGCTCGAAAAACAAAGAAAAAA   1980

Query   1981  ataaaaGGAATTCAGCAGGCCACTACAGGAGTCTCACAAGAAACCTCTGAAAATCCTGGT   2040
18665   1981  ATAAAAGGAATTCAGCAGGCCACTACAGGAGTCTCACAAGAAACCTCTGAAAATCCTGGT   2040

Query   2041  AACAAAACAATAGTTCCTGCAACGTTACCACAACTCACCCCTACCCTGGTGTCACTGTTG   2100
18665   2041  AACAAAACAATAGTTCCTGCAACGTTACCACAACTCACCCCTACCCTGGTGTCACTGTTG   2100

Query   2101  GAGGTTATTGAACCTGAAGTGTTATATGCAGGATATGATAGCTCTGTTCCAGACTCAACT   2160
18665   2101  GAGGTTATTGAACCTGAAGTGTTATATGCAGGATATGATAGCTCTGTTCCAGACTCAACT   2160
```

FIG. 7B

```
Query  2161  TGGAGGATCATGACTACGCTCAACATGTTAGGAGGGCGGCAAGTGATTGCAGCAGTGAAA  2220
18665  2161  TGGAGGATCATGACTACGCTCAACATGTTAGGAGGGCGGCAAGTGATTGCAGCAGTGAAA  2220

Query  2221  TGGGCAAAGGCAATACCAGGTTTCAGGAACTTACACCTGGATGACCAAATGACCCTACTG  2280
18665  2221  TGGGCAAAGGCAATACCAGGTTTCAGGAACTTACACCTGGATGACCAAATGACCCTACTG  2280

Query  2281  CAGTACTCCTGGATGTTTCTTATGGCATTTGCTCTGGGGTGGAGATCATATAGACAATCA  2340
18665  2281  CAGTACTCCTGGATGTTTCTTATGGCATTTGCTCTGGGGTGGAGATCATATAGACAATCA  2340

Query  2341  AGTGCAAACCTGCTGTGTTTTGCTCCTGATCTGATTATTAATGAGCAGAGAATGACTCTA  2400
18665  2341  AGTGCAAACCTGCTGTGTTTTGCTCCTGATCTGATTATTAATGAGCAGAGAATGACTCTA  2400

Query  2401  CCCTGCATGTACGACCAATGTAAACACATGCTGTATGTTTCCTCTGAGTTACACAGGCTT  2460
18665  2401  CCCTGCATGTACGACCAATGTAAACACATGCTGTATGTTTCCTCTGAGTTACACAGGCTT  2460

Query  2461  CAGGTATCTTATGAAGAGTATCTCTGTATGAAAACCTTACTGCTTCTCTCTTCAGTTCCT  2520
18665  2461  CAGGTATCTTATGAAGAGTATCTCTGTATGAAAACCTTACTGCTTCTCTCTTCAGTTCCT  2520

Query  2521  AAGGACGGTCTGAAGAGCCAAGAGCTATTTGATGAAATTAGAATGACCTACATCAAAGAG  2580
18665  2521  AAGGACGGTCTGAAGAGCCAAGAGCTATTTGATGAAATTAGAATGACCTACATCAAAGAG  2580

Query  2581  CTAGGAAAAGCCATTGTCAAGAGGGAAGGAAACTCCAGCCAGAACTGGCAGCGGTTTTAT  2640
18665  2581  CTAGGAAAAGCCATTGTCAAGAGGGAAGGAAACTCCAGCCAGAACTGGCAGCGGTTTTAT  2640

Query  2641  CAACTGACAAAACTCTTGGATTCTATGCATGAAGTGGTTGAAAATCTCCTTAACTATTGC  2700
18665  2641  CAACTGACAAAACTCTTGGATTCTATGCATGAA                             2673

Query  2701  TTCCAAACATTTTTGGATAAGACCATGAGTATTGAATTCCCCGAGATGTTAGCTGAAATC  2760

Query  2761  ATCACCAATCAGATACCAAAATATTCAAATGGAAATATCAAAAAACTTCTGTTTCATCAA  2820

Query  2821  AAGTGACTGCCTTAATAAGAATGGTTGCCTTAAAGAAAGTCGAATTAATAGCTTTTATTG  2880

Query  2881  TATAAACTATCAGTTTGTCCTGTAGAGgttttgttgttttattttttattgttttcatct  2940

Query  2941  gttgttttgttttAAATACGCACTACATGTGGTTTATAGAGGGCCAAGACTTGGCAACAG  3000

Query  3001  AAGCAGTTGAGTCGTCATCACTTTTCAGTGATGGGAGAGTAGATGGTGAAATTTATTAGT  3060

Query  3061  TAATATATCCCAGAAATTAGAAACCTTAATATGTGGACGTAATCTCCACAGTCAAAGAAG  3120

Query  3121  GATGGCACCTAAACCACCAGTGCCCAAAGTCTGTGTGATGAACTTTCTCTTCATACtttt  3180

Query  3181  tttCACAGTTGGCTGGATGAAATTTTCTAGACTTTCTGTTGGTGTATccccccccTGTAT  3240

Query  3241  AGTTAGGATAGCATTTTTGATTTATGCATGGAAACCTGaaaaaaaGTTTACAAGTGTATA  3300

Query  3301  TCAGAAAGGGAAGTTGTGCCTTTTATAGCTATTACTGTCTGGTTTTAACAATTTCCTTT  3360

Query  3361  ATATTTAGTGAACTACGCTTGCTCATTTTTTCTTACATAATTTTTATTCAAGTTATTGT  3420

Query  3421  ACAGCTGTTTAAGATGGGCAGCTAGTTCGTAGCTTTCCCAAATAAACTCTAAACATTAAT  3480

Query  3481  CAATCATCTGTGTGAAAATGGGTTGGTGCTTCTAACCTGATGGCACTTAGCTATCAGAAG  3540

Query  3541  ACCACAAAAATTGACTCAAATCTCCAGTATTCTTGTCaaaaaaaaaaaaaaaaaaGCTCA  3600

Query  3601  TATTTTGTATATATCTGCTTCAGTGGAGAATTATATAGGTTGTGCAAATTAACAGTCCTA  3660

Query  3661  ACTGGTATAGAGCACCTAGTCCAGTGACCTGCTGGGTAAACTGTGGATGATGGTTGCAAA  3720

Query  3721  AGACTAATTTAAAAAATAACTACCAAGAGGCCCTGTCTGTACCTAACGCCCTATTTTTGC  3780
```

FIG. 7C

```
Query  3781  AATGGCTATATGGCAAGAAAGCTGGTAAACTATTTGTCTTTCAGGACCTTTTGAAGTAGT  3840

Query  3841  TTGTATAACTTCTTAAAAGTTGTGATTCCAGATAACCAGCTGTAACACAGCTGAGAGACT  3900

Query  3901  TTTAATCAGACAAAGTAATTCCTCTCACTAAACTTTACCCAAAAACTAAATCTCTAATAT  3960

Query  3961  GGCAAAAATGGCTAGACACCCATTTTCACATTCCCATCTGTCACCAATTGGTTAATCTTT  4020

Query  4021  CCTGATGGTACAGGAAAGCTCAGCTACTGATTTTTGTGATTTAGAACTGTATGTCAGACA  4080

Query  4081  TCCATGTTTGTAAAACTACACATCCCTAATGTGTGCCATAGAGTTTAACACAAGTCCTGT  4140

Query  4141  GAATTTCTTCACTGTTGAAAATTATTTTAAACAAAATAGAAGCTGTAGTAGCCCTTTCTG  4200

Query  4201  TGTGCACCTTACCAACTTTCTGTAAACTCAAAACTTAACATATTTACTAAGCCACAAGAA  4260

Query  4261  ATTTGATTTCTATTCAAGGTGGCCAAATTATTTGTGTAATAGAAAACTGAAAATCTAATA  4320

Query  4321  TTAAAAATATGGAACTTCTAatatattttatatttagttatagtttcagatatatatca  4380

Query  4381  tatTGGTATTCACTAATCTGGGAAGGGAAGGGCTACTGCAGCTTTACATGCAATTTATTA  4440

Query  4441  AAATGATTGTAAAATAGCTTGTATAGTGTAAAATAAGAATGATTTTTAGATGAGATTGTT  4500

Query  4501  TTATCATGACATGTTATATATTTTTTGTAGGGGTCAAAGAAATGCTGATGGATAACCTAT  4560

Query  4561  ATGATTTATAGTTTGTACATGCATTCATACAGGCAGCGATGGTCTCAGAAACCAAACAGT  4620

Query  4621  TTGCTCTAGGGGAAGAGGGAGATGGAGACTGGTCCTGTGTGCAGTGAAGGTTGCTGAGGC  4680

Query  4681  TCTGACCCAGTGAGATTACAGAGGAAGTTATCCTCTGCCTCCCATTCTGACCACCCTTCT  4740

Query  4741  CATTCCAACAGTGAGTCTGTCAGCGCAGGTTTAGTTTACTCAATCTCCCCTTGCACTAAA  4800

Query  4801  GTATGTAAAGTATGTAAACAGGAGACAGGAAGGTGGTGCTTACATCCTTAAAGGCACCAT  4860

Query  4861  CTAATAGCGGGTTACTTTCACATACAGCCCTCCCCCAGCAGTTGAATGACAACAGAAGCT  4920

Query  4921  TCAGAAGTTTGGCAATAGTTTGCATAGAGGTACCAGCAATATGTAAATAGTGCAGAATCT  4980

Query  4981  CATAGGTTGCCAATAATACACTAATTCCTTTCTATCCTACAACAAGAGTTTATTTCCAAA  5040

Query  5041  TAAAATGAGGACAtgttttttgttttctttgaatgcttttgaatgttatttgttattttc  5100

Query  5101  agtattttggagaaattatttAATaaaaaaaCAATCATTTGCTTTTTGAATGCTCTCTAA  5160

Query  5161  AAGGGAATGTAATATTTTAAGATGGTGTGTAACCCGGCTGGATAAATTTTTGGTGCCTAA  5220

Query  5221  GAAAACTGCTTGAATATTCTTATCAATGACAGTGTTAAGTTTCAAAAAGAGCTTCTAAAA  5280

Query  5281  CGTAGATTATCATTCCTTTATAGAATGTTATGTGGTTAAAACCAGAAAGCACATCTCACA  5340
18665  2674                                 AATGTTATGTGGTTAAAACCAGAAAGCACATCTCACA  2710

Query  5341  CATTAATCTGATTTTCATCCCAACAATCTTGGCGCTCAAAAAATAGAACTCAATGAGAAA  5400
18665  2711  CATTAATCTGATTTTCATCCCAACAATCTTGGCGCTCAAAAAATAGAACTCAATGAGAAA  2770

Query  5401  AAGAAGATTATGTGCACTTCGTTGTCAATAATAAGTCAACTGATGCTCATCGACAACTAT  5460
18665  2771  AAGAAGATTATGTGCACTTCGTTGTCAATAATAAGTCAACTGATGCTCATCGACAACTAT  2830

Query  5461  AGGAGGCTTTTCATTAAATGGGAAAAGAAGCTGTGCCCTTTTAGGATACGTGGGGGAAAA  5520
18665  2831  AGGAGGCTTTTCATTAAATGGGAAAAGAAGCTGTGCCCTTTTAGGATACGTGGGGGAAAA  2890

Query  5521  GAAAGTCATCTTAATTATGTTTAATTGTGGATTTAAGTGCTATATGGTGGTGCTGTTTGA  5580
```

FIG. 7D

```
18665  2891  GAAAGTCATCTTAATTATGTTTAATTGTGGATTTAAGTGCTATATGGTGGTGCTGTTTGA  2950

Query  5581  AAGCAGATTTATTTCCTATGTATGTGTTATCTGGCCATCCCAACCCAAACTGTTGAAGTT  5640
18665  2951  AAGCAGATTTATTTCCTATGTATGTGTTATCTGGCCATCCCAACCCAAACTGTTGAAGTT  3010

Query  5641  TGTAGTAACTTCAGTGAGAGTTGGTTACTCACAACAAATCCTGAAAAGTATTTTTAGTGT  5700
18665  3011  TGTAGTAACTTCAGTGAGAGTTGGTTACTCACAACAAATCCTGAAAAGTATTTTTAGTGT  3070

Query  5701  TTGTAGGTATTCTGTGGGATACTATACAAGCAGAACTGAGGCACTTAGGACATAACACTT  5760
18665  3071  TTGTAGGTATTCTGTGGGATACTATACAAGCAGAACTGAGGCACTTAGGACATAACACTT  3130

Query  5761  TTGGGGTATATATATCCAAATGCCTAAAACTATGGGAGGAAACCTTGGCCACCCCAAAAG  5820
18665  3131  TTGGGGTATATATATCCAAATGCCTAAAACTATGGGAGGAAACCTTGGCCACCCCAAAAG  3190

Query  5821  GAAAACTAACATGATTTGTGTCTATGAAGTGCTGGATAATTAGCATGGGATGAGCTCTGG  5880
18665  3191  GAAAACTAACATGATTTGTGTCTATGAAGTGCTGGATAATTAGCATGGGATGAGCTCTGG  3250

Query  5881  GCATGCCATGAAGGAAAGCCACGCTCCCTTCAGAATTCAGAGGCAGGGAGCAATTCCAGT  5940
18665  3251  GCATGCCATGAAGGAAAGCCACGCTCCCTTCAGAATTCAGAGGCAGGGAGCAATTCCAGT  3310

Query  5941  TTCACCTAAGTCTCATAATTTTAGTTCCCTTTTAAAAACCCTGAAAACTACATCACCATG  6000
18665  3311  TTCACCTAAGTCTCATAATTTTAGTTCCCTTTTAAAAACCCTGAAAACTACATCACCATG  3370

Query  6001  GAATGAAAAATATTGTTATACAATACATTGATCTGTCAAACTTCCAGAACCATGGTAGCC  6060
18665  3371  GAATGAAAAATATTGTTATACAATACATTGATCTGTCAAACTTCCAGAACCATGGTAGCC  3430

Query  6061  TTCAGTGAGATTTCCATCTTGGCTGGTCACTCCCTGACTGTAGCTGTAGGTGAAtgtgtt  6120
18665  3431  TTCAGTGAGATTTCCATCTTGGCTGGTCACTCCCTGACTGTAGCTGTAGGTGAATGTGTT  3490

Query  6121  tttgtgtgtgtgtgtCTGGTTTTAGTGTCAGAAGGGAAATAAAAGTGTAAGGAGGACACT  6180
18665  3491  TTTGTGTGTGTGTGTCTGGTTTTAGTGTCAGAAGGGAAATAAAAGTGTAAGGAGGACACT  3550

Query  6181  TTAAACCCTTTGGGTGGAGTTTCGTAATTTCCCAGACTATTTTCAAGCAACCTGGTCCAC  6240
18665  3551  TTAAACCCTTTGGGTGGAGTTTCGTAATTTCCCAGACTATTTTCAAGCAACCTGGTCCAC  3610

Query  6241  CCAGGATTAGTGACCAGGTTTTCAGGAAAGGATTTGCTTCTCTCTAGAAAATGTCTGAAA  6300
18665  3611  CCAGGATTAGTGACCAGGTTTTCAGGAAAGGATTTGCTTCTCTCTAGAAAATGTCTGAAA  3670

Query  6301  GGATTTTATTTTCTGATGAAAGGCTGTATGAAAATACCCTCCTCAAATAACTTGCTTAAC  6360
18665  3671  GGATTTTATTTTCTGATGAAAGGCTGTATGAAAATACCCTCCTCAAATAACTTGCTTAAC  3730

Query  6361  TACATATAGATTCAAGTGTGTCAATATTCTATTTTGTATATTAAATGCTATATAATGGGG  6420
18665  3731  TACATATAGATTCAAGTGTGTCAATATTCTATTTTGTATATTAAATGCTATATAATGGGG  3790

Query  6421  ACAAATCTATATTATACTGTGTATGGCATTATTAAGAAGCTTTTTCATTATTTTTTATCA  6480
18665  3791  ACAAATCTATATTATACTGTGTATGGCATTATTAAGAAGCTTTTTCATTATTTTTTATCA  3850

Query  6481  CAGTAATTTTAAAATGTGTAAAAATTAAAACCAGTGACTCCTGTTTAAAAATAAAAGTTG  6540
18665  3851  CAGTAATTTTAAAATGTGTAAAAATTAAAACCAGTGACTCCTGTTTAAAAATAAAAGTTG  3910

Query  6541  TAGTTTTTTATTCATGCTGAATAATAATCTGTAGTTaaaaaaaaaGTGTCTTTTTACCTA  6600
18665  3911  TAGTTTTTTATTCATGCTGAATAATAATCTGTAGTTAAAAAAAAAGTGTCTTTTTACCTA  3970

Query  6601  CGCAGTGAAATGTCAGACTGTAAAACCTTGTGTGGAAATGTTTAACTTTTATTTTTTCAT  6660
18665  3971  CGCAGTGAAATGTCAGACTGTAAAACCTTGTGTGGAAATGTTTAACTTTTATTTTTTCAT  4030

Query  6661  TTAAATTTGCTGTTCTGGTATTACCAAACCACACATTTGTACCGAATTGGCAGTAAATGT  6720
18665  4031  TTAAATTTGCTGTTCTGGTATTACCAAACCACACATTTGTACCGAATTGGCAGTAAATGT  4090

Query  6721  TAGCCATTTACAGCAATGCCAAATATGGAGAAACATCATAATaaaaaaaTCTGCTTTTTC  6780
18665  4091  TAGCCATTTACAGCAATGCCAAATATGGAGAAACATCATAATAAAAAAATCTGCTTTTTC  4150

Query  6781  ATTA  6784
```

FIG. 7E 18665   4151   ATTA   4154

FIG. 7F

METHODS AND COMPOSITIONS RELATED TO GLUCOCORTICOID RECEPTOR ANTAGONISTS AND BREAST CANCER

CROSS-REFERENCES TO RELATED APPLICATIONS

This application is a Continuation of U.S. application Ser. No. 15/448,827, filed Mar. 3, 2017, which is a Continuation of U.S. application Ser. No. 14/296,127, filed Jun. 4, 2014 (now U.S. Pat. No. 9,623,032, issued Apr. 18, 2017), which is a Continuation of U.S. application Ser. No. 14/172,051, filed Feb. 4, 2014 (now U.S. Pat. No. 9,149,485, issued Oct. 6, 2015), which is a Continuation of U.S. application Ser. No. 13/071,363, filed Mar. 24, 2011 (now U.S. Pat. No. 8,710,035, issued Apr. 29, 2014), which claims priority to U.S. Provisional Application No. 61/317,182, filed on Mar. 24, 2010, the disclosures of which are hereby incorporated by reference in their entireties.

STATEMENT AS TO RIGHTS TO INVENTIONS MADE UNDER FEDERALLY SPONSORED RESEARCH AND DEVELOPMENT

This invention was made with government support under CA089208 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON AN ASCII TEXT FILE

The Sequence Listing written in file "SeqListing096487-1158267.TXT", created on Oct. 7, 2019, 231,396 bytes, machine format IBM-PC, MS-Windows operating system, is hereby incorporated by reference in its entirety for all purposes.

BACKGROUND OF THE INVENTION

I. Field of the Invention

Embodiments of this invention are directed generally to biology and medicine. In certain aspects methods involve determining the prognosis for a breast cancer patient. In other embodiments, there are methods and compositions for treating a breast cancer patient with a glucocorticoid antagonist.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002). In the absence of a strategy to reduce causative agents of breast cancer, early detection remains the best approach to reducing the mortality rate of this disease. It is widely held that breast cancer initiates as the pre-malignant stage of atypical ductal hyperplasia (ADH), progresses into the pre-invasive stage of ductal carcinoma in situ (DCIS), and culminates in the potentially lethal stage of invasive ductal carcinoma (IDC). This linear model of breast cancer progression has been the rationale for the use of detection methods such as mammography in the hope of diagnosing and treating breast cancer at earlier clinical stages (Ma et al., 2003).

As more molecular information is being collated, diseases such as breast cancer are being sub-divided according to genetic signatures linked to patient outcome, providing valuable information for the clinician. Emerging novel technologies in molecular medicine have already demonstrated their power in discriminating between disease sub-types that are not recognizable by traditional pathological criteria (Sorlie et al., 2001) and in identifying specific genetic events involved in cancer progression (Srinivas et al., 2002).

Endocrine therapy is a popular mode of treatment for all stages of breast cancer. A majority of breast cancers belong to the type in which growth is stimulated by the female sex hormones, estrogens and progesterone. Therefore some of the therapies are based on depriving the tumor of the hormone-induced growth stimulus. Some of the current modes of endocrine treatments include blockade of the estrogen receptor with an antiestrogen, e.g. tamoxifen; hormonal ablation by surgery (oophorectomy, adrenalectomy or hypophysectomy), radiotherapy or medically by administration of a luteinizing hormone-releasing hormone analogue (LH-RHa), e.g., goserelin; suppression of estrogen synthesis with aromatase inhibitors, e.g., anastrozole; pharmacological doses of estrogens and progestagens, e.g., megestrol acetate.

Despite recent advances, the challenge of cancer treatment, including breast cancer therapy remains. Progress is limited with respect to the development of specific treatment regimens to clinically distinct tumor types, and to personalize tumor treatment in order to maximize outcome and efficiency. Moreover, a number of patients exhibit chemotherapy resistance.

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, and apparatuses related to assessing, prognosing, and/or treating breast cancer patients. It concerns using information related to glucocorticoid receptor (GR) activity and/or expression in conjunction with information related to estrogen receptor (ER) activity or expression to identify patients with the least favorable prognosis based on current standards of care for breast cancer. Patients with relatively low levels of estrogen receptor expression and relatively high levels of glucocorticoid expression fall into a group of breast cancer patients with the least favorable prognosis (i.e., mortality rate).

Accordingly, methods concern evaluating a patient with breast cancer. Embodiments include evaluating a biological sample from a patient; evaluating breast cancer cells from a patient; evaluating a biological sample from a breast cancer patient; assessing a breast cancer patient; testing a breast cancer sample or biopsy; testing a breast tumor; prognosing a breast cancer patient; treating a breast cancer patient, particularly a patient with a particular profile related to ER and GR; determining a treatment for a breast cancer patient; altering a treatment plan for a breast cancer patient; reporting prognosis of a breast cancer patient; determining a prognosis score for a breast cancer patient; generating a prognosis score for a breast cancer patient; assessing the risk of mortality of a breast cancer patient generally or within a certain time frame, such as 150 months from end of cancer treatment; generating an ER and GR expression profile for a breast cancer patient; comparing a patient's ER and GR expression profile to a standardized profile; and/or, determining a breast cancer patient has a poor prognosis based on the patient's ER and GR status.

Embodiments also cover apparatuses, kits, and computer readable medium and systems for assessing the level or activity of ER and/or GR in a patient's breast cancer sample and determining a prognosis; and/or treating the patient accordingly. It is specifically contemplated that a breast cancer patient is a human. Accordingly, in human patients, ER refers to an estrogen receptor in a human and GR refers to a glucocorticoid receptor in a human.

Some embodiments include generating an expression profile for glucocorticoid receptor, which means obtaining the level of expression of GR directly or indirectly by measuring or assaying activity or expression. Methods include directly measuring or assaying the level of expression or activity refers to measuring or assaying a sample to determine the level of GR expression (protein or transcript) in the cell. Indirectly obtaining the level of expression includes measuring or assaying expression or activity of a gene or protein that correlates with GR expression or activity. In some embodiments, the level of GR expression can be indirectly obtained by measuring or assaying expression of a GR-responsive gene, which refers to a gene whose expression is affected in a dose-dependent manner by GR expression or activity. Expression refers to either protein expression or RNA (transcript) expression. Methods may involve either type of expression and a variety of assays are well known to those of skill in the art. For example, quantitative PCR may be performed to obtain RNA expression levels. The Affymetrix chip used in the Examples also provides information regarding RNA expression levels. Alternatively, reagents to detect protein expression levels may be employed in embodiments. Methods may involve probes, primers, and/or antibodies that are specific to GR or ER in order to assess expression levels.

In some embodiments, the activity level of GR is measured by assaying the level of GR expression. In additional embodiments, GR expression is GR transcript expression. In other embodiments, GR expression is GR protein expression. As discussed above, in some embodiments, the activity level of GR is measured by assaying the expression level of one or more GR-responsive genes. A GR-responsive gene may be one or more of the following: MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, or MAOA.

In some embodiments, there is a step of assaying or measuring the activity level of glucocorticoid receptor (GR) in a biological sample from the patient containing breast cancer cells. As discussed above, the activity level of GR can be obtained directly or indirectly. It is specifically contemplated that levels of glucocorticoid activity or expression refers to activity or expression of GR $\alpha$, GR $\beta$, or both. Unless specifically stated otherwise, the terms "glucocorticoid receptor" or "GR" refer to both forms. Embodiments discussed with respect to glucocorticoid receptor or GR may also be implemented solely with GR$\alpha$ or solely with GR$\beta$.

Methods may also include obtaining a level of estrogen receptor (ER) expression in breast cancer cells from the patient. The level can be obtained by obtaining the results of an assay that measured the level of ER expression. In some embodiments, the level is obtained by measuring or assaying the level of ER expression.

In some embodiments, the level of estrogen receptor expression in breast cancer cells from patient is obtained by measuring the level of estrogen receptor expression from the biological sample from the patient. In other embodiments, the level is obtained by receiving qualitative and/or quantitative data regarding the level.

In some embodiments, methods include identifying the patient as having or not having a risk factor for cancer recurrence based on the levels of ER and GR expression. Methods may involve categorizing the patient as ER+ or ER− based the level of estrogen receptor expression and a predetermined threshold value for ER expression. The term "ER+" refers to a classification of ER expression that indicates the patient expresses estrogen receptor in breast cancer cells at or above a certain level. The term "ER−" refers to a classification of ER expression that indicates the patient expresses estrogen receptor at a relatively low level in breast cancer cells, meaning at or below a certain level. In embodiments of the invention, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein.

Methods may involve measuring the activity level of glucocorticoid receptor in a biological sample from the patient containing breast cancer cells and measuring the expression level of estrogen receptor in the biological sample.

In certain embodiments, the predetermined threshold value for ER expression identifies a patient as ER+ if the patient's ER expression level is in the 25$^{th}$ percentile or greater compared to a normalized sample. This means the patient may be designated as having a level of ER expression that is at or above 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. It is contemplated that in some cases, a patient may be designated as ER+ if the patient's ER expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The patient may also be referred to as having a normal or high ER expression level. The higher the percentile, the higher the relative expression level.

In embodiments, methods may also involve categorizing the patient as GR+ or GR− based on a predetermined threshold value for GR activity. In some cases, a predetermined threshold value for GR activity is dependent on whether the patient is categorized as ER+ or ER−. Embodiments may involve a predetermined threshold value for GR activity that identifies a patient as GR+ if the patient is ER− and GR activity level is in the $65^{th}$ percentile or greater compared to a normalized sample. It is contemplated that in some cases, a patient may be designated as GR+ if the patient's GR expression level is at or above 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. The threshold value may or may not be dependent on ER expression levels or status. In some embodiments, the threshold value depends on whether the patient is ER− or not. The higher the percentile, the higher the relative expression level.

Methods may involve the use of a normalized sample or control that is based on one or more breast cancer samples that are not from the patient being tested.

In some embodiments, methods involve calculating a prognosis score for the patient based on the levels of ER and/or GR expression. Methods may alternatively or additionally involve reporting a prognosis score or report the levels of ER and/or GR expression. The score or report may contain or reflect raw data regarding expression levels or it may reflect a categorization of the expression levels obtained. A score could indicate the risk factor for mortality, recurrence, and/or both. The score could be a number within a numeric scale in which one end of the scale is most favorable and the other end is the least favorable with respect to a prognosis for breast cancer.

In certain embodiments, methods may involve identifying the patient as having a poor prognosis if the patient is determined to have a glucocorticoid receptor activity level at or above a certain threshold level and a level of estrogen receptor that is at or below a second threshold level. In each case, the threshold levels are specific for each of GR and ER. In certain embodiments, it is contemplated that a GR level in the 65th percentile or above based on breast cancer patients whose are in the $35^{th}$ percentile or below is indicative of a poor prognosis. In some embodiments, patients with a poor prognosis include a population of breast cancer patients that numbers approximately 10% or less.

Methods also include identifying the patient as having a poor prognosis if the patient is determined to have i) an activity level of glucocorticoid receptor that is higher than the activity level of glucocorticoid receptor in normalized control sample and ii) a expression level of estrogen receptor expression that is lower than the expression level of estrogen receptor in a normalized control sample. Consequently, methods of the invention include prognosing a breast cancer patient. In some cases, a patient is identified as having a relatively good prognosis.

Other embodiments include methods of treating a patient for breast cancer comprising: treating the patient for breast cancer after a biological sample from the patient containing breast cancer cells is analyzed for i) the activity level of glucocorticoid receptor and ii) the expression level of estrogen receptor. A patient may be treated with a different treatment protocol than the patient would have been treated with if the patient's biological sample had not been analyzed. In some embodiments, the patient is categorized as ER− and GR+ based on the activity level of the glucocorticoid receptor and the expression level of estrogen receptor. In some cases, the patient is treated with a more aggressive therapy than the patient would have been treated with if the patient had not been categorized as ER− and GR+. The term "more aggressive" refers to a treatment regimen that may include more drugs or drugs with more severe side effects and/or it may include an increased dosage or increased frequency of drugs. It may also include radiation or a combination of therapies. In some cases, the therapy includes one or more chemotherapeutics and/or biologics. In some embodiments, the patient is treated with a therapy comprising an anti-angiogenic agent. In additional embodiments, the therapy further comprises a chemotherapeutic agent in addition to the anti-angiogenic agent. Embodiments also include administering a glucocorticoid receptor antagonist and/or tyrosine kinase inhibitor.

Embodiments may also include where the patient is treated with more than one type of cancer therapy. This may be after the patient is determined to have a particular prognosis or after the status of the patient's GR and ER expression profile is known. In some embodiments, certain treatments are provided to an ER−/GR+ breast cancer patient who might have otherwise been treated with a less aggressive treatment for breast cancer. In some embodiments, a patient is treated with at least two of the following: radiation, chemotherapy, or a biologic. In particular embodiments, the patient may be treated with a kinase inhibitor and/or anti-angiogenic agent.

Methods may also involve obtaining a biological sample comprising breast cancer cells from the patient and categorizing the patient as i) GR+ or GR− based on the level of glucocorticoid activity assayed in the sample and compared to a predetermined threshold value for GR activity; and ii) ER+ or ER− based on the level of estrogen receptor expression assayed in the sample and compared to a predetermined threshold value for ER expression.

Any method may also include treating the patient for breast cancer, which may include directly administering or providing a cancer therapy. In some embodiments, a practitioner or doctor may prescribe a cancer therapy that the patient administers to herself.

To achieve these methods, a doctor, medical practitioner, or their staff may retrieve a biological sample from a patient for evaluation. The sample may be a biopsy, such as a breast tissue or tumor biopsy. The sample may be analyzed by the practitioner or their staff, or it may be sent to an outside or independent laboratory. The medical practitioner may be cognizant of whether the test is providing information regarding the patient's level of GR and/or ER expression or activity, or the medical practitioner may be aware only that the test indicates directly or indirectly that the test reflects that the patient has a particular prognosis or can be given a particular prognosis score. Furthermore, the practitioner may know the patient's ER or GR status, such as ER+ or ER−, or GR+ or GR−. Alternatively, she may be aware only that the test or assay indicates the patient has a poor prognosis, or the worst prognosis.

Embodiments also concern kits to determine glucocorticoid receptor status in breast cancer cells comprising: (a) one or more reagents for determining expression levels of NR3C1 in a biological sample; and (b) an algorithm and software encoding the algorithm for calculating a risk factor index from the expression of NR3C1 in a sample and the estrogen receptor status of the breast cancer cells to determine a prognosis or a prognosis score. Kits may also include one or more reagents for determining expression levels of ESR1 in the biological sample to provide estrogen receptor status.

Other embodiments include a computer readable medium having software modules for performing a method comprising the acts of: (a) comparing glucocorticoid receptor data obtained from a patient's breast cancer sample with a reference; and (b) providing an assessment of glucocorticoid receptor status to a physician for use in determining an appropriate therapeutic regimen for a patient. In further embodiments, the computer readable medium further comprises a software module for assessing estrogen receptor status of the patient's breast cancer sample.

Computer systems are also included. In some embodiments, they have a processor, memory, external data storage, input/output mechanisms, a display, for assessing glucocorticoid receptor activity, comprising: (a) a database; (b) logic mechanisms in the computer generating for the database a GR-responsive gene expression reference; and (c) a comparing mechanism in the computer for comparing the GR-responsive gene expression reference to expression data from a patient sample using a comparison model to determine a GR gene expression profile of the sample.

Other embodiments include an internet accessible portal for providing biological information constructed and arranged to execute a computer-implemented method for providing: (a) a comparison of gene expression data of one or more GR-responsive genes in a patient sample with a calculated reporter index; and (b) providing an assessment of GR activity or expression to a physician for use in determining an appropriate therapeutic regime for a patient.

In addition to compiling, collecting and or processing data related to GR status, methods, media and systems may also include the same embodiments with respect to data related to ER status. Such aspects may be instead of or in addition to the aspects related to GR status or data.

Embodiments also include methods of killing breast cancer cells comprising administering to a breast cancer patient an effective amount of a combination of anti-cancer compounds, wherein the anticancer compounds comprise a glucocorticoid receptor antagonist and a chemotherapeutic.

In other embodiments, there are methods for treating breast cancer in a patient comprising administering to the patient an effective amount of glucocorticoid receptor antagonist and a chemotherapeutic.

In further embodiments, methods are provided for treating chemotherapy-insensitive breast cancer cells comprising administering to a breast cancer patient an effective amount of a glucocorticoid receptor antagonist followed by chemotherapy.

Other methods include methods for treating breast cancer in a patient comprising: a) administering radiation or at least a first chemotherapeutic to the patient; b) subsequently administering an effective amount of a glucocorticoid receptor antagonist to the patient; and, c) administering radiation again or at least a second chemotherapeutic to the patient after the glucocorticoid receptor antagonist is administered to the patient.

In some embodiments, there are methods for treating breast cancer in a patient comprising: a) administering an effective amount of a glucocorticoid receptor antagonist to the patient, wherein the patient expresses detectable levels of GR prior to administration of the GR antagonist; b) then administering an effective amount of radiation or at least one chemotherapeutic.

It is contemplated that in methods described herein, breast cancer cells may undergo apoptosis following treatment set forth herein. Moreover, in some embodiments, the combination of a glucocorticoid receptor antagonist and an anticancer agent or compound induces more apoptosis than treatment with just the anticancer treatment alone. In other methods, it is specifically contemplated to exclude treatment with a synthetic glucocorticoid, such as dexamethasone.

Glucocorticoid receptor antagonists are known to those of skill in the art. It refers to a compound or substance that that does not provoke a biological response itself upon binding to the glucocorticoid receptor, but blocks or dampens agonist-mediated responses. Examples include, but are not limited to, beclometasone, betamethasone, budesonide, ciclesonide, flunisolide, fluticasone, mifepristone, mometasone, and triamcinolone. In additional embodiments, the glucocorticoid receptor antagonist has undetectable level or a lower level of activity as a progesterone receptor antagonist. In certain embodiments, the glucocorticoid receptor antagonist has greater than 10-fold, 50-fold, 100-fold, 200-fold, 300-fold, 400-fold, 500-fold, 1000-fold lower binding activity (or any range derivable therein) for another hormone receptor compared to its binding activity for glucocorticoid receptor. In specific embodiments the hormone receptor is estrogen receptor or progesterone receptor.

In some embodiments, a patient had been previously treated with an anti-cancer therapy, such as radiation, chemotherapy, or immunotherapy (or a combination or multiple therapies thereof). In certain embodiments, a first anti-cancer therapy prior to therapy with glucocorticoid receptor antagonist was last administered more than two weeks prior to the glucocorticoid receptor antagonist or its combination with a second anti-cancer therapy. In certain embodiments, this first anti-cancer therapy that does not include a glucocorticoid receptor antagonist was last administered to the breast cancer patient at least 7, 8, 9, 10, 11, 12, 13, 14 days, and/or 1, 2, 3, 4, or 5 weeks, and/or 1, 2, 3, 4, 5, 6, 7, 8, 9, 10, 11, or 12 months prior to treatment with a glucocorticoid receptor antagonist. Treatment methods may be applied to breast cancer or breast cancer cells that are chemo-resistant or breast cancer cells that are not chemo-sensitive. Moreover, treatment may be applied to breast cancer or to breast cancer cells that were previously administered a first apoptosis inducing agent, but were resistant to apoptosis.

In some embodiments, the breast cancer cells are determined to be resistant to apoptosis. In additional embodiments, the breast cancer or the breast cancer cells are determined not to be chemo-sensitive or are determined to be chemo-resistant. This determination may be based on the results of a genetic test or based on information obtained from an assessment of a tumor or the breast cancer after treatment with a first anti-cancer therapy. In specific embodiments, the first anti-cancer therapy is a chemotherapeutic, Herceptin®, radiation, a combination of chemotherapeutics, or a combination of one or more chemotherapeutic agents and Herceptin®.

In additional embodiments, the breast cancer cells express a detectable level of glucocorticoid receptor or its transcript. In some embodiments, the patient is determined to have breast cancer cells that express a detectable level of glucocorticoid receptor or its transcript. This may be determined directly or indirectly.

It is contemplated that breast cancer cells may be treated with a glucocorticoid receptor antagonist regardless of estrogen receptor status. Therefore, breast cancer cells may be estrogen receptor-negative (ER−) or estrogen receptor-positive (ER+), accordingly to a standardized and industry accepted test for ER status. In certain embodiments, the breast cancer cells do not express any detectable levels of ER; in other embodiments, ER expression is detectable in the breast cancer cells.

It is contemplated that breast cancer cells may be treated with a glucocorticoid receptor antagonist depending on or regardless of progesterone receptor status. Therefore, breast cancer cells may be progesterone receptor-negative (PR−) or progesterone receptor-positive (PR+), accordingly to a standardized and industry accepted test for ER status. In certain embodiments, the breast cancer cells do not express any detectable levels of PR; in other embodiments, PR expression is detectable in the breast cancer cells.

Methods involve treating breast cancer, particularly a chemo-resistant breast cancer, with a combination of therapies that includes a glucocorticoid receptor antagonist and an anticancer therapy that induces apoptosis (together they may be referred to as a combination of anti-cancer agents or compounds), such as a chemotherapeutic. In some embodiments, the chemotherapeutic is capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, or vinorelbin, or a combination of these agents. In other embodiments, therapy with a glucocorticoid receptor antagonist is combined Herceptin®, radiation, chemotherapeutic(s) and radiation, a combination of chemotherapeutics, or a combination of one or more chemotherapeutic agents and Herceptin®.

It is contemplated that in some embodiments of the combination therapy the glucocorticoid receptor antagonist is administered within 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof within administration of at least one or the combination of the anti-cancer agents or compounds. In specific embodiments, the glucocorticoid receptor antagonist is administered within 2 hours, 12 hours or 24 hours of administration of a anticancer agent or compound (or a combination of such agents or compounds).

It is specifically contemplated that treatment may continue or be repeated. In some embodiments, once treated with the combination of a glucocorticoid receptor antagonist and at least one anticancer agent or compound, all or part of the treatment may be repeated alone or in combination with a different anticancer agent or compound.

In certain embodiments, the glucocorticoid receptor antagonist is administered prior to as the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof prior to administration of at least one or the combination of the anti-cancer agents or compounds. It is specifically contemplated that in some embodiments, the glucocorticoid receptor antagonist is given prior to administration of the anticancer agent or compound but that the glucocorticoid receptor antagonist is also given concurrently with or after administration of the initial or a subsequent dose of the anticancer agent or compound. As discussed throughout, the anticancer agent or compound may be in a combination of such agents or compounds. In certain embodiments, the glucocorticoid receptor antagonist is administered up to three days prior to administering the anticancer agent or compound.

Additionally or alternatively, the glucocorticoid receptor antagonist is administered after administration of the other agent or therapy included in the combination therapy. In certain embodiments, the glucocorticoid receptor antagonist is administered 5, 10, 30, 45, 60 minutes, and/or 1, 2, 3, 4, 5, 6, 7, 8, 9, 10, 11, 12, 13, 14, 15, 16, 17, 18, 19, 20, 21, 22, 23, 24 hours, and/or 1, 2, 3, 4, 5, 6, 7 days, or any combination thereof after administration of at least one or the combination of the anti-cancer agents or compounds. It is specifically contemplated that in some embodiments, the glucocorticoid receptor antagonist is given after to administration of the anticancer agent or compound; such administration may be repeated. As discussed throughout, the anticancer agent or compound may be in a combination of such agents or compounds. In certain embodiments, the glucocorticoid receptor antagonist is administered up to three days after administering the anticancer agent or compound.

In certain embodiments, the breast cancer is an unresectable breast cancer. In further embodiments, the breast cancer is inflammatory breast cancer.

It is specifically contemplated that in some methods, dexamethasone has not been administered to the patient within 24 hours of administration of the glucocorticoid receptor antagonist.

Compositions are contemplated to include a glucocorticoid receptor antagonist and any other anticancer compound discussed herein, such a Herceptin or one or more chemotherapeutic compounds. In some embodiments, the composition is in a pharmaceutically acceptable formulation.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

In certain aspects, prognosis is an estimation of the likelihood of metastasis free survival of said patient over a predetermined period of time, e.g., over a period of 5 years.

In further aspects, prognosis is an estimation of the likelihood of death of disease of said patient over a predetermined period of time, e.g., over a period of 5 years.

The term "recurrence" refers to the detection of breast cancer in form of metastatic spread of tumor cells, local recurrence, contralateral recurrence or recurrence of breast cancer at any site of the body of the patient after breast cancer had been substantially undetectable or responsive to treatments.

As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, and/or duration of response in a patient or a group of patients susceptible to or diagnosed with a cancer.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation in comparison to a non-cancer cell or cancer cell that is not associated with the worst or poorest prognosis.

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A-F. Schematic of glucocorticoid receptor (GR) isoforms. GR alpha=SEQ ID NO:47; GR beta=SEQ ID NO:48

DETAILED DESCRIPTION OF THE INVENTION

Figure 1:
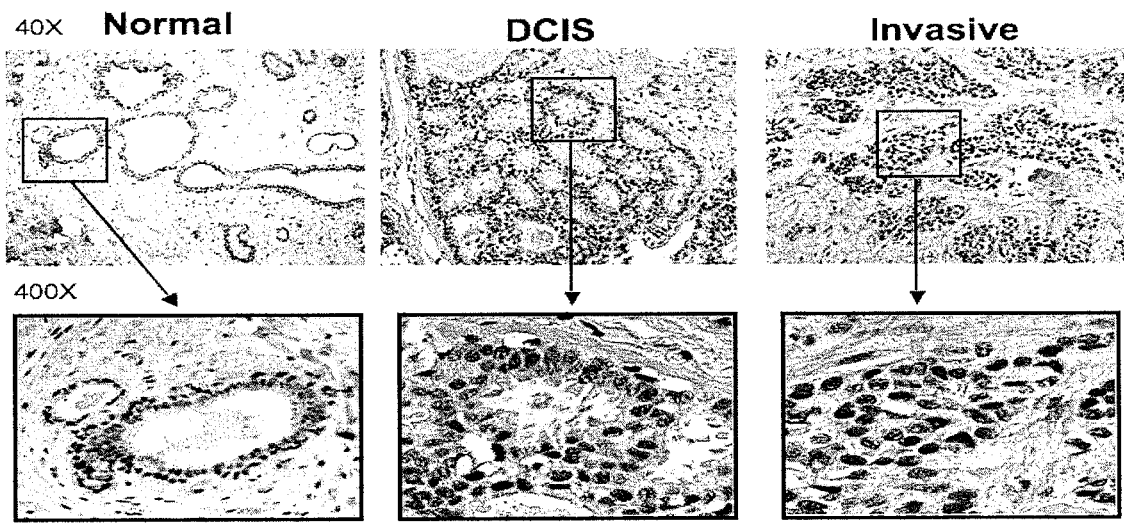
FIG. 1. Primary human breast ductal epithelium, DCIS (60%) invasive human cancers ('30-40%)exhibit significant glucocorticoid receptor expression.
Figure 2:
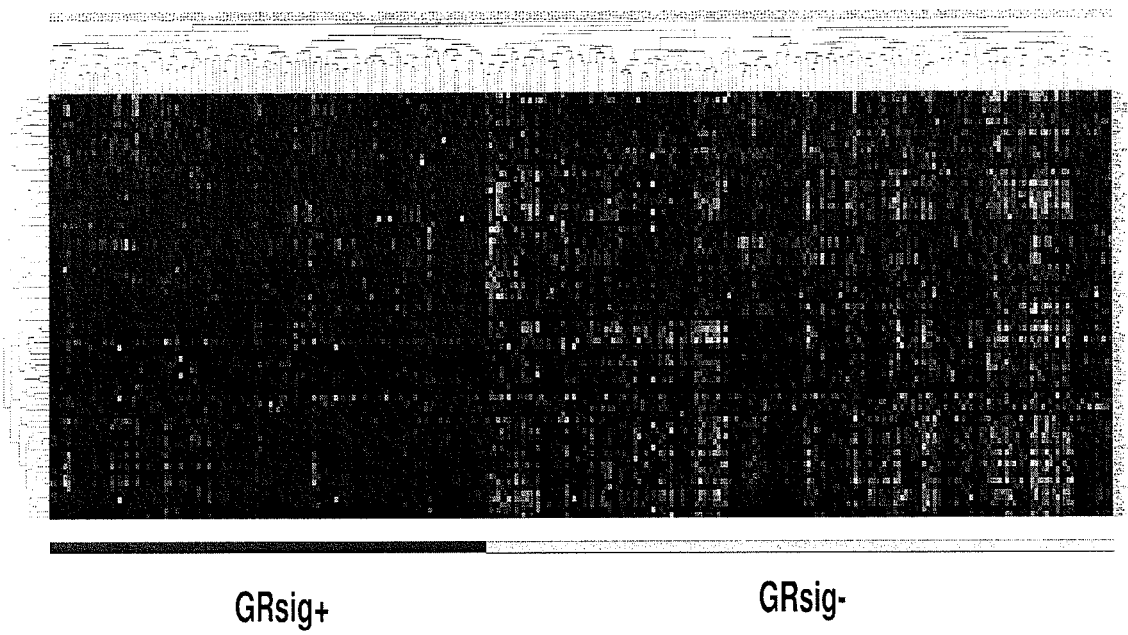
FIG. 2. Unsupervised cluster analysis identifies GR target gene signature (Sig+) vs Sig– tumors (n=68 genes) A GR-regulated gene expression set from MCF10A-Myc (ER–/GR+) cells treated+/– Dex from 30 m-24 h was used to perform a two dimensional unsupervised clustering analysis on the NKI-295 early breast cancer gene expression data set (n=2034 starting genes). GR-regulated genes (n=68) that separate these tumors into two groups (GRsig+=Red and GRsig–=Green) are shown in rows while each column represents a patient. Several EMT genes (e.g. Snail) and known anti-apoptotic genes are included.
Figure 3:
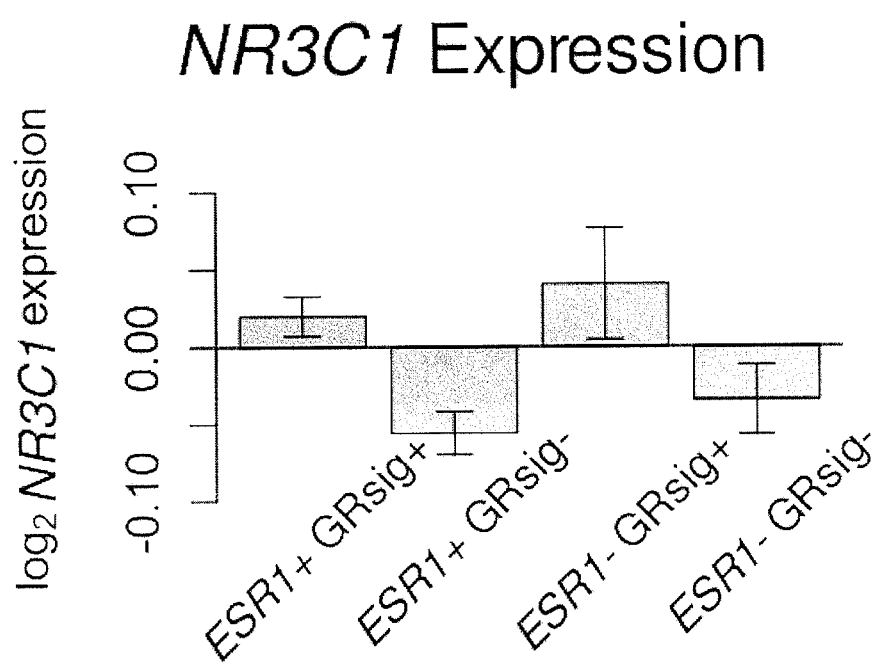
FIG. 3. NR3C1 expression correlates with GR signature gene expression. The GRsig+ vs. GRsig– tumor designations correlate with higher NR3C1 vs. lower expression, respectively. For ESR1+ tumors (orange) the P<.00001 and for ESR1– tumors (green) p=.7 (t test). Error bars are +/–SD.
Figure 4:
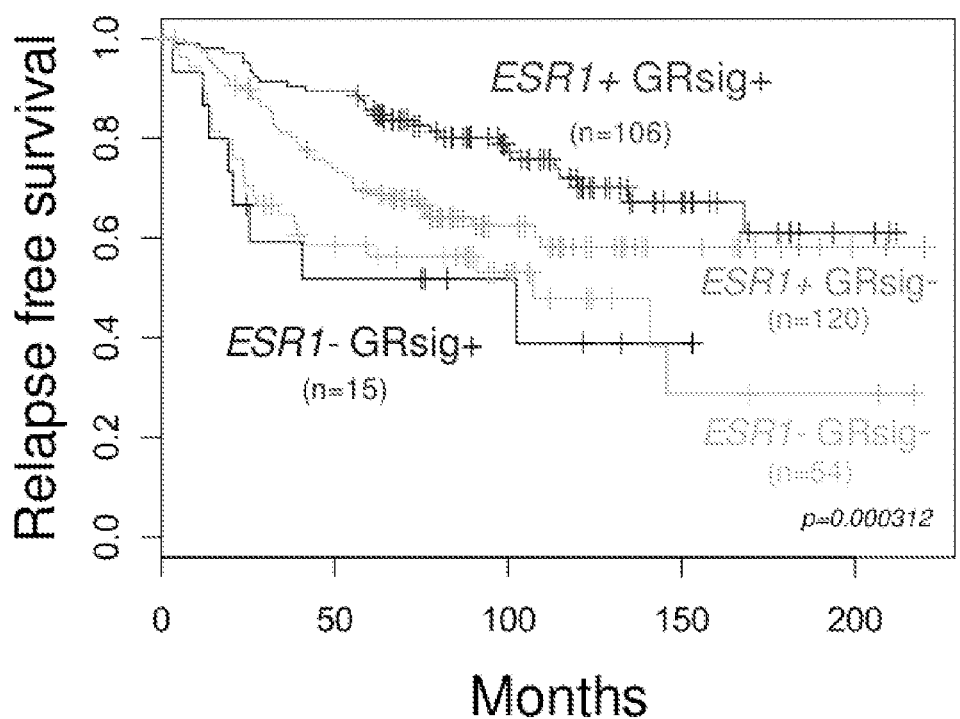
FIG. 4. RFS of GR gene expression signature. The GR signature predicts a differential prognosis for ESR1+ patients and ESR1– pts with respect to GR-signature expression. ESR1–/GR+ signature patients have the worst prognosis.
Figure 5:
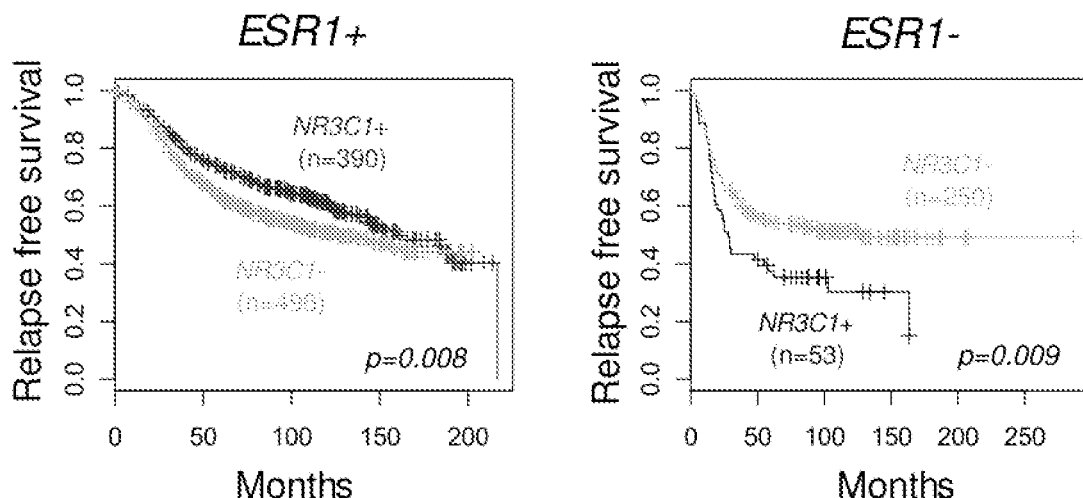
FIG. 5. Meta-analysis of NR3C1 expression and RFS.
Figure 6:
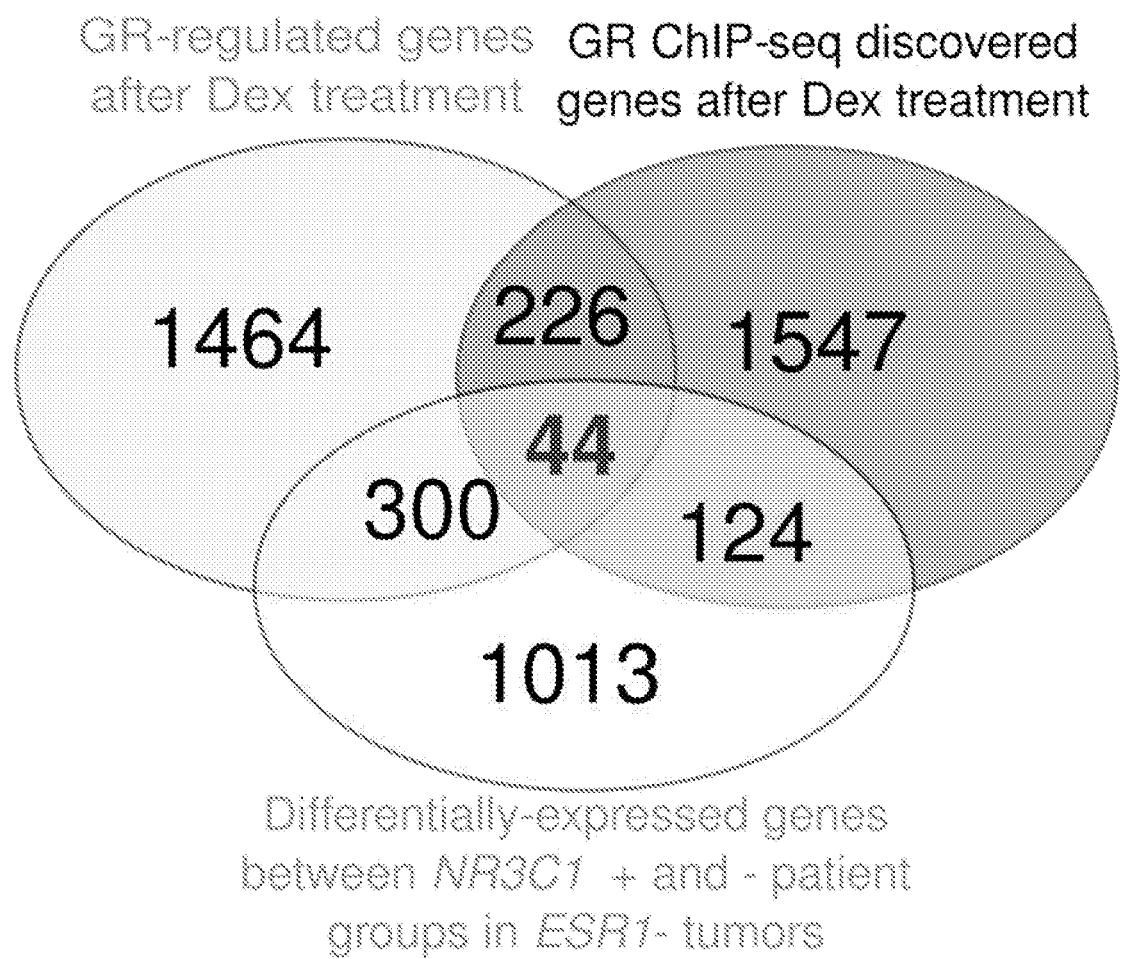
FIG. 6. Common genes differentially expressed in ESR1– and NR3C1+/– tumors, ChIP-seq and gene expression in Dex-treated MCF10A-Myc cells.

Glucocorticoid receptor (GR) activation initiates a potent cell survival signal in ER– breast cancer models. However, GR activity has not been previously examined in primary human breast cancers. Because anti-apoptotic signaling is believed to be an important determinant of breast cancer viability and relapse, the inventors contemplate that early stage primary human breast cancer demonstrates a correlation between high GR (NR3C1) and GR-mediated gene expression and cancer recurrence.

The Dutch NKI 295 data set was examined and the inventors determined that a gene expression signature of 68 GR-regulated genes (based on in vitro data) could cluster patients into different groups with differential outcome. In addition, it was found that GR-mediated gene expression correlated with NR3C1 expression levels. The inventors examined NR3C1 tumor expression in a much larger meta-dataset and again found that ER–/GR (NR3C1)+ patients did the worst. Moreover, key cell survival genes identified as GR gene targets from ChIP-seq experiments were differentially expressed.

I. Hormone Receptor Status of Breast Cancer

Intracellular receptors (IRs) form a class of structurally-related genetic regulators scientists have named "ligand dependent transcription factors" (R. M. Evans, Science, 240:889, 1988). Steroid receptors are a recognized subset of the IRs, including androgen receptor (AR), progesterone receptor (PR), estrogen receptor (ER), glucocorticoid receptor (GR), and mineralocorticoid receptor (MR). Regulation of a gene by such factors requires both the IR itself and a corresponding ligand, which has the ability to selectively bind to the IR in a way that affects gene transcription.

Naturally occurring as well as synthetic steroidal glucocorticoids (e.g., cortisol, cortisone, prednisolone, dexamethasone) have been widely used for over fifty years for the treatment of acute and chronic inflammatory and immune disorders. In particular, glucocorticoids have been prescribed for the treatment of rheumatoid arthritis, osteoarthritis, rheumatic fever, asthma, allergic rhinitis, systemic lupus erythematosus, chronic obstructive pulmonary disease, Crohn's disease, inflammatory bowel disease, and ulcerative colitis. However, the use of glucocorticoids is often associated with severe and sometimes irreversible side effects such as bone loss/osteoporosis, hyperglycemia, diabetes mellitus, hypertension, glaucoma, muscle atrophy, Cushing's syndrome, and psychosis.

Glucocorticoids exert their pharmacological effects by regulating gene transcription after the formation of a complex with the glucocorticoid receptor (GR). GR-glucocorticoid complex affects gene transcription by translocating to the nucleus after binding of the glucocorticoid where it acts as a dimer in binding to DNA glucocorticoid hormone response elements (GREs) in the promoter regions of particular genes. The GR-glucocorticoid/GRE complex then, in turn, activates (transactivation) or inhibits transcription of proximally located genes. Conversely, the GR-glucocorticoid complex may negatively regulate gene transcription by a process that does not involve binding to DNA. In this process, termed transrepression, following binding of the glucocorticoid, the complexed GR enters the nucleus where it acts as a monomer to directly interact (via protein-protein interaction) with other transcription factors, repressing their ability to induce gene transcription and thus protein expression.

Estrogen, mediated through the estrogen receptor (ER), plays a major role in regulating the growth and differentiation of normal breast epithelium (Pike et al. Epidemiologic Reviews (1993) 15(1):17-35; Henderson et al. Cancer Res. (1988) 48:246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., Annals of Oncology 11(8): 1057 (2000)). Thus, ER negative and ER positive breast cancers are two distinct disease entities rather than phenotypic variations of the same disease.

Relatively increased expression of these genes in primary ER-negative human breast tumors is associated with high GR expression and with an earlier relapse in ER-negative breast cancer patients (described herein). Activation of the glucocorticoid receptor (GR) in epithelial cells has been shown to initiate an anti-apoptotic (i.e., cell survival) signaling pathway that prevents breast (Wu et al, 2004) and ovarian cancer (Melhem et al, 2009) cell death in vitro and in vivo (Pang et al, 2006). Blocking or antagonizing GR activation with a GR antagonist such as mifepristone reverses cell survival signaling pathways initiated by the GR (Moran et al., 2000). Other GR antagonists (e.g., dexamethasone oxetanone) also reverse GR-mediated cell survival and potentiate apoptosis in response to cell stressors such as growth factor withdrawal (Mikosz et al, 2001). The mechanism(s) whereby GR activation protects from cell death includes the transcriptional upregulation of genes encoding anti-apoptotic proteins such as SGK1, MKP1, MCL1, and BIRC3. However, experiments with a glucocorticoid receptor antagonist, RU486, in conjunction with dexamethasone did not increase the number of apoptotic cells induced by paclitaxel, compared to paclitaxel alone (Wu et al., 2004).

II. Biomarkers and Evaluating Levels of Biomarkers

Biomarkers for prognosing human breast cancer patients have been identified. They include estrogen receptor (ER) in combination with the activity of the glucocorticoid receptor (GR) activity. It is contemplated that these biomarkers may be evaluated based on their gene products. In some embodiments, the gene product is the RNA transcript. In other embodiments, the gene product is the protein expressed by the RNA transcript. In still another embodiment is the evaluation of surrogate genes or gene targets of ER, GR, or ER and GR.

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene is preferably achieved by dividing the expression level of the individual marker gene to be normalized by the respective individual median expression of this marker genes, wherein said median expression is preferably calculated from multiple measurements of the respective gene in a sufficiently large cohort of test individuals. The test cohort preferably comprises at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, preferably more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous breast tissue cells or a heterogenous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.

2. The number of marker genes, the expression level of which is above their respective threshold level, is determined.

3. If a marker genes is expressed above its respective threshold level, then the expression level of the marker gene is taken to be "above the threshold level".

"A sufficiently large number", in this context, means preferably 30%, 50%, 80%, 90%, or 95% of the marker genes used.

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the ER or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second marker gene or activity; and (e) computing apparatus or device programmed to provide a unfavorable or poor prognosis if the data indicates a negative ER status and an increased or decreased expression level of said first marker gene or activity (e.g., GR expression or activity) with the predetermined first threshold value and, alternatively, the expression level of said second marker gene is above or below a predetermined second threshold level.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The GR nucleic acid and protein sequences are provided in GenBank accession number AY436590. The ER nucleic acid and protein sequences are provided in GenBank accession number NG_008493. The content of all of these GenBank Accession numbers is specifically incorporated herein by reference as of the filing date of this application.

The following biomarkers are provided for implementation with embodiments discussed herein. All of them designate nucleic acid sequences for the particular gene identifier. Nucleic acid sequences related to these gene designation can be found in the Genbank sequence data-bases. Additional biomarkers include the MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA genes.

One or more of the biomarkers can be used to prognose a human patient with breast cancer. The expression pattern of these biomarkers in breast cancer cells may be used to evaluate a patient to determine whether they are likely to respond to standard chemotherapy, likely not to respond to standard chemotherapy, or likely to relapse after standard chemotherapy.

The expression levels of breast cancer biomarkers can be compared to reference expression levels using various methods. These reference levels can be determined using expression levels of a reference based on all breast cancer patients or all breast cancer patients determined to be ER+and/or ER−. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments of the invention.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

A. Nucleic Acids

Screening methods based on differentially expressed gene products are well known in the art. In accordance with one aspect of the present invention, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Preferably, each probe/primer has relatively high sequence complexity and does not have any ambiguous residue (undetermined "n" residues).

The probes/primers preferably can hybridize to the target gene, including its RNA transcripts, under stringent or highly stringent conditions. In some embodiments, because each of the biomarkers has more than one human sequence, it is contemplated that probes and primers may be designed for use with each on of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as TaqMan, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products preferably are carried out when the PCR reactions are in the linear portion of their curves. In addition, relative concentrations of the amplifiable cDNAs preferably are normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array of the present invention can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods of the invention.

The present invention may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; W00138580; WO 0168255; WO 03020898; WO 03040410; WO 03053586; WO 03087297; WO 03091426; W003100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

B. Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies for this invention include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

III. Breast Cancer Therapy

Certain embodiments are directed to methods of treating breast cancer based on GR status of the breast cancer tissue. In some embodiments, the hormone receptor status is determined based on the expression of a hormone receptor such as the estrogen receptor (ER) in combination with the glucocorticoid receptor (GR).

In certain aspects, the hormone receptor status is high for GR and may also be low for one or more other hormone receptors such as the estrogen receptor. An individual having an elevated GR and low ER is likely to have a poor prognosis. In the event of a poor prognosis the physician may pursue a more aggressive therapy for those patients. In some embodiments, the method comprises identifying a breast cancer patient based on a hormone receptor status of patients having tumor tissue with elevated levels of GR expression.

In certain aspects, there may be provided methods for treating a subject determined to have cancer and with a predetermined expression profile of one or more biomarkers disclosed herein.

In a further aspect, biomarkers and related systems that can establish a prognosis of cancer patients in this invention can be used to identify patients who may get benefit of conventional single or combined modality therapy. In the same way, the invention can identify those patients who do not get much benefit from such conventional single or combined modality therapy and can offer them alternative treatment(s).

In certain aspects of the present invention, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Embodiments concern a glucocorticoid receptor antagonist. In some embodiments, the glucocorticoid receptor antagonist is a selective glucocorticoid receptor antagonist, as set forth in Clark, 2008, which is hereby incorporated by reference. In other embodiments, the glucocorticoid receptor antagonist is a non-selective glucocorticoid receptor antagonist, such as mifepristone. In certain embodiments, the glucocorticoid receptor antagonist is steroidal. In other embodiments, the glucocorticoid receptor antagonist is nonsteroidal. A glucocorticoid receptor antagonist includes those in the following classes of chemical compounds: octahydrophenanthrenes, spirocyclic dihydropyridines, triphenylmethanes and diaryl ethers, chromenes, dibenzyl anilines, dihydroisoquinolines, pyrimidinediones, azadecalins, and aryl pyrazolo azadecalins, and which are described in more detail in Clark, 2008, which is hereby incorporated by reference. Some embodiments of steroidal antagonists from Clark, 2008 are: RU-486, RU-43044, 11-monoaryl and 11,21 bisaryl steroids (including 11β-substituted steroids), 10β-substituted steroids, 11β-aryl conjugates of mifepristone, and phosphorous-containing mifepristone analogs. Further embodiments of nonsteroidal antagonists from Clark, 2008 are: octahydrophenanthrenes, spirocyclic dihydropyridines, triphenylmethanes and diaryl ethers, chromenes, dibenzyl anilines, dihyrdroquinolines, pyrimidinediones, azadecalins, aryl pyrazolo azadecalins (including 8a-benzyl isoquinolones, N-substituted derivatives, bridgehead alcohol and ethers, bridgehead amines). Additional specific examples include, but are not limited to the following specific antagonists: beclometasone, betamethasone, budesonide, ciclesonide, flunisolide, fluticasone, mifepristone, mometasone, and triamcinolone. Other examples include those described and/or depicted in U.S. Patent Application Publication 2010/0135956, which is hereby incorporated by reference. Even further examples include ORG-34517 (Merck), RU-43044, dexamethasone mesylate (Dex-Mes), dexamethasone oxetanone (Dex-Ox), deoxycorticosterone (DOC) (Peeters et al., 2008, which is hereby incorporated by reference in its entirety and Cho et al. 2005, which is hereby incorporated by reference in its entirety). In additional embodiments the glucocorticoid receptor antagonist may be CORT 0113083 or CORT 00112716, which are described in Belanoff et al. (2011), which is hereby incorporated by reference. It is specifically contemplated that one or more of the antagonists discussed herein or in the incorporated references may be excluded in embodiments of the invention. It is also contemplated that in some embodiments, more than one glucocorticoid receptor antagonist is employed, while in other embodiments, only one is employed as part of the therapeutic method (though it may be administered multiple times). It is contemplated that the second one may be administered concurrently with the first one or they may be administered at different times.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a breast cancer patient with a glucocorticoid receptor antagonist, which may be with or without a chemotherapeutic or a combination of chemotherapeutics.

Various combinations with a glucocorticoid receptor antagonist and an anticancer agent or compound (or a combination of such agents and/or compounds) may be employed, for example glucocorticoid receptor antagonist is "A" and the anticancer agent or compound (or a combination of such agents and/or compounds) given as part of an anticancer therapy regime, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8,CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine(9CI). Sorafenib is marketed as NEXAVAR.

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-.beta., lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R, 4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E, 6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be an anti-EGFR treatment. In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors. In a preferred embodiment of the method or use of the invention, the anti-EGFR agent is an antibody capable of binding to EGFR, i.e. an anti-EGFR antibody.

In a further embodiment, the anti-EGFR antibody is an intact antibody, i.e. a full-length antibody rather than a fragment. An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$ M or less, more preferably $10^{-10}$ M or less.

Particularly antibodies for use in the present invention include zalutumumab (2F8,), cetuximab (Erbitux), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

II. Kits

Certain aspects of the present invention also encompass kits for performing the diagnostic and prognostic methods of the invention. Such kits can be prepared from readily available materials and reagents. For example, such kits can comprise any one or more of the following materials: enzymes, reaction tubes, buffers, detergent, primers, probes, antibodies. In a preferred embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, for example, GR and/or ER, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers of the invention. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Tumor Biomarker Status

A. Results

The glucocorticoid receptor (GR) is highly expressed in the myoepithelium of the normal human breast and in a subset of both ERalpha-positive and negative human breast cancers. In vitro and in vivo experiments suggest that activation of the GR in ER− pre-malignant breast epithelial and cancer cells triggers cell survival pathways under stress conditions (e.g. chemotherapy) that usually induce apoptosis. The inventors examined the association between NR3C1 gene expression and GR target gene expression in human ER− breast cancers and found that ER− breast cancers with high NR3C1 expression also express GR target genes associated with EMT and anti-apoptotic signaling, and that those ER− patients with high NR3C1 gene expression have a significantly worse outcome than NR3C1-low patients. Interestingly, the high NR3C1 gene expression in the ER+ (ESR1-high) subset of patients suggests a slight better outcome, implying a crosstalk between the ER and the GR that is absent in ER− tumors.

Using a global approach of gene expression studies merged with data from GR ChIP-sequencing in ER− pre-malignant breast cells (MCF10A-Myc), the inventors have identified direct GR target genes are significantly associated with cell survival signaling pathways. Interestingly, a meta-analysis of the high NR3C1-expressing ER– tumors reveals that many genes identified by ChIP-sequencing/gene expression analysis are indeed differentially expressed in high versus low NR3C1-primary breast cancers. These results suggest that GR expression may be a functional biomarker in ER– breast cancer.

TABLE 1

Clinical studies used for meta-analysis

| GEO ID | # of pts | Reference |
|---|---|---|
| GSE9195 | 77 | Loi S, et al |
| GSE7390 | 189 | Desmedt C, et al |
| GSE6532 | 212 | Loi S, et al |
| GSE2603 | 73 | Minn A J, et al |
| GSE2990 | 183 | Sotiriou C, et al |
| GSE2034 | 280 | Wang Y X, et al |
| TOTAL | 1206 | |

TABLE 2

Differentially expressed genes with concordant expression by all three methods (33/44 genes)

| Gene expression after Dex-treatment in MCF10A-Myc | Gene expression in NR3C1 + vs. – tumors | GR-binding within distance to TSS after Dex-treatment in MCF10A-Myc | Genes |
|---|---|---|---|
| Up | Up | 10 kb | DUSP1, SGK1, SMARCA2, PTGDS, MCL1 |
| | | 10-100 kb | DPYSL2, STOM, LAPTM5, NNMT, SERPINF1, NRIP1, WIPF1, BIN1, IL1R1, ST3GAL5, SEMA4D, MAP3K5, SMARCA2, DPT, BIRC3, PTGDS, PHF15, MAOA, TFPI, SLC46A3, PIAS1, ACSL5, SESN1, C14orf139, LBH |
| Down | Down | 10 kb | NONE |
| | | 10-100 kb | SFN, SPP1, ERBB2 |
| Overlapping genes with NKI-285 gene signature | | | DUSP1, DPT, NNMT, SERPINF1, IL1R1, FN1, DPYSL2 |

B. Materials and Methods

Cell culture and glucocorticoid treatment: MCF10A-Myc cells were cultured in a 1:1 mixture of DMEM and Hams/F12 medium supplemented with 10% fetal bovine serum, hydrocortisone (0.5 μg/ml), EGF(10 ng/ml), insulin (5 ng/ml) and 100 U/ml penicillin/streptomycin were also added. The cells were then starved for three days of all growth factors and treated with dexamethasone (10-6M) and ethanol of the same volume as a control.

Microarray gene expression: MCF10A-Myc Cells: Time course (0.5 h, 2 h, 4 h and 24 h) microarray data were obtained using Affymetrix gene arrays (HG-U133A) (Wu et al., 2006). Genes that were induced or repressed ≥1.5 fold-change were considered to be regulated.

GR ChIP-Seq experiment and analysis for MCF10A-Myc Cells: Cells were collected for the ChIP assay following 1 hour of Dex (10-6M) or EtOH treatment. The ChIP assay was done basically following Millipore's ChIP Assay Kit instructions. The DNA input (1%) was also sequenced using Illumina's Solexa Sequencer. Short-tag reads (36 bp) were mapped to the Human Genome (UCSC, hg18) by using Maq aligner. GR-binding peaks were called by using MACS software. Known SGK1 and GILZ promoter GR binding-regions (GBRs) were used as positive controls to determine the FDR threshold for retrieving significant GBRs.

Human Primary Breast Cancer Analysis: 1) Data Collection: All the clinical data and raw CEL files (all Affymetrix HU-133A and HU-133+2) were obtained from GEO (see Table 1). Low quality arrays were removed by AffyPLM. Arrays were normalized by using RMA and then centered by mean within each study and pooled together. 2) Determination of ESR1 and NR3C1 positivity: Expression data of tumors with known ER IHC status were analyzed using ROC analysis. The Youden Index of the best ESR1 probe's ROC curve was used as the cut-off point to separate ESR1+ and ESR1– tumors. Due to the lack of tumors with both GR IHC and NR3C1 gene expression information, we were unable to use ROC analysis to determine the NR3C1 cutoff. Therefore, based on published and our unpublished GR IHC data, we used the percentiles of NR3C1 gene expression levels that correspond to the observed proportion of GR+ patients. 3) Clustering: Un-supervised clustering was performed by Cluster using Pearson correlation distance and complete-linkage method. Heat-maps were plotted by Treeview. 4) Statistical analysis: Relapse-free survival (RFS) Kaplan-Meier plot and log-rank test were done by using R's "survival" package. Microarray SAM analysis was performed by using R's "siggenes" package.

Tumor assessment. pAUC areas were calculated for all the probes on the chip by setting p=0.2 (meaning can separate at least 80% patients) for tumors with known ER status (n=1000). A probe was then selected that has biggest pAUC area, which is the ESR1 probe 205225_at. So, this probe is the best one that can separate ER IHC+versus –. Using the 205225_at probe, the Youden Index of its ROC curve was calculated, that is the max (sensitivity+specificity–1) as the cut-off value for ESR1+ and –. The range of ESR1 expression after normalization was [–5.223868-3.944120]. The Youden Index, i.e. the cut-off is –1.257434. In the n=1000, training set, n=773>–1.257434 (ESR1+), and n=227 <=–1.257434. (ESR1–) or i.e. 77.3% quantile This cut-off was applied to the entire dataset, n=898 (ESR+), n=308 (ESR–). In addition to the method, the ACTUAL Log 2 value cutoff is needed for ESR1 positivity in normalized meta-dataset, as well as the range of ESR1 values encountered following batched mean normalization. If in one study, samples are obtained from different hospitals, they were normalized separately. So, to be precisely accurate, the normalization is done within the samples from the same source.

The ESR1 probe ID from Affymetrix is 205225_at.

The NR3C1 probe ID from Affymetrix is 216321_s_at

The range for NR3C1 probe (216321_s_at) is [–3.145456 to 2.158716] for the entire data set. For ESR1+, the range is [–3.009359 2.158716] and for ESR1–, the range is [–3.145456 1.917823] Thus, the cut-off for ESR1+, is 0.172189, 55.98% quantile (or about 44% NR3C1+ percentage) and the cut-off for ESR1–, is 0.47332, 82.51% quantile (or about 17.5% NR3C1+ percentage). All the cut-off are log 2 values.

The cutoffs used are the best cut-off that can separate patients with a p<0.01. If the p-value is loosened to 0.05, the range can be widened.

For ESR1+ patients, NR3C1+ patients can be from about 35% to 60% (about 44% is the best). For ESR1− patients, NR3C1+ patients can be from about 30% to 15% (about 17.5% is the best)

Example 2

Figure 8:
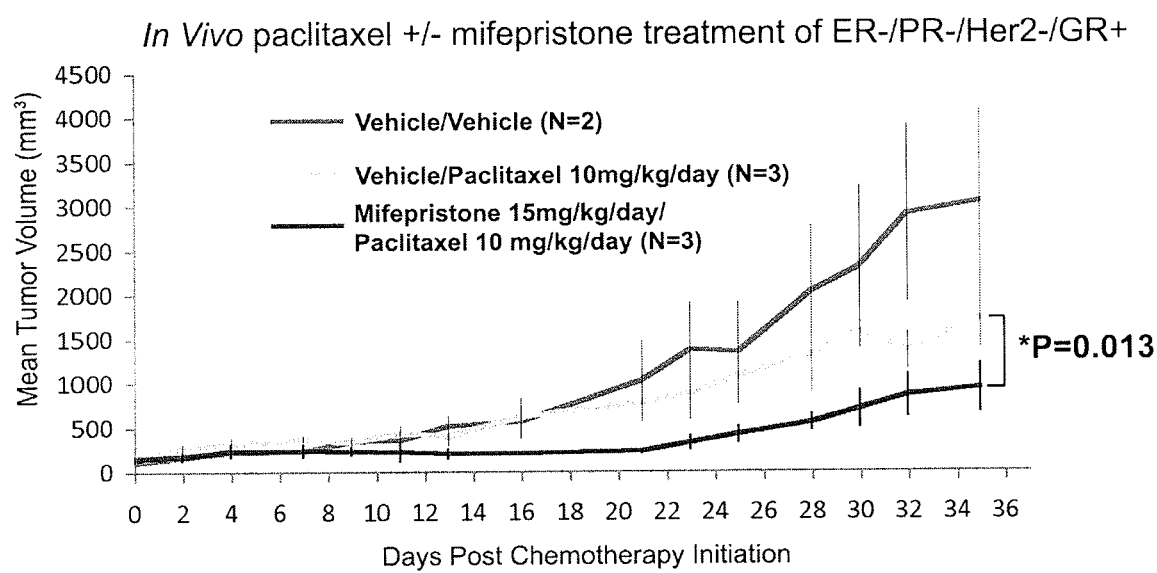
FIG. 8. Administration of mifepristone increases MDA-MB-231 tumor susceptibility to paclitaxel treatment in vivo.

Mifepristone Pretreatment Enhances Paclitaxel Anti-Tumor Effectiveness in Models of Human Breast Cancer Xenografted ER−/PR−/HER2− (GR+) MDA-MB-231 human breast cancer cells ($1 \times 10^7$ cells in 50 μl of PBS) were injected into the mammary fat pad of female Severe Combined Immunodeficient Mice (SCID) mice and allowed to grow until reaching approximately 100 mm$^3$. Mice were then injected intraperitoneally with either both vehicles, paclitaxel (10 mg/kg)+ the mifepristone vehicle, or the combination of mifepristone (15 mg/kg) administered two hours prior to paclitaxel (10 mg/kg) for five successive days. The longest (L) and shortest (S) diameters of the tumors were measured bi-weekly with electronic calipers and tumor volume was calculated using the formula for an ellipsoid sphere: volume=S2×L×0.52. Mifepristone pretreatment significantly decreased tumor volume over time (P=0.013) compared to treatment with paclitaxel alone (FIG. 8).

Example 3

Figure 9:
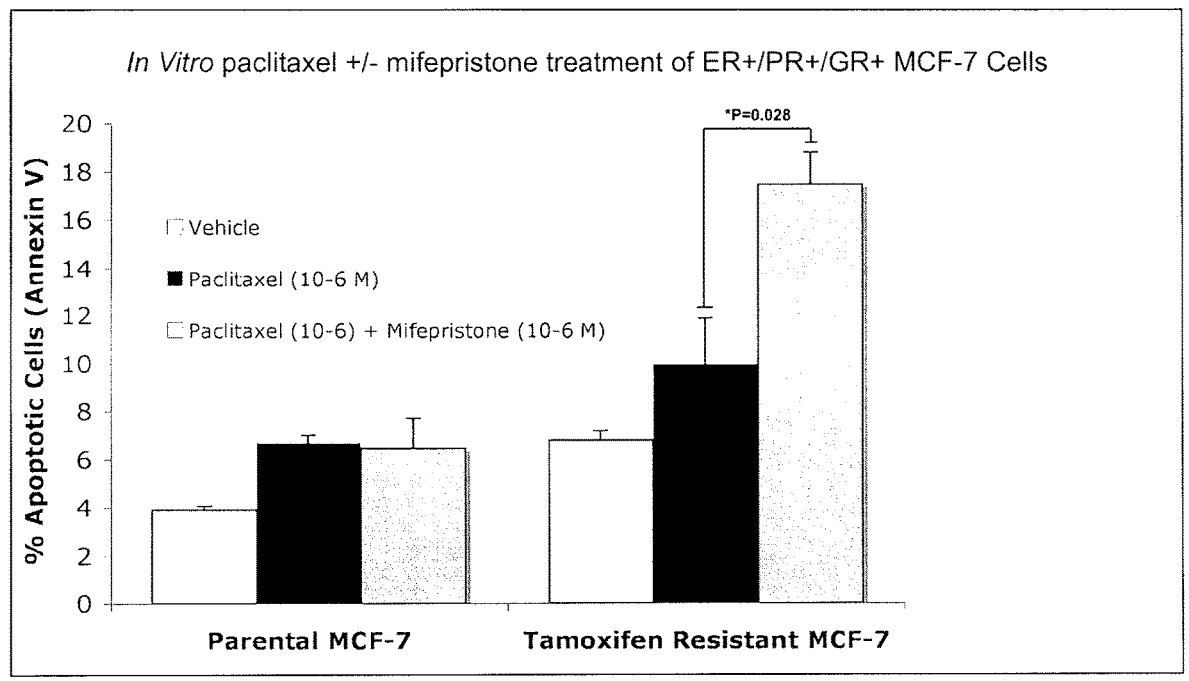
FIG. 9. Mifepristone pretreatment increases tamoxifen-resistant MCF-7 (T-R-MCF-7), but not parental MCF-7 cell susceptibility to paclitaxel in vitro.

Mifepristone Pretreatment Increases Tamoxifen-Resistant MCF-7 (T-R-MCF-7), but not Parental MCF-7 Cell Susceptibility to Paclitaxel in Vitro Parental MCF-7 (ER+/PR+/GR+) and T-R MCF-7 (ER+/PR+/GR+) cells were treated with the appropriate vehicle (ethanol for mifepristone and castor oil/saline for paclitaxel), paclitaxel alone ($10^{-6}$ M), and paclitaxel/mifepristone ($10^{-6}$ M). Apoptosis was measured using FITC conjugated-anti-Annexin V antibody labeling followed FACS analysis to determine the percentage of the total cell population undergoing apoptosis after 20 hours of treatment. Mean +/− SE is shown. Significantly more apoptosis (P=0.028) was observed in the T-R MCF-7 cells when treated with mifepristone/paclitaxel compared to paclitaxel alone (FIG. 9). No difference was seen in the parental MCF-7 cells.

```
                        Sequence Listing

NR3C1 GenBank AY436590-127687 bp, incorporated herein by reference
ESR1 GenBank NG_008493-419779 bp, incorporated herein by reference
SEQ ID NO: 1 NR3C1 mRNA
TTTTTAGAAAAAAAAATATATTTCCCTCCTGCTCCTTCTGCGTTCACAAGCTAAGTTGTTTATCTCGGC
TGCGGCGGGAACTGCGGACGGTGGCGGGCGAGCGGCTCCTCTGCCAGAGTTGATATTCACTGATGGACTC
CAAAGAATCATTAACTCCTGGTAGAGAAGAAAACCCCAGCAGTGTGCTTGCTCAGGAGAGGGGAGATGTG
ATGGACTTCTATAAAACCCTAAGAGGAGGAGCTACTGTGAAGGTTTCTGCGTCTTCACCCTCACTGGCTG
TCGCTTCTCAATCAGACTCCAAGCAGCGAAGACTTTTGGTTGATTTTCCAAAAGGCTCAGTAAGCAATGC
GCAGCAGCCAGATCTGTCCAAAGCAGTTTCACTCTCAATGGGACTGTATATGGGAGAGACAGAAACAAAA
GTGATGGGAAATGACCTGGGATTCCCACAGCAGGGCCAAATCAGCCTTTCCTCGGGGGAAACAGACTTAA
AGCTTTTGGAAGAAAGCATTGCAAACCTCAATAGGTCGACCAGTGTTCCAGAGAACCCCAAGAGTTCAGC
ATCCACTGCTGTGTCTGCTGCCCCCACAGAGAAGGAGTTTCCAAAAACTCACTCTGATGTATCTTCAGAA
CAGCAACATTTGAAGGGCCAGACTGGCACCAACGGTGGCAATGTGAAATTGTATACCACAGACCAAAGCA
CCTTTGACATTTTGCAGGATTTGGAGTTTTCTTCTGGGTCCCCAGGTAAAGAGACGAATGAGAGTCCTTG
GAGATCAGACCTGTTGATAGATGAAAACTGTTTGCTTTCTCCTCTGGCGGGAGAAGACGATTCATTCCTT
TTGGAAGGAAACTCGAATGAGGACTGCAAGCCTCTCATTTTACCGGACACTAAACCCAAAATTAAGGATA
ATGGAGATCTGGTTTTGTCAAGCCCCAGTAATGTAACACTGCCCCAAGTGAAAACAGAAAAAGAAGATTT
CATCGAACTCTGCACCCCTGGGGTAATTAAGCAAGAGAAACTGGGCACAGTTTACTGTCAGGCAAGCTTT
CCTGGAGCAAATATAATTGGTAATAAAATGTCTGCCATTTCTGTTCATGGTGTGAGTACCTCTGGAGGAC
AGATGTACCACTATGACATGAATACAGCATCCCTTTCTCAACAGCAGGATCAGAAGCCTATTTTTAATGT
CATTCCACCAATTCCCGTTGGTTCCGAAAATTGGAATAGGTGCCAAGGATCTGGAGATGACAACTTGACT
TCTCTGGGGACTCTGAACTTCCCTGGTCGAACAGTTTTTTCTAATGGCTATTCAAGCCCCAGCATGAGAC
CAGATGTAAGCTCTCCTCCATCCAGCTCCTCAACAGCAACAACAGGACCACCTCCCAAACTCTGCCTGGT
GTGCTCTGATGAAGCTTCAGGATGTCATTATGGAGTCTTAACTTGTGGAAGCTGTAAAGTTTTCTTCAAA
AGAGCAGTGGAAGGACAGCACAATTACCTATGTGCTGGAAGGAATGATTGCATCATCGATAAAATTCGAA
GAAAAAACTGCCCAGCATGCCGCTATCGAAATGTCTTCAGGCTGGAATGAACCTGGAAGCTCGAAAAAC
AAAGAAAAAAATAAAAGGAATTCAGCAGGCCACTACAGGAGTCTCACAAGAAACCTCTGAAAATCCTGGT
AACAAAACAATAGTTCCTGCAACGTTACCACAACTCACCCCTACCCTGGTGTCACTGTTGGAGGTTATTG
AACCTGAAGTGTTATATGCAGGATATGATAGCTCTGTTCCAGACTCAACTTGGAGGATCATGACTACGCT
CAACATGTTAGGAGGGCGGCAAGTGATTGCAGCAGTGAAATGGGCAAAGGCAATACCAGGTTTCAGGAAC
TTACACCTGGATGACCAAATGACCCTACTGCAGTACTCCTGGATGTTTCTTATGGCATTTGCTCTGGGGT
GGAGATCATATAGACAATCAAGTGCAAACCTGCTGTGTTTTGCTCCTGATCTGATTATTAATGAGCAGAG
AATGACTCTACCCTGCATGTACGACCAATGTAAACACATGCTGTATGTTTCCTCTGAGTTACACAGGCTT
CAGGTATCTTATGAAGAGTATCTCTGTATGAAAACCTTACTGCTTCTCTCTTCAGTTCCTAAGGACGGTC
TGAAGAGCCAAGAGCTATTTGATGAAATTAGAATGACCTACATCAAAGAGCTAGGAAAAGCCATTGTCAA
GAGGGAAGGAAACTCCAGCCAGAACTGGCAGCGGTTTTATCAACTGACAAAACTCTTGGATTCTATGCAT
GAAGTGGTTGAAAATCTCCTTAACTATTGCTTCCAAACATTTTTGGATAAGACCATGAGTATTGAATTCC
CCGAGATGTTAGCTGAAATCATCACCAATCAGATACCAAAATATTCAAATGGAAATATCAAAAAACTTCT
GTTTCATCAAAAGTGACTGCCTTAATAAGAATGGTTGCCTTAAAGAAAGTCGAATTAATAGCTTTTATTG
TATAAACTATCAGTTTGTCCTGTAGAGGTTTTGTTGTTTTATTTTTTATTGTTTTCATCTGTTGTTTTGT
TTTAAATACGCACTACATGTGGTTTATAGAGGGCCAAGACTTGGCAACAGAAGCAGTTGAGTCGTCATCA
CTTTTCAGTGATGGGAGAGTAGATGGTGAAATTTATTAGTTAATATATCCCAGAAATTAGAAACCTTAAT
ATGTGGACGTAATCTCCACAGTCAAAGAAGGATGGCACCTAAACCACCAGTGCCCAAAGTCTGTGTGATG
AACTTTCTCTTCATACTTTTTTTCACAGTTGGCTGGATGAAATTTTCTAGACTTTCTGTTGGTGTATCCC
CCCCCCTGTATAGTTAGGATAGCATTTTTGATTTATGCATGGAAACCTGAAAAAAGTTTACAAGTGTAT
ATCAGAAAAGGGAAGTTGTGCCTTTTATAGCTATTACTGTCTGGTTTTAACAATTTCCTTTATATTTAGT
GAACTACGCTTGCTCATTTTTTCTTACATAATTTTTTATTCAAGTTATTGTACAGCTGTTTAAGATGGGC
AGCTAGTTCGTAGCTTTCCCAAATAAACTCTAAACATTAATCAATCATCTGTGTGAAAATGGGTTGGTGC
```

```
TTCTAACCTGATGGCACTTAGCTATCAGAAGACCACAAAAATTGACTCAAATCTCCAGTATTCTTGTCAA
AAAAAAAAAAAAAAAAGCTCATATTTTGTATATATCTGCTTCAGTGGAGAATTATATAGGTTGTGCAAAT
TAACAGTCCTAACTGGTATAGAGCACCTAGTCCAGTGACCTGCTGGTAAACTGTGGATGATGGTTGCAA
AAGACTAATTTAAAAAATAACTACCAAGAGGCCCTGTCTGTACCTAACGCCCTATTTTTGCAATGGCTAT
ATGGCAAGAAAGCTGGTAAACTATTTGTCTTTCAGGACCTTTTGAAGTAGTTTGTATAACTTCTTAAAAG
TTGTGATTCCAGATAACCAGCTGTAACACAGCTGAGAGACTTTTAATCAGACAAAGTAATTCCTCTCACT
AAACTTTACCCAAAAACTAAATCTCTAATATGGCAAAAATGGCTAGACACCCATTTTCACATTCCCATCT
GTCACCAATTGGTTAATCTTTCCTGATGGTACAGGAAAGCTCAGCTACTGATTTTTGTGATTTAGAACTG
TATGTATGTCAGACATCCATGTTTGTAAAACTACACATCCCTAATGTGTGCCATAGAGTTTAACACAAGT
CCTGTGAATTTCTTCACTGTTGAAAATTATTTTAAACAAAATAGAAGCTGTAGTAGCCCTTTCTGTGTGC
ACCTTACCAACTTTCTGTAAACTCAAAACTTAACATATTTACTAAGCCACAAGAAATTTGATTTCTATTC
AAGGTGGCCAAATTATTTGTGTAATAGAAAACTGAAAATCTAATATTTAAAAATATGGAACTTCTAATATA
TTTTTATATTTAGTTATAGTTTCAGATATATATCATATTGGTATTCACTAATCTGGGAAGGGAAGGGCTA
CTGCAGCTTTACATGCAATTTATTAAAATGATTGTAAAATAGCTTGTATAGTGTAAAATAAGAATGATTT
TTAGATGAGATTGTTTTATCATGACATGTTATATATTTTTGTAGGGGTCAAAGAAATGCTGATGGATAA
CCTATATGATTTATAGTTTGTACATGCATTCATACAGGCAGCGATGGTCTCAGAAACCAAACAGTTTGCT
CTAGGGGAAGAGGGAGATGGAGACTGGTCCTGTGTGCAGTGAAGGTTGCTGAGGCTCTGACCCAGTGAGA
TTACAGAGGAAGTTATCCTCTGCCTCCCATTCTGACCACCCTTCTCATTCCAACAGTGAGTCTGTCAGCG
CAGGTTTAGTTTACTCAATCTCCCCTTGCACTAAAGTATGTAAAGTATGTAAACAGGAGACAGGAAGGTG
GTGCTTACATCCTTAAAGGCACCATCTAATAGCGGGTTACTTTCACATACAGCCCTTCCCCCAGCAGTTGA
ATGACAACAGAAGCTTCAGAAGTTTGGCAATAGTTTGCATAGAGGTACCAGCAATAGTGAAATAGTGCAG
AATCTCATAGGTTGCCAATAATACACTAATTCCTTTCTATCCTACAACAAGAGTTTATTTCCAAATAAAA
TGAGGACATGTTTTGTTTTCTTTGAATGCTTTTGAATGTTATTTGTTATTTTCAGTATTTTGGAGAAA
TTATTTAATAAAAAAAACAATCATTTGCTTTTTG

SEQ ID NO: 2 ESR1 Mrna (partial)
AGGAGCTGGC GGAGGGCGTT CGTCCTGGGA CTGCACTTGC TCCCGTCGGG TCGCCCGGCT
TCACCGGACC CGCAGGCTCC CGGGGCAGGG CCGGGGCCAG AGCTCGCGTG TCGGCGGGAC
ATGCGCTGCG TCGCCTCTAA CCTCGGGCTG TGCTCTTTTT CCAGGTGGCC CGCCGGTTTC
TGAGCCTTCT GCCCTGCGGG GACACGGTCT GCACCCTGCC CGCGGCCACG GACCATGACC
ATGACCCTCC ACACCAAAGC ATCTGGGATG GCCCTACTGC ATCAGATCCA AGGGAACGAG
CTGGAGCCCC TGAACCGTCC GCAGCTCAAG ATCCCCCTGG AGCGGCCCCT GGGCGAGGTG
TACCTGGACA GCAGCAAGCC CGCCGTGTAC AACTACCCCG AGGGCGCCGC CTACGAGTTC
AACGCCGCGG CCGCCGCCAA CGCGCAGGTC TACGGTCAGA CCGGCCTCCC CTACGGCCCC
GGGTCTGAGG CTGCGGCGTT CGGCTCCAAC GGCCTGGGGG GTTTCCCCCC ACTCAACAGC
GTGTCTCCGA GCCCGCTGAT GCTACTGCAC CCGCCGCCGC AGCTGTCGCC TTTCCTGCAG
CCCCACGGCC AGCAGGTGCC CTACTACCTG GAGAACGAGC CCAGCGGCTA CACGGTGCGC
GAGGCCGGCC CGCCGGCATT CTACAGGCCA AATTCAGATA ATCGACGCCA GGGTGGCAGA
GAAAGATTGG CCAGTACCAA TGACAAGGGA AGTATGGCTA TGGAATCTGC CAAGGAGACT
CGCTACTGTG CAGTGTGCAA TGACTATGCT TCAGGCTACC ATTATGGAGT CTGGTCCTGT
GAGGGCTGCA AGGCCTTCTT CAAGAGAAGT ATTCAAGGAC ATAACGACTA TATGTGTCCA
GCCACCAACC AGTGCACCAT TGATAAAAAC AGGAGGAAGA GCTGCCAGGC CTGCCGGCTC
CGCAAATGCT ACGAAGTGGG AATGATGAAA GGTGGGATAC GAAAAGACCG AAGAGGAGGG
AGAATGTTGA AACACAAGCG CCAGAGAGAT GATGGGGAGG GCAGGGGTGA AGTGGGGTCT
GCTGGAGACA TGAGAGCTGC CAACCTTTGG CCAAGCCCGC TCATGATCAA ACGCTCTAAG
AAGAACAGCC TGGCCTTGTC CCTGACGGCC GACCAGATGG TCAGTGCCTT GTTGGATGCT
GAGCCCCCCA TACTCTATTC CGAGTATGAT CCTACCAGAC CCTTCAGTGA AGCTTCGATG
ATGGGCTTAC TGACCAACCT GGCAGACAGG GAGCTGGTTC ACATGATCAA CTGGGCGAAG
AGGGTGCCAG GCTTTGTGGA TTTGACCCTC CATGATCAGG TCCACCTTCT AGAATGTGCC
TGGCTAGAGA TCCTGATGAT TGGTCTCGTC TGGCGCTCCA TGGAGCACCC AGGGAAGCTA
CTGTTTGCTC CTAACTTGCT CTTGGACAGG AACCAGGGAA AATGTGTAGA GGGCATGGTG
GAGATCTTCG ACATGCTGCT GGCTACATCA TCTCGGTTCC GCATGATGAA TCTGCAGGGA
GAGGAGTTTG TGTGCCTCAA ATCTATTATT TTGCTTAATT CTGGAGTGTA CACATTTCTG
TCCAGCACCC TGAAGTCTCT GGAAGAGAAG GACCATATCC ACCGAGTCCT GGACAAGATC
ACAGACACTT TGATCCACCT GATGGCCAAG GCAGGCCTGA CCCTGCAGCA GCAGCACCAG
CGGCTGGCCC AGCTCCTCCT CATCCTCTCC CACATCAGGC ACATGAGTAA CAAAGGCATG
GAGCATCTGT ACAGCATGAA GTGCAAGAAC GTGGTGCCCC TCTATGACCT GCTGCTGGAG
ATGCTGGACG CCCACCGCCT ACATGCGCCC ACTAGCCGTG GAGGGGCATC CGTGGAGGAG
ACGGACCAAA GCCACTTGGC CACTGCGGGC TCTACTTCAT CGCATTCCTT GCAAAAGTAT
TACATCACGG GGGAGGCAGA GGGTTTCCCT GCCACGGTCT GAGAGCTCCC TGGCTCCCAC
ACGGTTCAGA TAATCCCTGC TGCATTTTAC CCTCATCATG CACCACTTTA GCCAAATTCT
GTCTCCTGCA TACACTCCGG CATGCATCCA ACACCAATGG CTTTCTAGAT GAGTGGCCAT
TCATTTGCTT GCTCAGTTCT TAGTGGCACA TCTTCTGTCT TCTGTTGGGA ACAGCCAAAG
GGATTCCAAG GCTAAATCTT TGTAACAGCT CTCTTTCCCC CTTGCTATGT TACTAAGCGT
GAGGATTCCC GTAGCTCTTC ACAGCTGAAC TCAGTCTATG GGTTGGGGCT CAGATAACTC
TGTGCATTTA AGCTACTTGT AGAGACCCAG GCCTGGAGAG TAGACATTTT GCCTCTGATA
AGCACTTTTT AAATGGCTCT AAGAATAAGC CACAGCAAAG AATTTAAAGT GGCTCCTTTA
ATTGGTGACT TGGAGAAAGC TAGGTCAAGG GTTTATTATA GCACCCTCTT GTATTCCTAT
GGCAATGCAT CCTTTTATGA AAGTGGTACA CCTTAAAGCT TTTATATGAC TGTAGCAGAG
TATCTGGTGA TTGTCAATTC ATTCCCCCTA TAGGAATACA AGGGGCACAC AGGGAAGGCA
GATCCCCTAG TTGGCAAGAC TATTTTAACT TGATACACTG CAGATTCAGA TGTGCTGAAA
GCTCTGCCTC TGGCTTTCCG GTCATGGGTT CCAGTTAATT CATGCCTCCC ATGGACCTAT
GGAGAGCAGC AAGTTGATCT TAGTTAAGTC TCCCTATATG AGGGATAAGT TCCTGATTTT
TGTTTTTATT TTTGTGTTAC AAAAGAAAGC CCTCCCTCCC TGAACTTGCA GTAAGGTCAG
CTTCAGGACC TGTTCCAGTG GGCACTGTAC TTGGATCTTC CCGGCGTGTG TGTGCCTTAC
ACAGGGGTGA ACTGTTCACT GTGGTGATGC ATGATGAGGG TAAATGGTAG TTGAAAGGAG
CAGGGGCCCT GGTGTTGCAT TTAGCCCTGG GGCATGGAGC TGAACAGTAC TTGTGCAGGA
```

Sequence Listing

```
TTGTTGTGGC TACTAGAGAA CAAGAGGGAA AGTAGGGCAG AAACTGGATA CAGTTCTGAG
GCACAGCCAG ACTTGCTCAG GGTGGCCCTG CCACAGGCTG CAGCTACCTA GGAACATTCC
TTGCAGACCC CGCATTGCCC TTTGGGGGTG CCCTGGGATC CCTGGGGTAG TCCAGCTCTT
CTTCATTTCC CAGCGTGGCC CTGGTTGAA GAAGCAGCTG TCACAGCTGC TGTAGACAGC
TGTGTTCCTA CAATTGGCCC AGCACCCTGG GGCACGGGAA AAGGGTGGGG ACCGTTGCTG
TCACTACTCA GGCTGACTGG GGCCTGGTCA GATTACGTAT GCCCTTGGTG GTTTAGAGAT
AATCCAAAAT CAGGGTTTGG TTTGGGGAAG AAAATCCTCC CCCTTCCTCC CCCGCCCCGT
TCCCTACCGC CTCCACTCCT GCCAGCTCAT TTCCTTCAAT TTCCTTTGAC CTATAGGCTA
AAAAAGAAAG GCTCATTCCA GCCACAGGGC AGCCTTCCCT GGGCCTTTGC TTCTCTAGCA
CAATTATGGG TTACTTCCTT TTTCTTAACA AAAAGAATG TTTGATTTCC TCTGGGTGAC
CTTATTGTCT GTAATTGAAA CCCTATTGAG AGGTGATGTC TGTGTTAGCC AATGACCCAG
GTGAGCTGCT CGGGCTTCTC TTGGTATGTC TTGTTTGGAA AAGTGGATTT CATTCATTTC
TGATTGTCCA GTTAAGTGAT CACCAAAGGA CTGAGAATCT GGGAGGGCAA AAAAAAAAAA
AAAGTTTTTA TGTGCACTTA AATTGGGGA CAATTTATG TATCTGTGTT AAGGATATGT
TTAAGAACAT AATTCTTTTG TTGCTGTTTG TTTAAGAAGC ACCTTAGTTT GTTTAAGAAG
CACCTTATAT AGTATAATAT ATATTTTTTT GAAATTACAT TGCTTGTTTA TCAGACAATT
GAATGTAGTA ATTCTGTTCT GGATTTAATT TGACTGGGTT AACATGCAAA AACCAAGGAA
AAATATTTAG TTTTTTTTTT TTTTTTTGTA TACTTTTCAA GCTACCTTGT CATGTATACA
GTCATTTATG CCTAAAGCCT GGTGATTATT CATTTAAATG AAGATCACAT TCATATCAA
CTTTTGTATC CACAGTAGAC AAAATAGCAC TAATCCAGCT GCTATTGTT GGATACTGAA
TGACAGACAA TCTTATGTAG CAAAGATTAT GCCTGAAAAG GAAAATTATT CAGGGCAGCT
AATTTTGCTT TTACCAAAAT ATCAGTAGTA ATATTTTTGG ACAGTAGCTA ATGGGTCAGT
GGGTTCTTTT TAATGTTTAT ACTTAGATTT TCTTTTAAAA AAATTAAAAT AAAACAAAAA
AAAATTTCTA GGACTAGACG ATGTAATACC AGCTAAAGCC AAACAATTAT ACAGTGGAAG
GTTTTACATT ATTCATCCAA TGTGTTTCTA TTCATGTTAA GATACTACTA CATTTGAAGT
GGGCAGAGAA CATCAGATGA TTGAAATGTT CGCCCAGGGG TCTCCAGCAA CTTTGGAAAT
CTCTTTGTAT TTTTACTTGA AGTGCCACTA ATGGACAGCA GATATTTTCT GGCTGATGTT
GGTATTGGGT GTAGGAACAT GATTTAAAAA AAAACTCTTG CCTCTGCTTT CCCCCACTCT
GAGGCAAGTT AAAATGTAAA AGATGTGATT TATCTGGGGG GCTCAGGTAT GGTGGGGAAG
TGGATTCAGG AATCTGGGGA ATGGCAAATA TATTAAGAAG AGTATTGAAA GTATTTGGAG
GAAAATGGTT AATTCTGGGT GTGCACCAGG GTTCAGTAGA GTCCACTTCT GCCCTGGAGA
CCACAAATCA ACTAGCTCCA TTTACAGCCA TTTCTAAAAT GGCAGCTTCA GTTCTAGAGA
AGAAAGAACA ACATCAGCAG TAAAGTCCAT GGAATAGCTA GTGGTCTGTG TTTCTTTTCG
CCATTGCCTA GCTTGCCGTA ATGATTCTAT AATGCCATCA TGCAGCAATT ATGAGAGGCT
AGGTCATCCA AAGAGAAGAC CCTATCAATG TAGGTTGCAA AATCTAACCC CTAAGGAAGT
GCAGTCTTTG ATTTGATTTC CCTAGTAACC TTGCAGATAT GTTTAACCAA GCCATAGCCC
ATGCCTTTTG AGGGCTGAAC AAATAAGGGA CTTACTGATA ATTTACTTTT GATCACATTA
AGGTGTTCTC ACCTTGAAAT CTTATACACT GAAATGGCCA TTGATTTAGG CCACTGGCTT
AGAGTACTCC TTCCCCTGCA TGACACTGAT TACAAATACT TTCCTATTCA TACTTTCCAA
TTATGAGATG GACTGTGGGT ACTGGGAGTG ATCACTAACA CCATAGTAAT GTCTAATATT
CACAGGCAGA TCTGCTTGGG GAAGCTAGTT ATGTGAAAGG CAAATAGAGT CATACAGTAG
CTCAAAAGGC AACCATAATT CTCTTTGGTG CAGGTCTTGG GAGCGTGATC TAGATTACAC
TGCACCATTC CCAAGTTAAT CCCCTGAAAA CTTACTCTCA ACTGGAGCAA ATGAACTTTG
GTCCCAAATA TCCATCTTTT CAGTAGCGTT AATTATGCTC TGTTTCCAAC TGCATTTCCT
TTCCAATTGA ATTAAAGTGT GGCCTCGTTT TTAGTCATTT AAAATTGTTT TCTAAGTAAT
TGCTGCCTCT ATTATGGCAC TTCAATTTTG CACTGTCTTT TGAGATTCAA GAAAAATTTC
TATTCTTTTT TTTGCATCCA ATTGTGCCTG AACTTTTAAA ATATGTAAAT GCTGCCATGT
TCCAAACCCA TCGTCAGTGT GTGTGTTTAG AGCTGTGCAC CCTAGAAACA ACATATTGTC
CCATGAGCAG GTGCCTGAGA CACAGACCCC TTTGCATTCA CAGAGAGGTC ATTGGTTATA
GAGACTTGAA TTAATAAGTG ACATTATGCC AGTTTCTGTT CTCTCACAGG TGATAAACAA
TGCTTTTTGT GCACTACATA CTCTTCAGTG TAGAGCTCTT GTTTTATGGG AAAAGGCTCA
AATGCCAAAT TGTGTTTGAT GGATTAATAT GCCCTTTTGC CGATGCATAC TATTACTGAT
GTGACTCGGT TTTGTCGCAG CTTTGCTTTG TTTAATGAAA CACACTTGTA AACCTCTTTT
GCACTTTGAA AAAGAATCCA GCGGGATGCT CGAGCACCTG TAAACAATTT TCTCAACCTA
```

SEQ ID NO: 3-46 MCL1, SAP30, DUSP1, SGK1, SMARCA2, PTGDS, TNFRSF9, SFN, LAPTM5, GPSM2, SORT1, DPT, NRP1, ACSL5, BIRC3, NNMT, IGFBP6, PLXNC1, SLC46A3, C14orf139, PIAS1, IDH2, SERPINF1, ERBB2, PECAM1, LBH, ST3GAL5, IL1R1, BIN1, WIPF1, TFPI, FN1, FAM134A, NRIP1, RAC2, SPP1, PHF15, BTN3A2, SESN1, MAP3K5, DPYSL2, SEMA4D, STOM, and MAOA gene.

SEQ ID NO: 47 GR alpha.

SEQ ID NO: 48 GR beta.

SEQ ID NO: 49 NRR3C1 mRNA (complete)

REFERENCES

The following references, to the extent that they provide exemplary procedural or other details supplementary to those set forth herein, are specifically incorporated herein by reference.

U.S. Pat. No. 5,143,854
U.S. Pat. No. 5,202,231
U.S. Pat. No. 5,242,974
U.S. Pat. No. 5,288,644
U.S. Pat. No. 5,324,633
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,556,752
U.S. Pat. No. 5,561,071
U.S. Pat. No. 5,571,639
U.S. Pat. No. 5,580,726
U.S. Pat. No. 5,580,732
U.S. Pat. No. 5,593,839
U.S. Pat. No. 5,599,672
U.S. Pat. No. 5,599,695
U.S. Pat. No. 5,610;287
U.S. Pat. No. 5,624,711
U.S. Pat. No. 5,631,134
U.S. Pat. No. 5,639,603
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,744,305
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,871,928
U.S. Pat. No. 5,876,932
U.S. Pat. No. 5,919,626
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Patent Publn. 2010/0135956
Belanoff et al., *Eur. J. Pharmacol.*, 655(1-3):117-20, 2011.
Cho et al. *Biochemistry*, 44(9):3547-61, 2005.
Clark, *Curr. Top. Med. Chem.* 8(9):813-838, 2008.
Colleoni et al., *Annals of Oncology*, 11(8):1057, 2000.
Euopean Appln. EP 373 203
Euopean Appln. EP 785 280
Euopean Appln. EP 799 897
Evans, *Science*, 240:889, 1988.
Fodor et al., *Science*, 251:767-777, 1991.
Grover and Martin, *Carcinogenesis*, 23(7):1095-102, 2002.
Hacia et al., *Nature Genet.*, 14:441-449, 1996.
Harrison's Principles of Internal Medicine, Kasper et al. (Eds.), 16$^{th}$ Ed., Chapter 70, 2005.
Henderson et al. *Cancer Res.*, 48:246-253, 1988.
Keen and Davidson, *Cancer*, 97(3 Suppl):825-33, 2003.
Ma et al., *J. Immunol.*, 171(2):608-615, 2003.
MacBeath and Schreiber, *Science*, 289(5485):1760-3, 2000.
Melhem et al, *Clin. Cancer Res.*, 15(9):3196-204, 2009.
Mikosz et al., *J. Biol. Chem.*, 276:16649-54, 2001.
Moran et al., *Cancer Res.*, 60:867-872, 2000.
Pandey and Mann, *Nature*, 405(6788):837-46, 2000.
Pang and Conzen, *Cancer Biol. Ther. Cancer Biol. Ther.*, 5(8):933-40, 2006.
PCT Appln. WO 01/68255
PCT Appln. WO 03/020898
PCT Appln. WO 03/022421
PCT Appln. WO 03/023058
PCT Appln. WO 03/029485
PCT Appln. WO 03/040410
PCT Appln. WO 03/053586
PCT Appln. WO 03/066906
PCT Appln. WO 03/067217
PCT Appln. WO 03/076928
PCT Appln. WO 03/087297
PCT Appln. WO 03/091426
PCT Appln. WO 03/093810
PCT Appln. WO 03/100448A1
PCT Appln. WO 04/020085
PCT Appln. WO 04/027093
PCT Appln. WO 09/923256
PCT Appln. WO 09/936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/30347
PCT Appln. WO 96/31622
PCT Appln. WO 96/33980
PCT Appln. WO 97/10365
PCT Appln. WO 97/27317
PCT Appln. WO 9743450
PCT Appln. WO 99/35505
PCT Appln. WO 01/38580
PCT Appln. WO 03/100012
Pease et al., *Proc. Natl. Acad. Sci. USA*, 91:5022-5026, 1994.
Peeters et al., *Ann. NY Acad. Sci.*, 1148:536-41, 2008.
Pike et al., *Epidemiologic Revi.*, 15(1):17-35, 1993.

Shoemaker et al., *Nature Genetics*, 14:450-456, 1996.
Sims et al. *BMC Medical Genomics*, 1(42):1-14, 2008.
Sorlie et al., *Proc. Natl. Acad. Sci. USA*, 98:10869-10874., 2001.
Srinivas et al., *Clin. Chem.*, 48(8):1160-9, 2002.
UK Appln. 8 803 000
Wu et al., *Cancer Res.*, 64:1757-64, 2004.
Wu et al., *J. Clin. Invest.*, 114:560-568, 2004.
Wu et al., *Mol Endocrinol.*, 2006

What is claimed is:

1. A method of killing breast cancer cells comprising administering to a breast cancer patient an effective amount of a combination of anti-cancer compounds, wherein the breast cancer cells do not express detectable levels of estrogen receptor alpha, and wherein the anticancer compounds comprise a glucocorticoid receptor antagonist and a chemotherapeutic.

2. The method of claim 1, wherein the breast cancer cells were previously administered a first chemotherapeutic more than two weeks prior to the combination of anti-cancer compounds.

3. The method of claim 2, wherein the breast cancer cells that were previously administered a first chemotherapeutic are chemo-resistant.

4. The method of claim 3, wherein the breast cancer cells are determined not to be chemo-sensitive or are determined to be chemo-resistant.

5. The method of claim 1, wherein the breast cancer cells are glucocorticoid receptor-positive (GR+).

6. The method of claim 1, wherein the patient is determined to have breast cancer cells that are GR+.

7. The method of claim 1, wherein the combination of anti-cancer compounds is administered within 1 week of each anti-cancer compound.

8. The method of claim 7, wherein the combination of anti-cancer compounds is administered within 24 hours of each anti-cancer compound.

9. The method of claim 7, wherein the glucocorticoid receptor antagonist is administered prior to the chemotherapeutic.

10. The method of claim 9, wherein the glucocorticoid receptor antagonist is administered up to three days prior to administering the chemotherapeutic.

11. The method of claim 7, wherein the glucocorticoid receptor antagonist is administered after the chemotherapeutic is administered.

12. The method of claim 9, wherein the glucocorticoid receptor antagonist is also administered after the chemotherapeutic is administered.

13. The method of claim 1, wherein the glucocorticoid receptor antagonist is administered prior to and after administration of the chemotherapeutic.

14. The method of claim 13, wherein the glucocorticoid receptor antagonist is administered up to three days prior to administration of the chemotherapeutic.

15. The method of claim 1, wherein the glucocorticoid receptor antagonist has undetectable or a lower level of activity as a progesterone receptor antagonist.

16. The method of claim 15, wherein the glucocorticoid receptor antagonist does not have detectable progesterone receptor antagonist activity.

17. The method of claim 1, wherein the breast cancer is an unresectable breast cancer.

18. The method of claim 1, wherein dexamethasone has not been administered to the patient within 24 hours of administration of the glucocorticoid receptor antagonist.

19. The method of claim 1, wherein the breast cancer cells were previously administered a first apoptosis inducing agent more than two weeks prior to the glucocorticoid receptor antagonist.

20. The method of claim 19, wherein at least one apoptosis inducing agent is radiation, a chemotherapeutic, or an immunotherapy.

* * * * *

SEQUENCE LISTING

<160> NUMBER OF SEQ ID NOS: 49

<210> SEQ ID NO 1
<211> LENGTH: 4794
<212> TYPE: DNA
<213> ORGANISM: Homo sapiens
<220> FEATURE:
<223> OTHER INFORMATION: nuclear receptor subfamily 3, group C, member 1
      (NR3C1), glucocorticoid receptor cDNA

<400> SEQUENCE: 1

```
tttttagaaa aaaaaaatat atttccctcc tgctccttct gcgttcacaa gctaagttgt      60
ttatctcggc tgcggcggga actgcggacg gtggcgggcg agcggctcct ctgccagagt     120
tgatattcac tgatggactc caaagaatca ttaactcctg gtagaagaa aaacccagc      180 agtgtgcttg ctcaggagag gggagatgtg atggacttct ataaaaccct aagaggagga     240
gctactgtga aggtttctgc gtcttcaccc tcactggctg tcgcttctca atcagactcc     300
aagcagcgaa gacttttggt tgattttcca aaaggctcag taagcaatgc gcagcagcca     360
gatctgtcca aagcagtttc actctcaatg ggactgtata tgggagagac agaaacaaaa     420
gtgatgggaa atgacctggg attcccacag cagggccaaa tcagcctttc ctcggggaa      480 acagacttaa agcttttgga agaaagcatt gcaaacctca ataggtcgac cagtgttcca     540 gagaaccccca agagttcagc atccactgct gtgtctgctg ccccacaga gaaggagttt      600 ccaaaaactc actctgatgt atcttcagaa cagcaacatt tgaagggcca gactggcacc     660
aacggtggca atgtgaaatt gtataccaca gaccaaaagca cctttgacat tttgcaggat     720 ttggagttttt cttctgggtc cccaggtaaa gagacgaatg agagtccttg gagatcagac     780
ctgttgatag atgaaaactg tttgcttttct cctctggcgg gagaagacga ttcattcctt     840
ttggaaggaa actcgaatga ggactgcaag cctctcattt taccggacac taaacccaaa     900
attaaggata tggagatct ggttttgtca gccccagta atgtaacact gccccaagtg     960
aaaacagaaa agaagatttt catcgaactc tgcacccctg gggtaattaa gcaagagaaa    1020
ctgggcacag tttactgtca ggcaagcttt cctggagcaa atataattgg taataaaatg    1080
tctgccattt ctgttcatgg tgtgagtacc tctggaggac agatgtacca ctatgacatg    1140
aatacagcat ccctttctca acagcaggat cagaagccta ttttttaatgt cattccacca    1200 attcccgttg gttccgaaaa ttggaatagg tgccaaggat ctggagatga caacttgact    1260
tctctgggga ctctgaactt ccctggtcga acagtttttt ctaatggcta ttcaagcccc    1320
agcatgagac cagatgtaag ctctcctcca tccagctcct caacagcaac aacaggacca    1380
cctcccaaac tctgcctggt gtgctctgat gaagcttcag gatgtcatta tggagtctta    1440
acttgtggaa gctgtaaagt tttcttcaaa agagcagtgg aaggacagca cattaccta    1500 tgtgctggaa ggaatgattg catcatcgat aaaattcgaa gaaaaactg cccagcatgc    1560 cgctatcgaa aatgtcttca ggctggaatg aacctggaag ctcgaaaaac aaagaaaaaa    1620 ataaaggaa ttcagcaggc cactacagga gtctcacaag aaacctctga aatcctggt      1680 aacaaaacaa tagttcctgc aacgttacca caactcaccc ctacccctgg gtcactgttg    1740
gaggttattg aacctgaagt gttatatgca ggatatgata gctctgttcc agactcaact    1800
```

```
tggaggatca tgactacgct caacatgtta ggagggcggc aagtgattgc agcagtgaaa    1860
tgggcaaagg caataccagg tttcaggaac ttacacctgg atgaccaaat gaccctactg    1920
cagtactcct ggatgtttct tatggcattt gctctggggt ggagatcata tagacaatca    1980
agtgcaaacc tgctgtgttt tgctcctgat ctgattatta atgagcagag aatgactcta    2040
ccctgcatgt acgaccaatg taaacacatg ctgtatgttt cctctgagtt acacaggctt    2100
caggtatctt atgaagagta tctctgtatg aaaaccttac tgcttctctc ttcagttcct    2160
aaggacggtc tgaagagcca agagctattt gatgaaatta aatgaccta catcaaagag    2220 ctaggaaaag ccattgtcaa gagggaagga aactccagcc agaactggca gcggttttat    2280
caactgacaa aactcttgga ttctatgcat gaagtggttg aaaatctcct taactattgc    2340
ttccaaacat ttttggataa gaccatgagt attgaattcc ccgagatgtt agctgaaatc    2400
atcaccaatc agataccaaa atattcaaat ggaaatatca aaaaacttct gtttcatcaa    2460
aagtgactgc cttaataaga atggttgcct taaagaaagt cgaattaata gcttttattg    2520
tataaactat cagtttgtcc tgtagaggtt ttgttgtttt attttttatt gttttcatct    2580
gttgttttgt tttaaatacg cactacatgt ggtttataga gggccaagac ttggcaacag    2640
aagcagttga gtcgtcatca cttttcagtg atgggagagt agatggtgaa atttattagt    2700
taatatatcc cagaaattag aaaccttaat atgtggacgt aatctccaca gtcaaagaag    2760
gatggcacct aaaccaccag tgcccaaagt ctgtgtgatg aactttctct tcatactttt    2820
tttcacagtt ggctggatga attttctag actttctgtt ggtgtatccc cccccctgta    2880
tagttaggat agcattttg atttatgcat ggaaacctga aaaaagttt acaagtgtat    2940 atcagaaaag ggaagttgtg cctttatag ctattactgt ctggttttaa caattctt    3000 tatatttagt gaactacgct tgctcatttt ttcttacata attttttatt caagttattg    3060
tacagctgtt taagatgggc agctagttcg tagctttccc aaataaactc taaacattaa    3120
tcaatcatct gtgtgaaaat gggttggtgc ttctaacctg atggcactta gctatcagaa    3180
gaccacaaaa attgactcaa atctccagta ttccttgtcaa aaaaaaaaaa aaaaaagctc    3240 atatttgta tatatctgct tcagtggaga attatatagg ttgtgcaaat taacagtcct    3300
aactggtata gagcacctag tccagtgacc tgctgggtaa actgtggatg atggttgcaa    3360
aagactaatt taaaaataa ctaccaagag gccctgtctg tacctaacgc cctatttttg    3420
caatggctat atggcaagaa agctggtaaa ctatttgtct ttcaggacct tttgaagtag    3480
tttgtataac ttcttaaaag ttgtgattcc agataaccag ctgtaacaca gctgagagac    3540
ttttaatcag acaaagtaat tcctctcact aaactttacc caaaactaa atctctaata    3600 tggcaaaaat ggctagacac ccattttcac attcccatct gtcaccaatt ggttaatctt    3660
tcctgatggt acaggaaagc tcagctactg atttttgtga tttagaactg tatgtatgtc    3720
agacatccat gtttgtaaaa ctacacatcc ctaatgtgtg ccatagagtt aacacaagt    3780 cctgtgaatt tcttcactgt tgaaaattat tttaaacaaa atagaagctg tagtagccct    3840
ttctgtgtgc accttaccaa ctttctgtaa actcaaaact taacatattt actaagccac    3900
aagaaatttg atttctattc aaggtggcca aattatttgt gtaatagaaa actgaaaatc    3960
taatattaaa aatatggaac ttctaatata ttttatatt tagttatagt ttcagatata    4020
tatcatattg gtattcacta atctgggaag ggaagggcta ctgcagcttt acatgcaatt    4080
tattaaaatg attgtaaaat agcttgtata gtgtaaaata agaatgattt ttagatgaga    4140
```

```
ttgttttatc atgacatgtt atatatttt tgtaggggtc aaagaaatgc tgatggataa    4200
cctatatgat ttatagtttg tacatgcatt catacaggca gcgatggtct cagaaaccaa    4260
acagtttgct ctaggggaag agggagatgg agactggtcc tgtgtgcagt gaaggttgct    4320
gaggctctga cccagtgaga ttacagagga agttatcctc tgcctcccat tctgaccacc    4380
cttctcattc aacagtgag  tctgtcagcg caggtttagt ttactcaatc tccccttgca    4440
ctaaagtatg taaagtatgt aaacaggaga caggaaggtg gtgcttacat ccttaaaggc    4500
accatctaat agcgggttac tttcacatac agccctcccc cagcagttga atgacaacag    4560
aagcttcaga agtttggcaa tagtttgcat agaggtacca gcaatatgta aatagtgcag    4620
aatctcatag gttgccaata atacactaat tcctttctat cctacaacaa gagtttattt    4680
ccaaataaaa tgaggacatg ttttgtttt ctttgaatgc tttttgaatg ttatttgtta    4740
ttttcagtat tttggagaaa ttatttaata aaaaaaacaa tcatttgctt tttg           4794
```

<210> SEQ ID NO 2
<211> LENGTH: 6300
<212> TYPE: DNA
<213> ORGANISM: Homo sapiens
<220> FEATURE:
<223> OTHER INFORMATION: nuclear receptor subfamily 3, group A, member
      1, transcript variant 4 (NR3A1), estrogen receptor
      (ESR1, ER, ESR, ESRA, ESTRR) cDNA (partial)

<400> SEQUENCE: 2

```
aggagctggc ggagggcgtt cgtcctggga ctgcacttgc tcccgtcggg tcgcccggct      60
tcaccggacc cgcaggctcc cggggcaggg ccggggccag agctcgcgtg tcggcgggac     120
atgcgctgcg tcgcctctaa cctcgggctg tgctcttttt ccaggtggcc cgccggtttc     180
tgagccttct gccctgcggg gacacggtct gcaccctgcc cgcggccacg gaccatgacc     240
atgaccctcc acaccaaagc atctgggatg ccctactgc atcagatcca agggaacgag     300
ctggagcccc tgaaccgtcc gcagctcaag atcccctgg agcggcccct gggcgaggtg     360
tacctggaca gcagcaagcc cgccgtgtac aactaccccg agggcgccgc ctacgagttc     420
aacgccgcgg ccgccgccaa cgcgcaggtc tacggtcaga ccggcctccc ctacggcccc     480
gggtctgagg ctgcggcgtt cggctccaac ggcctggggg gtttccccc  actcaacagc     540
gtgtctccga gccgctgat gctactgcac ccgccgccgc agctgtcgcc tttcctgcag     600
ccccacggcc agcaggtgcc ctactacctg gagaacgagc ccagcggcta cacggtgcgc     660
gaggccggcc cgccggcatt ctacaggcca aattcagata tcgacgccgg ggtggcagag     720
aaagattgg  ccagtaccaa tgacaaggga agtatggcta tggaatctgc caaggagact     780
cgctactgtg cagtgtgcaa tgactatgct tcaggctacc attatggagt ctggtcctgt     840
gagggctgca aggccttctt caagagaagt attcaaggac ataacgacta tatgtgtcca     900
gccaccaacc agtgcaccat tgataaaaac aggaggaaga gctgccaggc ctgccggctc     960
cgcaaatgct acgaagtggg aatgatgaaa ggtgggatac gaaaagaccg aagaggaggg    1020
agaatgttga acacaagcg  ccagagagat gatgggagg  cagggtga  agtggggtct    1080
gctggagaca tgagagctgc caaccttttgg ccaagcccgc tcatgatcaa acgctctaag    1140
aagaacagcc tggccttgtc cctgacggcc gaccagatgg tcagtgcctt gttggatgct    1200
gagcccccca tactctattc cgagtatgat cctaccagac ccttcagtga agcttcgatg    1260
atgggcttac tgaccaacct ggcagacagg gagctggttc acatgatcaa ctgggcgaag    1320
agggtgccag gctttgtgga tttgacctc catgatcagg tccaccttct agaatgtgcc    1380
```

```
tggctagaga tcctgatgat tggtctcgtc tggcgctcca tggagcaccc agggaagcta    1440
ctgtttgctc ctaacttgct cttggacagg aaccagggaa aatgtgtaga gggcatggtg    1500
gagatcttcg acatgctgct ggctacatca tctcggttcc gcatgatgaa tctgcaggga    1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc    1680
acagacactt tgatccacct gatggccaag gcaggcctga ccctgcagca gcagcaccag    1740
cggctggccc agctcctcct catcctctcc cacatcaggc acatgagtaa caaaggcatg    1800
gagcatctgt acagcatgaa gtgcaagaac gtggtgcccc tctatgacct gctgctggag    1860
atgctggacg cccaccgcct acatgcgccc actagccgtg gagggcatc cgtggaggag     1920 acggaccaaa gccacttggc cactgcgggc tctacttcat cgcattcctt gcaaaagtat    1980
tacatcacgg gggaggcaga gggtttccct gccacggtct gagagctccc tggctcccac    2040
acggttcaga taatccctgc tgcattttac cctcatcatg caccacttta gccaaattct    2100
gtctcctgca tacactccgg catgcatcca acaccaatgg ctttctagat gagtggccat    2160
tcatttgctt gctcagttct tagtggcaca tcttctgtct tctgttggga acagccaaag    2220
ggattccaag gctaaatctt tgtaacagct ctctttcccc cttgctatgt tactaagcgt    2280
gaggattccc gtagctcttc acagctgaac tcagtctatg ggttggggct cagataactc    2340
tgtgcattta agctacttgt agagacccag gcctggagag tagacatttt gcctctgata    2400 agcactttt aaatggctct aagaataagc cacagcaaag aatttaaagt ggctccttta     2460
attggtgact tggagaaagc taggtcaagg gtttattata gcaccctctt gtattcctat    2520
ggcaatgcat cctttatga aagtggtaca ccttaaagct tttatatgac tgtagcagag     2580
tatctggtga ttgtcaattc attccccta taggaataca aggggcacac agggaaggca    2640
gatcccctag ttggcaagac tatttaact tgatacactg cagattcaga tgtgctgaaa     2700
gctctgcctc tggctttccg gtcatgggtt ccagttaatt catgcctccc atggacctat    2760
ggagagcagc aagttgatct tagttaagtc tccctatatg agggataagt tcctgatttt    2820
tgtttttatt tttgtgttac aaaagaaagc cctccctccc tgaacttgca gtaaggtcag    2880
cttcaggacc tgttccagtg ggcactgtac ttggatcttc ccggcgtgtg tgtgccttac    2940 acagggtga actgttcact gtggtgatgc atgatgaggg taaatggtag ttgaaaggag     3000
caggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttggggtg ccctgggatc cctggggtag tccagctctt     3240
cttcatttcc cagcgtggcc ctggttggaa gaagcagctg tcacagctgc tgtagacagc    3300
tgtgttccta caattggccc agcacccctgg ggcacgggag aagggtgggg accgttgctg   3360
tcactactca ggctgactgg ggcctggtca gattacgtat gcccttggtg gtttagagat    3420
aatccaaaat cagggtttgg tttggggaag aaaatcctcc cccttcctcc cccgcccgt    3480 tccctaccgc ctccactcct gccagctcat ttccttcaat ttcctttgac ctataggcta    3540
aaaaagaaag gctcattcca gccacagggc agccttccct gggcctttgc ttctctagca    3600
caattatggg ttacttcctt tttcttaaca aaaagaatg tttgatttcc tctgggtgac     3660
cttattgtct gtaattgaaa ccctattgag aggtgatgtc tgtgttagcc aatgacccag    3720
```

```
gtgagctgct cgggcttctc ttggtatgtc ttgtttggaa aagtggattt cattcatttc    3780
tgattgtcca gttaagtgat caccaaagga ctgagaatct ggggagggcaa aaaaaaaaa     3840 aaagttttta tgtgcactta aatttgggga caattttatg tatctgtgtt aaggatatgt    3900
ttaagaacat aattcttttg ttgctgtttg tttaagaagc accttagttt gtttaagaag    3960
caccttatat agtataatat atattttttt gaaattacat tgcttgttta tcagacaatt    4020
gaatgtagta attctgttct ggatttaatt tgactgggtt aacatgcaaa aaccaaggaa    4080
aaatatttag tttttttttt tttttttgta tacttttcaa gctaccttgt catgtataca    4140
gtcatttatg cctaaagcct ggtgattatt catttaaatg aagatcacat ttcatatcaa    4200
cttttgtatc cacagtagac aaaatagcac taatccagat gcctattgtt ggatactgaa    4260
tgacagacaa tcttatgtag caaagattat gcctgaaaag gaaaattatt cagggcagct    4320
aattttgctt ttaccaaaat atcagtagta atattttttgg acagtagcta atgggtcagt    4380
gggttctttt taatgtttat acttagattt tcttttaaaa aattaaaat aaaacaaaaa    4440 aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtggggaag    4800
tggattcagg aatctgggga atggcaaata tattaagaag agtattgaaa gtatttggag    4860
gaaaatggtt aattctgggt gtgcaccagg gttcagtaga gtccacttct gccctggaga    4920 ccacaaaatca actagctcca tttacagcca tttctaaaat ggcagcttca gttctagaga    4980
agaaagaaca acatcagcag taaagtccat ggaatagcta gtggtctgtg tttctttttcg    5040 ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220
atgccttttg agggctgaac aaataaggga cttactgata atttactttt gatcacatta    5280
aggtgttctc accttgaaat cttatacact gaaatggcca ttgatttagg ccactggctt    5340
agagtactcc ttcccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctctttggtg caggtcttgg gagcgtgatc tagattacac    5580
tgcaccattc ccaagttaat ccctgaaaa cttactctca actggagcaa atgaactttg    5640
gtcccaaata tccatctttt cagtagcgtt aattatgctc tgtttccaac tgcatttcct    5700
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820
tattcttttt tttgcatcca attgtgcctg aacttttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agttctgtt ctctcacagg tgataaacaa    6060 tgcttttttgt gcactacata ctcttcagtg tagagctctt gttttatggg aaaaggctca    6120
```

-continued

| | |
|---|---|
| aatgccaaat tgtgtttgat ggattaatat gccctttttgc cgatgcatac tattactgat | 6180 |
| gtgactcggt tttgtcgcag cttttgctttg tttaatgaaa cacacttgta aacctctttt | 6240 |
| gcactttgaa aaagaatcca gcgggatgct cgagcacctg taaacaattt tctcaaccta | 6300 |

<210> SEQ ID NO 3
<211> LENGTH: 4107
<212> TYPE: DNA
<213> ORGANISM: Homo sapiens
<220> FEATURE:
<223> OTHER INFORMATION: MCL1 glucocorticoid receptor-responsive gene

<400> SEQUENCE: 3

| | |
|---|---|
| gcgcaaccct ccggaagctg ccgccccttt cccctttttat gggaatactt tttttaaaaa | 60 |
| aaaagagttc gctggcgcca ccccgtagga ctggccgccc taaaaccgtg ataaaggagc | 120 |
| tgctcgccac ttctcacttc cgcttccttc cagtaaggag tcggggtctt ccccagtttt | 180 |
| ctcagccagg cggcggcggc gactggcaat gtttggcctc aaaagaaacg cggtaatcgg | 240 |
| actcaacctc tactgtgggg gggccggctt ggggccggc agcggcggcg ccacccgccc | 300 |
| gggagggcga cttttggcta cggagaagga ggcctcggcc cggcgagaga taggggagg | 360 |
| ggaggccggc gcggtgattg gcggaagcgc cggcgcaagc ccccgtcca ccctcacgcc | 420 |
| agactcccgg agggtcgcgc ggccgccgcc cattggcgcc gaggtccccg acgtcaccgc | 480 |
| gacccccgcg aggctgctttt tcttcgcgcc cacccgccgc gcggcgccgc ttgaggagat | 540 |
| ggaagcccg gccgctgacg ccatcatgtc gcccgaagag gagctggacg ggtacgagcc | 600 |
| ggagcctctc gggaagcggc cggctgtcct gccgctgctg gagttggtcg gggaatctgg | 660 |
| taataacacc agtacggacg ggtcactacc ctcgacgccg ccgccagcag aggaggagga | 720 |
| ggacgagttg taccggcagt cgctggagat tatctctcgg taccttcggg agcaggccac | 780 |
| cggcgccaag gacacaaagc caatgggcag gtctgggcc accagcagga aggcgctgga | 840 |
| gaccttacga cgggttgggg atggcgtgca gcgcaaccac gagacggcct tccaaggcat | 900 |
| gcttcggaaa ctggacatca aaacgaagag cgatgtgaaa tcgttgtctc gagtgatgat | 960 |
| ccatgttttc agcgacggcg taacaaactg gggcaggatt gtgactctca tttcttttgg | 1020 |
| tgcctttgtg gctaaacact tgaagaccat aaaccaagaa agctgcatcg aaccattagc | 1080 |
| agaaagtatc acagacgttc tcgtaaggac aaaacgggac tggctagtta acaaagagg | 1140 |
| ctgggatggg tttgtggagt tcttccatgt agaggaccta aaggtggca tcaggaatgt | 1200 |
| gctgctggct tttgcaggtg ttgctggagt aggagctggt ttggcatatc taataagata | 1260 |
| gccttactgt aagtgcaata gttgactttt aaccaaccac caccaccacc aaaaccagtt | 1320 |
| tatgcagttg gactccaagc tgtaacttcc tagagttgca ccctagcaac ctagccagaa | 1380 |
| aagcaagtgg caagaggatt atggctaaca agaataaata catgggaaga gtgctcccca | 1440 |
| ttgattgaag agtcactgtc tgaaagaagc aaagttcagt ttcagcaaca aacaaacttt | 1500 |
| gtttgggaag ctatggagga ggacttttag atttagtgaa gatggtaggg tggaaagact | 1560 |
| taatttcctt gttgagaaca ggaaagtggc cagtagccag gcaagtcata gaattgatta | 1620 |
| cccgccgaat tcattaattt actgtagtgt taagagaagc actaagaatg ccagtgacct | 1680 |
| gtgtaaaagt tacaagtaat agaactatga ctgtaagcct cagtactgta caagggaagc | 1740 |
| ttttcctctc tctaattagc tttcccagta tacttcttag aaagtccaag tgttcaggac | 1800 |
| ttttatacct gttatacttt ggcttggttt ccatgattct tactttatta gcctagttta | 1860 |

```
tcaccaataa tacttgacgg aaggctcagt aattagttat gaatatggat atcctcaatt    1920
cttaagacag cttgtaaatg tatttgtaaa aattgtatat atttttacag aaagtctatt    1980
tctttgaaac gaaggaagta tcgaatttac attagttttt ttcatacccct tttgaacttt    2040
gcaacttccg taattaggaa cctgttcctt acagcttttc tatgctaaac tttgttctgt    2100
tcagttctag agtgtataca gaacgaattg atgtgtaact gtatgcagac tggttgtagt    2160
ggaacaaatc tgataactat gcaggtttaa attttcttat ctgattttgg taagtattcc    2220
ttagataggt ttttctttga aacctgggga ttgagaggtt gatgaatgga aattctttca    2280
cttcattata tgcaagtttt caataattag gtctaagtgg agttttaagg ttactgatga    2340
cttacaaata atgggctctg attgggcaat actcatttga gttccttcca tttgacctaa    2400
tttaactggt gaaatttaaa gtgaattcat gggctcatct ttaaagcttt tactaaaaga    2460
ttttcagctg aatggaactc attagctgtg tgcatataaa aagatcacat caggtggatg    2520
gagagacatt tgatcccttg tttgcttaat aaattataaa atgatggctt ggaaaagcag    2580
gctagtctaa ccatggtgct attattaggc ttgcttgtta cacacacagg tctaagccta    2640
gtatgtcaat aaagcaaata cttactgttt tgtttctatt aatgattccc aaaccttgtt    2700
gcaagtttt gcattggcat ctttggattt cagtcttgat gtttgttcta tcagacttaa    2760
ccttttattt cctgtccttc cttgaaattg ctgattgttc tgctccctct acagatattt    2820
atatcaattc ctacagcttt cccctgccat ccctgaactc tttctagccc ttttagattt    2880
tggcactgtg aaacccctgc tggaaacctg agtgaccctc cctccccacc aagagtccac    2940
agacctttca tctttcacga acttgatcct gttagcaggt ggtaatacca tgggtgctgt    3000
gacactaaca gtcattgaga ggtgggagga agtcccttt ccttggactg gtatcttttc    3060
aactattgtt ttatcctgtc tttgggggca atgtgtcaaa agtcccctca ggaattttca    3120
gaggaaagaa cattttatga ggctttctct aaagtttcct ttgtatagga gtatgctcac    3180
ttaaatttac agaagagggt gagctgtgtt aaacctcaga gttaaaagc tactgataaa    3240
ctgaagaaag tgtctatatt ggaactaggg tcatttgaaa gcttcagtct cggaacatga    3300
cctttagtct gtggactcca tttaaaaata ggtatgaata agatgactaa gaatgtaatg    3360
gggaagaact gccctgcctg cccatctcag agccataagg tcatctttgc tagagctatt    3420
tttacctatg tatttatcgt tcttgatcat aagccgctta tttatatcat gtatctctaa    3480
ggacctaaaa gcactttatg tagttttttaa ttaatcttaa gatctggtta cggtaactaa    3540
aaaagcctgt ctgccaaatc cagtggaaac aagtgcatag atgtgaattg gttttttaggg    3600
gccccacttc ccaattcatt aggtatgact gtggaaatac agacaaggat cttagttgat    3660
attttgggct tggggcagtg agggcttagg acaccccaag tggtttggga aaggaggagg    3720
ggagtggtgg gtttataggg ggaggaggag gcaggtggtc taagtgctga ctggctacgt    3780
agttcgggca aatcctccaa aagggaaagg gaggatttgc ttagaaggat ggcgctccca    3840
gtgactactt tttgacttct gtttgtctta cgcttctctc agggaaaaac atgcagtcct    3900
ctagtgtttc atgtacattc tgtgggggt gaacaccttg gttctggtta aacagctgta    3960
cttttgatag ctgtgccagg aagggttagg accaactaca aattaatgtt ggttgtcaaa    4020
tgtagtgtgt ttccctaact ttctgttttt cctgagaaaa aaaataaat ctttattca    4080
aatacaggga aaaaaaaaaa aaaaaaa                                      4107
```

<210> SEQ ID NO 4
<211> LENGTH: 1126

```
<212> TYPE: DNA
<213> ORGANISM: Homo sapiens
<220> FEATURE:
<223> OTHER INFORMATION: SAP30 glucocorticoid receptor-responsive gene

<400> SEQUENCE: 4
tccccatgtg acagtgagcg gggtccccgc tccaggagac gctcgagtct gcgtcccggc     60
cctcagcact gtccactgtt tcggtgccag cagagaccag caggcccggg acagttggtg    120
tttggccgtg ccgctgtcta acttggtgtg cagagtgaat tgccgctgcc ggagcggaga    180
gaggcggagc ggccaggaga gaggggattt ctgtcagcgc cggcctcggg agctcggaga    240
catgaacggc ttcacgcctg acgagatgag ccgcggcggg gatgcggccg ccgcagtggc    300
cgcagtggtc gctgccgcgg ccgccgccgc ctcggcgggg aacgggaccg gcgcgggcac    360
cggggctgag gtgccgggcg cggggcggt ctcagcggct gggcccccgg gggcggccgg    420
gccgggcccc gggcaactgt gctgcctgcg ggaggatggt gagcggtgcg gccgggcggc    480
aggcaacgcc agcttcagca agaggatcca gaagagcatc tcccagaaga aggtgaagat    540
cgagctggat aagagcgcaa ggcatcttta catatgtgat tatcataaaa acttaattca    600
gagtgttcga aacagaagaa agagaaaagg gagtgatgat gatggaggtg attcacctgt    660
tcaagatatt gatacccag aggttgattt ataccaatta caagtaaata cacttaggag    720
atacaaaaga cacttcaagc taccaaccag accaggactt aataaagcac aacttgttga    780
gatagttggt tgccacttta ggtctattcc agtgaatgaa aaagacacct taacatattt    840
catctactca gtgaagaatg acaagaacaa atcagatctc aaggttgata gtggtgttca    900
ctaggagacg tggaattgag actaataact tggatgttaa cactgtttac tgttttttca    960
catgtagaaa tgttctttgt gtattttttc tacagaggat tttctctgat tttatttct    1020 ttgtttctga ctctaataat tagttggaaa ctcatataaa atgagctttc ctaaattaaa   1080 tctatttaa ataaggtta ttactattaa aaaaaaaaaa aaaaaa                    1126

<210> SEQ ID NO 5
<211> LENGTH: 2040
<212> TYPE: DNA
<213> ORGANISM: Homo sapiens
<220> FEATURE:
<223> OTHER INFORMATION: DUSP1 glucocorticoid receptor-responsive gene

<400> SEQUENCE: 5
tcgctgcgaa ggacatttgg gctgtgtgtg cgacgcgggt cggaggggca gtcgggggaa     60
ccgcgaagaa gccgaggagc ccggagcccc gcgtgacgct cctctctcag tccaaaagcg    120
gcttttggtt cggcgcagag agacccgggg gtctagcttt tcctcgaaaa gcgccgccct    180
gcccttggcc ccgagaacag acaaagagca ccgcagggcc gatcacgctg ggggcgctga    240
ggccggccat ggtcatggaa gtgggcaccc tggacgctgg aggcctgcgg gcgctgctgg    300
gggagcgagc ggcgcaatgc ctgctgctgg actgccgctc cttcttcgct ttcaacgccg    360
gccacatcgc cggctctgtc aacgtgcgct tcagcaccat cgtgcggcgc cgggccaagg    420
gcgccatggg cctggagcac atcgtgccca acgccgagct ccgcggccgc ctgctggccg    480
gcgcctacca cgccgtggtg ttgctggacg agcgcagcgc cgccctggac ggcgccaagc    540
gcgacggcac cctggccctg ggcggccgcg cgctctgccg cgaggcgcgc gccgcgcaag    600
tcttcttcct caaaggagga tacgaagcgt tttcggcttc ctgccccgag ctgtgcagca    660
aacagtcgac ccccatgggg ctcagccttc ccctgagtac tagcgtccct gacagcgcgg    720
```

```
aatctgggtg cagttcctgc agtaccccac tctacgatca gggtggcccg gtggaaatcc    780 tgcccttct  gtacctgggc agtgcgtatc acgcttcccg caaggacatg ctggatgcct    840
tgggcatcac tgccttgatc aacgtctcag ccaattgtcc caaccatttt gagggtcact    900
accagtacaa gagcatccct gtggaggaca accacaaggc agacatcagc tcctggttca    960
acgaggccat tgacttcata gactccatca agaatgctgg aggaagggtg tttgtccact   1020
gccaggcagg catttcccgg tcagccacca tctgccttgc ttaccttatg aggactaatc   1080
gagtcaagct ggacgaggcc tttgagtttg tgaagcagag gcgaagcatc atctctccca   1140
acttcagctt catgggccag ctgctgcagt ttgagtccca ggtgctggct ccgcactgtt   1200
cggcagaggc tgggagcccc gccatggctg tgctcgaccg aggcacctcc accaccaccg   1260
tgttcaactt ccccgtctcc atccctgtcc actccacgaa cagtgcgctg agctaccttc   1320
agagccccat tacgacctct cccagctgct gaaaggccac gggaggtgag gctcttcaca   1380
tcccattggg actccatgct ccttgagagg agaaatgcaa taactctggg aggggctcga   1440
gagggctggt ccttatttat ttaacttcac ccgagttcct ctgggtttct aagcagttat   1500
ggtgatgact tagcgtcaag acatttgctg aactcagcac attcgggacc aatatatagt   1560
gggtacatca agtccatctg acaaaatggg gcagaagaga aaggactcag tgtgtgatcc   1620
ggtttctttt tgctcgcccc tgttttttgt agaatctctt catgcttgac atacctacca   1680
gtattattcc cgacgacaca tatacatatg agaatatacc ttatttattt ttgtgtaggt   1740
gtctgccttc acaaatgtca ttgtctactc ctagaagaac caaataccct aattttgttt    1800
tttgagtact gtactatcct gtaaatatat cttaagcagg tttgttttca gcactgatgg   1860
aaaataccag tgttgggttt tttttagtt gccaacagtt gtatgtttgc tgattattta    1920
tgacctgaaa taatatattt cttcttctaa gaagacattt tgttacataa ggatgacttt   1980
tttatacaat ggaataaatt atggcatttc tattgaaatt tcaaaaaaaa aaaaaaaaa    2040
```

<210> SEQ ID NO 6
<211> LENGTH: 3208
<212> TYPE: DNA
<213> ORGANISM: Homo sapiens
<220> FEATURE:
<223> OTHER INFORMATION: SGK1 glucocorticoid receptor-responsive gene

<400> SEQUENCE: 6

```
agatattcat gaaccgttgc ttcttccagc ctcgccttct cgctccctct gcctttctgg     60
cgctgttctc cctccctccc tctggcttct gctctttctt actccttctc tcagctgctt    120
aactacagct cccactggaa cttgcacaat caaaaacaac tctcctctct caagccgcct    180
ccaggagcgc atcacctgga gaagagcgac tcgctcccg cgccggccgc ggaagagcag     240
ccaggtagct gggggcgggg aggcgtaccc ttctcccgct cggtaagagc cacagcatct    300
ccccggagat tggccgtatc ccaccgtccg gcccccaggg tcctgcagcg gtgatgcata    360
tgtttcggag caatgatgga aggagaaaag ccgctgtcgg tggcaactga agtggggag     420 aggttgctgc agtagctggt gctgcagaat gcgcgagtga agaactgagc cccgctagat    480
tctccatccc gctcagtctt cattaactgt ctgcaggagg taaaccgggg aaacagatat    540
gcactaacca ggcgggtgcc aacctggatc tataactgtg aattccccac ggtggaaaat    600
ggtaaacaaa gacatgaatg gattcccagt caagaaatgc tcagccttcc aattttttaa    660
gaagcgggta cgaaggtgga tcaagagccc aatggtcagt gtggacaagc atcagagtcc    720
cagcctgaag tacaccggct cctccatggt gcacatccct ccaggggagc cagacttcga    780
```

```
gtcttccttg tgtcaaacat gcctgggtga acatgctttc caaagagggg ttctccctca      840
ggagaacgag tcatgttcat gggaaactca atctgggtgt gaagtgagag agccatgtaa      900
tcatgccaac atcctgacca agcccgatcc aagaaccttc tggactaatg atgatccagc      960
tttcatgaag cagaggagga tgggtctgaa cgactttatt cagaagattg ccaataactc     1020
ctatgcatgc aaacaccctg aagttcagtc catcttgaag atctcccaac ctcaggagcc     1080
tgagcttatg aatgccaacc cttctcctcc accaagtcct tctcagcaaa tcaaccttgg     1140
cccgtcgtcc aatcctcatg ctaaaccatc tgactttcac ttcttgaaag tgatcggaaa     1200
gggcagtttt ggaaaggttc ttctagcaag acacaaggca gaagaagtgt tctatgcagt     1260
caaagtttta cagaagaaag caatcctgaa aaagaaagag gagaagcata ttatgtcgga     1320
gcggaatgtt ctgttgaaga atgtgaagca ccctttcctg gtgggccttc acttctcttt     1380
ccagactgct gacaaattgt actttgtcct agactacatt aatggtggag agttgttcta     1440
ccatctccag agggaacgct gcttcctgga accacgggct cgtttctatg ctgctgaaat     1500
agccagtgcc ttgggctacc tgcattcact gaacatcgtt tatagagact aaaaccaga     1560 gaatattttg ctagattcac agggacacat tgtccttact gacttcggac tctgcaagga     1620
gaacattgaa cacaacagca caacatccac cttctgtggc acgccggagt atctcgcacc     1680
tgaggtgctt cataagcagc cttatgacag gactgtggac tggtggtgcc tgggagctgt     1740
cttgtatgag atgctgtatg gcctgccgcc ttttatagc cgaaacacag ctgaaatgta     1800
cgacaacatt ctgaacaagc ctctccagct gaaaccaaat attacaaatt ccgcaagaca     1860
cctcctggag ggcctcctgc agaaggacag gacaaagcgg ctcggggcca aggatgactt     1920
catggagatt aagagtcatg tcttcttctc cttaattaac tgggatgatc tcattaataa     1980
gaagattact ccccctttta acccaaatgt gagtgggccc aacgacctac ggcactttga     2040
ccccgagttt accgaagagc ctgtccccaa ctccattggc aagtcccctg acagcgtcct     2100
cgtcacagcc agcgtcaagg aagctgccga ggctttccta ggcttttcct atgcgcctcc     2160
cacggactct ttcctctgaa ccctgttagg gcttggtttt aaaggatttt atgtgtgttt     2220
ccgaatgttt tagttagcct tttggtggag ccgccagctg acaggacatc ttacaagaga     2280
atttgcacat ctctggaagc ttagcaatct tattgcacac tgttcgctgg aagcttttg     2340 aagagcacat tctcctcagt gagctcatga ggttttcatt tttattcttc cttccaacgt     2400
ggtgctatct ctgaaacgag cgttagagtg ccgccttaga cggaggcagg agtttcgtta     2460
gaaagcggac gctgttctaa aaaaggtctc ctgcagatct gtctgggctg tgatgacgaa     2520
tattatgaaa tgtgcctttt ctgaagagat tgtgttagct ccaaagcttt tcctatcgca     2580
gtgtttcagt tctttatttt cccttgtgga tatgctgtgt gaaccgtcgt gtgagtgtgg     2640
tatgcctgat cacagatgga ttttgttata agcatcaatg tgacacttgc aggacactac     2700
aacgtgggac attgtttgtt tcttccatat ttggaagata aatttatgtg tagacttttt     2760
tgtaagatac ggttaataac taaaatttat tgaaatggtc ttgcaatgac tcgtattcag     2820
atgcttaaag aaagcattgc tgctacaaat atttctattt ttagaaaggg ttttttatgga     2880 ccaatgcccc agttgtcagt cagagccgtt ggtgttttc attgtttaaa atgtcacctg     2940
taaaatgggc attatttatg tttttttttt tgcattcctg ataattgtat gtattgtata     3000
aagaacgtct gtacattggg ttataacact agtatattta aacttacagg cttatttgta     3060
atgtaaacca ccatttttaat gtactgtaat taacatggtt ataatacgta caatccttcc     3120
```

| | |
|---|---:|
| ctcatcccat cacacaactt tttttgtgtg tgataaactg attttggttt gcaataaaac | 3180 |
| cttgaaaaat atttacatat aaaaaaaa | 3208 |

<210> SEQ ID NO 7
<211> LENGTH: 5758
<212> TYPE: DNA
<213> ORGANISM: Homo sapiens
<220> FEATURE:
<223> OTHER INFORMATION: SMARCA2 glucocorticoid receptor-responsive gene

<400> SEQUENCE: 7

| | |
|---|---:|
| tttctgtact ctgggtgact cagagaggga agagattcag ccagcacact cctcgcgagc | 60 |
| aagcattact ctactgactg gcagagacag gagaggtaga tgtccacgcc cacagaccct | 120 |
| ggtgcgatgc cccacccagg gccttcgccg gggcctgggc cttcccctgg gccaattctt | 180 |
| gggcctagtc caggaccagg accatcccca ggttccgtcc acagcatgat ggggccaagt | 240 |
| cctggacctc caagtgtctc ccatcctatg ccgacgatgg ggtccacaga cttcccacag | 300 |
| gaaggcatgc atcaaatgca taagcccatc gatggtatac atgacaaggg gattgtagaa | 360 |
| gacatccatt gtggatccat gaagggcact ggtatgcgac cacctcaccc aggcatgggc | 420 |
| cctccccaga gtccaatgga tcaacacagc caaggttata tgtcaccaca cccatctcca | 480 |
| ttaggagccc cagagcacgt ctccagccct atgtctggag gaggcccaac tccacctcag | 540 |
| atgccaccaa gccagccggg ggccctcatc ccaggtgatc cgcaggccat gagccagccc | 600 |
| aacagaggtc cctcaccttt cagtcctgtc cagctgcatc agcttcgagc tcagattta | 660 |
| gcttataaaa tgctggcccg aggccagccc ctccccgaaa cgctgcagct tgcagtccag | 720 |
| gggaaaagga cgttgcctgg cttgcagcaa caacagcagc agcaacagca gcagcagcag | 780 |
| cagcagcagc agcagcagca gcagcaacag cagccgcagc agcagccgcc gcaaccacag | 840 |
| acgcagcaac aacagcagcc ggcccttgtt aactacaaca gaccatctgg cccggggccg | 900 |
| gagctgagcg gcccgagcac cccgcagaag ctgccggtgc ccgcgcccgg cggccggccc | 960 |
| tcgcccgcgc ccccgcagc cgcgcagccg cccgcggccg cagtgcccgg gccctcagtg | 1020 |
| ccgcagccgg ccccggggca gccctcgccc gtcctccagc tgcagcagaa gcagagccgc | 1080 |
| atcagcccca tccagaaacc gcaaggcctg acccccgtgg aaattctgca agagcgggaa | 1140 |
| tacagacttc aggcccgcat agctcatagg atacaagaac tggaaaatct gcctggctct | 1200 |
| ttgccaccag atttaagaac caaagcaacc gtggaactaa aagcacttcg gttactcaat | 1260 |
| ttccagcgtc agctgagaca ggaggtggtg gcctgcatgc gcagggacac gacccctggag | 1320 |
| acggctctca actccaaagc atacaaacgg agcaagcgcc agactctgag agaagctcgc | 1380 |
| atgaccgaga gctggagaa gcagcagaag attgagcagg agaggaaacg ccgtcagaaa | 1440 |
| caccaggaat acctgaacag tattttgcaa catgcaaaag attttaagga atatcatcgg | 1500 |
| tctgtggccg gaaagatcca gaagctctcc aaagcagtgg caacttggca tgccaacact | 1560 |
| gaaagagagc agaagaagga gacagagcgg attgaaaagg agaatgcg gcgactgatg | 1620 |
| gctgaagatg aggagggtta tagaaaactg attgatcaaa agaaagacag gcgtttagct | 1680 |
| tacctttgc agcagaccga tgagtatgta gccaatctga ccaatctggt ttgggagcac | 1740 |
| aagcaagccc aggcagccaa agagaagaag aagaggagga ggaggaagaa gaaggctgag | 1800 |
| gagaatgcag agggtgggga gtctgccctg ggaccggatg gagagcccat agatgagagc | 1860 |
| agccagatga gtgacctccc tgtcaaagtg actcacacag aaaccggcaa ggttctgttc | 1920 |
| ggaccagaag cacccaaagc aagtcagctg gacgcctggc tggaaatgaa tcctggttat | 1980 |

```
gaagttgccc ctagatctga cagtgaagag agtgattctg attatgagga agaggatgag    2040
gaagaagagt ccagtaggca ggaaaccgaa gagaaaatac tcctggatcc aaatagcgaa    2100
gaagtttctg agaaggatgc taagcagatc attgagacag ctaagcaaga cgtggatgat    2160
gaatacagca tgcagtacag tgccaggggc tcccagtcct actacaccgt ggctcatgcc    2220
atctcggaga gggtggagaa acagtctgcc ctcctaatta atgggaccct aaagcattac    2280
cagctccagg gcctggaatg gatggtttcc ctgtataata acaacttgaa cggaatctta    2340
gccgatgaaa tggggcttgg aaagaccata cagaccattg cactcatcac ttatctgatg    2400
gagcacaaaa gactcaatgg cccctatctc atcattgttc cccttcgac tctatctaac    2460 tggacatatg aatttgacaa atgggctcct tctgtggtga agatttctta caagggtact    2520
cctgccatgc gtcgctccct tgtccccag ctacggagtg gcaaattcaa tgtcctcttg    2580
actacttatg agtatattat aaaagacaag cacattcttg caaagattcg gtggaaatac    2640
atgatagtgg acgaaggcca ccgaatgaag aatcaccact gcaagctgac tcaggtcttg    2700
aacactcact atgtggcccc cagaaggatc ctcttgactg ggaccccgct gcagaataag    2760
ctccctgaac tctgggccct cctcaacttc ctcctcccaa caatttttaa gagctgcagc    2820
acatttgaac aatggttcaa tgctccattt gccatgactg gtgaaagggt ggacttaaat    2880
gaagaagaaa ctatattgat catcaggcgt ctacataagg tgttaagacc attttttacta    2940 aggagactga agaaagaagt tgaatcccag cttcccgaaa aagtggaata tgtgatcaag    3000
tgtgacatgt cagctctgca gaagattctg tatcgccata tgcaagccaa ggggatcctt    3060
ctcacagatg gttctgagaa agataagaag gggaaaggag gtgctaagac acttatgaac    3120
actattatgc agttgagaaa aatctgcaac cacccatata tgtttcagca cattgaggaa    3180 tccttttgctg aacacctagg ctattcaaat ggggtcatca atggggctga actgtatcgg    3240
gcctcaggga gtttgagct gcttgatcgt attctgccaa aattgagagc gactaatcac    3300
cgagtgctgc tttctgcca gatgacatct ctcatgacca tcatggagga ttattttgct    3360
tttcggaact tccttttacct acgccttgat ggcaccacca agtctgaaga tcgtgctgct    3420
ttgctgaaga aattcaatga acctggatcc cagtatttca ttttcttgct gagcacaaga    3480
gctggtggcc tgggcttaaa tcttcaggca gctgatacag tggtcatctt tgacagcgac    3540
tggaatcctc atcaggatct gcaggcccaa gaccgagctc accgcatcgg gcagcagaac    3600
gaggtccggg tactgaggct ctgtaccgtg aacagcgtgg aggaaaagat cctcgcggcc    3660
gcaaaataca agctgaacgt ggatcagaaa gtgatccagg cggcatgtt tgaccaaaag    3720 tcttcaagcc acgagcggag ggcattcctg caggccatct ggagcatga ggaggaaaat    3780 gaggaagaag atgaagtacc ggacgatgag actctgaacc aaatgattgc tcgacgagaa    3840
gaagaatttg accttttat gcggatggac atggaccggc ggagggaaga tgcccggaac    3900
ccgaaacgga agccccgttt aatgaggaag atgagctgc cctcctggat cattaaggat    3960
gacgctgaag tagaaaggct cacctgtgaa gaagaggagg agaaaatatt tgggaggggg    4020
tcccgccagc gccgtgacgt ggactacagt gacgccctca cggagaagca gtggctaagg    4080
gccatcgaag acggcaattt ggaggaaatg gaagaggaag tacggcttaa gaagcgaaaa    4140
agacgaagaa atgtggataa agatcctgca aaagaagatg tggaaaaagc taagaagaga    4200
agaggccgcc ctcccgctga gaactgtca ccaaatcccc ccaaactgac aaagcagatg    4260
aacgctatca tcgatactgt gataaactac aaagataggt gtaacgtgga gaaggtgccc    4320
```

```
agtaattctc agttggaaat agaaggaaac agttcagggc gacagctcag tgaagtcttc    4380
attcagttac cttcaaggaa agaattacca gaatactatg aattaattag gaagccagtg    4440
gatttcaaaa aaataaagga aaggattcgt aatcataagt accggagcct aggcgacctg    4500
gagaaggatg tcatgcttct ctgtcacaac gctcagacgt tcaacctgga gggatcccag    4560
atctatgaag actccatcgt cttacagtca gtgtttaaga gtgcccggca gaaaattgcc    4620
aaagaggaag agagtgagga tgaaagcaat gaagaggagg aagaggaaga tgaagaagag    4680
tcagagtccg aggcaaaatc agtcaaggtg aaaattaagc tcaataaaaa agatgacaaa    4740
ggccgggaca aagggaaagg caagaaaagg ccaaatcgag aaaagccaa acctgtagtg     4800 agcgattttg acagcgatga ggagcaggat gaacgtgaac agtcagaagg aagtgggacg    4860
gatgatgagt gatcagtatg gaccttttc cttggtagaa ctgaattcct tcctcccctg     4920
tctcatttct acccagtgag ttcatttgtc atataggcac tgggttgttt ctatatcatc    4980
atcgtctata aactagcttt aggatagtgc cagacaaaca tatgatatca tggtgtaaaa    5040
aacacacaca tacacaaata tttgtaacat attgtgacca aatgggcctc aaagattcag    5100
attgaaacaa acaaaaagct tttgatggaa aatatgtggg tggatagtat atttctatgg    5160
gtgggtctaa tttggtaacg gtttgattgt gcctggtttt atcacctgtt cagatgagaa    5220 gattttttgtc ttttgtagca ctgataacca ggagaagcca ttaaaagcca ctggttatttt   5280 tatttttcat caggcaattt tcgaggtttt tatttgttcg gtattgtttt tttacactgt    5340
ggtacatata agcaacttta ataggtgata aatgtacagt agttagattt cacctgcata    5400
tacatttttc cattttatgc tctatgatct gaacaaaagc ttttttgaatt gtataagatt   5460 tatgtctact gtaaacattg cttaatttt ttgctcttga tttaaaaaaa agttttgttg    5520
aaagcgctat tgaatattgc aatctatata gtgtattgga tggcttcttt tgtcaccctg    5580
atctcctatg ttaccaatgt gtatcgtctc cttctcccta aagtgtactt aatctttgct    5640
ttctttgcac aatgtctttg gttgcaagtc ataagcctga ggcaaataaa attccagtaa    5700
tttcgaagaa tgtggtgttg gtgctttcct aataaagaaa taatttagct tgacaaaa     5758
```

<210> SEQ ID NO 8
<211> LENGTH: 837
<212> TYPE: DNA
<213> ORGANISM: Homo sapiens
<220> FEATURE:
<223> OTHER INFORMATION: PTGDS glucocorticoid receptor-responsive gene

<400> SEQUENCE: 8

```
gctcctcctg cacacctccc tcgctctccc acaccactgg caccaggccc cggacacccg      60
ctctgctgca ggagaatggc tactcatcac acgctgtgga tgggactggc cctgctgggg     120
gtgctgggcg acctgcaggc agcaccggag gcccaggtct ccgtgcagcc caacttccag    180
caggacaagt tcctggggcg ctggttcagc gcgggcctcg cctccaactc gagctggctc    240
cgggagaaga aggcggcgtt gtccatgtgc aagtctgtgg tggcccctgc cacggatggt    300
ggcctcaacc tgacctccac cttcctcagg aaaaaccagt gtgagacccg aaccatgctg    360
ctgcagcccg cggggtccct cggctcctac agctaccgga gtccccactg gggcagcacc    420
tactccgtgt cagtggtgga gaccgactac gaccagtacg cgctgctgta cagccagggc    480
agcaagggcc ctggcgagga cttccgcatg gccacccctct acagccgaac ccagaccccc    540
agggctgagt taaggagaa attcaccgcc ttctgcaagg cccagggctt cacagaggat    600
accattgtct tcctgcccca aaccgataag tgcatgacgg aacaatagga ctccccaggg    660
```

```
ctgaagctgg gatcccggcc agccaggtga ccccacgct ctggatgtct ctgctctgtt    720
ccttccccga gccctgccc cggctccccg ccaaagcaac cctgcccact caggcttcat    780
cctgcacaat aaactccgga agcaagtcag taaaaaaaaa aaaaaaaaaa aaaaaaa     837
```

<210> SEQ ID NO 9
<211> LENGTH: 6001
<212> TYPE: DNA
<213> ORGANISM: Homo sapiens
<220> FEATURE:
<223> OTHER INFORMATION: TNFRSF9 glucocorticoid receptor-responsive gene

<400> SEQUENCE: 9

```
caaggaggga tcccacagat gtcacagggc tgtcacagag ctgtggtggg aatttcccat     60
gagaccccgc ccctggctga gtcaccgcac tcctgtgttt gacctgaagt cctctcgagc    120
tgcagaagcc tgaagaccaa ggagtggaaa gttctccggc agccctgaga tctcaagagt    180
gacatttgtg agaccagcta atttgattaa aattctcttg gaatcagctt tgctagtatc    240
atacctgtgc cagatttcat catgggaaac agctgttaca acatagtagc cactctgttg    300
ctggtcctca actttgagag acaagatca ttgcaggatc cttgtagtaa ctgcccagct    360
ggtacattct gtgataataa caggaatcag atttgcagtc cctgtcctcc aaatagtttc    420
tccagcgcag gtggacaaag gacctgtgac atatgcaggc agtgtaaagg tgttttcagg    480
accaggaagg agtgttcctc caccagcaat gcagagtgtg actgcactcc agggtttcac    540
tgcctggggg caggatgcag catgtgtgaa caggattgta acaaggtca agaactgaca    600 aaaaaaggtt gtaaagactg ttgctttggg acatttaacg atcagaaacg tggcatctgt    660
cgaccctgga caaactgttc tttggatgga aagtctgtgc ttgtgaatgg gacgaaggag    720
agggacgtgg tctgtggacc atctccagcc gacctctctc cgggagcatc ctctgtgacc    780
ccgcctgccc ctgcgagaga gccaggacac tctccgcaga tcatctcctt ctttcttgcg    840
ctgacgtcga ctgcgttgct cttcctgctg ttcttcctca cgctccgttt ctctgttgtt    900
aaacggggca gaaagaaact cctgtatata ttcaaacaac catttatgag accagtacaa    960
actactcaag aggaagatgg ctgtagctgc cgatttccag aagaagaaga aggaggatgt   1020
gaactgtgaa atggaagtca atagggctgt tgggactttc ttgaaaagaa gcaaggaaat   1080
atgagtcatc cgctatcaca gctttcaaaa gcaagaacac catcctacat aatacccagg   1140
attcccccaa cacacgttct tttctaaatg ccaatgagtt ggcctttaaa aatgcaccac   1200
tttttttttt tttttgacag gtctcactc tgtcacccag gctggagtgc agtggcacca   1260
ccatggctct ctgcagcctt gacctctggg agctcaagtg atcctcctgc ctcagtctcc   1320
tgagtagctg gaactacaag gaagggccac cacacctgac taactttttt gttttttgtt   1380
tggtaaagat ggcatttcac catgttgtac aggctggtct caaactccta ggttcacttt   1440
ggcctcccaa agtgctggga ttacagacat gaactgccag gccggccaa aataatgcac   1500 cacttttaac agaacagaca gatgaggaca gagctggtga taaaaaaaaa aaaaaaaaag   1560
cattttctag ataccactta acaggtttga gctagttttt ttgaaatcca agaaaatta    1620 tagtttaaat tcaattacat agtccagtgg tccaactata attataatca aaatcaatgc   1680
aggtttgttt tttggtgcta atatgacata tgacaataag ccacgaggtg cagtaagtac   1740
ccgactaaag tttccgtggg ttctgtcatg taacacgaca tgctccaccg tcagggggga   1800
gtatgagcag agtgcctgag tttagggtca aggacaaaaa acctcaggcc tggaggaagt   1860
```

```
tttggaaaga gttcaagtgt ctgtatatcc tatggtcttc tccatcctca caccttctgc    1920
ctttgtcctg ctcccttta agccaggtta cattctaaaa attcttaact tttaacataa    1980
tattttatac caaagccaat aaatgaactg catatgatag gtatgaagta cagtgagaaa    2040
attaacacct gtgagctcat tgtcctacca cagcactaga gtgggggccg ccaaactccc    2100
atggccaaac ctggtgcacc atttgccttt gtttgtctgt tggtttgctt gagacagtct    2160
tgctctgttg cccaggctgg aatggagtgg ctattcacag gcacaatcat agcacacttt    2220
agccttaaac tcctgggctc aagtgatcca cccgcctcag tctcccaagt agctgggatt    2280
acaggtgcaa acctggcatg cctgccattg tttggcttat gatctaagga tagcttttta    2340 aatttattc attttatttt tttttgagac agtgtctcac tctgtctccc aggctggagt    2400
acagtggtac aatcttggat caccgcctcc cagtttcaag tgatctccct gcctcagcct    2460
cctaagtagc tgggactaca ggtatgtgcc accacgcctg gctaatttt atattttag     2520 tagagacggg gtttcaccat gttgtccagg ctggtctcaa actcctgacc tcaggtgatc    2580
tgcccacctc tgcctcccaa agtgctggga ttacaggcat gagccaccat gcctggccat    2640
ttcttacact tttgtatgac atgcctattg caagcttgcg tgcctctgtc ccatgttatt    2700
ttactctggg atttaggtgg agggagcagc ttctatttgg aacattggcc atcgcatggc    2760
aaatgggtat ctgtcacttc tgctcctatt tagttggttc tactataacc tttagagcaa    2820
atcctgcagc caagccaggc atcaataggg cagaaaagta tattctgtaa ataggggtga    2880
ggagaagata tttctgaaca atagtctact gcagtaccaa attgcttttc aaagtggctg    2940
ttctaatgta ctcccgtcag tcatataagt gtcatgtaag tatcccattg atccacatcc    3000
ttgctaccct ctggtactat caggtgccct taattttgcc aagccagtgg gtatagaatg    3060
agatctcact gtggtcttag tttgcatttg cttggttact gatgagcacc ttgtcaaata    3120
tttatatacc atttgtgttt attttttta ataaaatgct tgctcatgct tttttgccca    3180
tttgcaaaaa aacttggggc cgggtgcagt ggctcatgcc tgtagtccca gctctttggg    3240
aggccaaggt gggcagatcg cttgagccca ggagttcgag accagccttg caacatggc     3300 gaaaccctgt ctttacaaaa aatacaaaaa ttagccgggt gtggtggtgt gcacctgaag    3360
tcccagctac tcagtaggtt cgctttgagc ctgggaggca gaggttgcag tgagctggga    3420
ccgcatcact acacttcagc ctgggcaaca gagaaaaacc ttttctcaga aacaaacaaa    3480
cccaaatgtg gttgtttgtc ctgattccta aaaggtcttt atgtattcta gataataatc    3540
tttggtcagt tatatgtgtt aaaaaatatc ttctttgtgg ccaggcacgg tagctcacac    3600
ctgtaatccc agcactttgc ggggctgagg tgggtggatc atctgaggtc aagagttcaa    3660
gatcagcctg gccaacacag tgaaacccca tctctactaa acatgtacaa aacttagctg    3720
ggtatggtgg cgggtgcctg taaccccagc tgctccagag gctgtggcag aagaatcgct    3780
tgaacccagg aggcagaggt tgcagcgagc caagattgtg ccattgcact ccagactggg    3840
tgacaagagt gaaattctgc ctatctatct atctatctat ctatatctat atatatatat    3900
atatatatcc tttgtaattt attttccct tttaaaatt ttttataaaa ttctttttta     3960
tttttatttt tagcagaggt gaggtttctg aggtttcatt atgttgccca ggctggtctt    4020
gaactcctga gctcaagtga tcctcccacc tcagccttcc aaagtgctgg aattgcagac    4080
atgagccacc gcgcccctcc tgtttttctc taattaatgg tgtctttctt tgtctttctg    4140
gtaataagca aaaagttctt catttgattt ggttaaattt ataactgttt tctcatatgg    4200
ttaacatttt ttcttgcctg gctaaagaaa tccttttctg cccaatacta taaagaggtt    4260
```

```
tgcccacatt ttattccaaa agttttaagt tttgtctttc atcttgaagt ctaatgtatc    4320
aggaactggc ttttgtgcct gttgggaggt agtgatccaa ttccatgtct tgcatgtagg    4380
taaccactgg tccctgcgcc atgtattcaa tacgtcgtct ttctcctgcg ggtctgcaat    4440
ctcacctacc atccatcaag tttccatagg gccatgggtc tgcttctggg ctccctgttc    4500
tgttccattg tcaatttgtc tatcctgtgc cagtatcaca ctgtgtttat tacaatagct    4560
ttgtaacagc tctcgatatc cggtaggaca tctccctcca ccttcttttt ctacttcaga    4620
agtgtcttag ctaggtcagg cacggtggct cacgcctgta atcccagcac tttgggaggc    4680
cgacgcggat ggatcacctg aggtcaggag ttttgagaca gcctggccaa catggtgaaa    4740
ccccatctct actaaaaaat acaaaaatta gtcaggcatg gtggcatgtg cctgtaatcc    4800
cagctatttg ggaggctgag gccggagaat tgcttgaacc cggggggcgg aggttgcagt    4860
gagccgagat cgtaccattg cactccagcc tgggtgacag agcgaaactc tgtctcagga    4920 aaaaaagaa aagagatgtc ttggttattc ttggttcttt attattcaat ataaatttta     4980
gaagctgaat ttgaaaagat ttggattgga atttcattaa atctacaggt caatttaggg    5040
agagttgata attttacaga attgagtcat ctggtgttcc aataagaata agagaacaat    5100
tattggctgt acaattcttg ccaaatagta ggcaaagcaa agcttaggaa gtatactggt    5160
gccatttcag gaacaaagct aggtgcgaat atttttgtct ttctgaatca tgatgctgta    5220
agttctaaag tgatttctcc tcttggcttt ggacacatgg tgtttaatta cctactgctg    5280
actatccaca aacagaaaga gactggtcat gccccacagg gttggggtat ccaagataat    5340
ggagcgaggc tctcatgtgt cctaggttac acaccgaaaa tccacagtt attctgtgaa     5400 gaaaggaggc tatgtttatg atacagactg tgatatttt atcatagcct attctggtat     5460
catgtgcaaa agctataaat gaaaaacaca ggaacttggc atgtgagtca ttgctccccc    5520
taaatgacaa ttaataagga aggaacattg agacagaata aaatgatccc cttctgggtt    5580
taatttagaa agttccataa ttaggtttaa tagaaataaa tgtaaatttc tatgattaaa    5640
aataaattag cacatttagg gatacacaaa ttataaatca ttttctaaat gctaaaaaca    5700
agctcaggtt ttttcagaa gaaagtttta atttttttc tttagtggaa gatatcactc      5760
tgacggaaag ttttgatgtg aggggcggat gactataaag tgggcatctt cccccacagg    5820
aagatgtttc catctgtggg tgagaggtgc ccaccgcagc tagggcaggt tacatgtgcc    5880
ctgtgtgtgg taggacttgg agagtgatct ttatcaacgt ttttatttaa aagactatct    5940
aataaaacac aaaactatga tgttcacagg aaaaaaagaa taagaaaaaa agaaaaaaaa    6000
a                                                                   6001
```

<210> SEQ ID NO 10
<211> LENGTH: 1336
<212> TYPE: DNA
<213> ORGANISM: Homo sapiens
<220> FEATURE:
<223> OTHER INFORMATION: SFN glucocorticoid receptor-responsive gene

<400> SEQUENCE: 10

```
gagagacaca gagtccggca ttggtcccag gcagcagtta gcccgccgcc cgcctgtgtg      60
tccccagagc catggagaga gccagtctga tccagaaggc caagctggca gagcaggccg     120
aacgctatga ggacatggca gccttcatga aaggcgccgt ggagaagggc gaggagctct     180
cctgcgaaga gcgaaacctg ctctcagtag cctataagaa cgtggtgggc ggccagaggg     240
```

```
ctgcctggag ggtgctgtcc agtattgagc agaaaagcaa cgaggagggc tcggaggaga    300
aggggcccga ggtgcgtgag taccgggaga aggtggagac tgagctccag ggcgtgtgcg    360
acaccgtgct gggcctgctg gacagccacc tcatcaagga ggccggggac gccgagagcc    420
gggtcttcta cctgaagatg aagggtgact actaccgcta cctggccgag gtggccaccg    480
gtgacgacaa gaagcgcatc attgactcag cccggtcagc ctaccaggag gccatggaca    540
tcagcaagaa ggagatgccg cccaccaacc ccatccgcct gggcctggcc ctgaactttt    600
ccgtcttcca ctacgagatc gccaacagcc ccgaggaggc catctctctg gccaagacca    660
ctttcgacga ggccatggct gatctgcaca ccctcagcga ggactcctac aaagacagca    720
ccctcatcat gcagctgctg cgagacaacc tgacactgtg gacggccgac aacgccgggg    780
aagaggggg cgaggctccc caggagcccc agagctgagt gttgcccgcc accgccccgc    840
cctgcccct ccagtccccc accctgccga gaggactagt atgggtggg aggccccacc    900
cttctccct aggcgctgtt cttgctccaa agggctccgt ggagagggac tggcagagct    960
gaggccacct ggggctgggg atcccactct tcttgcagct gttgagcgca cctaaccact   1020
ggtcatgccc ccaccctgc tctccgcacc cgcttcctcc cgaccccagg accaggctac   1080
ttctcccctc ctcttgcctc cctcctgccc ctgctgcctc tgatcgtagg aattgaggag   1140
tgtcccgcct gtggctgag aactggacag tggcagggc tggagatggg tgtgtgtgtg   1200
tgtgtgtgtg tgtgtgtgtg tgtgcgcgcg cgccagtgca agaccgagat tgagggaaag   1260
catgtctgct gggtgtgacc atgtttcctc tcaataaagt tccctgtga cactcaaaaa   1320
aaaaaaaaa aaaaaa                                                   1336
```

<210> SEQ ID NO 11
<211> LENGTH: 2240
<212> TYPE: DNA
<213> ORGANISM: Homo sapiens
<220> FEATURE:
<223> OTHER INFORMATION: LAPTM5 glucocorticoid receptor-responsive gene

<400> SEQUENCE: 11

```
ggagggcagc cagcagcttc cccttctctg ccctgctcca ggcaccaggc tctttcccct     60
tcagtgtctc agaggagggg acggcagcac catggacccc cgcttgtcca ctgtccgcca    120
gacctgctgc tgcttcaatg tccgcatcgc aaccaccgcc ctggccatct accatgtgat    180
catgagcgtc ttgttgttca tcgagcactc agtagaggtg gcccatggca aggcgtcctg    240
caagctctcc cagatgggct acctcaggat cgctgacctg atctccagct tcctgctcat    300
caccatgctc ttcatcatca gcctgagcct actgatcggc gtagtcaaga accgggagaa    360
gtacctgctg cccttcctgt ccctgcaaat catggactat ctcctgtgcc tgctcaccct    420
gctgggctcc tacattgagc tgcccgccta cctcaagttg gcctcccgga gccgtgctag    480
ctcctccaag ttccccctga tgacgctgca gctgctggac ttctgcctga gcatcctgac    540
cctctgcagc tcctacatgg aagtgcccac ctatctcaac ttcaagtcca tgaaccacat    600
gaattacctc cccagccagg aggatatgcc tcataaccag ttcatcaaga tgatgatcat    660
cttttccatc gccttcatca ctgtcctttat cttcaaggtc tacatgttca agtgcgtgtg    720
gcggtgctac agattgatca agtgcatgaa ctcggtggag gagaagagaa actccaagat    780
gctccagaag gtggtcctgc cgtcctacga ggaagccctg tctttgccat cgaagacccc    840
agaggggggc ccagcaccac ccccatactc agaggtgtga ccctcgccag gccccagccc    900
cagtgctggg aggggtggag ctgcctcata atctgctttt ttgctttggt ggcccctgtg    960
```

```
gcctgggtgg gccctcccgc ccctccctgg caggacaatc tgcttgtgtc tccctcgctg    1020
gcctgctcct cctgcagggc ctgtgagctg ctcacaactg ggtcaacgct ttaggctgag    1080
tcactcctcg ggtctctcca taattcagcc caacaatgct tggtttattt caatcagctc    1140
tgacacttgt ttagacgatt ggccattcta aagttggtga gtttgtcaag caactatcga    1200
cttgatcagt tcagccaagc aactgacaaa tcaaaaccc acttgtcagt tcagtaaaat    1260
aatttggtca acaacagtc tattgcattg atttataaat agttgtcagt tcacatagca    1320
atttaatcaa gtaatcatta attagttacc ccctatatat aaatatatgt aatcaatttc    1380
ttcaaatagc ttgcttacat gataatcaat tagccaacca tgagtcattt agaatagtga    1440
taaatagaat acacagaata gtgatgaaat tcaatttaaa aaatcacgtt agcctccaaa    1500
ccatttaatt caaatgaacc catcaactgg atgccaactc tggcgaatgt aggacctctg    1560
agtggctgta taattgttaa ttcaaatgaa attcatttaa acagttgaca aactgtcatt    1620
caacaattag ctccaggaaa taacagttat ttcatcataa aacagtccct tcaaacacac    1680
aattgttctg ctgaagagtt gtcatcaaca atccaatgct cacctattca gttgctctgt    1740
ggtcagtgtg gctgcataac agtggattcc atgaaaggag tcattttagt gatgagctgc    1800
cagtccattc ccaggccagg ctgtcgctgg ccatccattc agtcgattca gtcataggcg    1860
aatctgttct gcccgaggct tgtggtcaag caaaaattca gccctgaaat caggcacatc    1920
tgttcgttgg actaaaccca caggttagtt cagtcaaagc aggcaacccc cttgtgggca    1980
ctgaccctgc cactggggtc atggcggttg tggcagctgg ggaggtttgg ccccaacagc    2040
cctcctgtgc ctgcttccct gtgtgtcggg gtcctccagg gagctgaccc agaggtggag    2100
gccacggagg cagggtctct ggggactgtc ggggggtaca gagggagaag gctctgcaag    2160
agctccctgg caatacccc ttgtgtaatt gctttgtgtg cgacagggag gaagtttcaa    2220
taaagcagca acaagcttct                                                2240
```

<210> SEQ ID NO 12
<211> LENGTH: 3039
<212> TYPE: DNA
<213> ORGANISM: Homo sapiens
<220> FEATURE:
<223> OTHER INFORMATION: GPSM2 glucocorticoid receptor-responsive gene

<400> SEQUENCE: 12

```
aggcgcagag gagggcggtg ttgagaccgg cggagcggcg ggaccectag gtggcggagg      60 gacgctccgg gaaagcgagg ggcgctacga gctctggccc acgtgacctg ccggggggcg     120 gagcagggg cgcgccggcc tcctgcggtg ccctgcctt ggggaggggc cgtgaccacc       180
cgtctgtcgc ccgaggcggc cgccgctgca ccttcaccgc gtacccggga cccgcccgcc     240
cgcgggagaa atgttgctga agtgctgctg aaagggccag agatgcaagg atttgggata     300
cattttgaac ctttaagctg tctgacattg acctcctttc attattaata aagaagaatc     360
aggagcttag gatgtattaa caccaactca ttaatatact aaccggacaa tgttctacaa     420
acaattctac attgtaaagg actggattgg cacaaaataa aataattta ttttattcag     480 cttataatat gactcgatgg aggaaaattt gataagcatg agaagacc attctttca       540 tgttcgttac agaatggaag cttcttgcct agagctggcc ttggaagggg aacgtctatg     600
taaatcagga gactgccgcg ctggcgtgtc attctttgaa gctgcagttc aagttggaac     660
tgaagaccta aaaacactta gcgctattta cagccagttg ggcaatgctt atttctattt     720
```

```
gcatgattat gccaaagcat tagaatatca ccatcatgat ttaacccttg caaggactat    780
tggagaccag ctgggggaag cgaaagctag tggtaatctg ggaaacacct taaaagttct    840
tgggaatttt gacgaagcca tagtttgttg tcagcgacac ctagatattt ccagagagct    900
taatgacaag gtgggagaag caagagcact ttacaatctt gggaatgtgt atcatgccaa    960
agggaaaagt tttggttgcc ctggtcccca ggatgtagga gaatttccag aagaagtgag   1020
agatgctctg caggcagccg tggattttta tgaggaaaac ctatcattag tgactgcttt   1080
gggtgaccga gcggcacaag gacgtgcctt tggaaatctt ggaaacacac attacctcct   1140
tggcaacttc agggatgcag ttatagctca tgagcagcgt ctccttattg caaaagaatt   1200
tggagataaa gcagctgaaa gaagagcata tagcaacctt ggaaatgcat atatatttct   1260
tggtgaattt gaaactgcct cggaatacta caagaagaca ctactgttgg cccgacagct   1320
taaagaccga gctgtagaag cacagtcttg ttacagtctt ggaaatacat atactttact   1380
tcaagactat gaaaaggcca ttgattatca tctgaagcac ttagcaattg ctcaagagct   1440
gaatgataga attggtgaag gaagagcatg ttggagctta ggaaatgcat acacagcact   1500
aggaaatcat gatcaagcaa tgcattttgc tgaaaagcac ttggaaattt caagagaggt   1560
tggggataaa agtggtgaac taacagcacg acttaatctc tcagaccttc aaatggttct   1620
tggtctgagc tacagcacaa ataactccat aatgtctgaa aatactgaaa ttgatagcag   1680
tttgaatggt gtacgcccca agttgggacg ccggcatagt atgaaaaata tggaacttat   1740
gaagttaaca ccagaaaagg tacagaactg gaacagtgaa attcttgcta agcaaaaacc   1800
tcttattgcc aaaccttctg caaagctact ctttgtcaac agactgaagg ggaaaaaata   1860
caaaacgaat tcctccacta aagttctcca agatgccagt aattctattg accaccgaat   1920
tccaaattct cagaggaaaa tcagtgcaga tactattgga gatgaagggt ctttgactt    1980 attaagccga tttcaaagca ataggatgga tgatcagaga tgttgcttac aagaaaagaa   2040
ctgccataca gcttcaacaa caacttcttc cactcccccct aaaatgatgc taaaaacatc   2100
atctgttcct gtggtatccc ccaacacgga tgagttttta gatcttcttg ccagctcaca   2160
gagtcgccgc ctgatgacc agagggctag tttcagtaat ttgccagggc ttcgtctaac   2220
acaaaacagc cagtcggtac ttagccacct gatgactaat gacaacaaag aggctgatga   2280 agatttctttt gacatccttg taaaatgtca aggatccaga ttagatgatc aaagatgtgc   2340
tccaccacct gctaccacaa agggtccgac agtaccagat gaagacttt tcagccttat    2400 tttacggtcc cagggaaaga gaatggatga acagagagtt cttttacaaa gagatcaaaa   2460
cagagacact gactttgggc taaaggactt tttgcaaaat aatgctttgt tggagtttaa   2520
aaattcaggg aaaaaatcgg cagaccatta gttactatgg atttatttt tttcctttca   2580 aacacggtaa ggaaacaatc tattactttt ttccttaaaa ggagaattta tagcactgta   2640
atacagctta aaatattttt agaatgatgt aaatagttaa ccttcagtag tctattaagg   2700
cattaatact tctctggaca tgcgcgtttg agggtggagg ggtcctgtaa ggtgcttcat   2760
cgtctgtgat tactgcttgg gatgtgttct ttggcagctt gtgagattac tttacctagt   2820
gtttataaag taggaagtta agtgaatcat agattagaat ttaatactct tatgaaaata   2880
attttttaac atcttaattg acaatggcgt ttttttatac ataaccatgg atgtagtggg   2940
aaacaatgtt gtttggtaaa aataatgtac ttgatcaatg taaaaagta tataaaatag    3000 tcttactaaa aatctaggtt ttttttttcct ccaaaaaaa                          3039
```

<210> SEQ ID NO 13
<211> LENGTH: 7018
<212> TYPE: DNA
<213> ORGANISM: Homo sapiens
<220> FEATURE:
<223> OTHER INFORMATION: SORT1 glucocorticoid receptor-responsive gene

<400> SEQUENCE: 13

| | | | | | |
|---|---|---|---|---|---|
| ggcggcgcg | ccgggcggca | ggtgtcggcg | tcggcggcat | tcggcggcga | tggagcggcc | 60 |
| ctggggagct | gcggacggcc | tctcgcgctg | gccccatggc | ctcggcctcc | tcctcctcct | 120 |
| gcagctgctg | ccgccgtcga | ccctcagcca | ggaccggctg | gacgcgccgc | cgccgcccgc | 180 |
| tgcgccgctg | ccgcgctggt | ctggccccat | cggggtgagc | tggggggctgc | gggcggccgc | 240 |
| agccgggggc | gcgtttcccc | gcggcggccg | ttggcgtcgc | agcgcgccgg | gcgaggacga | 300 |
| ggagtgcggc | cgggtccggg | acttcgtcgc | caagctggcc | aacaacacgc | accagcatgt | 360 |
| gtttgatgat | ctcagaggct | cagtatcctt | gtcctgggtt | ggagatagca | ctggggtcat | 420 |
| tctagtcttg | actaccttcc | atgtaccact | ggtaattatg | actttttggac | agtccaagct | 480 |
| atatcgaagt | gaggattatg | ggaagaactt | taaggatatt | acagatctca | tcaataacac | 540 |
| ctttattcgg | actgaatttg | gcatggctat | tggtcctgag | aactctggaa | aggtggtgtt | 600 |
| aacagcagag | gtgtctggag | gaagtcgtgg | aggaagaatc | ttcagatcat | cagattttgc | 660 |
| gaagaatttt | gtgcaaacag | atctccctt | tcatcctctc | actcagatga | tgtatagccc | 720 |
| tcagaattct | gattatcttt | tagctctcag | cactgaaaat | ggcctgtggg | tgtccaagaa | 780 |
| ttttgggggga | aaatgggaag | aaatccacaa | agcagtatgt | ttggccaaat | ggggatcaga | 840 |
| caacaccatc | ttctttacaa | cctatgcaaa | tggctcctgc | aaagctgacc | ttggggctct | 900 |
| ggaattatgg | agaacttcag | acttgggaaa | aagcttcaaa | actattggtg | tgaaaatcta | 960 |
| ctcatttggt | cttggggac | gtttccttt | tgcctctgtg | atggctgata | aggataccac | 1020 |
| aagaaggatc | cacgttttcaa | cagatcaagg | ggacacatgg | agcatggccc | agctcccctc | 1080 |
| cgtgggacag | gaacagttct | attctattct | ggcagcaaat | gatgacatgg | tattcatgca | 1140 |
| tgtagatgaa | cctggagaca | ctgggtttgg | cacaatcttt | acctcagatg | atcgaggcat | 1200 |
| tgtctattcc | aagtctttgg | accgacatct | ctacactacc | acaggcggag | agacggactt | 1260 |
| taccaacgtg | acctcctcc | gcggcgtcta | cataacaagc | gtgctctccg | aagataattc | 1320 |
| tatccagacc | atgatcactt | ttgaccaagg | aggaaggtgg | acgcacctga | ggaagcctga | 1380 |
| aaacagtgaa | tgtgatgcta | cagcaaaaaa | caagaatgag | tgcagccttc | atattcatgc | 1440 |
| ttcctacagc | atctcccaga | aactgaatgt | tccaatggcc | ccactctcag | agccgaatgc | 1500 |
| cgtaggcatt | gtcattgctc | atggtagcgt | ggggatgcc | atctcagtga | tggttccaga | 1560 |
| tgtgtacatc | tcagatgatg | ggggttactc | ctggacaaag | atgctggaag | acccccacta | 1620 |
| ttacaccatc | ctggattctg | gaggcatcat | tgtggccatt | gagcacagca | gccgtcctat | 1680 |
| caatgtgatt | aagttctcca | cagacgaagg | tcaatgctgg | caaacctaca | cgttcaccag | 1740 |
| ggacccatc | tatttcactg | gcctagcttc | agaacctgga | gctaggtcca | tgaatatcag | 1800 |
| catttggggc | ttcacagaat | cttttcctgac | cagccagtgg | gtctcctaca | ccattgattt | 1860 |
| taaagatatc | cttgaaagga | actgtgaaga | gaaggactat | accatatggc | tggcacactc | 1920 |
| cacagaccct | gaagattatg | aagatggctg | catttttgggc | tacaaagaac | agtttctgcg | 1980 |
| gctacgcaag | tcatccgtgt | gtcagaatgg | tcgagactac | gttgtgacca | gcagccctc | 2040 |
| catctgcctc | tgttcctgg | aggactttct | ctgtgatttt | ggctactacc | gtccagaaaa | 2100 |

-continued

```
tgactccaag tgtgtggaac agccagaact gaagggccac gacctggagt tttgtctgta    2160
cggaagagaa gaacacctaa caacaaatgg gtaccggaaa attccagggg acaaatgcca    2220 gggtgggta  aatccagttc gagaagtaaa agacttgaaa aagaaatgca caagcaactt    2280
tttgagtccg gaaaaacaga attccaagtc aaattctgtt ccaattatcc tggccatcgt    2340
gggattgatg ctggtcacag tcgtagcagg agtgctcatt gtgaagaaat atgtctgtgg    2400
gggaaggttc ctggtgcatc gatactctgt gctgcagcag catgcagagg ccaatggtgt    2460
ggatggtgtg gatgctttgg acacagcctc ccacactaat aaaagtggtt atcatgatga    2520
ctcagatgag gacctcttgg aatagctctt cagaggagct ggacccagca tggatggtgg    2580
aaccacagta cctcttacac tccctgtggc tccaacttca ggaaataaat ttcccattgc    2640
gagggaccca gctctgtttc tgctgcttcc atcaaagcca aaaggaccta cactaaagaa    2700
atgcagggtg ggggtgggga accctgagca cttttttaca attggctctg agaaaaaggg    2760
agacatttta aattctttaa cttcttattt ctcgtcctgt ctctttgcaa agtatgggct    2820
tttttgtttt tgttttttaa gggaaacgaa atggaattcg aagggacctt ttcactaacc    2880
ccacttctgt gtgttctgca tggcgcctgc cccagggcat ctgccaactc cagtatcagc    2940
tctcacagtg tacttggtac catccctggg ctctgctggc gagacgaaac agctgtagag    3000
atgaaaacag gctgcagagg ctggcacagc ctggccggct tttctccatc tgggacagt    3060 cctactccaa gaacactgca caccagctcc tcacacagat cccacttact cttttttttt    3120
ttttcagaga ccacagacca cagtgatttt tcttttcct tgtttaatta ggcaataccc    3180
ttgttaattg cccctttggca actaacttaa ccatgtgctt cccacacagt acatcaggaa    3240
aacttacagg gcaatatttt taacttgggg caggaagaag ggagcagcag agaattgact    3300
agatatagca cctattaaaa gagaactctt gcttcttctg agattttca agctgtgctt    3360 tgtgtgtgtg ccagtagact tacgcaagga cagggtacaa acttagctgg aagtctgccc    3420
aggctgaatg atctcttccc tagagttgat tgtcgggtac acagtgtgaa cccccgaaga    3480
cggaacctca cagtcttcca tgttcccttc ttaactgtcg tgtggctcgt tgctaaatca    3540
tgacaatggc tgcctatctg ctgcttctta ggttgctgtt gtacatggaa ccaggactag    3600
agattttttc agatttatag acttaaaaaa ttagaatttt attaccaggc tttccttctc    3660 acccctttt tctgactttg ccaagtaatt tgttgacacg aaaatttggg aggaaccaat    3720
tgaaaacaca cttccagtct agatgatgct ttgtgtgata cattaagttc ttattttgga    3780
ttaaaagaag ttttccattt gatacttctc taaattaaat aaattataga atgtagttgg    3840
gtggattttg gggtggccat atagtaatgg aaagctgcaa taattagttt taatacagct    3900
tgaatatttg ctatatagaa atatagtatg gaaagttttt ggtcttaatg tagctactgt    3960
gcgggtcaca gtttctccca atgattatga ctgggacatt ctttggtaga taccatttgc    4020
tactagttta ttttgtggct agaaagtcag ttttgtgtgt ttttttttt ttttatttga    4080 agtgccaaat taactttagt cagaatgtga gcagatggct aagttctctc ctccccagaa    4140
tggattaaca gctgcgtgga aagtggggga gagagtggat ggagactttt agagatgtta    4200
aaactgcagt agaatgaaat gagtcaggga gcttcagtta gaaaataaag ttgaggcagt    4260
ttttgtgaag ataatatggt tagggctgga gtgcactagt cttttgctt  attcattttg    4320 catggtttta aaattaaaaa taattccgaa gatacaccag ctcacaaatg aaaacgtcag    4380
cctctgcccc accctccctc ctgcccaaag tgaatttggt actcagaaaa gaactgttta    4440
taccactcac ctttctccca gcatgtactc actgtgggca gatgcaccaa tacatggtaa    4500
```

```
tcctcttact cattttaaga cgtaggaaac tcaatattct tctctaacca tatacgatag    4560
ggctcttcgc ttttaatgat atctgggatt tctgtggaac ttggcaaatt ttcagagcac    4620
cttcactcac ataatgtcat ttgaacctca caatgttctt gggatggagt cagttgttca    4680
gggtccccgt gtgtgtgata agcagtgctg gctggctgtc ttcagaactc ttggaaatct    4740
ttacacatgc gagtgctaac cactttgagc aaggctgcct tcttgtagat gacttgctgt    4800
tctttatgac agggatcagt ggcatttgtt tcctagcagt atttagcacc tttttgccac    4860
cttggtgaac agaaaattgt attttcctgt ctttcatggc tgaaaacaaa agtaatggga    4920
attttaaata cgtttgcaga aactgcccct cccctcattg agggtcactg ctcaagagtg    4980
caggagtgga ctctccactg atgggtctcc ctccccatcc tggtttccac cccgggctgg    5040
ctagctctgt tggtttgaag actgacagcc agcctggctc attctcatta ttggctagtt    5100
agctttcttt atcaacctgc tcactcacaa atgtgtgccc tcagccagag agtaagaaag    5160
cccaaatctg ttacagcttc taaaaaaata gatttctaat ttgtcctact catgttagga    5220
gcattatctt tgaaggtaaa acatagtgta tcattgtgta aactcccagg cttgatgtag    5280
cagaagagat catttctgga ggcttcagca atggaattta gcattataag agagattgga    5340
caaaccagtc caaagtggtc cgagttctta aatccaggta gggaactcac tcttctttct    5400
tctctggacc taattgggca ttgggcttta gtgagaccac agaccaggcc cgtctctcct    5460
gtaggctttt aattcaatgg caactctatt tcaaagaata aaagcctttg agagttgcg    5520 gcagttctgg gggcgggctc aggagagtcc atagatcagc cgtaactgga acgtagaatc    5580
tacgtctgcc tctgaatgga cttcccacct cctctctctt gctctgatgc ttgcctctgg    5640
gcctctccat gcccaaggtg gtctttcatc cttgacaggc tggtaatgtg ctggccacct    5700
ccagctcctg catcgagtct gtaaaccaga gctggttctc atggccttcg tcacgatacc    5760
aggatacgga ggggagccca gggccatcca tacccacccc agggtaacgg ggctggcctg    5820
gcattagtca ttatttagtt tccaggccaa ccatccagat agagattccc tctttccttt    5880
gagcagtgct ctcaagagct ccgtgcctgt ccacaatgac ctagagtgca tcctgctcat    5940
tgtcagtgta gcccctcgcc cctatattca tccaggatac ttggaagtgc taaaatagga    6000
agggattcgg ctttcaactt tgctaccatc ttccctgaag caggaaaatg aacatggact    6060
taaatgttct ttgaaaaaac caaagtttta agatttgctg tgtgatgaag tgacagggag    6120
ggccggagtc agcaggtgcc agactttctg ttctgtctgc catgggtttg tccagctcag    6180
gtagctctag gagcaccatc ctgccctagc agagcccagg ccttgccctc atgaagcatc    6240
attgaaatag caggagcatg ttgatttctt ggttaggttg cattataata acaagagtca    6300
gaacattaat tcgaaacaac ttgcagtatg catttcttca caccagtaca ttcttaagtg    6360
tacttgttta taaggaataa cataaactaa tctgtaccctt tatatatatg tgtgtgtaca    6420
tatatacata tataaactgt atagtgtaca tggtaatgat ttattgctat gccccagatc    6480
cttaatgtag ttctcatcct ccgcatgccc tcagccacaa gcgggtgact gactgttccc    6540
tgatgatttg gcccacctcc tgtgtttgga cctctaggga ggagggtttt ggtcatactc    6600
tccttatcct cgtgcacaga aatgctcagg gtccccatgt gcctgttgtt cagccctctc    6660
tcttgttccc tttctgagca tgtggtcctt cccaggctg tgggacagct gccttcccac    6720
gaaagtgtaa agcagtatta agatcattac tgcatgtgcc ctaaaaaccc aagtttcta    6780 ttcccttagg acagaaaatt gcatgtgagg tgggataatc gagtttcagt gacccacgtc    6840
```

```
agttacacat taaagccaga ccccatgata aaattccaca aaatggaaat aaaactcaaa    6900
tttctttagc attgtgtaaa taaatctgaa tgtgtttaac tttgtactgg taattttctg    6960
tatatttgga atatttgggt taaaaataaa acagactgga ctttgttacc tgacctac     7018
```

<210> SEQ ID NO 14
<211> LENGTH: 1749
<212> TYPE: DNA
<213> ORGANISM: Homo sapiens
<220> FEATURE:
<223> OTHER INFORMATION: DPT glucocorticoid receptor-responsive gene

<400> SEQUENCE: 14

```
gtgacattgt ttgccaaaat cccaggcagc atggacctca gtcttctctg ggtacttctg      60
cccctagtca ccatggcctg gggccagtat ggcgattatg gatacccata ccagcagtat     120
catgactaca gcgatgatgg gtgggtgaat ttgaaccggc aaggcttcag ctaccagtgt     180
ccccaggggc aggtgatagt ggccgtgagg agcatcttca gcaagaagga aggttctgac     240
agacaatgga actacgcctg catgcccacg ccacagagcc tcggggaacc cacggagtgc     300
tggtgggagg agatcaacag ggctggcatg aatggtacc agacgtgctc caacaatggg      360
ctggtggcag gattccagag ccgctacttc gagtcagtgc tggatcggga gtggcagttt     420
tactgttgtc gctacagcaa gaggtgccca tattcctgct ggctaacaac agaatatcca     480
ggtcactatg tgaggaaat ggacatgatt cctacaatt atgattacta tatccgagga      540
gcaacaacca ctttctctgc agtggaaagg gatcgccagt ggaagttcat aatgtgccgg     600
atgactgaat acgactgtga atttgcaaat gtttagattt gccacatacc aaatctgggt     660
gaaaggaaag gggccgggga caggagggtg tccacatatg ttaacatcag ttggatctcc     720
tatagaagtt tctgctgctc tcttttcttc tccctgagct ggtaactgca atgccaactt     780
cctgggcctt tctgactagt atcacacttc taataaaatc cacaattaaa ccatgtttct     840
cacttttcac atgtttcata gcaactgctt tatatgactg atgatggctt ccttgcacac     900
cacatataca gtgcgcatgc ttacagccgg gcttctggag caccagctgc agcctggcta     960
ctgcttttta ctgcagaatg aactgcaagt tcagcatagt ggaggggaga ggcagaactg    1020
gaggagaggt gcagtgaagg ttctctacag ctaagcctgt ttgaatgata cgtaggttcc    1080
ccaccaaaag caggctttct gccctgaggg acatcttccc actcccctgc tccacatgag    1140
ccatgcatgc ttagcaatcc aagtgcagag ctctttgctc caggagtgag gagactggga    1200
ggtgaaatgg ggaaatggaa gggttttggag gcagagctga aaacagggtt ggaaggattt    1260
cctgaattag aagacaaacg ttagcatacc cagtaaggaa aatgagtgca ggggccaggg    1320
gaacccgtga ggatcactct caaatgagat taaaaacaag gaagcagaga atggtcagag    1380
aatgggattc agattgggaa cttgtgggga tgagagtgac caggttgaac tgggaagtgg    1440
aaaaaggagt ttgagtcact ggcacctaga agcctgccca cgattcctag gaaggctggc    1500
agacaccctg gaaccctggg gagctactgg caaactctcc tggattgggc ctgattttt    1560 tggtgggaaa ggctgccctg gggatcaact ttccttctgt gtgtggctca ggagttcttc    1620
tgcagagatg gcgctatctt tcctcctcct gtgatgtcct gctcccaacc atttgtactc    1680
ttcattacaa aagaaataaa aatattaacg ttcactatgc tgaaaataaa aaaaaaaaaa    1740
aaaaaaaaaa                                                           1749
```

<210> SEQ ID NO 15
<211> LENGTH: 2478

<212> TYPE: DNA
<213> ORGANISM: Homo sapiens
<220> FEATURE:
<223> OTHER INFORMATION: NRP1 glucocorticoid receptor-responsive gene

<400> SEQUENCE: 15

| | | | | |
|---|---|---|---|---|
| gcagttggtg | aaactcctct | gtctcccgct | catcttttca | ttgctcgttc | ccctccttcc | 60 |
| cgcagacacc | cggacctccc | ctgggcgcca | gctccgcggc | tccaacgggt | ccagaaacaa | 120 |
| gccggatttt | ttttttttct | tcctggaaat | tggctttggt | gtgtgttgcc | ctacctccct | 180 |
| cctcccctc | ccacccacag | ccccccccg | gccttttttt | tttttttttt | ttttttgag | 240 |
| acatggcccg | ggcagtggct | cctggaagag | gaacaagtgt | gggaaaaggg | agaggaagcc | 300 |
| ggagctaaat | gacaggatgc | aggcgacttg | agacacaaaa | agagaagcgt | tcctctcgga | 360 |
| tccaggcatt | gcctcgctgc | tttcttttct | ccaagacggg | ctgaggattg | tacagctcta | 420 |
| ggcggagttg | gggctcttcg | gatcgcttag | attctcctct | ttgctgcatt | tcccccacg | 480 |
| tcctcgttct | cccgcgtctg | cctgcggacc | cggagaaggg | agaatggaga | ggggctgcc | 540 |
| gctcctctgc | gccgtgctcg | ccctcgtcct | cgcccggcc | ggcgcttttc | gcaacgataa | 600 |
| atgtggcgat | actataaaaa | ttgaaagccc | cgggtacctt | acatctcctg | gttatcctca | 660 |
| ttcttatcac | ccaagtgaaa | aatgcgaatg | gctgattcag | gctccggacc | ataccagag | 720 |
| aattatgatc | aacttcaacc | ctcacttcga | tttggaggac | agagactgca | agtatgacta | 780 |
| cgtggaagtc | ttcgatggag | aaaatgaaaa | tggacatttt | aggggaaagt | tctgtggaaa | 840 |
| gatagcccct | cctcctgttg | tgtcttcagg | gccatttctt | tttatcaaat | ttgtctctga | 900 |
| ctacgaaaca | catggtgcag | gattttccat | acgttatgaa | attttcaaga | gaggtcctga | 960 |
| atgttcccag | aactacacaa | cacctagtgg | agtgataaag | tccccggat | tccctgaaaa | 1020 |
| atatcccaac | agccttgaat | gcacttatat | tgtctttgcg | ccaaagatgt | cagagattat | 1080 |
| cctggaattt | gaaagctttg | acctggagcc | tgactcaaat | cctccagggg | ggatgttctg | 1140 |
| tcgctacgac | cggctagaaa | tctgggatgg | attccctgat | gttggccctc | acattgggcg | 1200 |
| ttactgtgga | cagaaaacac | caggtcgaat | ccgatcctca | tcgggcattc | tctccatggt | 1260 |
| tttttacacc | gacagcgcga | tagcaaaaga | aggtttctca | gcaaactaca | gtgtcttgca | 1320 |
| gagcagtgtc | tcagaagatt | tcaaatgtat | ggaagctctg | ggcatggaat | caggagaaat | 1380 |
| tcattctgac | cagatcacag | cttcttccca | gtatagcacc | aactggtctg | cagagcgctc | 1440 |
| ccgcctgaac | taccctgaga | atgggtggac | tcccggagag | gattcctacc | gagagtggat | 1500 |
| acaggtagac | ttgggccttc | tgcgctttgt | cacggctgtc | gggacacagg | gcgccatttc | 1560 |
| aaaagaaacc | aagaagaaat | attatgtcaa | gacttacaag | atcgacgtta | gctccaacgg | 1620 |
| ggaagactgg | atcaccataa | agaaggaaa | caaacctgtt | ctctttcagg | gaaacaccaa | 1680 |
| ccccacagat | gttgtggttg | cagtattccc | caaaccactg | ataactcgat | tgtccgaat | 1740 |
| caagcctgca | acttgggaaa | ctggcatatc | tatgagattt | gaagtatacg | gttgcaagat | 1800 |
| aacagattat | ccttgctctg | gaatgttggg | tatggtgtct | ggacttattt | ctgactccca | 1860 |
| gatcacatca | tccaaccaag | gggacagaaa | ctggatgcct | gaaaacatcc | gcctggtaac | 1920 |
| cagtcgctct | ggctgggcac | ttccacccgc | acctcattcc | tacatcaatg | agtggctcca | 1980 |
| aatagacctg | ggggaggaga | agatcgtgag | gggcatcatc | attcagggtg | gaagcaccg | 2040 |
| agagaacaag | gtgttcatga | ggaagttcaa | gatcgggtac | agcaacaacg | gctcggactg | 2100 |
| gaagatgatc | atggatgaca | gcaaacgcaa | ggcgaagtct | tttgagggca | acaacaacta | 2160 |

-continued

```
tgatacacct gagctgcgga cttttccagc tctctccacg cgattcatca ggatctaccc      2220
cgagagagcc actcatggcg gactggggct cagaatggag ctgctgggct gtgaagtgga      2280
agcccctaca gctggaccga ccactcccaa cgggaacttg gtggatgaat gtgatgacga      2340
ccaggccaac tgccacagtg gaacaggtga tgacttccag ctcacaggtg gcaccactgt      2400
gctggccaca gaaaagccca cggtcataga cagcaccata caatcaggta tcaaataaaa      2460
tacgaaatgt gacagatt                                                    2478
```

<210> SEQ ID NO 16
<211> LENGTH: 3372
<212> TYPE: DNA
<213> ORGANISM: Homo sapiens
<220> FEATURE:
<223> OTHER INFORMATION: ACSL5 glucocorticoid receptor-responsive gene

<400> SEQUENCE: 16

```
taaaaccagg aagtgaagtc cccgagcacg ttagaaagcc tgacatggcc tgactcggga        60
cagctcagag cagggcagaa ctggggacac tctgggccgg ccttctgcct gcatggacgc       120
tctgaagcca ccctgtctct ggaggaacca cgagcgaggg aagaaggaca gggactcgtg       180
tggcaggaag aactcagagc cgggaagccc ccattcacta gaagcactga gagatgcggc       240
cccctcgcag ggtctgaatt tcctgctgct gttcacaaag atgcttttta tctttaactt       300
tttgttttcc ccacttccga ccccggcgtt gatctgcatc ctgacatttg gagctgccat       360
cttcttgtgg ctgatcacca gacctcaacc cgtcttacct cttcttgacc tgaacaatca       420
gtctgtggga attgagggag gagcacggaa gggggtttcc cagaagaaca atgacctaac       480
aagttgctgc ttctcagatg ccaagactat gtatgaggtt ttccaaagag gactcgctgt       540
gtctgacaat gggccctgct gggatatag aaaaccaaac cagccctaca gatggctatc       600
ttacaaacag gtgtctgata gagcagagta cctgggttcc tgtctcttgc ataaaggtta       660
taaatcatca ccagaccagt tgtcggcat cttttgctcag aataggccag agtggatcat      720
ctccgaattg gcttgttaca cgtactctat ggtagctgta cctctgtatg acaccttggg       780
accagaagcc atcgtacata ttgtcaacaa ggctgatatc gccatggtga tctgtgacac       840
accccaaaag gcattggtgc tgatagggaa tgtagagaaa ggcttcaccc cgagcctgaa       900
ggtgatcatc cttatggacc cctttgatga tgacctgaag caaagagggg agaagagtgg       960
aattgagatc ttatccctat atgatgctga gaacctaggc aaagagcact tcagaaaacc      1020
tgtgcctcct agcccagaag acctgagcgt catctgcttc accagtggga ccacaggtga      1080
ccccaaagga gccatgataa cccatcaaaa tattgtttca aatgctgctg cctttctcaa      1140
atgtgtggag catgcttatg agcccactcc tgatgatgtg ccatatcct acctccctct       1200 ggctcatatg tttgagagga ttgtacaggc tgttgtgtac agctgtggag ccagagttgg      1260
attcttccaa ggggatattc ggttgctggc tgacgacatg aagactttga agccacatt      1320 gtttcccgcg gtgcctcgac tccttaacag gatctacgat aaggtacaaa atgaggccaa      1380
gacacccttg aagaagttct tgttgaagct ggctgttttcc agtaaattca agagcttca       1440 aaagggtatc atcaggcatg atagtttctg ggacaagctc atctttgcaa agatccagga      1500
cagcctgggc ggaagggttc gtgtaattgt cactggagct gccccccatgt ccacttcagt    1560 catgacattc ttccgggcag caatgggatg tcaggtgtat gaagcttatg gtcaaacaga     1620
atgcacaggt ggctgtacat ttacattacc tgggactgg acatcaggtc acgttgggt     1680 gccctggct tgcaattacg tgaagctgga agatgtggct gacatgaact actttacagt      1740
```

```
gaataatgaa ggagaggtct gcatcaaggg tacaaacgtg ttcaaaggat acctgaagga   1800
ccctgagaag acacaggaag ccctggacag tgatggctgg cttcacacag agacattgg    1860 tcgctggctc ccgaatggaa ctctgaagat catcgaccgt aaaaagaaca ttttcaagct   1920
ggcccaagga gaatacattg caccagagaa gatagaaaat atctacaaca ggagtcaacc   1980
agtgttacaa attttgtac acggggagag cttacggtca tccttagtag gagtggtggt    2040
tcctgacaca gatgtacttc cctcatttgc agccaagctt ggggtgaagg gctcctttga   2100
ggaactgtgc caaaaccaag ttgtaaggga agccatttta gaagacttgc agaaaattgg   2160
gaaagaaagt ggcctttaaaa cttttgaaca ggtcaaagcc attttcttc atccagagcc    2220 attttccatt gaaaatgggc tcttgacacc aacattgaaa gcaaagcgag gagagctttc   2280
caaatacttt cggacccaaa ttgacagcct gtatgagcac atccaggatt aggataaggt   2340
acttaagtac ctgccggccc actgtgcact gcttgtgaga aaatggatta aaaactattc   2400
ttacatttgt tttgcctttc tcctattttt ttttaacct gttaaactct aaagccatag     2460
cttttgtttt atattgagac ataatgtg taaacttagt tcccaaataa atcaatcctg      2520
tctttcccat cttcgatgtt gctaatatta aggcttcagg gctactttta tcaacatgcc    2580
tgtcttcaag atcccagttt atgttctgtg tccttcctca tgatttccaa ccttaatact    2640
attagtaacc acaagttcaa gggtcaaagg gaccctctgt gccttcttct ttgttttgtg   2700
ataaacataa cttgccaaca gtctctatgc ttatttacat cttctactgt tcaaactaag   2760
agatttttaa attctgaaaa actgcttaca attcatgttt tctagccact ccacaaacca   2820
ctaaaatttt agttttagcc tatcactcat gtcaatcata tctatgagac aaatgtctcc   2880
gatgctcttc tgcgtaaatt aaattgtgta ctgaagggaa aagtttgatc ataccaaaca   2940
tttcctaaac tctctagtta gatatctgac ttgggagtat taaaaattgg gtctatgaca   3000
tattgtccaa aaggaatgct gttcttaaag cattatttac agtaggaact ggggagtaaa   3060
tctgttccct acagtttgct gctgagctgg aagctgtggg ggaaggagtt gacaggtggg   3120
cccagtgaac ttttccagta aatgaagcaa gcactgaata aaaacctcct gaactgggaa   3180
caaagatcta caggcaagca agatgcccac acaacaggct tatttctgt gaaggaacca    3240 actgatctcc cccaccccttg gattagagtt cctgctctac cttacccaca gataacacat   3300
gttgtttcta cttgtaaatg taaagtcttt aaaataaact attacagata cttaaaaaaa   3360 aaaaaaaaa aa                                                         3372
```

<210> SEQ ID NO 17
<211> LENGTH: 5243
<212> TYPE: DNA
<213> ORGANISM: Homo sapiens
<220> FEATURE:
<223> OTHER INFORMATION: BICR3 glucocorticoid receptor-responsive gene

<400> SEQUENCE: 17

```
agcgtgagac tcgcgccctc cggcacggaa aaggccaggc gacaggtgtc gcttgaaaag   60
actgggcttg tccttgctgg tgcatgcgtc gtcggcctct gggcagcagg tttacaaagg   120
aggaaaacga cttcttctag attttttttt cagtttcttc tataaatcaa acatctcaa    180 aatggagacc taaaatcctt aaagggactt agtctaatct cgggaggtag ttttgtgcat   240
gggtaaacaa attaagtatt aactggtgtt ttactatcca aagaatgcta atttttataaa  300 catgatcgag ttatataagg tataccataa tgagtttgat tttgaatttg atttgtggaa   360
```

```
ataaaggaaa agtgattcta gctggggcat attgttaaag cattttttc agagttggcc      420 aggcagtctc ctactggcac attctcccat tatgtagaat agaaatagta cctgtgtttg     480
ggaaagattt taaaatgagt gacagttatt tggaacaaag agctaataat caatccactg     540
caaattaaag aaacatgcag atgaaagttt tgacacatta aaatacttct acagtgacaa     600
agaaaaatca agaacaaagc ttttgatat gtgcaacaaa tttagaggaa gtaaaaagat      660
aaatgtgatg attggtcaag aaattatcca gttatttaca aggccactga tattttaaac    720
gtccaaaagt ttgtttaaat gggctgttac cgctgagaat gatgaggatg agaatgatgg    780
ttgaaggtta cattttagga aatgaagaaa cttagaaaat taatataaag acagtgatga    840
atacaaagaa gattttata caatgtgta aaattttggg ccagggaaag gaatattgaa      900
gttagataca attacttacc tttgagggaa ataattgttg gtaatgagat gtgatgtttc    960
tcctgccacc tggaaacaaa gcattgaagt ctgcagttga aaagcccaac gtctgtgaga   1020
tccaggaaac catgcttgca aaccactggt aaaaaaaaaa aaaaaaaaaa aaaaagcca    1080 cagtgacttg cttattggtc attgctagta ttatcgactc agaacctctt tactaatggc   1140
tagtaaatca taattgagaa attctgaatt ttgacaaggt ctctgctgtt gaaatggtaa   1200
atttattatt ttttttgtca tgataaattc tggttcaagg tatgctatcc atgaaataat   1260
ttctgaccaa aactaaattg atgcaatttg attatccatc ttagcctaca gatggcatct   1320
ggtaactttt gactgtttta aaaataaat ccactatcag agtagatttg atgttggctt    1380
cagaaacatt tagaaaaaca aaagttcaaa aatgttttca ggaggtgata agttgaataa   1440
ctctacaatg ttagttcttt gaggggaca aaaaatttaa aatctttgaa aggtcttatt    1500
ttacagccat atctaaatta tcttaagaaa attttttaaca aagggaatga aatatatatc   1560
atgattctgt ttttccaaaa gtaacctgaa tatagcaatg aagttcagtt ttgttattgg   1620
tagtttgggc agagtctctt tttgcagcac ctgttgtcta ccataattac agaggacatt   1680
tccatgttct agccaagtat actattagaa taaaaaaact taacattgag ttgcttcaac   1740
agcatgaaac tgagtccaaa agaccaaatg aacaaacaca ttaatctctg attatttatt   1800
ttaaatagaa tatttaattg tgtaagatct aatagtatca ttatacttaa gcaatcatat   1860
tcctgatgat ctatgggaaa taactattat ttaattaata ttgaaaccag gttttaagat   1920
gtgttagcca gtcctgttac tagtaaatct ctttatttgg agagaaattt tagattgttt   1980
tgttctcctt attagaagga ttgtagaaag aaaaaaatga ctaattggag aaaaattggg   2040
gatatatcat atttcactga attcaaaatg tcttcagttg taaatcttac cattatttta   2100
cgtacctcta agaaataaaa gtgcttctaa ttaaaatatg atgtcattaa ttatgaaata   2160
cttcttgata acagaagttt taaaatagcc atcttagaat cagtgaaata tggtaatgta   2220 ttatttttcct cctttgagtt aggtcttgtg cttttttttc ctggccacta aatttcacaa   2280
tttccaaaaa gcaaataaa catattctga atattttgc tgtgaaacac ttgacagcag    2340
agctttccac catgaaaaga agcttcatga gtcacacatt acatctttgg gttgattgaa   2400
tgccactgaa acattctagt agcctggaga agttgaccta cctgtggaga tgcctgccat   2460
taaatggcat cctgatggct aatacacat cactcttctg tgaagggttt taattttcaa    2520
cacagcttac tctgtagcat catgtttaca ttgtatgtat aaagattata caaggtgca    2580 attgtgtatt tcttccttaa aatgtatcag tataggattt agaatctcca tgttgaaact   2640
ctaaatgcat agaaataaaa ataataaaaa attttcatt ttggcttttc agcctagtat    2700
taaaactgat aaaagcaaag ccatgcacaa aactacctcc ctagagaaag gctagtccct   2760
```

| | |
|---|---|
| tttcttcccc attcatttca ttatgaacat agtagaaaac agcatattct tatcaaattt | 2820 |
| gatgaaaagc gccaacacgt ttgaactgaa atacgacttg tcatgtgaac tgtaccgaat | 2880 |
| gtctacgtat tccactttc ctgctggggt tcctgtctca gaaaggagtc ttgctcgtgc | 2940 |
| tggtttctat tacactggtg tgaatgacaa ggtcaaatgc ttctgttgtg gcctgatgct | 3000 |
| ggataactgg aaaagaggag acagtcctac tgaaaagcat aaaaagttgt atcctagctg | 3060 |
| cagattcgtt cagagtctaa attccgttaa caacttggaa gctacctctc agcctacttt | 3120 |
| tccttcttca gtaacaaatt ccacacactc attacttccg ggtacagaaa acagtggata | 3180 |
| tttccgtggc tcttattcaa actctccatc aaatcctgta aactccagag caaatcaaga | 3240 |
| tttttctgcc ttgatgagaa gttcctacca ctgtgcaatg aataacgaaa atgccagatt | 3300 |
| acttactttt cagacatggc cattgacttt tctgtcgcca acagatctgg caaaagcagg | 3360 |
| cttttactac ataggacctg agacagagt ggcttgcttt gcctgtggtg gaaaattgag | 3420 |
| caattgggaa ccgaaggata atgctatgtc agaacacctg agacattttc ccaaatgccc | 3480 |
| atttatagaa aatcagcttc aagacacttc aagatacaca gtttctaatc tgagcatgca | 3540 |
| gacacatgca gcccgctta aaacattctt taactggccc tctagtgttc tagttaatcc | 3600 |
| tgagcagctt gcaagtgcgg gttttttatta tgtgggtaac agtgatgatg tcaaatgctt | 3660 |
| ttgctgtgat ggtggactca ggtgttggga atctggagat gatccatggg ttcaacatgc | 3720 |
| caagtggttt ccaaggtgtg agtacttgat aagaattaaa ggacaggagt tcatccgtca | 3780 |
| agttcaagcc agttaccctc atctacttga acagctgcta tccacatcag acagcccagg | 3840 |
| agatgaaaat gcagagtcat caattatcca ttttgaacct ggagaagacc attcagaaga | 3900 |
| tgcaatcatg atgaatactc ctgtgattaa tgctgccgtg gaaatgggct ttagtagaag | 3960 |
| cctggtaaaa cagacagttc agagaaaaat cctagcaact ggagagaatt atagactagt | 4020 |
| caatgatctt gtgttagact tactcaatgc agaagatgaa ataagggaag aggagagaga | 4080 |
| aagagcaact gaggaaaaag aatcaaatga tttattatta atccggaaga atagaatggc | 4140 |
| acttttttcaa catttgactt gtgtaattcc aatcctggat agtctactaa ctgccggaat | 4200 |
| tattaatgaa caagaacatg atgttattaa acagaagaca cagacgtctt tacaagcaag | 4260 |
| agaactgatt gatacgattt tagtaaaagg aaatattgca gccactgtat tcagaaactc | 4320 |
| tctgcaagaa gctgaagctg tgttatatga gcatttattt gtgcaacagg acataaaata | 4380 |
| tattcccaca gaagatgttt cagatctacc agtggaagaa caattgcgga gactacaaga | 4440 |
| agaaagaaca tgtaaagtgt gtatggacaa agaagtgtcc atagtgttta ttccttgtgg | 4500 |
| tcatctagta gtatgcaaag attgtgctcc ttctttaaga agtgtcctta tttgtaggag | 4560 |
| tacaatcaag ggtacagttc gtacatttct ttcatgaaga agaaccaaaa catcgtctaa | 4620 |
| actttagaat taatttatta aatgtattat aactttaact tttatcctaa tttggtttcc | 4680 |
| ttaaaatttt tatttattta caactcaaaa acattgttt tgtgtaacat atttatatat | 4740 |
| gtatctaaac catatgaaca tatatttttt agaaactaag agaatgatag cttttgttc | 4800 |
| ttatgaacga aaagaggta gcactacaaa cacaatattc aatcaaaatt tcagcattat | 4860 |
| tgaaattgta agtgaagtaa aacttaagat atttgagtta accttaaaga atttaaata | 4920 |
| ttttggcatt gtactaatac cgggaacatg aagccaggtg tggtggtatg tgcctgtagt | 4980 |
| cccaggctga ggcaagagaa ttacttgagc ccaggagttt gaatccatcc tgggcagcat | 5040 |
| actgagaccc tgcctttaaa aacaaacaga acaaaaacaa aacaccaggg acacatttct | 5100 | ctgtcttttt tgatcagtgt cctatacatc gaaggtgtgc atatatgttg aatgacattt     5160 tagggacatg gtgtttttat aaagaattct gtgagaaaaa atttaataaa gcaacaaaaa     5220 ttactcttaa aaaaaaaaaa aaa                                             5243

<210> SEQ ID NO 18
<211> LENGTH: 1579
<212> TYPE: DNA
<213> ORGANISM: Homo sapiens
<220> FEATURE:
<223> OTHER INFORMATION: NNMT glucocorticoid receptor-responsive gene

<400> SEQUENCE: 18
gaggaggtgc ttgccagaca ctgggtcatg gcagtggtcg gtgaagctgc agttgcctag       60 ggcaggatg gagagagagt ctgggcatga ggagagggtc tcgggatgtt tggctggact      120
agattttaca gaaagcctta tccaggcttt taaaattact ctttccagac ttcatctgag      180
actccttctt cagccaacat tccttagccc tgaatacatt tcctatcctc atctttccct      240 tcttttttt cctttctttt acatgtttaa atttaaacca ttcttcgtga cccctttttct     300 tgggagattc atggcaagaa cgagaagaat gatggtgctt gttaggggat gtcctgtctc      360
tctgaacttt ggggtcctat gcattaaata attttcctga cgagctcaag tgctccctct      420
ggtctacaat ccctggcggc tggccttcat cccttgggca agcattgcat acagctcatg      480
gccctccctc taccataccc tccaccccg ttcgcctaag ctcccttctc cgggaatttc      540
atcatttcct agaacagcca gaacatttgt ggtctatttc tctgttagtg tttaaccaac      600
catctgttct aaaagaaggg ctgaactgat ggaaggaatg ctgttagcct gagactcagg      660
aagacaactt ctgcagggtc actccctggc ttctggagga aagagaagga gggcagtgct      720
ccagtggtac agaagtgaga cataatggaa tcaggcttca cctccaagga cacctatcta      780
agccatttta accctcggga ttacctagaa aaatattaca agtttggttc taggcactct      840
gcagaaagcc agattcttaa gcaccttctg aaaaatcttt tcaagatatt ctgcctagac      900
ggtgtgaagg gagacctgct gattgacatc ggctctggcc ccactatcta tcagctcctc      960
tctgcttgtg aatcctttaa ggagatcgtc gtcactgact actcagacca gaacctgcag     1020
gagctggaga agtggctgaa gaaagagcca gaggcctttg actggtcccc agtggtgacc     1080
tatgtgtgtg atcttgaagg gaacagagtc aagggtccag agaaggagga gaagttgaga     1140
caggcggtca agcaggtgct gaagtgtgat gtgactcaga gccagccact gggggccgtc     1200
cccttacccc cggctgactg cgtgctcagc acactgtgtc tggatgccgc ctgcccagac     1260
ctccccacct actgcagggc gctcaggaac ctcggcagcc tactgaagcc aggggcttc      1320 ctggtgatca tggatgcgct caagagcagc tactacatga ttggtgagca gaagttctcc     1380
agcctccccc tgggccggga ggcagtagag gctgctgtga agaggctgg ctacacaatc      1440 gaatggtttg aggtgatctc gcaaagttat tcttccacca tggccaacaa cgaaggactt     1500 ttctcccctgg tggcgaggaa gctgagcaga cccctgtgat gcctgtgacc tcaattaaag     1560
caattccttt gacctgtca                                                  1579

<210> SEQ ID NO 19
<211> LENGTH: 980
<212> TYPE: DNA
<213> ORGANISM: Homo sapiens
<220> FEATURE:
<223> OTHER INFORMATION: IGFBP6 glucocorticoid receptor-responsive gene

<400> SEQUENCE: 19

```
gcggcggcgg gcagcagctg cgctgcgact gctctggaag gagaggacgg ggcacaaacc      60
ctgaccatga ccccccacag gctgctgcca ccgctgctgc tgctgctagc tctgctgctc     120
gctgccagcc caggaggcgc cttggcgcgg tgcccaggct gcgggcaagg ggtgcaggcg     180
ggttgtccag ggggctgcgt ggaggaggag gatgggggt cgccagccga gggctgcgcg      240
gaagctgagg gctgtctcag gagggagggg caggagtgcg gggtctacac ccctaactgc     300
gccccaggac tgcagtgcca tccgcccaag gacgacgagg cgcctttgcg ggcgctgctg     360
ctcggccgag gccgctgcct tccggcccgc gcgcctgctg ttgcagagga gaatcctaag     420
gagagtaaac cccaagcagg cactgcccgc ccacaggatg tgaaccgcag agaccaacag     480
aggaatccag gcacctctac cacgccctcc cagcccaatt ctgcgggtgt ccaagacact     540
gagatgggcc catgccgtag acatctggac tcagtgctgc agcaactcca gactgaggtc     600
taccgagggg ctcaaacact ctacgtgccc aattgtgacc atcgaggctt ctaccggaag     660
cggcagtgcc gctcctccca ggggcagcgc cgaggtccct gctggtgtgt ggatcggatg     720
ggcaagtccc tgccagggtc tccagatggc aatggaagct cctcctgccc cactgggagt     780
agcggctaaa gctgggggat agaggggctg caggccact ggaaggaaca tggagctgtc      840
atcactcaac aaaaaaccga ggccctcaat ccaccttcag gccccgcccc atgggcccct    900
caccgctggt tggaaagagt gttggtgttg gctggggtgt caataaagct gtgcttgggg    960
tcgctgaaaa aaaaaaaaaa                                                 980

<210> SEQ ID NO 20
<211> LENGTH: 7346
<212> TYPE: DNA
<213> ORGANISM: Homo sapiens
<220> FEATURE:
<223> OTHER INFORMATION: PLXNC1 glucocorticoid receptor-responsive gene

<400> SEQUENCE: 20
gcgaggagga aacggtgccg gagcgcgcag ggcttgctgc cgccaccgcc gctgcacagg      60
ctgccggagc gagcctgccg cgcgccgccc tccccgctct ccttcctggg cgagctgcgg     120
ggatggggcg gccgcgggag cccgagcgcg cgcaggaacc gccgccgccg ccgcccgcgt     180
ctccgttgcc gcgcgcctga gccgccgtcg ccgccgcgcg ccctgcccgg ggcggcccc     240 cccagcccca tggaggtctc ccggaggaag gcgccgccgc gccccccgcg ccccgcagcg     300
ccactgcccc tgctcgccta tctgctggca ctggcggctc ccggccgggg cgcggacgag     360
cccgtgtggc ggtcggagca agccatcgga gccatcgcgg cgagccagga ggacggcgtg     420
tttgtggcga gcggcagctg cctggaccag ctggactaca gcctggagca cagcctctcg     480
cgcctgtacc gggaccaagc gggcaactgc acagagccgg tctcgctggc gcccccgcg     540 cggccccggc ccgggagcag cttcagcaag ctgctgctgc cctaccgcga ggggcggcc     600 ggcctcgggg gctgctgct caccggctgg accttcgacc ggggcgcctg cgaggtgcgg     660
cccctgggca acctgagccg caactccctg cgcaacggca ccgaggtggt gtcgtgccac     720
ccgcagggct cgacgccgg cgtggtgtac cgcgcgggcc ggaacaaccg ctggtacctg     780
gcggtggccg ccacctacgt gctgcctgag ccggagacgc cgagccgctg caaccccgcg     840
gcatccgacc acgacacggc catcgcgctc aaggacacgg aggggcgcag cctggccacg     900
caggagctgg ggcgcctcaa gctgtgcgag ggcgcgggca gcctgcactt cgtgacgcc      960 tttctctgga acggcagcat ctacttcccc tactaccccct acaactacac gagcggcgct    1020
```

```
gccaccggct ggcccagcat ggcgcgcatc gcgcagagca ccgaggtgct gttccagggc    1080
caggcatccc tcgactgcgg ccacggccac cccgacggcc gccgcctgct cctctcctcc    1140
agcctagtgg aggccctgga cgtctgggcg ggagtgttca gcgcggccgc tggagagggc    1200
caggagcggc gctcccccac caccacggcg ctctgcctct tcagaatgag tgagatccag    1260
gcgcgcgcca agagggtcag ctgggacttc aagacggccg agagccactg caaagaaggg    1320
gatcaacctg aaagagtcca accaatcgca tcatctacct tgatccattc cgacctgaca    1380
tccgtttatg gcaccgtggt aatgaacagg actgttttat tcttggggac tggagatggc    1440
cagttactta aggttattct tggtgagaat ttgacttcaa attgtccaga ggttatctat    1500
gaaattaaag aagagacacc tgttttctac aaactcgttc ctgatcctgt gaagaatatc    1560
tacatttatc taacagctgg gaaagaggtg aggagaattc gtgttgcaaa ctgcaataaa    1620
cataaatcct gttcggagtg tttaacagcc acagaccctc actgcggttg gtgccattcg    1680
ctacaaaggt gcactttttca aggagattgt gtacattcag agaacttaga aaactggctg    1740
gatatttcgt ctggagcaaa aaagtgccct aaaattcaga taattcgaag cagtaaagaa    1800
aagactacag tgactatggt gggaagcttc tctccaagac actcaaagtg catggtgaag    1860
aatgtggact ctagcaggga gctctgccag aataaaagtc agcccaaccg gacctgcacc    1920
tgtagcatcc caaccagagc aacctacaaa gatgtttcag ttgtcaacgt gatgttctcc    1980
ttcggttctt ggaattttatc agacagattc aactttacca actgctcatc attaaaagaa    2040
tgcccagcat gcgtagaaac tggctgcgcg tggtgtaaaa gtgcaagaag gtgtatccac    2100
cccttcacag cttgcgaccc ttctgattat gagagaaacc aggaacagtg tccagtggct    2160
gtcgagaaga catcaggagg aggaagaccc aaggagaaca aggggaacag aaccaaccag    2220
gctttacagg tcttctacat taagtccatt gagccacaga agtatcgac attagggaaa    2280 agcaacgtga tagtaacggg agcaaacttt acccgggcat cgaacatcac aatgatcctg    2340
aaaggaacca gtacctgtga taaggatgtg atacaggtta gccatgtgct aaatgacacc    2400
cacatgaaat tctctcttcc atcaagccgg aaagaaatga aggatgtgtg tatccagttt    2460
gatggtggga actgctcttc tgtgggatcc ttatcctaca ttgctctgcc acattgttcc    2520
cttatatttc ctgctaccac ctggatcagt ggtggtcaaa atataaccat gatgggcaga    2580
aattttgatg taattgacaa cttaatcatt tcacatgaat taaaaggaaa cataaatgtc    2640
tctgaatatt gtgtggcgac ttactgcggg ttttttagccc ccagtttaaa gagttcaaaa    2700
gtgcgcacga atgtcactgt gaagctgaga gtacaagaca cctacttgga ttgtggaacc    2760
ctgcagtatc gggaggaccc cagattcacg gggtatcggg tggaatccga ggtggacaca    2820
gaactggaag tgaaaattca aaagaaaat gacaacttca acatttccaa aaaagacatt    2880
gaaattactc tcttccatgg ggaaaatggg caattaaatt gcagttttga aaatattact    2940
agaaatcaag atcttaccac catcctttgc aaaattaaag gcatcaagac tgcaagcacc    3000
attgccaact cttctaagaa agttcgggtc aagctgggaa acctggagct ctacgtcgag    3060
caggagtcag ttccttccac atggtatttt ctgattgtgc tccctgtctt gctagtgatt    3120
gtcatttttg cggccgtggg ggtgaccagg cacaaatcga aggagctgag tcgcaaacag    3180
agtcaacaac tagaattgct ggaaagcgag ctccggaaag agatacgtga cggctttgct    3240
gagctgcaga tggataaatt ggatgtggtt gatagttttg gaactgttcc cttccttgac    3300
tacaaacatt ttgctctgag aactttcttc cctgagtcag gtggcttcac ccacatcttc    3360
actgaagata tgcataacag agacgccaac gacaagaatg aaagtctcac agctttggat    3420
```

```
gccctaatct gtaataaaag ctttcttgtt actgtcatcc acacccttga aaagcagaag    3480
aacttttctg tgaaggacag gtgtctgttt gcctccttcc taaccattgc actgcaaacc    3540
aagctggtct acctgaccag catcctagag gtgctgacca gggacttgat ggaacagtgt    3600
agtaacatgc agccgaaact catgctgaga cgcacggagt ccgtcgtcga aaactcctc    3660 acaaactgga tgtccgtctg cctttctgga tttctccggg agactgtcgg agagcccttc    3720
tatttgctgg tgacgactct gaaccagaaa attaacaagg gtcccgtgga tgtaatcact    3780
tgcaaagccc tgtacacact taatgaagac tggctgttgt ggcaggttcc ggaattcagt    3840
actgtggcat taaacgtcgt cttttgaaaaa atcccggaaa acgagagtgc agatgtctgt    3900
cggaatattt cagtcaatgt tctcgactgt gacaccattg ccaagccaa agaaaagatt    3960 ttccaagcat tcttaagcaa aaatggctct ccttatggac ttcagcttaa tgaaattggt    4020
cttgagcttc aaatgggcac acgacagaaa gaacttctgg acatcgacag ttcctccgtg    4080
attcttgaag atggaatcac caagctaaac accattggcc actatgagat atcaaatgga    4140
tccactataa aagtctttaa gaagatagca aattttactt cagatgtgga gtactcggat    4200
gaccactgcc atttgatttt accagattcg gaagcattcc aagatgtgca aggaaagaga    4260
catcgaggga agcacaagtt caaagtaaaa gaaatgtatc tgacaaagct gctgtcgacc    4320
aaggtggcaa ttcattctgt gcttgaaaaa cttttagaa gcatttggag tttacccaac    4380
agcagagctc catttgctat aaaatacttt tttgactttt tggacgccca ggctgaaaac    4440
aaaaaaatca cagatcctga cgtcgtacat atttggaaaa caaacagcct tcctcttcgc    4500
ttctgggtaa acatcctgaa gaaccctcag tttgtctttg acattaagaa gacaccacat    4560
atagacggct gtttgtcagt gattgcccag gcattcatgg atgcattttc tctcacagag    4620
cagcaactag ggaaggaagc accaactaat aagcttctct atgccaagga tatcccaacc    4680
tacaaagaag aagtaaaatc ttattacaaa gcaatcaggg atttgcctcc attgtcatcc    4740
tcagaaatgg aagaattttt aactcaggaa tctaagaaac atgaaaatga atttaatgaa    4800
gaagtggcct tgacagaaat ttacaaatac atcgtaaaat attttgatga gattctaaat    4860
aaactagaaa gagaacgagg gctggaagaa gctcagaaac aactcttgca tgtaaaagtc    4920
ttatttgatg aaaagaagaa atgcaagtgg atgtaagcac tctggggcct ggcttaatct    4980
ggcaaagttc ttcagacgac ttgggagcaa aatggctgct tgagctactc tgtgtcgtta    5040
atttgttgtt tgcacatagg ttccactttg ggcactgtct ttttaagaga ccaaggcaca    5100
tgcacagctt ttagaaagca taccaaccct tgtgcctgtg tgtataccgt gggaacccct    5160
ctgtaaatag agttgaagtg gttgttgcaa acagcctcct tgtttacaga gaatacaagg    5220
ccagtaagcg aatgtcagta ttgtaactac agtctccact taagcacaat gatataagtg    5280
gttttgtttg aaaactacag ctatgtagca cttgtgctac actgcacctc tgcattgtaa    5340
agggatactg ccagtgctca aaacaaaatg tgaaatgagt catttggaaa caaggtgggg    5400
gtgttagggc aacctcgagg atttgcagca ttgaaacttt ccccagtagt tcttggaaaa    5460
gctgaccgca gaatttggta gtgtacactt agcatttgtg agtgtgtgtg tgtgtttaaa    5520
ccaaaaacta acagtgttgc aacattgttg aaagggctcg tgttttcag tggtcatcaa    5580 ctgcactcca tcaaactcac ctccatttca ccaaggagct ctaaagtaag gagagtgggc    5640
tttatttaaa tgaacagcat tttaaccaga tactttgtcc taatgtatgt tcctttctt    5700 catctgtttt ttcatactaa atgtatttga tagtggacat gttggatatt atacaaaaaaa    5760
```

```
atcattaatt catttctgtt ccaaaacctt tgatcagaac gatctgtgga agagtaactc    5820
catttctata tgagtgagtg tctccttgct ttagatttct ggtgaaccct gtggttatga    5880
atacttgtgt gtgatttaaa aaaaaaaaga tacattttac atttcatcga attgctgttc    5940
acactggagt attatatata aatatatata tttgaggccc aaggcctgaa aaatattagt    6000
atacaacttg gtatcttagt cttactatgt acttttttgaa agtattcctc gcaggagaaa    6060
gaatttaaaa tacccatttt attcatgcct ttctttttaa agaattctct atccagttat    6120
actgtagtct ttttagtgct gatttttttaa ttcctgaatt tttgctgctc atgaccagtt    6180
ttaataccac tgtgttttcc ttctattaaa ccagaagaag taaacagcat aattggcaac    6240
tcttgagctt ttcttgtggc aggcaccttt tacccttggt gctccaaatc ccccatctag    6300
gaaagaaaat tttttcaagt caaataacat tgatcacata ttccttgaaa tcatttacca    6360
acactgtatg gagcattagg atttaaatat gaatttgtct taaaggcaat tccttttttgc    6420 ttctgtatta tctggaaaag catgagagag gtgacacctc aacaaactga tcagagaaaa    6480
taagcagtta ctaccctgat aggcaccttc ccaatcctgt tgcttttgac cattgtctgt    6540
ccaacggaca cacctcaaac aaacaaaact accaaataga tgacagatca gaataaaggt    6600
gagaggtctg gtccccattg aaggctgcta cagtcttcaa agaggtgaag gagttcataa    6660
gagaacaaca gtaggaaagt tgagagccaa gggtaggaga gttgcccaaa agacttcccc    6720
tactacttta gggtactgaa aactcaaagg atcagctaca gctttatcta agtatttact    6780
aaatgctaca tgagggtgtc cctgtccagc tttctggcac atgagtcctg tgtggagagt    6840
tacctcctct tccagggact gtgctgttgg gaactttggg caagtcactt acctctttgt    6900
gcctcaattt ctgtataata tttctaagct acctcactga ggtggtatga agattcacta    6960
atgtatgtag cgtgtttgtc aatcctccag tgaaaagcac tatctagatc acattttgga    7020
tcacattagc caaatgcagt aaatggccaa attagatgtg tgctgaagac aatcagtcac    7080
tgggtctata ttaaacagca accagagcaa caaatggcaa acaatttcta ttttcaagtt    7140
tctttgcata tttttttggt gcaaaaccat ttataaactt tttttttctaa cactagtgtc    7200 tacagcagca ttcaaaaaaa ttctgttacc ttttctgtat taggatttaa agtctatttc    7260
ttattgtata cctgattgaa gctgttcttg gagatgaatg ttttaaatgt ctatatccaa    7320
aaaataaaca ttttgatgta actgtg                                         7346

<210> SEQ ID NO 21
<211> LENGTH: 2828
<212> TYPE: DNA
<213> ORGANISM: Homo sapiens
<220> FEATURE:
<223> OTHER INFORMATION: SLC46A3 glucocorticoid receptor-responsive gene

<400> SEQUENCE: 21
agaacagtga cagcgccgcg gcagccgacc ccgcctcctc ggcggacagc gatgctcagc      60
tggctgcggc cgagtcatcg cctagcgctg cagggccgc tgaccgaccg acggaggcgc     120
cgattggccg attgtccact gcgcagaagg agcagctgct ccgcgccccg ccgcgccgcg     180
ctgaggccga ggtccgcagg gccgcgggga agccgagggc tgccggagaa ccctgcaggt     240
gtcactcggg acgcggaagt gcgcttgccg aggtttgctt tacaatacgc ttgagactcc     300
ccgacaagcg taatttggtc gagttcgacg ggaaagtact ctccccaccc cagcgccggc     360
cgcgtagtcc gaggttactg tccccggcgc gtcctctgtt gccccagtcc agaggctgcc     420
cttgaacccg ggcgcgcacg agcgcagggc atccgaggcg acagcccctg gcacggcccg     480
```

```
acctgtaccc agcctggcag gaagactgta atcgtgggaa tacagctacc tacccaggca      540
atatgaagat tttatttgta gaacctgcca ttttccttag tgcatttgct atgactttga      600
ccggtccact gacaacgcaa tatgtttatc ggagaatatg ggaagaaact ggcaactaca      660 cttttttcatc tgatagcaat atttctgagt gtgaaaaaaa caaaagcagc ccaattttg       720
```

```
acctgtaccc agcctggcag gaagactgta atcgtgggaa tacagctacc tacccaggca      540
atatgaagat tttatttgta gaacctgcca ttttccttag tgcatttgct atgactttga      600
ccggtccact gacaacgcaa tatgtttatc ggagaatatg ggaagaaact ggcaactaca      660
cttttttcatc tgatagcaat atttctgagt gtgaaaaaaa caaaagcagc ccaattttg      720
cattccagga ggaagttcag aaaaaagtgt cacgttttaa tctgcagatg acataagtg      780
gattaattcc tggtctagtg tctacattca tacttttgtc tattagtgat cactacggac      840
gaaaattccc tatgattttg tcttccgttg gtgctcttgc aaccagcgtt tggctctgtt      900
tgctttgcta ttttgccttt ccattccagc ttttgattgc atctaccttc attggtgcat      960
tttgtggcaa ttataccaca ttttggggag cttgctttgc ctatatagtt gatcagtgta     1020
aagaacacaa acaaaaaaca attcgaatag ctatcattga ctttctactt ggacttgtta     1080
ctggactaac aggactgtca tctggctatt ttattagaga gctaggtttt gagtggtcgt     1140
ttctaattat tgctgtgtct cttgctgtta atttgatcta tattttatttt tttctcggag    1200
atccagtgaa agagtgttca tctcagaatg ttactatgtc atgtagtgaa ggcttcaaaa     1260
acctatttta ccgaacttac atgctttttta agaatgcttc tggtaagaga cgattttttgc   1320
tctgtttgtt acttttttaca gtaatcactt atttttttgt ggtaattggc attgccccaa    1380
tttttatcct ttatgaattg gattcaccac tctgctggaa tgaagttttt ataggttatg     1440
gatcagcttt gggtagtgcc tcttttttga ctagtttcct aggaatatgg cttttttctt     1500
attgtatgga agatattcat atggccttca ttgggatttt taccacgatg acaggaatgg     1560
ctatgaccgc gtttgccagt acaacactga tgatgttttt agccagggtg ccgttccttt     1620
tcactattgt gccattctct gttctacggt ccatgttgtc aaaagtggtt cgttcgactg     1680
aacaaggtac cctgtttgct tgtattgctt tcttagaaac acttggagga gtcactgcag     1740
tttctacttt taatggaatt tactcagcca ctgttgcttg gtaccctggc ttcactttcc     1800
tgctgtctgc tggtctgtta ctacttccag ccatcagtct atgtgttgtc aagtgtacca     1860
gctggaatga gggaagctat gaacttctta tacaagaaga atccagtgaa gatgcttcag     1920
acagagcctg ttaagctgct attgatagtc ggagcttata tactgtgact tctgaagact     1980
atacatgaat tccacaatca gtgctttgtt gatacaaaat ccttaaaagg gaggcacttt     2040
aaagaatatg tatttttcac ttttcttaat atgtttcatc ggtgacaggc atgataatat     2100
ttctatatgt aatgggtaat tgggaaaaaa tagatgataa ataaaattgc tctaagaag     2160
ttaaaaaact gaatgaacag ctaatactgg tataaagtaa ctaatgtttg gagccaacat     2220
ttgttccttg tgtcagcaaa aggatattca cattccatga tccctggctg agaattctgc     2280
ctctagtctt tcttacccag ctgttgtcta tccttgttca attataaata ctgctaaggg     2340
cattttttaaa atacgatctt gtactcctta aatttgaatc cgtcagcacg gtcactcata    2400
ggaaaatgat caaacaagca agccagtcat gatttgactc cttcccatct catttcttac    2460
tgccttacgc tcatcctgag gtccaccttg gtctctaaaa acaccatgtg ttctcatgcc    2520
tccatgtctt ttcacacact gttccatttg ctcttcctcc cacattacat tgaaactttc    2580
aagcctcagt cgaaacattg cttcttctgg atagcagcct tcttgacatc cctcctcact    2640
ccccagtccc tacagggctt ccatagctct ttgtgtgcac ttcgatccca gcattttcca    2700
tcgacttgta attgtttctg ctacctgaca atcatcgcct tgagtactgg gacaaccttt    2760
gattactcat tatatcctca ataaatattt gttgaactaa aaaaaaaaaa aaaaaaaaa     2820
```

| aaaaaaaa | 2828 |

<210> SEQ ID NO 22
<211> LENGTH: 2840
<212> TYPE: DNA
<213> ORGANISM: Homo sapiens
<220> FEATURE:
<223> OTHER INFORMATION: C14orf139 glucocorticoid receptor-responsive gene

<400> SEQUENCE: 22

| gtttttgtgc aggaacagcc cctcccgtct ttgtcctggc ggtgagcacc cagggctaag | 60 |
| cttttgaaca ctttctttgt gtttggattc agcccaggca atgcatattt gctttcattt | 120 |
| cttcttgagc ttgaggagct cctgggtgca aatcttggaa aatgaggatc tctgagcctt | 180 |
| tccaggccag ctctttgttt tgtagcagac aattgaggct ttgaaaagga aagtgggtgg | 240 |
| gggcacccca caggtggccc tcatcaccca attgccagtg cctgcaggct gcttcagcag | 300 |
| aggcccagag tcaaagagga cttaaaacca gctgtcgttt ctcccttagc ttctgtgtat | 360 |
| gagagaaacg acttctgttt ttcaaagtaa gaacaaggag gaatttgttt ctaaaagaac | 420 |
| attaaaacac aggctcgtgg tctaaaagca aatggttcag caggatgttc agggccttaa | 480 |
| agcacagtca gcaggactca gcatctccca gcacctgctc tccggttgtc atggtaacat | 540 |
| catccccaac ccaaccacct tgtccagccg agagacagca atcataagga gggacctcgg | 600 |
| tttcccccga ggatcctggg cttcctttct gaaacgcttg cttctgagct cagcaaccag | 660 |
| gaacaccagg ccagcccatc cccagcacct ctgtggagat gagggacaaa gtcctacagt | 720 |
| ccctcttcct gttctgatga gaaagggagg gaagaaaaca taccccgagc gcctgcaata | 780 |
| tggtcatgac actttcaaaa agcctgtgct atggagtcat gatcagaaac cagagtgtgg | 840 |
| agagggtcag cagcctgcct cagagcagcc agctaggcgg ggagtggtaa atttgggact | 900 |
| tgtacccagg catgactggc tccgagccca gtgctccact ctatggaatg ttccctgggc | 960 |
| ctcagttgct ttcctttcct ttgcaggccg cgggctgctg ccactctggc agctggtgag | 1020 |
| ttagctggag ggcaacattc caaagcaggg gcagcatgct gctttcctcc tgtgcccact | 1080 |
| cctgcgggga agtccgttga ctcccaccgc tgaagggagc tggcaacacc aggatgaggt | 1140 |
| cccaggggac gggagcaggt acccactgtc tgtctacctt cccactggaa aagcacggac | 1200 |
| aggccagccc ttgcggggc aggcagagga cagagttggc tttgcgcggt ctctgcctgc | 1260 |
| tgagcagttc caattcctct catgggagaa acaaggaggc agtcgcttgt gcatgttcca | 1320 |
| gaagttttac tggggaggag gaagcgggaca gaggaagctg tgtgtgcatg tgaaggggtg | 1380 |
| ggcagggtgg gagggatgca cgcgtatgtg agcatagcat gtgtgagtac tacacacatc | 1440 |
| tccatgcaga agcacaactg ggcagccctg gcttccagct ctgggcttca gcacaacaga | 1500 |
| caccagcctg tggtctctca gaagccaggg agaccacatc gggctcagga cgttttaccc | 1560 |
| aaagtccaga gttttatgc ctctccctgg cattctccat aaagaaggga aggtcagatg | 1620 |
| accccttaga tctgtgtcat ctgggaattt ccttgggctg gtttagacac gatgccctct | 1680 |
| ttttctcagg atagcagata acctgctttg aaagagggct taattctgtg ggtcctaaat | 1740 |
| tttctccttt ctctctctct ttctgtgtgt gtgtgttggg aaaatggcaa gtttccaata | 1800 |
| ccagctttgg aggaacgatt acgttttccc tccaatttca gtccgaaag accagagccc | 1860 |
| tcattccaaa gccccccacc cagatggatt ttttcgtttc atttgtcatc cgtcccatgg | 1920 |
| gagggcccca tgtctcctca gaacccatcc tggaggcagc aggtcgggta gagtgagttt | 1980 |

```
ggcctgctca tgacctccac ccctgagatt gtgaacaagg atgtctgggg cgatgctgag    2040 aatgttttg aagctgctcc cagatgacgc tgatgatcac accagattga gtgctgcgat     2100
cgccttgagt ccaacctctg cataaacgag gttctcataa acaagttcac tctaccctaa    2160
gctaagtcta tgtgagcaaa cccacttcat cctttgtacc tggagacctg gttacactaa    2220
cctgatactg acctgttcat gtagctggaa tggtgtgttt catgcagtgt ggaccaagca    2280
atggcatggg gtgtgtgtgt gtgtgtgtgt gtgtctgtgt gtgtgtgttt gtgtatgcgt    2340
tcacacttgt gtgtgtatat gtgcatgtag atgctgcata aatgattttt gatgtcaaag    2400
acaaacacat tccattgttt taaatattct attatgtaaa caatacgcag agggaccata    2460
tctactcttg tcatattatt tgtgatggta aacatgcat ttgcaataaa ttaagctttc      2520
tgggaaggca agcagtattg gagccaaacg actgtctcgg aacatgtgtg tgttatctcg    2580
gttcatatca agtccaaagc taatggagcc ttccccgcca tccagggagg aacaccagga    2640
ccccggagtt tcttcttagt gctatatttt aaagttgcat tgacgttttc ctccccttcc    2700 tttgtgcaa gttggaagta gcagtgttct aaaagatggt ttgacgtttt tgctgttgtt     2760
ttatgttttt aaaaatgtat ctgctttgtg tttggaaata aaaatctcta ttttggtcta    2820
tgaaaaaaaa aaaaaaaaa                                                 2840
```

<210> SEQ ID NO 23
<211> LENGTH: 2309
<212> TYPE: DNA
<213> ORGANISM: Homo sapiens
<220> FEATURE:
<223> OTHER INFORMATION: PIAS1 glucocorticoid receptor-responsive gene

<400> SEQUENCE: 23

```
gcggggggcgg gccggggcgg ggccaggccg gctagagggg cgggtctagc ggcggccccc     60
ggcgaagttc actgcgcttg cgctgacaga cgcaagatgg cggacagtgc ggaactaaag    120
caaatggtta tgagccttag agtttctgaa ctccaagtac tgttgggcta cgccgggaga    180
aacaagcacg gacgcaaaca cgaacttctc acaaaagccc tgcatttgct aaaggctggc    240
tgtagtcctg ctgtgcaaat gaaaattaag gaactctata gcggcggtt cccacagaaa     300 atcatgacgc ctgcagactt gtccatcccc aacgtacatt caagtcctat gccagcaact    360
ttgtctccat ctaccattcc acaactcact tacgatggtc accctgcatc atcgccatta    420
ctccctgttt ctcttctggg acctaaacat gaactggaac tcccacatct acatcagct     480 cttcacccag tccatccgga tataaaactt caaaaattac cattttatga tttactggat    540
gaactgataa aacccaccag tctagcatca gacaacagtc agcgctttcg agaaacctgt    600
tttgcatttg ccttgacacc acaacaagtg cagcaaatca gtagttccat ggatattct    660 gggaccaaat gtgacttcac agtacaggtc cagttaaggt tttgtttatc agaaaccagt    720
tgtccacaag aagatcactt cccacccaat ctttgtgtga agtgaatac aaaaccttgc     780 agccttccag gttaccttcc acctacaaaa aatggcgtgg aaccaaagcg acccagccga    840
ccaattaata tcacctcact tgtccgactg tccacaacag taccaaacac gattgttgtt    900
tcttggactg cagaaattgg aagaaactat tccatgcgca tatatcttgt aaaacagttg    960
tcctcaacag ttcttcttca gaggttacga gcaaagggaa taaggaatcc ggatcattct    1020
agagctttaa ttaaagagaa gttgactgcg gatccagaca gtgaaatagc tacaaccagc    1080
ctaagggttt ctctactatg tccacttggt aaaatgcggc tgacaattcc gtgtcgggcc    1140
cttacatgtt ctcatctaca atgttttgac gcaactcttt acattcagat gaatgagaaa    1200
```

```
aaaccaacct gggtttgtcc tgtctgtgat aagaaggctc catatgaaca ccttattatt    1260
gatggcttgt ttatggaaat cctaaagtac tgtacagact gtgatgaaat acaatttaag    1320
gaggatggca cttgggcacc gatgagatca aaaaaggaag tacaggaagt ttctgcctct    1380
tacaatggag tcgatggatg cttgagctcc acattggagc atcaggtagc gtctcaccac    1440
cagtcctcaa ataaaaacaa gaaagtagaa gtgattgacc taaccataga cagttcatct    1500
gatgaagagg aagaagagcc atctgccaag aggacctgtc cttccctatc tcccacatca    1560
ccactaaata ataaaggcat tttaagtctt ccacatcaag catctccagt atcccgcacc    1620
ccaagccttc ctgctgtaga cacaagctac attaatacct ccctcatcca agactatagg    1680
catcctttcc acatgacacc catgccttac gacttacaag gattagattt ctttcctttc    1740
ttatcaggag acaatcagca ttacaacacc tccttgcttg ccgctgcagc agcagcagtt    1800
tcagatgatc aagacctcct acactcgtct cggttttttcc cgtataccto ctcacagatg    1860 tttcttgatc agttaagtgc aggaggcagt acttctctgc caaccaccaa tggaagcagt    1920
agtggcagta acagcagcct ggtttcttcc aacagcctaa gggaaagcca tagccacacc    1980
gtcacaaaca ggagcagcac ggacacggca tccatctttg gcatcatacc agacattatt    2040
tcattggact gattcccagg ccctgctgct cccatcccca ccccagatcg aatgaacttg    2100
gcagaaagaa gagaactttg tgctctgttt taccttactc tgtttagaaa agtatacaag    2160
cgtgtttttt ttcctttttt tagggaaaaa attaaaagaa atgtacagag aacaaaacta    2220
tattttcagt tttacttttg tatataaatc taagactgcc tgtgtgataa aacacttgtt    2280
taaaaaaaaa aaaaaaaaa aaaaaaaaa                                       2309
```

<210> SEQ ID NO 24
<211> LENGTH: 1740
<212> TYPE: DNA
<213> ORGANISM: Homo sapiens
<220> FEATURE:
<223> OTHER INFORMATION: IDH2 glucocorticoid receptor-responsive gene

<400> SEQUENCE: 24

```
ccagcgttag cccgcggcca ggcagccggg aggagcggcg cgcgctcgga cctctcccgc     60
cctgctcgtt cgctctccag cttgggatgg ccggctacct gcgggtcgtg cgctcgctct    120
gcagagcctc aggctcgcgg ccggcctggg cgccggcggc cctgacagcc ccacctcgc    180 aagagcagcc gcggcgccac tatgccgaca aaaggatcaa ggtggcgaag cccgtggtgg    240
agatggatgg tgatgagatg acccgtatta tctggcagtt catcaaggag aagctcatcc    300
tgccccacgt ggacatccag ctaaagtatt ttgacctcgg gctcccaaac cgtgaccaga    360
ctgatgacca ggtcaccatt gactctgcac tggccaccca gaagtacagt gtggctgtca    420
agtgtgccac catcaccccc tgatgaggccc gtgtggaaga gttcaagctg aagaagatgt    480
ggaaaagtcc caatggaact atccggaaca tcctgggggg gactgtcttc cgggagccca    540
tcatctgcaa aaacatccca cgcctagtcc ctggctggac caagcccatc accattggca    600
ggcacgccca tggcgaccag tacaaggcca cagactttgt ggcagaccgg gccggcactt    660
tcaaaatggt cttcacccca aaagatggca gtggtgtcaa ggagtgggaa gtgtacaact    720
tccccgcagg cggcgtgggc atgggcatgt acaacaccga cgagtccatc tcaggttttg    780
cgcacagctg cttccagtat gccatccaga agaaatggcc gctgtacatg agcaccaaga    840
acaccatact gaaagcctac gatgggcgtt tcaaggacat cttccaggag atctttgaca    900
```

```
agcactataa gaccgacttc gacaagaata agatctggta tgagcaccgg ctcattgatg      960
acatggtggc tcaggtcctc aagtcttcgg gtggctttgt gtgggcctgc aagaactatg     1020
acggagatgt gcagtcagac atcctggccc agggctttgg ctcccttggc ctgatgacgt     1080
ccgtcctggt ctgccctgat gggaagacga ttgaggctga ggccgctcat ggaccgtca     1140 cccgccacta tcgggagcac cagaagggcc ggcccaccag caccaacccc atcgccagca     1200
tctttgcctg gacacgtggc ctggagcacc ggggaagct ggatgggaac caagacctca     1260
tcaggtttgc ccagatgctg gagaaggtgt gcgtggagac ggtggagagt ggagccatga     1320
ccaaggacct ggcgggctgc attcacggcc tcagcaatgt gaagctgaac gagcacttcc     1380
tgaacaccac ggacttcctc gacaccatca gagcaacct ggacagagcc ctgggcaggc     1440
agtaggggga ggcgccaccc atggctgcag tggaggggcc agggctgagc cggcgggtcc     1500
tcctgagcgc ggcagagggt gagcctcaca gcccctctct ggaggccttt ctaggggatg     1560 ttttttttata agccagatgt ttttaaaagc atatgtgtgt ttcccctcat ggtgacgtga    1620
ggcaggagca gtgcgtttta cctcagccag tcagtatgtt ttgcatactg taatttatat    1680 tgccccttgga acacatggtg ccatatttag ctactaaaaa gctcttcaca aaaaaaaaa    1740
```

<210> SEQ ID NO 25
<211> LENGTH: 1552
<212> TYPE: DNA
<213> ORGANISM: Homo sapiens
<220> FEATURE:
<223> OTHER INFORMATION: SERPINF1 glucocorticoid receptor-responsive gene

<400> SEQUENCE: 25

```
ggtcgcttta agaaaggagt agctgtaatc tgaagcctgc tggacgctgg attagaaggc       60
agcaaaaaaa gctctgtgct ggctggagcc ccctcagtgt gcaggcttag agggactagg      120
ctgggtgtgg agctgcagcg tatccacagg ccccaggatg caggccctgg tgctactcct      180
ctgcattgga gccctcctcg gcacagcag ctgccagaac cctgccagcc ccccggagga      240
gggctcccca gaccccgaca gcacagggc gctggtggag gaggaggatc ctttcttcaa      300
agtccccgtg aacaagctgg cagcggctgt ctccaacttc ggctatgacc tgtacccggt      360
gcgatccagc acgagcccca cgaccaacgt gctcctgtct cctctcagtg tggccacggc      420
cctctcggcc ctctcgctgg gagcgagca gcgaacagaa tccatcattc accgggctct      480
ctactatgac ttgatcagca gcccagacat ccatggtacc tataaggagc tccttgacac      540
ggtcactgcc ccccagaaga acctcaagag tgcctcccgg atcgtctttg agaagaagct      600
gcgcataaaa tccagctttg tggcacctct ggaaaagtca tatgggacca ggcccagagt      660
cctgacgggc aaccctcgct tggacctgca agagatcaac aactgggtgc aggcgcagat      720
gaaagggaag ctcgccaggt ccacaaagga aattcccgat gagatcagca ttctccttct      780
cggtgtggcg cacttcaagg ggcagtgggt aacaaagttt gactccagaa agacttccct      840
cgaggatttc tacttggatg aagagaggac cgtgagggtc cccatgatgt cggaccctaa      900
ggctgtttta cgctatggct tggattcaga tctcagctgc aagattgccc agctgcctt      960 gaccggaagc atgagtatca tcttcttcct gccccctgaaa gtgacccaga atttgaccttt     1020 gatagaggag agcctcacct ccgagttcat tcatgacata gaccgagaac tgaagaccgt     1080
gcaggcggtc ctcactgtcc ccaagctgaa gctgagttat gaaggcgaag tcaccaagtc     1140
cctgcaggag atgaagctgc aatccttgtt tgattcacca gactttagca agatcacagg     1200
```

```
caaacccatc aagctgactc aggtggaaca ccgggctggc tttgagtgga acgaggatgg    1260
ggcgggaacc accccagcc cagggctgca gcctgcccac ctcaccttcc cgctggacta    1320
tcaccttaac cagcctttca tcttcgtact gagggacaca gacacagggg cccttctctt    1380
cattggcaag attctggacc ccaggggccc ctaatatccc agtttaatat tccaataccc    1440
tagaagaaaa cccgagggac agcagattcc acaggacacg aaggctgccc ctgtaaggtt    1500
tcaatgcata caataaaaga gctttatccc taaaaaaaaa aaaaaaaaa aa             1552
```

<210> SEQ ID NO 26
<211> LENGTH: 4816
<212> TYPE: DNA
<213> ORGANISM: Homo sapiens
<220> FEATURE:
<223> OTHER INFORMATION: ERBB2 glucocorticoid receptor-responsive gene

<400> SEQUENCE: 26

```
gttcccggat ttttgtgggc gcctgccccg cccctcgtcc ccctgctgtg tccatatatc      60
gaggcgatag ggttaaggga aggcggacgc ctgatgggtt aatgagcaaa ctgaagtgtt     120
ttccatgatc ttttttgagt cgcaattgaa gtaccacctc ccgagggtga ttgcttcccc     180 atgcgggta gaacctttgc tgtcctgttc accactctac ctccagcaca gaatttggct     240
tatgcctact caatgtgaag atgatgagga tgaaaacctt tgtgatgatc cacttccact     300
taatgaatgg tggcaaagca aagctatatt caagaccaca tgcaaagcta ctccctgagc     360
aaagagtcac agataaaacg ggggcaccag tagaatggcc aggacaaacg cagtgcagca     420
cagagactca gaccctggca gccatgcctg cgcaggcagt gatgagagtg acatgtactg     480
ttgtggacat gcacaaaagt gagtgtgcac cggcacagac atgaagctgc ggctccctgc     540
cagtcccgag acccacctgg acatgctccg ccacctctac cagggctgcc aggtggtgca     600
gggaaacctg gaactcacct acctgcccac caatgccagc ctgtccttcc tgcaggatat     660
ccaggaggtg cagggctacg tgctcatcgc tcacaaccaa gtgaggcagg tcccactgca     720
gaggctgcgg attgtgcgag gcacccagct cttttgaggac aactatgccc tggccgtgct     780
agacaatgga gacccgctga caataccac ccctgtcaca ggggcctccc aggaggcct     840 gcgggagctg cagcttcgaa gcctcacaga gatcttgaaa ggaggggtct tgatccagcg     900 gaaccccag ctctgctacc aggacacgat tttgtggaag acatcttcc acaagaacaa     960 ccagctggct ctcacactga tagacaccaa ccgctctcgg gcctgccacc cctgttctcc    1020
gatgtgtaag ggctcccgct gctggggaga gagttctgag gattgtcaga gcctgacgcg    1080
cactgtctgt gccggtggct gtgcccgctg caagggggcca ctgcccactg actgctgcca    1140
tgagcagtgt gctgccggct gcacgggccc caagcactct gactgcctgg cctgcctcca    1200
cttcaaccac agtggcatct gtgagctgca ctgcccagcc ctggtcacct acaacacaga    1260
cacgtttgag tccatgccca atccgagggg ccggtataca ttcggcgcca gctgtgtgac    1320
tgcctgtccc tacaactacc tttctacgga cgtgggatcc tgcacccttcg tctgcccct    1380 gcacaaccaa gaggtgacag cagaggatgg aacacagcgg tgtgagaagt gcagcaagcc    1440
ctgtgcccga gtgtgctatg gtctgggcat ggagcacttg cgagaggtga gggcagttac    1500
cagtgccaat atccaggagt tgctggctg caagaagatc tttgggagcc tggcatttct    1560
gccggagagc tttgatgggg acccagcctc caacactgcc ccgctccagc cagagcagct    1620
ccaagtgttt gagactctgg aagagatcac aggttaccta tacatctcag catggccgga    1680
cagcctgcct gacctcagcg tcttccagaa cctgcaagta atccggggac gaattctgca    1740
```

```
caatggcgcc tactcgctga ccctgcaagg gctgggcatc agctggctgg ggctgcgctc   1800
actgagggaa ctgggcagtg gactggccct catccaccat aacacccacc tctgcttcgt   1860
gcacacggtg ccctgggacc agctctttcg gaacccgcac caagctctgc tccacactgc   1920
caaccggcca gaggacgagt gtgtgggcga gggcctggcc tgccaccagc tgtgcgcccg   1980
agggcactgc tggggtccag ggcccaccca gtgtgtcaac tgcagccagt tccttcgggg   2040
ccaggagtgc gtggaggaat gccgagtact gcaggggctc cccagggagt atgtgaatgc   2100
caggcactgt ttgccgtgcc accctgagtg tcagcccag aatggctcag tgacctgttt   2160
tggaccggag gctgaccagt gtgtggcctg tgcccactat aaggaccctc ccttctgcgt   2220
ggcccgctgc cccagcggtg tgaaacctga cctctcctac atgcccatct ggaagtttcc   2280
agatgaggag ggcgcatgcc agccttgccc catcaactgc acccactcct gtgtggacct   2340
ggatgacaag ggctgccccg ccgagcagag agccagccct ctgacgtcca tcatctctgc   2400
ggtggttggc attctgctgg tcgtggtctt ggggtggtc tttgggatcc tcatcaagcg   2460
acggcagcag aagatccgga agtacacgat gcggagactg ctgcaggaaa cggagctggt   2520
ggagccgctg acacctagcg gagcgatgcc caaccaggcg cagatgcgga tcctgaaaga   2580
gacggagctg aggaaggtga aggtgcttgg atctggcgct tttggcacag tctacaaggg   2640
catctggatc cctgatgggg agaatgtgaa aattccagtg gccatcaaag tgttgaggga   2700
aaacacatcc cccaaagcca caaagaaat cttagacgaa gcatacgtga tggctggtgt   2760
gggctcccca tatgtctccc gccttctggg catctgcctg acatccacgg tgcagctggt   2820
gacacagctt atgccctatg gctgcctctt agaccatgtc cgggaaaacc gcggacgcct   2880
gggctcccag gacctgctga actggtgtat gcagattgcc aagggggatga gctacctgga   2940 ggatgtgcgg ctcgtacaca gggacttggc cgctcggaac gtgctggtca agagtcccaa   3000
ccatgtcaaa attacagact cgggctggc tcggctgctg acattgacg agacagagta   3060 ccatgcagat gggggcaagg tgcccatcaa gtggatggcg ctggagtcca ttctccgccg   3120
gcggttcacc caccagagtg atgtgtggag ttatggtgtg actgtgtggg agctgatgac   3180 ttttgggggcc aaaccttacg atgggatccc agcccgggag atccctgacc tgctggaaaa   3240
gggggagcgg ctgccccagc cccccatctg caccattgat gtctacatga tcatggtcaa   3300
atgttggatg attgactctg aatgtcggcc aagattccgg gagttggtgt ctgaattctc   3360
ccgcatggcc agggacccc agcgctttgt ggtcatccag aatgaggact gggcccagc   3420 cagtcccttg gacagcacct tctaccgctc actgctggag gacgatgaca tggggggacct   3480 ggtggatgct gaggagtatc tggtacccca gcagggcttc ttctgtccag accctgcccc   3540
gggcgctggg ggcatggtcc accacaggca ccgcagctca tctaccagga gtggcggtgg   3600
ggacctgaca ctagggctgg agccctctga agaggaggcc cccaggtctc cactggcacc   3660
ctccgaaggg gctggctccg atgtatttga tggtgacctg ggaatggggg cagccaaggg   3720
gctgcaaagc ctccccacac atgaccccag ccctctacag cggtacagtg aggacccac   3780 agtacccctg ccctctgaga ctgatggcta cgttgccccc ctgacctgca gccccagcc   3840 tgaatatgtg aaccagccag atgttcggcc ccagccccct tcgccccgag agggccctct   3900
gcctgctgcc cgacctgctg gtgccactct ggaaaggccc aagactctct cccagggaa   3960 gaatggggtc gtcaaagacg tttttgcctt tgggggtgcc gtggagaacc ccgagtactt   4020 gacacccag ggaggagctg cccctcagcc ccaccctcct cctgccttca gcccagcctt   4080
```

| | |
|---|---:|
| cgacaacctc tattactggg accaggaccc accagagcgg ggggctccac ccagcacctt | 4140 |
| caaagggaca cctacggcag agaacccaga gtacctgggt ctggacgtgc cagtgtgaac | 4200 |
| cagaaggcca agtccgcaga agccctgatg tgtcctcagg gagcagggaa ggcctgactt | 4260 |
| ctgctggcat caagaggtgg gagggccctc cgaccacttc caggggaacc tgccatgcca | 4320 |
| ggaacctgtc ctaaggaacc ttccttcctg cttgagttcc cagatggctg aaggggtcc | 4380 |
| agcctcgttg gaagaggaac agcactgggg agtctttgtg gattctgagg ccctgcccaa | 4440 |
| tgagactcta gggtccagtg gatgccacag cccagcttgg ccctttcctt ccagatcctg | 4500 |
| ggtactgaaa gccttaggga agctggcctg agaggggaag cggccctaag ggagtgtcta | 4560 |
| agaacaaaag cgacccattc agagactgtc cctgaaacct agtactgccc cccatgagga | 4620 |
| aggaacagca atggtgtcag tatccaggct ttgtacagag tgcttttctg tttagttttt | 4680 |
| acttttttg ttttgttttt ttaaagatga aataaagacc caggggagaa atgggtgttg | 4740 |
| tatgggagg caagtgtggg gggtccttct ccacacccac tttgtccatt tgcaaatata | 4800 |
| ttttggaaaa cagcta | 4816 |

```
<210> SEQ ID NO 27
<211> LENGTH: 6831
<212> TYPE: DNA
<213> ORGANISM: Homo sapiens
<220> FEATURE:
<223> OTHER INFORMATION: PECAM1 glucocorticoid receptor-responsive gene

<400> SEQUENCE: 27
```

| | |
|---|---:|
| ccaggcccca ttgttcccgg tttccagcca tggctgccat tacctgacca gcgccacagc | 60 |
| cggtctctct gcaggcgccg ggagaagtga ccagagcaat ttctgctttt cacagggcgg | 120 |
| gtttctcaac ggtgacttgt gggcagtgcc ttctgctgag cgagtcatgg cccgaaggca | 180 |
| gaactaactg tgcctgcagt cttcactctc aggatgcagc cgaggtgggc ccaaggggcc | 240 |
| acgatgtggc ttggagtcct gctgaccctt ctgctctgtt caagccttga gggtcaagaa | 300 |
| aactctttca caatcaacag tgttgacatg aagagcctgc cggactggac ggtgcaaaat | 360 |
| gggaagaacc tgaccctgca gtgcttcgcg gatgtcagca ccacctctca cgtcaagcct | 420 |
| cagcaccaga tgctgttcta taggatgac gtgctgtttt acaacatctc ctccatgaag | 480 |
| agcacagaga gttatttat tcctgaagtc cggatctatg actcagggac atataaatgt | 540 |
| actgtgattg tgaacaacaa agagaaaacc actgcagagt accaggtgtt ggtggaagga | 600 |
| gtgcccagtc ccagggtgac actggacaag aaagaggcca tccaaggtgg gatcgtgagg | 660 |
| gtcaactgtt ctgtcccaga ggaaaaggcc ccaatacact tcacaattga aaaacttgaa | 720 |
| ctaaatgaaa aaatggtcaa gctgaaaaga gagaagaatt ctcgagacca gaattttgtg | 780 |
| atactggaat tccccgttga ggaacaggac cgcgttttat ccttccgatg tcaagctagg | 840 |
| atcatttctg ggatccatat gcagacctca gaatctacca agagtgaact ggtcaccgtg | 900 |
| acggaatcct tctctacacc caagttccac atcagcccca ccggaatgat catggaagga | 960 |
| gctcagctcc acattaagtg caccattcaa gtgactcacc tggcccagga gtttccagaa | 1020 |
| atcataattc agaaggacaa ggcgattgtg gcccacaaca acatggcaa caaggctgtg | 1080 |
| tactcagtca tggccatggt ggagcacagt ggcaactaca cgtgcaaagt ggagtccagc | 1140 |
| cgcatatcca aggtcagcag catcgtggtc aacataacag aactattttc caagcccgaa | 1200 |
| ctggaatctt ccttcacaca tctggaccaa ggtgaaagac tgaacctgtc ctgctccatc | 1260 |
| ccaggagcac ctccagccaa cttcaccatc cagaaggaag atacgattgt gtcacagact | 1320 |

-continued

| | |
|---|---|
| caagatttca ccaagatagc ctcaaagtcg acagtggga cgtatatctg cactgcaggt | 1380 |
| attgacaaag tggtcaagaa aagcaacaca gtccagatag tcgtatgtga aatgctctcc | 1440 |
| cagcccagga tttcttatga tgcccagttt gaggtcataa aaggacagac catcgaagtc | 1500 |
| cgttgcgaat cgatcagtgg aactttgcct atttcttacc aacttttaaa aacaagtaaa | 1560 |
| gttttggaga atagtaccaa gaactcaaat gatcctgcgg tattcaaaga caaccccact | 1620 |
| gaagacgtcg aataccagtg tgttgcagat aattgccatt cccatgccaa aatgttaagt | 1680 |
| gaggttctga gggtgaaggt gatagccccg gtggatgagg tccagatttc tatcctgtca | 1740 |
| agtaaggtgt ggagtctgg agaggacatt gtgctgcaat gtgctgtgaa tgaaggatct | 1800 |
| ggtcccatca cctataagtt ttacagagaa aaagagggca aaccttcta tcaaatgacc | 1860 |
| tcaaatgcca cccaggcatt ttggaccaag cagaaggcta gcaaggaaca ggagggagag | 1920 |
| tattactgca cagccttcaa cagagccaac cacgcctcca gtgtccccag aagcaaaata | 1980 |
| ctgacagtca gagtcattct tgccccatgg aagaaaggac ttattgcagt ggttatcatc | 2040 |
| ggagtgatca ttgctctctt gatcattgcg gccaaatgtt attttctgag gaaagccaag | 2100 |
| gccaagcaga tgccagtgga aatgtccagg ccagcagtac cacttctgaa ctccaacaac | 2160 |
| gagaaaatgt cagatcccaa tatggaagct aacagtcatt acggtcacaa tgacgatgtc | 2220 |
| agaaaccatg caatgaaacc aataaatgat aataaagagc ctctgaactc agacgtgcag | 2280 |
| tacacggaag ttcaagtgtc ctcagctgag tctcacaaag atcaggaaa aaggacaca | 2340 |
| gagacagtgt acagtgaagt ccggaaagct gtccctgatg ccgtggaaag cagatactct | 2400 |
| agaacggaag gctcccttga tggaacttag acagcaaggc cagatgcaca tccctggaag | 2460 |
| gacatccatg ttccgagaag aacagataat ccctgtattt caagacctct gtgcacttat | 2520 |
| ttatgaacct gccctgctcc cacagaacac agcaattcct caggctaagc tgccggttct | 2580 |
| taaatccatc ctgctaagtt aatgttgggt agaaagagat acagaggggc tgttgaattt | 2640 |
| cccacatacc ctccttccac caagttggaa catccttgga aattggaaga gcacaagagg | 2700 |
| agatccaggg caaggccatt gggatattct gaaacttgaa tattttgttt tgtgcagaga | 2760 |
| taaagacctt ttccatgcac cctcatacac agaaaccaat tttcttttt atactcaatc | 2820 |
| atttctagcg catggcctgg ttagaggctg gttttttctc ttttcctttg gtccttcaaa | 2880 |
| ggcttgtagt tttggctagt ccttgttctt tggaaataca cagtgctgac cagacagcct | 2940 |
| cccctgtcc cctctatgac ctcgccctcc acaaatggga aaccagact acttgggagc | 3000 |
| accgcctgtg aaataccaac ctgaagcacac cgttcattca ggcaacgcac aaaacagaaa | 3060 |
| atgaaggtgg aacaagcaca gatgttcttc aactgttttt gtctacactc tttctctttt | 3120 |
| cctctaccat gctgaaggct gaaagacagg aagatggtgc catcagcaaa tattattctt | 3180 |
| aattgaaaac ttgaaatgtg tatgtttctt actaattttt aaaaatgtat tccttgccag | 3240 |
| ggcaggcaag gtggctcacg cctgtaatcc cagcacttca ggaggctgag gtgggcggat | 3300 |
| cacctgaggt caggagtttg agaccagcct gatgaaaccc tgtctctact aaaaatacaa | 3360 |
| gaattagccg ggcgtggtgg cgcatgcctg tagtatcagc tactcaagag gctgaggtga | 3420 |
| gattatcgct tgaacccagg aaacggaggt tgtagtgagc ggagatcgcg ccactgcact | 3480 |
| ccagcctgag tgacagagtg agaatccatc tcaaaaaaaa caaaaaacaa aattgcttgc | 3540 |
| taaagaagtg gtctcctgag gtcttaagac attcctgaca gtgtcttgag tgggtgggag | 3600 |
| agaggctgct gtcattgcgc tgtggaattt cacagatgag aaccacgcct agccaaaatc | 3660 |

```
acttttcctg tttgcctcag tgacacagct gcagggaccc tcgtggatgt tgtattaaat    3720
aaatttgacc tttgctcttt gcagatctgt gaaatgttgt cttctgaggg gccacatgca    3780
tctatagtgc tgaggactcc ttgggcctct gaagtcacag agagaaccga gcaggtctat    3840
gttttgttt tgttgttttg agacggagat tcgctcttgt tgcccgggct ggactgcagc    3900
ggcgcaacct ctgctcactg caacctccgc ctcctgggtt caagcagttc tcctgtctca    3960
gcctcccgag tagctgggat tacaggcaca tgtcaccacg cctggctaat ttttgtattt    4020
ttagtagaga tgggtttca ccacgttggc caggctgatc tcgaatgcct gacctttggt    4080
gatctgcccg ccttgtcctc atgtgtgctc acaggcctt tgggttggga ttgcaggcgt    4140
gagccaccat gcccagccta gactcttttg acaatatgat gaaagctgtt ggttcctttc    4200
cccaacacac acacaccgag ttgtatcacg aaaatgtcat acaatttcca ggttttctga    4260
gtggtgggct cagattgagg tcaaaggatc agacgacctc taacgacctt catgtctctg    4320
ttgatgatct ggggacagcc agatcccctg tgtccaggga gttccttagt cccttgccac    4380
caccagagaa gggcaattgc cacgggagct gcaaagaccc tattcctact cctggtgcct    4440
tacttatgca gcacgactga attttttgtt ttgttttgtt ttgttgagac aggggcttgc    4500
tctgttgccc aggctggagt gcagtggcac aacaatggct caccgcagcc tcgaacccct    4560
gggctcaagc gatcctccca tctcagcttc ctgggtagct gggaccagag gcgtgagccg    4620
ccatagctgg ctaattttta attttttttt tgcagagatg aggtttcacc atggtgccca    4680
ggctggtctc gaacttctgg gctcaagtga tcctccctcc ttggcctcgc aaagtgctgg    4740
gattgcaggc atgagccacc gccccggcc tgtggagcac acatgagttt aaaattactt    4800
tcccttctgc ctatatttcc gaggaggaaa cttcatgcgc agggatcttt cttagtggat    4860
ttaatggcta aaaggtctgt ctgaatccag gacgctggct ttagccttcc tcggcagctg    4920
ccgtaaccc ggtgtctaaa cctgaagcat cccaggagca cccactccag gagttttctc    4980
ggccgcggaa ctcattagtt agagcgccct cttgtgttct catgtggtaa tcggtcactg    5040
aaggacttaa aatggtcctt agccaacaca cagtaaaact tttccctctt ctgaccccaa    5100
gaggtcagcc acccatttca tgagcatata ctggtcgccc catcagcgtt ctctgattgg    5160
ctaactgaac ccactccccg acctagactc aagacaggcg aagtgacgct taggtcaaca    5220
ttcactcact aaagcaacga ctgtcgggcg attttgtctc ccgctggttt tggaatggtg    5280
tctggagaca ttttttggttg tcacagctgg gtgggtgtgc tcccggcatc tggtgggtag    5340
aaaccaagca tgctcctaaa catcctacag gcacagaacc gtctcccacg accaagcatg    5400
atcaagtccc aaatgccaat aatggccagg ttgagaaact ctgcacagaa gcatccagtt    5460
atttgtctgt ttgctcaaca agcttgtgct catcatgctc tgtgttcctg acgctgtgct    5520
gggtgttggc ggtgggaaga ttacaagagt cacatggcag ctgtcctcct ggaaggtaca    5580
acccagtaga gatgcagact aacagagagc caattacaaa gcagtgtgac aagcgtcatg    5640
gtggaaaatt aaaagctcaa acaagggcac atggagggg cttccaacac agactttggg    5700
ggatccagga aggtctaaga ggaaagtggg tctcaccaaa gccttgacca taggcagagg    5760
gtaccagtgg aaaaggtggg gtgaagaaca ttgaggacaa aaggaagaag tgcaggaagg    5820
ccctgaggca agggagtggg gggtgccctg gagggatggc agcagggcag tctgtcagac    5880
ccaagtggcc tccagcccta gaagccaatt agtcctcctc aaaaagctgt cactgtcccc    5940
taagaattgc tgccaggctc ccactggcct gactcagtct ttgagagtct taaggaggag    6000
gtctctgaaa ggtacacacc aagaactctc cccagcacag ctgttttaa gactctccac    6060
```

-continued

| | |
|---|---|
| cagcgtcatt ggcgtgttgg gaagaaaccc tctgccacag aggccagctt cagcctttgc | 6120 |
| ctaacaccgc aagggcaaat ggaaaggtaa acgggaagga gatgtctccc cagcaggcta | 6180 |
| tttgaggaca gtcttccctg cagaagatct caacctgggg tccacagagt ggaaatgtta | 6240 |
| gagtagggag ctaggcaaac atgagcagga caggtgaggg cccccacagg aatgtcaggc | 6300 |
| taccatcagg tgatggtcag gtggttgtta aactgtctct gtaaataat aattggttgc | 6360 |
| agccagctcc aagcaaggac agtctctcaa tagatacaaa acaccctgat ctggtgatca | 6420 |
| gccgcttccc gataagatct caggagctgg gcaagcagcc tggagcatgc gcaccaagag | 6480 |
| gcaaaatggc ggaatttaac cagtatatga cctaccttcc tctgggaacg cacgactggt | 6540 |
| aaggggaaaa atgcctcaag tgagcatgcg cgcaacttca gtaatcacac tgtgcatgcg | 6600 |
| accccttcca gtgctggca ggtcaccaca tacgcggaca gcctgctgca agggaagaat | 6660 |
| caggggagat gagacgtaaa tcccagaact atgccaaata cataaaaccc caagttaagg | 6720 |
| gtcaggcagg gcacttagat ctctcaagtt gcctgcctga cccaagtgta gtgtacttcc | 6780 |
| ttttgttcct gctctaaaac ttttaataa actctcactc ctgctctaaa a | 6831 |

<210> SEQ ID NO 28
<211> LENGTH: 2956
<212> TYPE: DNA
<213> ORGANISM: Homo sapiens
<220> FEATURE:
<223> OTHER INFORMATION: LBH glucocorticoid receptor-responsive gene

<400> SEQUENCE: 28

| | |
|---|---|
| ggggctgagt gctcagtgga gagcggggag ttgtgtccac cttgccgacg tcgctagccg | 60 |
| tggggctgtc ctgggaaggc ggacggcgag cgcccggtgt ccgcactcgg ccgcctgccg | 120 |
| tgcccgtctg cgcccgtgtc atcctcactc gggacgcagg gaccgttttt aaatcacagg | 180 |
| ggcgtgtgtc agcctgccct aggacttcat gtctatatat ttccccattc actgccccga | 240 |
| ctatctgaga tcggccaaga tgactgaggt gatgatgaac acccagccca tggaggagat | 300 |
| cggcctcagc ccccgcaagg atggcctttc ctaccagatc ttcccagacc cgtcagattt | 360 |
| tgaccgctgc tgcaaactga aggaccgtct gccctccata gtggtggaac ccacagaagg | 420 |
| ggaggtggag agcggggagc tccggtggcc ccctgaggag ttcctggtcc aggaggatga | 480 |
| gcaagataac tgcgaagaga cagcgaaaga aaataaagag cagtagagtc cctgtggact | 540 |
| cccatgggtc ataccagcca gcatctgttc ctgaactgtg ttttccat catgacggaa | 600 |
| gaagagagtg agccgcaatt gttctgaaaa tgtcaaacga ggcttctgtt ttgcacctgc | 660 |
| agatcaccga gttggttttc ttttctttc ttgcctttt tttttttga aatttgccga | 720 |
| gcagtggagc cctctgacaa tttgcaaggc cctctgagaa aggaagctgc ttagagccag | 780 |
| ggggttagtg ggtgagggga gcgagtgctg tttttgagat cattatctga actcaggcag | 840 |
| cctagtagag gcagtggtgg gattccaatg ggtcttggtg ggtgggaggt ggggcatgtg | 900 |
| caaagcaagc aaggaacatt tggggtaaga aaacaaacat gaggcaaaag aaaaaataca | 960 |
| tgtttttaag aaaacattga gcagagaact gcagccagga tgcgctcagc agacattcac | 1020 |
| tctggctgct gggacatcag aaaacaaagt cttcatctct ctctccagtt tcacccaccc | 1080 |
| caccctttgc tttcatttca ggtgtgttgg tctatatgac agggaggaga gtaaaggaga | 1140 |
| gcaggagcaa ttggctgcct gcaaagccag ctggaggtga agtgcaggaa aggaaaggtc | 1200 |
| accccattct actccatggc ctctctgctc ccagctgtgg taggctcaca tagccagtgt | 1260 |

```
gatcggtttt taagaggcag tgcttttcag cttttctccc tgatatatcc attttgcttc   1320
ccagcacttt ttaggagtag tgagagcact tcctgccctt gttggaagcc ccagggtgga   1380
cactcagcac gaaggtctct cccttaactg ctgcccttcc aagacttgct cccgagatgg   1440
agtgggcgtg gtcttccagg ctggcccttc cttctcctca ccgccacctt ccctgcccca   1500
gccccagcag ccatgggtac atgggtcccc agctcaccta tggattcccg ccagtctgcc   1560
cagctgcagt actcacgccc catgggggat cttggtctgt ttttcttgtg ggagcctagt   1620
ggagagcaga cgtggctttt tatgtgtctt gttggggagg tgacttgcat ggtggggaca   1680
aggctgtcgt ggcaaccttg ggatcgagtt tgagactaaa ggatgtcatg agatccctgg   1740
cttctcccca tgttgttccc ggacaagggc agaagggagg catggcaagg gacctctgct   1800
gtccttactc aacagtggtc ctcatccctc cccacctccc actgcttcct gcaagggcac   1860
cagttgtatg agaaagttgg cctttggact taggatttct tattgtagct aagagccatc   1920
tgaagcagca ggttgcagga caaatgcttc agtccgccga gagcagtacc gtgtggccaa   1980
gaggtggact cagagcccttc cttgagctaa actcggccaa ccaaggcacg cagcatgtcc   2040
cctcaggtct ccagtcagtc caggttgacc ctcagttctg gacgtgtgta tatagctgta   2100
tttaatacct caaggtcatt gtggctctgg ggatgccggg gcaggaggac gagggtgcgc   2160
tgtggacaca gcagtccgcg gaattccgtt ctgggaagcc aatggtcgcc ggcacccctt   2220
gcttcctccc tctgttgtct gcctgtgtga cacacatcaa tggcaataac ttcttccaac   2280
tcctcgcaga agtgggagag gccggcagcc tgcaccgaga ggggctttcc tctctcttgc   2340
tccccgcttc gttctgtttt ggctgcagag agtggttcat ccatactctc attccctcgc   2400
ctccccttgt ggacgggggt cttgcctttt caattcctgt gttttggtgt cttcccttat   2460
ctgctaccct gaatcacctg tcctggtctt gctgtgtgat gggaacatgc ttgtaaactg   2520
cgtaacaaat ctactttgtg tatgtgtctg tttatggggg tggtttatta tttttgctgg   2580
tccctagacc actttgtatg accgtttgca gtctgagcag gccaggggct gacagctaat   2640
gtcaggaccc tcagcggtgg agcctgctgg ggggacccag ctgctcttgg acaagtggct   2700
gagctcctat ctggcctcct ctttttttttt ttttcaagta atttgtgtgt atttctaact   2760
gattgtattg aaaaaattcc tagtatttca gtaaaaatgc ctgttgtgag atgaacctcc   2820
tgtaacttct atctgttctt ttttgaggct caggagaaaa ctagcatttt ttttttttcca   2880 aactactttt tgtcactgtg acagttgtaa ataaagtttg aaaatgcttt ccactctgaa   2940
aaaaaaaaaa aaaaaa                                                   2956
```

<210> SEQ ID NO 29
<211> LENGTH: 2262
<212> TYPE: DNA
<213> ORGANISM: Homo sapiens
<220> FEATURE:
<223> OTHER INFORMATION: ST3GAL5 glucocorticoid receptor-responsive gene

<400> SEQUENCE: 29

```
ctggggagta atagcatggg caaccattat cctgtctcgc cgccacccag gacatggctt     60
ctgttccaat gccaagtgag tacacctatg tgaaactgag aagtgattgc tcgaggcctt    120
ccctgcaatg gtacacccga gctcaaagca agatgagaag gcccagcttg ttattaaaag    180
acatcctcaa atgtacattg cttgtgtttg gagtgtggat cctttatatc ctcaagttaa    240
attatactac tgaagaatgt gacatgaaaa aaatgcatta tgtggaccct gaccatgtaa    300
agagagctca gaaatatgct cagcaagtct tgcagaagga atgtcgtccc aagtttgcca    360
```

```
agacatcaat ggcgctgtta tttgagcaca ggtatagcgt ggacttactc cctttttgtgc    420 agaaggcccc caaagacagt gaagctgagt ccaagtacga tcctccttttt gggttccgga    480 agttctccag taaagtccag accctcttgg aactcttgcc agagcacgac ctccctgaac     540
acttgaaagc caagacctgt cggcgctgtg tggttattgg aagcggagga atactgcacg    600
gattagaact gggccacacc ctgaaccagt tcgatgttgt gataaggtta aacagtgcac     660
cagttgaggg atattcagaa catgttggaa ataaaactac tataaggatg acttatccag    720
agggcgcacc actgtctgac cttgaatatt attccaatga cttatttgtt gctgttttat     780
ttaagagtgt tgatttcaac tggcttcaag caatggtaaa aaaggaaacc ctgccattct     840
gggtacgact cttcttttgg aagcaggtgg cagaaaaaat cccactgcag ccaaaacatt    900 tcaggattttt gaatccagtt atcatcaaag agactgcctt tgacatcctt cagtactcag     960
agcctcagtc aaggttctgg ggccgagata agaacgtccc cacaatcggt gtcattgccg    1020
ttgtcttagc cacacatctg tgcgatgaag tcagtttggc gggttttgga tatgacctca    1080
atcaacccag aacacctttg cactacttcg acagtcaatg catggctgct atgaactttc     1140
agaccatgca taatgtgaca acggaaacca agttcctctt aaagctggtc aaagagggag    1200
tggtgaaaga tctcagtgga ggcattgatc gtgaattttg aacacagaaa acctcagttg    1260
aaaatgcaac tctaactctg agagctgttt ttgacagcct tcttgatgta tttctccatc     1320
ctgcagatac tttgaagtgc agctcatgtt tttaactttt aatttaaaaa cacaaaaaaa    1380
attttagctc ttcccacttt ttttttccta tttatttgag gtcagtgttt gtttttgcac    1440 accatttttgt aaatgaaact taagaattga attggaaaga cttctcaaag agaattgtat    1500
gtaacgatgt tgtattgatt tttaagaaag taatttaatt tgtaaaactt ctgctcgttt    1560
acactgcaca ttgaatacag gtaactaatt ggaaggagag gggaggtcac tcttttgatg    1620
gtggccctga acctcattct ggttccctgc tgcgctgctt ggtgtgaccc acggaggatc    1680
cactcccagg atgacgtgct ccgtagctct gctgctgata ctgggtctgc gatgcagcgg    1740
cgtgaggcct gggctggttg gagaaggtca caacccttct ctgttggtct gccttctgct    1800
gaaagactcg agaaccaacc agggaagctg tcctggaggt ccctggtcgg agagggacat    1860
agaatctgtg acctctgaca actgtgaagc caccctgggc tacagaaacc acagtcttcc    1920
cagcaattat tacaattctt gaattccttg gggattttttt actgcccttt caaagcactt    1980
aagtgttaga tctaacgtgt tccagtgtct gtctgaggtg acttaaaaaa tcagaacaaa     2040
acttctatta tccagagtca tgggagagta caccctttcc aggaataatg ttttgggaaa    2100
cactgaaatg aaatcttccc agtattataa attgtgtatt taaaaaaaag aaactttttct    2160 gaatgcctac ctggcggtgt ataccaggca gtgtgccagt ttaaaaagat gaaaaagaat    2220
aaaaactttt gaggaaaaaa aaaaaaaaaa aaaaaaaaa aa                         2262
```

<210> SEQ ID NO 30
<211> LENGTH: 4909
<212> TYPE: DNA
<213> ORGANISM: Homo sapiens
<220> FEATURE:
<223> OTHER INFORMATION: IL1R1 glucocorticoid receptor-responsive gene

<400> SEQUENCE: 30

```
tagacgcacc ctctgaagat ggtgactccc tcctgagaag ctggaccccct tggtaaaaga     60 caaggccttc tccaagaaga atatgaaagt gttactcaga cttatttgtt tcatagctct    120
```

| | |
|---|---|
| actgatttct tctctggagg ctgataaatg caaggaacgt gaagaaaaaa taattttagt | 180 |
| gtcatctgca aatgaaattg atgttcgtcc ctgtcctctt aacccaaatg aacacaaagg | 240 |
| cactataact tggtataaag atgacagcaa gacacctgta tctacagaac aagcctccag | 300 |
| gattcatcaa cacaaagaga aactttggtt tgttcctgct aaggtggagg attcaggaca | 360 |
| ttactattgc gtggtaagaa attcatctta ctgcctcaga attaaaataa gtgcaaaatt | 420 |
| tgtggagaat gagcctaact tatgttataa tgcacaagcc atatttaagc agaaactacc | 480 |
| cgttgcagga gacggaggac ttgtgtgccc ttatatggag ttttttaaaa atgaaaataa | 540 |
| tgagttacct aaattacagt ggtataagga ttgcaaacct ctacttcttg acaatataca | 600 |
| ctttagtgga gtcaaagata ggctcatcgt gatgaatgtg gctgaaaagc atagagggaa | 660 |
| ctatacttgt catgcatcct acacatactt gggcaagcaa tatcctatta cccgggtaat | 720 |
| agaatttatt actctagagg aaaacaaacc cacaaggcct gtgattgtga gcccagctaa | 780 |
| tgagacaatg gaagtagact tgggatccca gatacaattg atctgtaatg tcaccggcca | 840 |
| gttgagtgac attgcttact ggaagtggaa tgggtcagta attgatgaag atgacccagt | 900 |
| gctaggggaa gactattaca gtgtggaaaa tcctgcaaac aaaagaagga gtaccctcat | 960 |
| cacagtgctt aatatatcgg aaattgaaag tagattttat aaacatccat ttacctgttt | 1020 |
| tgccaagaat acacatggta tagatgcagc atatatccag ttaatatatc cagtcactaa | 1080 |
| tttccagaag cacatgattg gtatatgtgt cacgttgaca gtcataattg tgtgttctgt | 1140 |
| tttcatctat aaaatcttca agattgacat tgtgctttgg tacagggatt cctgctatga | 1200 |
| ttttctccca ataaaagctt cagatggaaa gacctatgac gcatatatac tgtatccaaa | 1260 |
| gactgttggg aagggtctac cctctgactg tgatatttt tgtgtttaaag tcttgcctga | 1320 |
| ggtcttggaa aaacagtgtg gatataagct gttcatttat ggaagggatg actacgttgg | 1380 |
| ggaagacatt gttgaggtca ttaatgaaaa cgtaaagaaa agcagaagac tgattatcat | 1440 |
| tttagtcaga gaaacatcag gcttcagctg gctgggtggt tcatctgaag agcaaatagc | 1500 |
| catgtataat gctcttgttc aggatggaat taaagttgtc ctgcttgagc tggagaaaat | 1560 |
| ccaagactat gagaaaatgc cagaatcgat taaattcatt aagcagaaac atggggctat | 1620 |
| ccgctggtca ggggacttta cacagggacc acagtctgca aagacaaggt tctggaagaa | 1680 |
| tgtcaggtac cacatgccag tccagcgacg gtcaccttca tctaaacacc agttactgtc | 1740 |
| accagccact aaggagaaac tgcaaagaga ggctcacgtg cctctcgggt agcatggaga | 1800 |
| agttgccaag agttctttag gtgcctcctg tcttatggcg ttgcaggcca ggttatgcct | 1860 |
| catgctgact tgcagagttc atggaatgta actatatcat cctttatccc tgaggtcacc | 1920 |
| tggaatcaga ttattaaggg aataagccat gacgtcaata gcagcccagg cacttcaga | 1980 |
| gtagagggct tgggaagatc tttttaaaaag gcagtaggcc cggtgtggtg gctcacgcct | 2040 |
| ataatcccag cactttggga ggctgaagtg ggtggatcac cagaggtcag gagttcgaga | 2100 |
| ccagcccagc caacatggca aaaccccatc tctactaaaa atacaaaaat gagctaggca | 2160 |
| tggtggcaca cgcctgtaat cccagctaca cctgaggctg aggcaggaga attgcttgaa | 2220 |
| ccggggagac ggaggttgca gtgagccgag tttgggccac tgcactctag cctggcaaca | 2280 |
| gagcaagact ccgtctcaaa aaagggcaa taaatgccct ctctgaatgt ttgaactgcc | 2340 |
| aagaaaaggc atggagacag cgaactagaa gaaagggcaa gaaggaaata gccaccgtct | 2400 |
| acagatggct tagttaagtc atccacagcc caagggcggg gctatgcctt gtctggggac | 2460 |
| cctgtagagt cactgacccct ggagcggctc tcctgagagg tgctgcaggc aaagtgagac | 2520 |

```
tgacacctca ctgaggaagg gagacatatt cttggagaac tttccatctg cttgtatttt    2580
ccatacacat ccccagccag aagttagtgt ccgaagaccg aatttttattt tacagagctt    2640 gaaaactcac ttcaatgaac aaagggattc tccaggattc caaagttttg aagtcatctt    2700
agctttccac aggagggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc tccgtctgc aatgtcccctt gcacagccca    2880 cacatgaacc atccttccca tgatgccgct cttctgtcat cccgctcctg ctgaaacacc    2940
tcccaggggc tccacctgtt caggagctga agcccatgct ttcccaccag catgtcactc    3000
ccagaccacc tccctgccct gtcctccagc ttcccctcgc tgtcctgctg tgtgaattcc    3060
caggttggtc tggtggccat gtcgcctgcc cccagcactc ctctgtctct gctcttgcct    3120
cgacccttcc tcctcctttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt taattttgc aattattcta    3480 attttatata tagagaaagt gacctatttt ttaaaaaat cacactctaa gttctattga    3540
acctaggact tgagcctcca tttctggctt ctagtctggt gttctgagta cttgatttca    3600
ggtcaataac ggtcccccct cactccacac tggcacgttt gtgagaagaa atgacatttt    3660
gctaggaagt gaccgagtct aggaatgctt ttattcaaga caccaaattc caaacttcta    3720
aatgttggaa ttttcaaaaa ttgtgtttag atttttatgaa aaactcttct actttcatct    3780
attctttccc tagaggcaaa catttcttaa aatgtttcat tttcattaaa aatgaaagcc    3840
aaatttatat gccaccgatt gcaggacaca agcacagttt taagagttgt atgaacatgg    3900
agaggacttt tggtttttat atttctcgta tttaatatgg gtgaacacca acttttattt    3960
ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
ctgctgttcc aacagacagg gcctagcttt catttgacac acagactaca gccagaagcc    4140
catggagcag ggatgtcacg tcttgaaaag cctattagat gttttacaaa tttaattttg    4200
cagattattt tagtctgtca tccagaaaat gtgtcagcat gcatagtgct aagaaagcaa    4260
gccaatttgg aaacttaggt tagtgacaaa attggccaga gagtgggggt gatgatgacc    4320
aagaattaca agtagaatgg cagctggaat ttaaggaggg acaagaatca atggataagc    4380
gtgggtggag gaagatccaa acagaaaagt gcaaagttat tccccatctt ccaagggttg    4440
aattctggag gaagaagaca cattcctagt tccccgtgaa cttcctttga cttattgtcc    4500
ccactaaaac aaaacaaaaa acttttaatg ccttccacat taattagatt ttcttgcagt    4560 tttttttatgg cattttttta aagatgccct aagtgttgaa gaagagtttg caaatgcaac    4620
aaaatattta attaccggtt gttaaaactg gtttagcaca atttatattt tccctctctt    4680
gcctttctta tttgcaataa aaggtattga gccattttttt aaatgacatt tttgataaat    4740
tatgtttgta ctagttgatg aaggagtttt tttaacctg tttatataat tttgcagcag    4800
aagccaaatt ttttgtatat taaagcacca aattcatgta cagcatgcat cacggatcaa    4860
```

<210> SEQ ID NO 31
<211> LENGTH: 2210
<212> TYPE: DNA
<213> ORGANISM: Homo sapiens
<220> FEATURE:
<223> OTHER INFORMATION: BIN1 glucocorticoid receptor-responsive gene

<400> SEQUENCE: 31

| | | |
|---|---|---|
| tagactgtac ttattttcca ataaaatttt caaactttgt actgttaaa | | 4909 |

| | | |
|---|---|---|
| cgcgcccctc cctcctcgcg gacctggcgg tgccggcgcc cggagtggcc ctttaaaagg | | 60 |
| cagcttattg tccggagggg gcgggcgggg ggcgccgacc gcggcctgag gcccggcccc | | 120 |
| tccctctcc ctccctctgt ccccgcgtcg ctcgctggct agctcgctgg ctcgctcgcc | | 180 |
| cgtccggcgc acgctccgcc tccgtcagtt ggctccgctg tcgggtgcgc ggcgtggagc | | 240 |
| ggcagccggt ctggacgcgc ggccggggct ggggctggg agcgcggcgc gcaagatctc | | 300 |
| cccgcgcgag agcggcccct gccaccgggc gaggcctgcg ccgcgatggc agagatgggc | | 360 |
| agtaaagggg tgacggcggg aaagatcgcc agcaacgtgc agaagaagct cacccgcgcg | | 420 |
| caggagaagg ttctccagaa gctggggaag gcagatgaga ccaaggatga gcagtttgag | | 480 |
| cagtgcgtcc agaatttcaa caagcagctg acggagggca cccggctgca gaaggatctc | | 540 |
| cggacctacc tggcctccgt caaagccatg cacgaggctt ccaagaagct gaatgagtgt | | 600 |
| ctgcaggagg tgtatgagcc cgattggccc ggcaggatg aggcaaacaa gatcgcagag | | 660 |
| aacaacgacc tgctgtggat ggattaccac cagaagctgg tggaccaggc gctgctgacc | | 720 |
| atggacacgt acctgggcca gttccccgac atcaagtcac gcattgccaa gcgggggcgc | | 780 |
| aagctggtgg actacgacag tgcccggcac cactacgagt cccttcaaac tgccaaaaag | | 840 |
| aaggatgaag ccaaaattgc caaggccgag gaggagctca tcaaagccca gaaggtgttt | | 900 |
| gaggagatga atgtggatct gcaggaggag ctgccgtccc tgtggaacag ccgcgtaggt | | 960 |
| ttctacgtca acacgttcca gagcatcgcg ggcctggagg aaaacttcca caggagatg | | 1020 |
| agcaagctca accagaacct caatgatgtg ctggtcggcc tggagaagca cacgggagc | | 1080 |
| aacaccttca cggtcaaggc ccagcccaga aagaaaagta aactgttttc gcggctgcgc | | 1140 |
| agaaagaaga acagtgacaa cgcgcctgca aaagggaaca gagcccttc gcctccagat | | 1200 |
| ggctcccctg ccgccacccc cgagatcaga gtcaaccacg agccagagcc ggccggcggg | | 1260 |
| gccacgcccg ggccacccct ccccaagtcc ccatctcagc cagcagaggc ctcggaggtg | | 1320 |
| gcgggtggga cccaacctgc ggctggagcc caggagccag gggagacggc ggcaagtgaa | | 1380 |
| gcagcctcca gctctcttcc tgctgtcgtg gtggagacct tcccagcaac tgtgaatggc | | 1440 |
| accgtggagg gcggcagtgg ggccgggcgc ttggacctgc ccccaggttt catgttcaag | | 1500 |
| gtacaggccc agcacgacta cacggccact gacacagacg agctgcagct caaggctggt | | 1560 |
| gatgtggtgc tggtgatccc cttccagaac cctgaagagc aggatgaagg ctggctcatg | | 1620 |
| ggcgtgaagg agagcgactg gaaccagcac aaggagctgg agaagtgccg tggcgtcttc | | 1680 |
| cccgagaact tcactgagag ggtcccatga cggcggggcc caggcagcct ccgggcgtgt | | 1740 |
| gaagaacacc tcctcccgaa aaatgtgtgg ttcttttttt tgttttgttt tcgttttca | | 1800 |
| tcttttgaag agcaaaggga aatcaagagg agaccccag gcagaggggc gttctcccaa | | 1860 |
| agattaggtc gttttccaaa gagccgcgtc ccggcaagtc cggcggaatt caccagtgtt | | 1920 |
| cctgaagctg ctgtgtcctc tagttgagtt tctggcgccc ctgcctgtgc ccgcatgtgt | | 1980 |
| gcctggccgc agggcggggc tgggggctgc cgagccacca tgcttgcctg aagcttcggc | | 2040 |

```
cgcgccaccc gggcaagggt cctctttttcc tggcagctgc tgtgggtggg gcccagacac    2100
cagcctagcc tggctctgcc ccgcagacgg tctgtgtgct gtttgaaaat aaatcttagt    2160
gttcaaaaca aaatgaaaca aaaaaaaaat gataaaaact ctcaaaaaaa               2210
```

<210> SEQ ID NO 32
<211> LENGTH: 4664
<212> TYPE: DNA
<213> ORGANISM: Homo sapiens
<220> FEATURE:
<223> OTHER INFORMATION: WIPF1 glucocorticoid receptor-responsive gene

<400> SEQUENCE: 32

```
gcagcctccc ggcgctgagc gcttttcctg cccgcccggc tcagccctgc ggaccccggg      60 agaagttttcc cagaaaaaat gcccagcgcg gcgcggggct gcggagtcgt ccggagccgc    120
tgcgcgattt atcagcaaga ctgttgaacg cataactgcc caagatgcct gtccctcccc    180
ctccagcacc cccgccgccc ccgacgtttg cactggccaa tacagagaag cctaccttga    240
ataagacaga gcaggctggg agaaatgctc tcctttctga tatcagcaaa gggaagaaac    300
taaagaagac ggtcaccaat gacagaagtg caccaatact ggacaaacct aaaggagctg    360
gtgctggagg cggtggtggt ggcttttggtg gaggcggcgg atttggcgga ggaggtggtg    420
gcggaggcgg tggaagtttt ggaggggggcg gacctccagg tctgggagga ttgttccagg    480
ctggaatgcc gaagctgaga tccacggcca acagggataa tgattctgga ggaagccgac    540
caccattgtt gccaccggga ggaagatcca catctgcgaa accctttttca cccccaagtg    600 gcccagggag gtttcctgtg ccttctccag gccacagaag tggtccccca gagcctcaga    660
ggaaccgaat gccgccccca aggcccgacg tgggctcaaa gcctgatagc attcctcctc    720
cagtacctag tactccaaga cccattcaat caagtccgca caaccggggg tccccaccag    780
tgcccggagg ccccaggcag cccagcccccg ggcccactcc tcccccttttc cctggaaacc    840 gcggcactgc tttgggagga ggctcaatac gtcagtcccc cttgagctcc tcctcgccct    900
tctccaaccg gcctccctg ccgcctaccc ccagcagggc cttggatgac aaaccccctc    960
caccacctcc tccagtgggc aacaggccct ccatccacag ggaagcggtt ccccctcctc   1020
ctcctcagaa caacaagcct ccagtgcctt ccactccgcg gccttcggcc tcctcacagg   1080
ccccacctcc gccgccacct cccagcaggc ccgggccgcc tcctctgcct ccaagttcca   1140
gcggcaatga cgaaacccca agactccac agcggaatct gtccctcagt tcgtccacgc   1200
ccccgttacc ttcgccagga cgttcaggtc ctcttcctcc cccgcccagt gagagacccc   1260
cacctccagt gagggacccg ccaggccgat caggcccccct ccaccacct cctccagtaa   1320 gcagaaacgg cagcacatct cgggccctgc ctgctacccc tcagttgcca tccaggagtg   1380
gagtagacag tcccaggagt ggacccaggc ctcccttcc tcctgatagg cccagtgctg   1440
gggcacctcc cccacctcca ccatcaacat ctattagaaa tggcttccaa gactctccat   1500
gtgaagatga gtgggaaagc agattctact tccatccgat ttccgatttg ccacctccag   1560
agccatatgt acaaacgacc aaaagttatc ccagcaaact ggcaagaaac gaaagccgga   1620
gtggatccaa ccgaagagaa aggggtgctc caccactccc tcccatcccg aggtgatctt   1680
tgcctgctct tctctacca agctcaagag ctgcttctgt tgctatctaa gaactgcata   1740
ccctcctccc tgcttcttcc cttgtgcctc atgtatgggc aggaggaaag gtgggagggg   1800
gagtgggaat atgcgtgtgt gggtgggaat cggtaagaaa tgcacctagc tttcatatt    1860
```

```
gtgtttattc tccaggctat tgcttgcttc agctgcagcc tgcctgtgct ggctgctggg    1920
gtcgataggc ttttgtcgta ataggcagag atgacttgca tcccagcttt ccaccaacca    1980
aattcaaaca ttcactgctt atttgttaca gactgtaatt attaaagtcc ctgagagctg    2040
ttttctcccg ttccttttc gcatgcttgg cctcctctct gtttctatga accacagacc    2100
acctaagcaa gctgctgagt aagggctcac tggaaacttg cagtcacagg atgtccaatc    2160
tttggcagtc cgagcttggc tctaggacag agctgtccaa tagaaatata atgtgagccc    2220
catatacaat ttttacattt ctaatatatt ttaaacaagt gaagttaata tgcatccaaa    2280
atatttcaac ctgtaatcaa cataaaattt taatgagata ttttatatta tttttttggta   2340 ctgaatcttc aaaatccaga gtgtatttta cacttaccgc acatctccat tcagactagt    2400 cacatttta agtgctcagt agccacatgt ggctggtggc tactggatta gacagcacga    2460
gtctggaaga tggaagctag tgcagaaacc tcttgtttaa aaacaaaaa aggcaagatg    2520 ggcttgagcg attcaagagg caactaaaaa taaaattagg acccagcacc ttgtttgaca    2580
cacagtttga ccttcgattt tcctccctta acttccctct tcccttaata tctgtataca    2640
agtgttgctt caaagtacca aggtcagaaa ttgattcagt acggtttact aaagtcatgt    2700
ggaataaagc cattggaaac aaatggaaag cctgtcggga cttctgggct cagaaccagc    2760
tggctcacgc actccacttg tcagctggac ttctgccttg tgaaatggaa gcagcctttg    2820
ttcctttctg gctgagcaag ctcctgaggc tgggagagac taggaaggct tggtaggagg    2880 ggaaaaagt caggaaaaga tatcaaatca gaaacatgga agaagaaggg aaccgatttg     2940
agttggtggg caaaactcta aaaatctaaa tctgatgctt atgtaagggt tgagcgaatt    3000
agggagattg ctagtggaaa ttggagggaa tttgttttgc atcatttgtc taggatctat    3060
gcaaatatag ctcccactaaa ggaccatagg gaagagccag ccttgccttt cttatatga    3120 ttttgtttac aaaattttac tgggactttt aaatctagct atagagttgg gaaaaaatat    3180
ttccacttag atattttaca tggttttgtt taaaattacc attacttgtt ttttaaaaac    3240
acatgaccac atatgtatat gtatatctac ctaaacattg tatcatggtt tcagtatgtt    3300
attcatgtat tactgggaga tgctaccaag aaaccaaccc aaagaaaatt ctgaaaaata    3360
catttctatt tatagaataa atgtttcatt tatataaaag caaagaact tagagttcta    3420 ataaatggga tgtctaataa attatgaagt tactgatttg aatatattat atttttataa    3480
cttccttgcc aaagtcctga tttagtacat tagagaacct gtgtttcctc tctcctctac    3540
cattcatctc tcttccatac agtcatttgg gcttttttact caaagagaat caagaaataa    3600
taaggtataa caagcttggc aaagtgttgg cttttttaaaa aaaattttt ttaatctcta    3660 gcagtttggt aatttagcag catcatttat ttgggattct tttatctgat ttcaacagtg    3720
aaaaacatcc ctatgataaa gcctaatgac ccatttcaca aaagatggaa tttgcccttc    3780
ctagaaaata tgacggagaa aagtctgact cagagaaagt gagtctgaat tttataaggg    3840
gtagtaagaa ttggacaatt cctttgcata tctgaacttg gcaggtaccg ttctaaatct    3900
gaaacagggt gatagctcaa agttgccatt catccagaat agattgtttt agaatgtagt    3960
gtttaagtga ctgtttcatt aatacaccta cacccttct ttgaaagttt gcaacctaat     4020
tgcatctaaa actatgaata agttctgtgg taaaatctta aactatggaa aattacaaaa    4080
atgaattttt cttcccctgaa atcagagctt acatgtgtgt tttttaataa catttttcaga   4140 taaatgtatt caacatgtaa tacagtattt taacattcac ctcttatttt atattgaaat    4200
gtattacagt attaaaactc agtggtcagt atttatttca ctatgcattt tatttagtaa    4260
```

```
aagccaggag aaatgtttaa tccaatggtg ccttactttg tgatttaaaa gaaatcaact      4320 ttttttatg tctaagtagt agattatttg catatttgta aaaactgtta ggtctttata       4380 tttaaagtg taataccagt tttgttattt tagtagcaga aatgggatga ttgttaaagt       4440
tccccaaaaa tgttggcatg aaattaattt ttccctcctt atagtcaagg accgtagagg      4500
aagaaaaact ttttttcat accatgcact atgtaaacag acacattttg ctatctgtgt      4560
catcaggata gtgtaagtgg tagggtagag actaccctag acatctgcat ctttgtaagt     4620
tagccagaca ataaagaaaa gcagaatgaa aaaaaaaaa aaaa                       4664

<210> SEQ ID NO 33
<211> LENGTH: 1166
<212> TYPE: DNA
<213> ORGANISM: Homo sapiens
<220> FEATURE:
<223> OTHER INFORMATION: TFPI glucocorticoid receptor-responsive gene

<400> SEQUENCE: 33
attcccaact gccagtgatc tctgaagccg actctgaggc tccctctttg ctctaacaga      60
cagcagcgac tttaggctgg ataatagtca aattcttacc tcgctctttc actgctagta     120
agatcagatt gcgtttcttt cagttactct tcaatcgcca gtttcttgat ctgcttctaa     180
aagaagaagt agagaagata atcctgtct tcaatacctg gaaggaaaaa caaaataacc      240
tcaactccgt tttgaaaaaa acattccaag aactttcatc agagatttta cttagatgat     300
ttacacaatg aagaaagtac atgcactttg ggcttctgta tgcctgctgc ttaatcttgc     360
ccctgcccct cttaatgctg attctgagga agatgaagaa cacacaatta tcacagatac     420
ggagttgcca ccactgaaac ttatgcattc attttgtgca ttcaaggcgg atgatggccc     480
atgtaaagca atcatgaaaa gatttttctt caatattttc actcgacagt gcgaagaatt     540
tatatatggg ggatgtgaag gaaatcagaa tcgatttgaa agtctggaag agtgcaaaaa     600
aatgtgtaca agagataatg caaacaggat tataaagaca acattgcaac aagaaaagcc     660
agatttctgc ttttttggaag aagatcctgg aatatgtcga ggttatatta ccaggtattt     720
ttataacaat cagacaaaac agtgtgaacg tttcaagtat ggtggatgcc tgggcaatat     780
gaacaatttt tgagacactgg aagaatgcaa gaacatttgt gaagatggtc cgaatggttt     840
ccaggtggat aattatggaa cccagctcaa tgctgtgaat aactccctga ctccgcaatc     900
aaccaaggtt cccagccttt ttgttacaaa agaaggaaca aatgatggtt ggaagaatgc     960
ggctcatatt taccaagtct ttctgaacgc cttctgcatt catgcatcca tgttctttct    1020
aggattggat agcatttcat gcctatgtta atatttgtgc ttttggcatt tccttaatat    1080
ttatatgtat acgtgatgcc tttgatagca tactgctaat aaagttttaa tatttacatg    1140
catagtaaaa aaaaaaaaaa aaaaaa                                         1166

<210> SEQ ID NO 34
<211> LENGTH: 8449
<212> TYPE: DNA
<213> ORGANISM: Homo sapiens
<220> FEATURE:
<223> OTHER INFORMATION: FN1 glucocorticoid receptor-responsive gene

<400> SEQUENCE: 34
gcccgcgccg gctgtgctgc acaggggag gagagggaac cccaggcgcg agcgggaaga       60
ggggacctgc agccacaact tctctggtcc tctgcatccc ttctgtccct ccacccgtcc     120
```

-continued

```
ccttccccac cctctggccc ccaccttctt ggaggcgaca accccgggga ggcattagaa      180 gggattttc  ccgcaggttg cgaagggaag caaacttggt ggcaacttgc ctcccggtgc      240
gggcgtctct cccccaccgt ctcaacatgc ttaggggtcc ggggcccggg ctgctgctgc      300
tggccgtcca gtgcctgggg acagcggtgc cctccacggg agcctcgaag agcaagaggc      360
aggctcagca aatggttcag ccccagtccc cggtggctgt cagtcaaagc aagcccggtt      420
gttatgacaa tggaaaacac tatcagataa atcaacagtg ggagcggacc tacctaggca      480
atgcgttggt ttgtacttgt tatggaggaa gccgaggttt aactgcgag  agtaaacctg      540 aagctgaaga gacttgcttt gacaagtaca ctgggaacac ttaccgagtg ggtgacactt      600
atgagcgtcc taaagactcc atgatctggg actgtacctg catcgggct  gggcgaggga      660 gaataagctg taccatcgca aaccgctgcc atgaagggg  tcagtcctac aagattggtg      720
acacctggag gagaccacat gagactggtg gttacatgtt agagtgtgtg tgtcttggta      780
atggaaaagg agaatggacc tgcaagccca tagctgagaa gtgttttgat catgctgctg      840
ggacttccta tgtggtcgga gaaacgtggg agaagcccta ccaaggctgg atgatggtag      900
attgtacttg cctgggagaa ggcagcggac gcatcacttg cacttctaga aatagatgca      960
acgatcagga cacaaggaca tcctatagaa ttggagacac ctggagcaag aaggataatc     1020
gaggaaacct gctccagtgc atctgcacag gcaacggccg aggagagtgg aagtgtgaga     1080
ggcacacctc tgtgcagacc acatcgagcg gatctggccc cttcaccgat gttcgtgcag     1140
ctgtttacca accgcagcct caccccage  ctcctcccta tggccactgt gtcacagaca     1200
gtggtgtggt ctactctgtg gggatgcagt ggctgaagac acaaggaaat aagcaaatgc     1260
tttgcacgtg cctgggcaac ggagtcagct gccaagagac agctgtaacc cagacttacg     1320
gtggcaactc aaatggagag ccatgtgtct taccattcac ctacaatggc aggacgttct     1380
actcctgcac cacagaaggg cgacaggacg gacatctttg gtgcagcaca acttcgaatt     1440
atgagcagga ccagaaatac tcttttctgca cagaccacac tgttttggtt cagactcgag     1500
gaggaaattc caatggtgcc ttgtgccact tccccttcct atacaacaac cacaattaca     1560
ctgattgcac ttctgagggc agaagagaca acatgaagtg gtgtgggacc acacagaact     1620
atgatgccga ccagaagttt gggttctgcc ccatggctgc ccacgaggaa atctgcacaa     1680
ccaatgaagg ggtcatgtac cgcattggag atcagtggga taagcagcat gacatggcgtc    1740 acatgatgag gtgcacgtgt gttgggaatg gtcgtgggga atggacatgc attgcctact     1800
cgcagcttcg agatcagtgc attgttgatg acatcactta caatgtgaac gacacattcc     1860
acaagcgtca tgaagagggg cacatgctga actgtacatg cttcggtcag gtcggggca      1920 ggtggaagtg tgatcccgtc gaccaatgcc aggattcaga gactgggacg ttttatcaaa     1980
ttggagattc atgggagaag tatgtgcatg gtgtcagata ccagtgctac tgctatggcc     2040
gtggcattgg ggagtggcat tgccaacctt tacagaccta ccaagctcca gtggtcctg      2100 tcgaagtatt tatcactgag actccgagtc agcccaactc ccaccccatc cagtggaatg     2160
caccacagcc atctcacatt tccaagtaca ttctcaggtg gagacctaaa aattctgtag     2220
gccgttggaa ggaagctacc ataccaggcc acttaaactc ctacaccatc aaaggcctga     2280
agcctggtgt ggtatacgag ggccagctca tcagcatcca gcagtacggc caccaagaag     2340
tgactcgctt tgacttcacc accaccagca ccagcacacc tgtgaccagc aacaccgtga     2400
caggagagac gactcccttt tctcctcttg tggccacttc tgaatctgtg accgaaatca     2460
cagccagtag ctttgtggtc tcctgggtct cagcttccga caccgtgtcg ggattccggg     2520
```

```
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cgggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccagggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960
gcacttttga taacctgagt cccggcctgg agtacaatgt cagtgtttac actgtcaagg    4020
atgacaagga aagtgtccct atctctgata ccatcatccc agctgttcct cctcccactg    4080
acctgcgatt caccaacatt ggtccagaca ccatgcgtgt cacctgggct ccaccccat     4140 ccattgattt aaccaacttc ctggtgcgtt actcacctgt gaaaaatgag gaagatgttg    4200
cagagttgtc aatttctcct tcagacaatg cagtggtctt aacaaatctc ctgcctggta    4260
cagaatatgt agtgagtgtc tccagtgtct acgaacaaca tgagagcaca cctcttagag    4320
gaagacagaa aacaggtctt gattccccaa ctggcattga cttttctgat attactgcca    4380 actctttttac tgtgcactgg attgctcctc gagccaccat cactggctac aggatccgcc    4440
atcatcccga gcacttcagt gggagacctc gagaagatcg ggtgccccac tctcggaatt    4500
ccatcaccct caccaacctc actccaggca cagagtatgt ggtcagcatc gttgctctta    4560
atggcagaga ggaaagtccc ttattgattg ccaacaatc aacagtttct gatgttccga     4620
gggacctgga agttgttgct gcgacccca ccagcctact gatcagctgg gatgctcctg     4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
```

-continued

```
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct tgcagcccac agtggagtat gtggttagtg    5100
tctatgctca gaatccaagc ggagagagtc agcctctggt tcagactgca gtaaccaaca    5160
ttgatcgccc taaaggactg gcattcactg atgtggatgt cgattccatc aaaattgctt    5220
gggaaagccc acaggggcaa gtttccaggt acagggtgac ctactcgagc cctgaggatg    5280
gaatccatga gctattccct gcacctgatg gtgaagaaga cactgcagag ctgcaaggcc    5340
tcagaccggg ttctgagtac acagtcagtg tggttgcctt gcacgatgat atggagagcc    5400 agccctgat tggaacccag tccacagcta ttcctgcacc aactgacctg aagttcactc    5460
aggtcacacc cacaagcctg agcgcccagt ggacaccacc caatgttcag ctcactggat    5520
atcgagtgcg ggtgaccccc aaggagaaga ccggaccaat gaaagaaatc aaccttgctc    5580
ctgacagctc atccgtggtt gtatcaggac ttatggtggc caccaaatat gaagtgagtg    5640
tctatgctct taaggacact ttgcaagca gaccagctca gggagttgtc accactctgg    5700
agaatgtcag cccaccaaga agggctcgtg tgacagatgc tactgagacc accatcacca    5760
ttagctggag aaccaagact gagacgatca ctggcttcca agttgatgcc gttccagcca    5820
atggccagac tccaatccag agaaccatca agccagatgt cagaagctac accatcacag    5880
gtttacaacc aggcactgac tacaagatct acctgtacac cttgaatgac aatgctcgga    5940
gctcccctgt ggtcatcgac gcctccactg ccattgatgc accatccaac ctgcgtttcc    6000
tggccaccac acccaattcc ttgctggtat catggcagcc gccacgtgcc aggattaccg    6060
gctacatcat caagtatgag aagcctgggt ctcctcccag agaagtggtc cctcggcccc    6120
gccctggtgt cacagaggct actattactg gcctggaacc gggaaccgaa tatacaattt    6180
atgtcattgc cctgaagaat aatcagaaga gcgagcccct gattggaagg aaaaagacag    6240
acgagcttcc ccaactggta acccttccac accccaatct tcatggacca gagatcttgg    6300
atgttccttc cacagttcaa aagaccccct tcgtcaccca ccctgggtat gacactggaa    6360
atggtattca gcttcctggc acttctggtc agcaacccag tgttgggcaa caaatgatct    6420
ttgaggaaca tggttttagg cggaccacac cgcccacaac ggccacccc ataaggcata    6480 ggccaagacc ataccgcccg aatgtaggac aagaagctct ctctcagaca accatctcat    6540 gggcccatt ccaggacact tctgagtaca tcatttcatg tcatcctgtt ggcactgatg    6600 aagaacccttt acagttcagg gttcctggaa cttctaccag tgccactctg acaggcctca    6660
ccagaggtgc cacctacaac atcatagtgg aggcactgaa agaccagcag aggcataagg    6720
ttcgggaaga ggttgttacc gtgggcaact ctgtcaacga aggcttgaac caacctacgg    6780
atgactcgtg ctttgacccc tacacagttt cccattatgc cgttggagat gagtgggaac    6840
gaatgtctga atcaggcttt aaactgttgt gccagtgctt aggctttgga agtggtcatt    6900
tcagatgtga ttcatctaga tggtgccatg acaatggtgt gaactacaag attggagaga    6960
agtgggaccg tcaggagaa aatggccaga tgatgagctg cacatgtctt gggaacggaa    7020
aaggagaatt caagtgtgac cctcatgagg caacgtgtta tgatgatggg aagacatacc    7080
acgtaggaga acagtggcag aaggaatatc tcggtgccat ttgctcctgc acatgctttg    7140
gaggccagcg gggctggcgc tgtgacaact gccgcagacc tgggggtgaa cccagtcccg    7200
aaggcactac tggccagtcc tacaaccagt attctcagag ataccatcag agaacaaaca    7260
```

```
ctaatgttaa ttgcccaatt gagtgcttca tgcctttaga tgtacaggct gacagagaag      7320
attcccgaga gtaaatcatc tttccaatcc agaggaacaa gcatgtctct ctgccaagat      7380
ccatctaaac tggagtgatg ttagcagacc cagcttagag ttcttctttc tttcttaagc      7440
cctttgctct ggaggaagtt ctccagcttc agctcaactc acagcttctc caagcatcac      7500
cctgggagtt tcctgagggt tttctcataa atgagggctg cacattgcct gttctgcttc      7560
gaagtattca ataccgctca gtattttaaa tgaagtgatt ctaagatttg gtttgggatc      7620
aataggaaag catatgcagc caaccaagat gcaaatgttt tgaaatgata tgaccaaaat      7680
tttaagtagg aaagtcaccc aaacacttct gctttcactt aagtgtctgg cccgcaatac      7740
tgtaggaaca agcatgatct tgttactgtg atattttaaa tatccacagt actcactttt      7800
tccaaatgat cctagtaatt gcctagaaat atctttctct tacctgttat ttatcaattt      7860
ttcccagtat ttttatacgg aaaaaattgt attgaaaaca cttagtatgc agttgataag      7920
aggaatttgg tataattatg gtgggtgatt attttttata ctgtatgtgc caaagcttta      7980
ctactgtgga aagacaactg ttttaataaa agatttacat tccacaactt gaagttcatc      8040
tatttgatat aagacacctt cggggggaaat aattcctgtg aatattcttt ttcaattcag      8100
caaacatttg aaaatctatg atgtgcaagt ctaattgttg atttcagtac aagattttct      8160
aaatcagttg ctacaaaaac tgattggttt ttgtcacttc atctcttcac taatggagat      8220
agctttacac tttctgcttt aatagattta agtggacccc aatatttatt aaaattgcta      8280
gtttaccgtt cagaagtata atagaaataa tctttagttg ctcttttcta accattgtaa      8340
ttcttccctt cttccctcca cctttccttc attgaataaa cctctgttca aagagattgc      8400
ctgcaaggga aataaaaatg actaagatat taaaaaaaaa aaaaaaaa                   8449

<210> SEQ ID NO 35
<211> LENGTH: 4625
<212> TYPE: DNA
<213> ORGANISM: Homo sapiens
<220> FEATURE:
<223> OTHER INFORMATION: FAM134A glucocorticoid receptor-responsive gene

<400> SEQUENCE: 35
agcgctccgc agtcacgtga cgctcgtccg caacctctgc tgtcctccgc ggcgccccct        60
tccgcctgac gcgcccccgg cggcggccgc gcagccctgg ctcctcgcgg gctcgggcgg       120
cggctgcggc ggggctatgg cgagcggcgg tggcggggggt aacactggcg cgggtggggg      180
gccggggatg ggcctgagcc tgggcctggg tctgggtctg agcctaggca tgagtgaggc      240
caccagtgag gcagaggagg aggcggccac ggccgaggcg gtgggacgcc tggccacgac      300
gctgtggctg cggctccgcg gctgggaggc ggtgctggcg gcgcgcagc ggttgctggt      360 gtgggagaag ccgctgcaca gcctggtcac ggcggccgcg ctcaacggcc tcttctggtt      420
gctgtcttcc tcgtccctcc ggcccttctt cctactcagc gtctcacttt tggcctattt      480
tctgctggat ctctggcagc ctcgctttct ccctgacgtt tcagcatcat ccccagagga      540
gccacactct gacagtgagg gtgcggggtc aggcgcccgg ccgcacctgc tgagtgtgcc      600
cgagttgtgc agatacctgg ctgagagctg gctcaccttc cagattcacc tgcaggagct      660
gctgcagtac aagaggcaga atccagctca gttctgcgtt cgagtctgct ctggctgtgc      720
tgtgttggct gtgttgggac actatgttcc agggattatg atttcctaca ttgtcttgtt      780
gagtatcctg ctgtggcccc tggtggttta tcatgagctg atccagagga tgtacactcg      840
```

| | |
|---|---|
| cctggagccc ctgctcatgc agctggacta cagcatgaag gcagaagcca atgccctgca | 900 |
| tcacaaacac gacaagagga agcgtcaggg gaagaatgca ccccaggag gtgatgagcc | 960 |
| actggcagag acagagagtg aaagcgaggc agagctggct ggcttctccc cagtggtgga | 1020 |
| tgtgaagaaa acagcattgg ccttggccat tacagactca gagctgtcag atgaggaggc | 1080 |
| ttctatcttg gagagtggtg gcttctccgt atcccgggcc acaactccgc agctgactga | 1140 |
| tgtctccgag gatttggacc agcagagcct gccaagtgaa ccagaggaga ccctaagccg | 1200 |
| ggacctaggg gagggagagg agggagagct ggcccctccc gaagacctac taggccgtcc | 1260 |
| tcaagctctg tcaaggcaag ccctggactc ggaggaagag gaagaggatg tggcagctaa | 1320 |
| ggaaaccttg ttgcggctct catccccct ccactttgtg aacacgcact tcaatggggc | 1380 |
| agggtccccc ccagatggag tgaaatgctc ccctggagga ccagtggaga cactgagccc | 1440 |
| cgagacagtg agtggtggcc tcactgctct gcccggcacc ctgtcacctc cactttgcct | 1500 |
| tgttggaagt gacccagccc cctcccttc cattctccca cctgttcccc aggactcacc | 1560 |
| ccagcccctg cctgcccctg aggaagaaga ggcactcacc actgaggact ttgagttgct | 1620 |
| ggatcagggg gagctggagc agctgaatgc agagctgggc ttggagccag agacaccgcc | 1680 |
| aaaacccct gatgctccac ccctggggcc cgacatccat tctctggtac agtcagacca | 1740 |
| agaagctcag gccgtggcag agccatgagc cagccgttga ggaaggagct gcaggcacag | 1800 |
| tagggcttcc tggctaggag tgttgctgtt tcctcctttg cctaccactc tggggtgggg | 1860 |
| cagtgtgtgg ggaagctggc tgtcggatgg tagctattcc accctctgcc tgcctgcctg | 1920 |
| cctgctgtcc tgggcatggt gcagtacctg tgcctaggat tggttttaaa tttgtaaata | 1980 |
| attttccatt tgggttagtg gatgtgaaca gggctaggga agtccttccc acagcctgcg | 2040 |
| cttgcctccc tgcctcatct ctattctcat tccactatgc cccaagccct ggtggtctgg | 2100 |
| cccttttcttt ttcctcctat cctcagggac ctgtgctgct ctgccctcat gtcccacttg | 2160 |
| gttgtttagt tgaggcactt tataattttt ctcttgtctt gtgttccttt ctgctttatt | 2220 |
| tccctgctgt gtcctgtcct tagcagctca accccatcct tgccagctc ctcctatccc | 2280 |
| gtgggcactg ccaagctttt agggaggctc ctggtctggg aagtaaagag taaacctggg | 2340 |
| gcagtgggtc aggccagtag ttacactctt aggtcactgt agtctgtgta accttcactg | 2400 |
| catccttgcc ccattcagcc cggccttca tgatgcagga gagcagggat cccgcagtac | 2460 |
| atggcgccag cactggagtt ggtgagcatg tgctctctct tgagattagg agcttcctta | 2520 |
| ctgctcctct gggtgatcca agtgtagtgg gaccccctac tagggtcagg aagtggacac | 2580 |
| taacatctgt gcaggtgttg acttgaaaaa taaagtgttg attggctaga actgctgcct | 2640 |
| ccctgactgt gagctgcctt ccacaccctg cactgcactg tgttctctcc tcacccttaa | 2700 |
| cctgcttcac tccagtctgt tctggctgtt tattaccttg ttgcaaaaca gggccgaagc | 2760 |
| aaggattacc ttgacaaccc tagcttctcc ttagccatct tccttgacag tgtgatctgt | 2820 |
| ttagtgagat ttagcatgtg tgaataaagt atatgcagga ggaaattgct ttgtcttccc | 2880 |
| aatcggtaga aattcgggac cataaaaatt gtgttttacc atgtggccta caaccttaac | 2940 |
| actgcttct taagaagtct tcacccatct acatgctaac aactcactca gcctggattt | 3000 |
| atctttactg gggaagccaa acaagcaata gaggaccttt acctgtgtta gaaatgagtt | 3060 |
| ggagccaagg aacactgaag aaatagtatc ttaacagtta ctgagtccat tgtatgtgct | 3120 |
| tggctctgct ctgagtgatt tatatgtatt aagattttc ctcacaggtc agatatatac | 3180 |
| tgttactaac ttcatttat agacaggtta agcttcctga aggccacagg tcccagtaaa | 3240 |

```
ttgtggagcc agaacccaaa cccaagaagt tttggcttca gcaaatgcat cagacagccc    3300
ctgtccatta atagggcaca ggtaggaaga tgcacaagga tgtgggaact atagagaacc    3360
aatctgatgc cttggcttaa caaagagtgg acatggcaag ccttcctctt tggggaagaa    3420
aagcccagaa ctgagcagat ggcctccttt atgagttcat gtcctccgcc ttcagctgga    3480
ggtaccatat ggcgatgcta cctgtctttc tgctggaggt accatatggt aatgctgcct    3540
ggctgtctgc tggaggtacc atatggtaat gctgcctgtc tttctgaggt tgactttat    3600
gccatgtctt tcctaagtgt gtaagaattt ttctgtttgc ttcacatttg actgagaatc    3660
attctagggt ttgattgagc ccctgtcctg tgccactaaa ggaactcgaa ctttttcatca   3720
cttagagatt tcagagggga atggaaaaac agttctaatc aataagcaag caattcaaga   3780
aaaatagaat taatcaggca atgactgcaa catgtcctat cttaatcta ttttcttatt     3840
aagcttggac attgacaata gaaccagaag cttgtagctg gatcaaaata ttctccatag   3900
gcctggagtt tcatgagggt ctattctttt gttgttgttg ttttggtttt ttgttttttg   3960
tgggtttttt ttttttttt tttgagacgg agtcttgttc tgttgcccag gctggagtgc    4020
aatggtgcag tcttggttca ctgcaacctc tgcctcccag gttcaaacaa ttctcctgcc   4080
tcagccgtcc aagtagctgg gattacaggt gcatgccacg atgcctggct atttttgta   4140
ttttagtag aggtgggggtt tcaccatgtt ggccaggctg gtctcgaact cctgacctca   4200
ggtgattcac ccacctcggc ctcccaaagt gctgggatta caggtgtgag ccacggcgcc   4260
cagcctcatg agggtctatt ctttacattc accatggtct gatggttgct acatgtttgt   4320
ctatgattttt tttttctat tatcaggtgt cttggccggt tcatgcccca cgatgaaagg   4380
gccagaggtt ttcatatgag taaaagaaaa aagcagaaat gtgaaaccta caattaggct   4440
aaacaaaaat caactggaaa agtacaggct gaggggagaa gagttggcta catgtttatg   4500
ttaggggagg agggagtaca ttttagctat gtattcaaac agctaatagt ttaatgttgc   4560
tgcttataaa cttaatttta ggctgcatta ataaaagtgt agtctccaaa acaaaaaaaa   4620
aaaaa                                                               4625
```

<210> SEQ ID NO 36
<211> LENGTH: 7556
<212> TYPE: DNA
<213> ORGANISM: Homo sapiens
<220> FEATURE:
<223> OTHER INFORMATION: NRIP1 glucocorticoid receptor-responsive gene

<400> SEQUENCE: 36

```
gcaggcgcct tcgcggaccg agcctgacgg agccggaggc tgggagccgc ggcggcctgg    60
ggaagtgttt ggattgtgag ctatttcaga actgttctca ggactcatta ttttaacatt   120
tgggagaaac acagccagaa gatgcacact tgactgaagg aggacaggga atctgaagac   180
tccggatgac atcagagcta cttttcaaca gccttctcaa ttttctttct cagaaagcag   240
aggctcagag cttggagaca gacgaacact gatatttgca tttaatgggg aacaaaagat   300
gaagaaggaa aaggaatata ttcactaagg attctatctg cttactgcta cagacctatg   360
tgttaaggaa ttcttctcct cctccttgcg tagaagttga tcagcactgt ggtcagactg   420
catttatctt gtcattgcca gaagaaatct tggacagaat gtaacagtac gtctctctct   480
gattgcgatg gaaggtgata aactgatact ccttattaa agttacatcg cactcaccac    540
agaaaaccat tctttaaagt gaatagaaac caagcccttg tgaacacttc tattgaacat    600
```

```
gactcatgga gaagagcttg gctctgatgt gcaccaggat tctattgttt taacttacct    660
agaaggatta ctaatgcatc aggcagcagg gggatcaggt actgccgttg acaaaaagtc    720
tgctgggcat aatgaagagg atcagaactt taacatttct ggcagtgcat ttcccacctg    780
tcaaagtaat ggtccagttc tcaatacaca tacatatcag gggtctggca tgctgcacct    840
caaaaaagcc agactgttgc agtcttctga ggactggaat gcagcaaagc ggaagaggct    900
gtctgattct atcatgaatt taaacgtaaa gaaggaagct ttgctagctg gcatggttga    960
cagtgtgcct aaaggcaaac aggatagcac attactggcc tctttgcttc agtcattcag   1020
ctctaggctg cagactgttg ctctgtcaca acaaatcagg cagagcctca aggagcaagg   1080
atatgccctc agtcatgatt ctttaaaagt ggagaaggat ttaaggtgct atggtgttgc   1140
atcaagtcac ttaaaaactt tgttgaagaa agtaaagtt aaagatcaaa agcctgatac    1200
gaatcttcct gatgtgacta aaaacctcat cagagatagg tttgcagagt ctcctcatca   1260
tgttggacaa agtggaacaa aggtcatgag tgaaccgttg tcatgtgctg caagattaca   1320
ggctgttgca agcatggtgg aaaaagggc tagtcctgcc acctcaccta aacctagtgt    1380
tgcttgtagc cagttagcat tacttctgtc aagcgaagcc catttgcagc agtattctcg   1440
agaacacgct ttaaaaacgc aaaatgcaaa tcaagcagca agtgaaagac ttgctgctat   1500
ggccagattg caagaaaatg ccagaagga tgttggcagt taccagctcc caaaggaat     1560 gtcaagccat cttaatggtc aggcaagaac atcatcaagc aaactgatgg ctagcaaaag   1620
tagtgctaca gtgtttcaaa atccaatggg tatcattcct tcttccccta aaaatgcagg   1680
ttataagaac tcactggaaa gaaacaatat aaaacaagct gctaacaata gtttgctttt   1740
acatcttctt aaaagccaga ctatacctaa gccaatgaat ggacacagtc acagtgagag   1800
aggaagcatt tttgaggaaa gtagtacacc tacaactatt gatgaatatt cagataacaa   1860
tcctagtttt acagatgaca gcagtggtga tgaaagttct tattccaact gtgttcccat   1920
agacttgtct tgcaaacacc gaactgaaaa atcagaatct gaccaacctg tttccctgga   1980
taacttcact caatccttgc taaacacttg ggatccaaaa gtcccagatg tagatatcaa   2040
agaagatcaa gataccctcaa agaattctaa gctaaactca caccagaaag taacacttct   2100
tcaattgcta cttggccata agaatgaaga aaatgtagaa aaaaacacca gccctcaggg   2160
agtacacaat gatgtgagca agttcaatac acaaaattat gcaaggactt ctgtgataga   2220 aagcccagt acaaatcgga ctactccagt gagcactcca cctttactta catcaagcaa    2280
agcagggtct cccatcaatc tctctcaaca ctctctggtc atcaaatgga attccccacc   2340
atatgtctgc agtactcagt ctgaaaagct aacaaatact gcatctaacc actcaatgga   2400
ccttacaaaa agcaaagacc caccaggaga gaaaccagcc caaatgaag gtgcacagaa    2460 ctctgcaacg tttagtgcca gtaagctgtt acaaaattta gcacaatgtg gaatgcagtc   2520
atccatgtca gtggaagagc agagacccag caaacagctg ttaactggaa acacagataa   2580
accgataggt atgattgata gattaaatag ccctttgctc tcaaataaaa caaatgcagt   2640
tgaagaaaat aaagcattta gtagtcaacc aacaggtcct gaaccagggc tttctggttc   2700
tgaaatagaa aatctgcttg aaagacgtac tgtcctccag ttgctcctgg ggaaccccaa   2760
caaagggaag agtgaaaaaa aagagaaaac tcccttaaga gatgaaagta ctcaggaaca   2820
ctcagagaga gctttaagtg aacaaatact gatggtgaaa ataaaatctg agccttgtga   2880
tgacttacaa attcctaaca caaatgtgca cttgagccat gatgctaaga gtgccccatt   2940
cttgggtatg gctcctgctg tgcagagaag cgcacctgcc ttaccagtgt ccgaagactt   3000
```

```
taaatcggag cctgtttcac ctcaggattt ttctttctcc aagaatggtc tgctaagtcg    3060
attgctaaga caaaatcaag atagttacct ggcagatgat tcagacagga gtcacagaaa    3120
taatgaaatg gcacttctag aatcaaagaa tctttgcatg gtccctaaga aaaggaagct    3180
ttatactgag ccattagaaa atccatttaa aaagatgaaa aacaacattg ttgatgctgc    3240
aaacaatcac agtgccccag aagtactgta tgggtccttg cttaaccagg aagagctgaa    3300
atttagcaga aatgatcttg aatttaaata tcctgctggt catggctcag ccagcgaaag    3360
tgaacacagg agttgggcca gagagagcaa aagctttaat gttctgaaac agctgcttct    3420
ctcagaaaac tgtgtgcgag atttgtcccc gcacagaagt aactctgtgg ctgacagtaa    3480
aaagaaagga cacaaaaata atgtgaccaa cagcaaacct gaatttagca tttcttcttt    3540
aaatggactg atgtacagtt ccactcagcc cagcagttgc atggataaca ggacattttc    3600
atacccaggt gtagtaaaaa ctcctgtgag tcctactttc cctgagcact tgggctgtgc    3660
agggtctaga ccagaatctg gcttttgaa tgggtgttcc atgcccagtg agaaaggacc    3720
cattaagtgg gttatcactg atgcggagaa gaatgagtat gaaaaagact ctccaagatt    3780
gaccaaaacc aacccaatac tatattacat gcttcaaaaa ggaggcaatt ctgttaccag    3840
tcgagaaaca caagacaagg acatttggag ggaggcttca tctgctgaaa gtgtctcaca    3900
ggtcacagcc aaagaagagt tacttcctac tgcagaaacg aaagcttctt tctttaattt    3960
aagaagccct tacaatagcc atatgggaaa taatgcttct cgcccacaca gcgcaaatgg    4020
agaagtttat ggacttctgg gaagcgtgct aacgataaag aaagaatcag aataaaatgt    4080
acctgccatc cagttttgga tcttttaaa actaatgagt atgaacttga gatctgtata    4140
aataagagca tgatttgaaa aaagcatgg tataattgaa actttttca ttttgaaaag    4200 tattggttac tggtgatgtt gaaatatgca tactaattt tgcttaacat tagatgtcat    4260
gaggaaacta ctgaactagc aattggttgt ttaacacttc tgtatgcatc agataacaac    4320
tgtgagtagc ctatgaatga aattctttta taaatattag gcataaatta aaatgtaaaa    4380
ctccattcat agtggattaa tgcattttgc tgcctttatt agggtacttt attttgcttt    4440
tcagaagtca gcctacataa cacatttta aagtctaaac tgttaaacaa ctcttttaaag    4500 gataattatc caataaaaaa aaacctagtg ctgattcaca gcttattatc caattcaaaa    4560
ataaattaga aaatatatg cttacattt tcacttttgc taaaaagaaa aaaaaaggt    4620 gtttattttt aactcttgga agaggtttttg tggttcccaa tgtgtctgtc ccaccctgat    4680 cctttcaat atatatttct ttaaaccttg tgctacttag taaaaattga ttacaattga    4740
gggaagtttg atagatcctt taaaaaaaag gcagatttcc atttttttgta ttttaactac    4800 tttactaaat taatactcct cctttacag aattagaaaa gttaacattt atctttaggt    4860
ggtttcctga aaagttgaat atttaagaaa ttgtttttaa cagaagcaaa atggcttttc    4920
tttggacagt tttcaccatc tcttgtaaaa gttaattctc accattcctg tggtacctgc    4980
gagtgttatg accaggattc cttaaacctg aactcagacc acttgcatta gaaccatctg    5040
gagcacttgt tttaaaatgc agattcatag gcagcatctc agatctacag aacaagaatc    5100
tctgctaagt ggacctggaa tcttccatct gcatcttaac atgctctcta ggtgtttctt    5160
gtgtttgaga accatgactt atgactttcc tcagaacatg agactgtaaa acaaaaacaa    5220
aaaactatgt gatgcctcta ttttcccaa tacagtcaca catcagctca aatttgcaa    5280 tattgtagtt catatattac cgttatgtct ttggaaatcg ggttcagaac acttttttatg   5340
```

| | | |
|---|---|---|
| acaaaaattg ggtggagggg ataactttca tatctggctc aacatctcag gaaaatctgt | 5400 |
| gattatttgt gtgttctaat gagtaacatc tacttagtta gccttaggga tggaaaaaca | 5460 |
| gggccactta ccaaactcag gtgattccag gatggtttgg aaacttctcc tgaatgcatc | 5520 |
| cttaacctt attaaaacca ttgtcctaag aacaatgcca acaaagctta caacatttag | 5580 |
| tttaaaccca agaagggcac taaactcaga ttgactaaat aaaaagtaca aagggcacat | 5640 |
| atacgtgaca gaattgtaca caatcactcc attggatctt ttactttaaa gtagtgatga | 5700 |
| aaagtacatg ttgatactgt cttagaagaa attaatatat tagtgaagcc acatggggtt | 5760 |
| tcagttgcga acaggtctg tttttatgtt cagtttgtac aatccacaat tcattcacca | 5820 |
| gatattttgt tcttaattgt gaaccaggtt agcaaatgac ctatcaaaaa ttattctata | 5880 |
| atcactacta gttaggatat tgatttaaaa ttgttctact tgaagtggtt tctaagattt | 5940 |
| ttatattaaa aataggtgtg atttcctaat atgatctaaa accctaaatg gttattttc | 6000 |
| ctcagaatga tttgtaaata gctactggaa atattataca gtaataggag tgggtattat | 6060 |
| gcaacatcat ggagaagtga aggcataggc ttattctgac ataaaattcc actggccagt | 6120 |
| tgaatatatt ctattccatg tccatactat gacaatctta ttgtcaacac tatataaata | 6180 |
| agcttttaaa caagtcattt ttcttgatcg ttgtggaagg tttggagcct tagaggtatg | 6240 |
| tcagaaaaaa tatgttggta ttctcccttg ggtaggggga aatgacccttt ttacaagaga | 6300 |
| gtgaaattta ggtcagggaa aagaccaagg gccagcattg ctacttttgt gtgtgtgtgt | 6360 |
| gtgggttttg ttttgttttt ttggttggct ggttgttttc gttgttgtta acaaaggaat | 6420 |
| gagaatatgt aatacttaaa taaacatgac cacgaagaat gctgttctga tttactagag | 6480 |
| aatgttccca atttgaattt agggtgattt taaagaacag tgagaaaggg catacatcca | 6540 |
| cagattcact ttgtttatgc atatgtagat acaaggatgc acatatacac attttcaagg | 6600 |
| actattttag atatctagac aatttcttct aataaagtca tttgtgaaag ggtactacag | 6660 |
| cttattgaca tcagtaaggt agcattcatt acctgtttat tctctgctgc atcttacaga | 6720 |
| agagtaaaact ggtgagagta tatttttat atatatatat atatatatat atataatatg | 6780 |
| tatatatata tatattgact tgttacatga agatgttaaa atcggttttt aaaggtgatg | 6840 |
| taaatagtga tttccttaat gaaaaataca tattttgtat tgttctaatg caacagaaaa | 6900 |
| gccttttaat ctctttggtt cctgtatatt ccatgtataa gtgtaaatat aatcagacag | 6960 |
| gtttaaaagt tgtgcatgta tgtatacagt tgcaagtctg gacaaatgta tagaataaac | 7020 |
| cttttattta agttgtgatt acctgctgca tgaaaagtgc atgggggacc ctgtgcatct | 7080 |
| gtgcatttgg caaaatgtct taacaaatca gatcagatgt tcatcctaac atgacagtat | 7140 |
| tccatttctg gacatgacgt ctgtggttta agctttgtga agaatgtgc tttgattcga | 7200 |
| agggtcttaa agaatttttt taatcgtcaa ccactttaa acataaagaa ttcacacaac | 7260 |
| tactttcatg aattttttaa tcccattgca acattattc caagagtatc ccagtattag | 7320 |
| caatactgga atataggcac attaccattc atagtaagaa ttctggtgtt tacacaacca | 7380 |
| aatttgatgc gatctgctca gtaatataat ttgccatttt tattagaaat ttaatttctt | 7440 |
| catgtgatgt catgaaactg tacatactgc agtgtgaatt ttttgtttt gtttttaat | 7500 |
| cttttagtgt ttacttcctg cagtgaattt gaataaatga gaaaaaatgc attgtc | 7556 |

<210> SEQ ID NO 37
<211> LENGTH: 1516
<212> TYPE: DNA
<213> ORGANISM: Homo sapiens

```
<220> FEATURE:
<223> OTHER INFORMATION: RAC2 glucocorticoid receptor-responsive gene

<400> SEQUENCE: 37
tgccccacca ccgctgctcc tcagcaggcg cctcaccagc ctccacaccc cttgcgcccg      60
cagaaacgcg cctggccctg agctgtcacc accgacactc tccaggctcc ggacacgatg     120
caggccatca agtgtgtggt ggtgggagat ggggccgtgg gcaagacctg ccttctcatc     180
agctacacca ccaacgcctt tcccggagag tacatcccca ccgtgtttga caactattca     240
gccaatgtga tggtggacag caagccagtg aacctggggc tgtgggacac tgctgggcag     300
gaggactacg accgtctccg gccgctctcc tatccacaga cggacgtctt cctcatctgc     360
ttctccctcg tcagcccagc ctcttatgag aacgtccgcg ccaagtggtt cccagaagtg     420
cggcaccact gccccagcac acccatcatc tggtgggca ccaagctgga cctgcgggac      480
gacaaggaca ccatcgagaa actgaaggag aagaagctgg ctcccatcac ctacccgcag     540
ggcctggcac tggccaagga gattgactcg gtgaaatacc tggagtgctc agctctcacc     600
cagagaggcc tgaaaaccgt gttcgacgag gccatccggg ccgtgctgtg ccctcagccc     660
acgcggcagc agaagcgcgc ctgcagcctc tctaggggt tgcacccccag cgctcccacc     720 tagatgggtc tgatcctcca ggatccccac ccaaagcctg atggcacccc ggctggccat     780
gctgtcccct ccctgtggcg tttcttagca gatggctgca gagcttcgtt gatggtcttt     840
tctgtactgg aggcctcctg aggccaggaa cgtgcaaatt tgcaggtgct gcatcccaag     900
cccctcatgc tcctgccttc ctgagggcca gagggagcc ccaggaccca ttaagccacc       960
cccgtgttcc tgccgtcagt gccaactgcc gcatgtggaa gcatctaccc gttcactcca    1020
gtccacgccc acgcctgact cccctctgga aactgcaggc cagatggttg ctgccacaac    1080
ttgtgtacct tcagggatgg ggctcttact ccctcctgag gccagctgct ctaatatcga    1140
tggtcctgct tgccagagag ttcctctacc cagcaaaaat gagtgtctca gaagtgtgct    1200
cctctggcct cagttctcct cttttggaac aacataaaac aaatttaatt ttctacgcct    1260
ctggggatat ctgctcagcc aatggaaaat ctgggttcaa ccagcccctg ccatttctta    1320
agactttctg ctgcactcac aggatcctga gctgcactta cctgtgagag tcttcaaact    1380
tttaaacctt gccagtcagg acttttgcta ttgcaaatag aaaacccaac tcaacctgct    1440
taagcagaaa ataaatttat tgattcaaaa aaaaaaaaa aaaaaaaaaa aaaaaaaaaa     1500
aaaaaaaaaa aaaaaa                                                    1516

<210> SEQ ID NO 38
<211> LENGTH: 1641
<212> TYPE: DNA
<213> ORGANISM: Homo sapiens
<220> FEATURE:
<223> OTHER INFORMATION: SPP1 glucocorticoid receptor-responsive gene

<400> SEQUENCE: 38
ctccctgtgt tggtggagga tgtctgcagc agcatttaaa ttctgggagg gcttggttgt      60
cagcagcagc aggaggaggc agagcacagc atcgtcggga ccagactcgt ctcaggccag     120
ttgcagcctt ctcagccaaa cgccgaccaa ggaaaactca ctaccatgag aattgcagtg     180
atttgctttt gcctcctagg catcacctgt gccataccag ttaaacaggc tgattctgga     240
agttctgagg aaaagcagct ttacaacaaa tacccagatg ctgtggccac atggctaaac    300
cctgacccat ctcagaagca gaatctccta gccccacaga atgctgtgtc ctctgaagaa    360
```

```
accaatgact ttaaacaaga gacccttcca agtaagtcca acgaaagcca tgaccacatg      420
gatgatatgg atgatgaaga tgatgatgac catgtggaca gccaggactc cattgactcg      480
aacgactctg atgatgtaga tgacactgat gattctcacc agtctgatga gtctcaccat      540
tctgatgaat ctgatgaact ggtcactgat tttcccacgg acctgccagc aaccgaagtt      600
ttcactccag ttgtccccac agtagacaca tatgatggcc gaggtgatag tgtggtttat      660
ggactgaggt caaaatctaa gaagtttcgc agacctgaca tccagtaccc tgatgctaca      720
gacgaggaca tcacctcaca catggaaagc gaggagttga atggtgcata caaggccatc      780
cccgttgccc aggacctgaa cgcgccttct gattgggaca gccgtgggaa ggacagttat      840
gaaacgagtc agctggatga ccagagtgct gaaacccaca gccacaagca gtccagatta      900
tataagcgga aagccaatga tgagagcaat gagcattccg atgtgattga tagtcaggaa      960
ctttccaaag tcagccgtga attccacagc catgaatttc acagccatga agatatgctg     1020
gttgtagacc ccaaaagtaa ggaagaagat aaacacctga aatttcgtat ttctcatgaa     1080
ttagatagtg catcttctga ggtcaattaa aaggagaaaa aatacaattt ctcactttgc     1140
atttagtcaa aagaaaaaat gctttatagc aaaatgaaag agaacatgaa atgcttcttt     1200
ctcagtttat tggttgaatg tgtatctatt tgagtctgga ataactaat gtgtttgata     1260 attagtttag tttgtggctt catggaaact ccctgtaaac taaaagcttc agggttatgt     1320
ctatgttcat tctatagaag aaatgcaaac tatcactgta ttttaatatt tgttattctc     1380
tcatgaatag aaatttatgt agaagcaaac aaaatacttt tacccactta aaaagagaat     1440
ataacatttt atgtcactat aatctttgt tttttaagtt agtgtatatt ttgttgtgat     1500 tatcttttg tggtgtgaat aaatcttta tcttgaatgt aataagaatt tggtggtgtc     1560
aattgcttat ttgttttccc acggttgtcc agcaattaat aaaacataac ctttttact     1620 gcctaaaaaa aaaaaaaaa a                                                1641
```

<210> SEQ ID NO 39
<211> LENGTH: 6463
<212> TYPE: DNA
<213> ORGANISM: Homo sapiens
<220> FEATURE:
<223> OTHER INFORMATION: PHF15 glucocorticoid receptor-responsive gene

<400> SEQUENCE: 39

```
ctctcttgct cgctcgctcc ctctctctcc tgctggctgc ctgttctagg aagccagcgc       60
ggagaggggg gggatgcaca gcacagggga gagagattgc gcatgttggt cagtcgtgtt      120
ttaaagagta cagtgcgggg aggctgagag gggcgcatgc aacaacaact tttggaagga      180
tggaagagaa gaggcgaaaa tactccatca gcagtgacaa ctctgacacc actgacagtc      240
atgcgacatc tacatccgca tcaagatgct ccaaactgcc cagcagcacc aagtcgggct      300
ggccccgaca gaacgaaaag aagccctccg aggttttccg gacagacttg atcacagcca      360
tgaagatccc ggactcatac cagctcagcc cggatgacta ctacatcctg gcagacccat      420
ggcgacagga atgggagaaa ggtgtgcagg tgcctgccgg ggcagaggcc atcccagagc      480
ccgtggtgag gatcctccca ccactggaag gcccccctgc ccaggcatcc ccgagcagca      540
ccatgcttgg tgagggctcc cagcctgatt ggccagggg cagccgctat gacttggacg      600
agattgatgc ctactggctg gagctcatca actcggagct taaggagatg gagaggccgg      660
agctggacga gctgacatta gagcgtgtgc tggaggagct ggagaccctg tgccaccaga      720
atatggccag ggccattgag acgcaggagg ggctgggcat cgagtacgac gaggatgttg      780
```

-continued

```
tctgcgacgt gtgtcgctct cctgagggcg aggatggcaa cgagatggtc ttctgtgaca    840
agtgcaacgt ctgtgtgcat caggcatgct acgggatcct caaggtgccc acgggcagct    900
ggctgtgccg gacgtgtgcc ctgggtgtcc agccaaagtg cctgctctgc cccaagcgag    960
gaggagcctt gaagcccact agaagtggga ccaagtgggt gcatgtcagc tgtgccctat   1020
ggattcctga ggtcagcatc ggctgcccag agaagatgga gcccatcacc aagatctcgc   1080
atatcccagc cagccgctgg gctctgtcct gcagcctctg caaggaatgc acaggcacct   1140
gcatccagtg ttccatgcct tcctgcgtca cagcgttcca tgtcacatgc gcctttgacc   1200
acggcctgga aatgcggact atattagcag acaacgatga ggtcaagttc aagtcattct   1260
gccaggagca cagtgacggg ggcccacgta atgagcccac atctgagccc acggaaccca   1320
gccaggctgg cgaggacctg gaaaaggtga ccctgcgcaa gcagcggctg cagcagctag   1380
aggaggactt ctacgagctg gtggagccgg ctgaggtggc tgagcggctg acctggctg    1440 aggcactggt cgacttcatc taccagtact ggaagctgaa gaggaaagcc aatgccaacc   1500
agccgctgct gaccccaag accgacgagg tggacaacct ggcccagcag gagcaggacg    1560
tcctctaccg ccgcctgaag ctcttcaccc atctgcggca ggacctagag agggttagaa   1620
atctgtgcta catggtgaca aggcgcgaga gaacgaaaca cgccatctgc aaactccagg   1680
agcagatatt ccacctgcag atgaaactta ttgaacagga tctgtgtcga ggcctgtcca   1740
cctcattccc catcgatggc accttcttca acagctggct ggcacagtcg gtgcagatca   1800
cagcagagaa catggccatg agcgagtggc cactgaacaa tgggcaccgc gaggaccctg   1860
ctccagggct gctgtcagag gaactgctgc aggacgagga gacactgctc agcttcatgc   1920
gggacccctc gctgcgacct ggtgaccctg ctaggaaggc ccgaggccgc acccgcctgc   1980
ctgccaagaa gaaaccacca ccaccaccac cgcaggacgg gcctggttca cggacgactc   2040
cagacaaagc ccccaagaag acctgggggcc aggatgcagg cagtggcaag gggggtcaag   2100
ggccacctac caggaagcca ccacgtcgga catcttctca cttgccgtcc agccctgcag   2160
ccggggactg tcccatccta gccaccctg aaagccccc gccactggcc ctgagaccc     2220 cggacgaggc agcctcagta gctgctgact cagatgtcca agtgcctggc cctgcagcaa   2280
gccctaagcc tttgggccgg ctccggccac cccgcgagag caaggtaacc cggagattgc   2340
cgggtgccag gcctgatgct gggatgggac caccttcagc tgtggctgag aggcccaagg   2400
tcagcctgca ttttgacact gagactgatg ctacttctc tgatgggag atgagcgact    2460 cagatgtaga ggccgaggac ggtgggtgc agcggggtcc ccgggaggca ggggcagagg   2520
aggtggtccg catgggcgta ctggcctcct aactcacccc cttccctgtc ccaggccctg   2580
ccctggtccc cccacaaggc ctcagcccag tcacaactgc catttccagt ctctgctgag   2640
tgtcccagac cctcgaggct gccactccgt cgtggtttta ttttaatat agagagagtt    2700 ttgaattcta cactgttgtc tttcctctgt gctggcctag acattagga ttccttccac    2760 ggctccggcc gctaggaccc tgccaggtcc cgcgcaccat ccctgccctg cccacgtggt   2820
attgctgggc tcctggctag atgcaagcaa ggtggacaag agctcaggac tccagcccac   2880
tgccactggg tgacacagac tgtcgtttgg gcattatttc atggcagatg gccagtcca    2940 gggcctaccc cgccttgccc ccagatccca ctggggtcca tttgggggt cctgctacac    3000 tccaccgatc cccaaggaag tataataaac gatacccagc cagagtctac tcactgtcac   3060
aagcacaacg agtttatatg agaaagcact gaggggggtgc agagggcccg ctagttccag   3120
```

```
gggaactgaa agctgttcct gatcagcccg tatcatctga ggcctgcctg cccacccctgc    3180
caccctcccc tcccttgctg ctctgcccct gccagtgccc agcccagcgg ctctgggaag    3240
gggttcccag aatccctcct gagctgtgcc atttactcag gggactccca acagccagc     3300
tgccagtgca ggtggagggc tgtaggggag ggccagtgcc cagacagggt catggggctc    3360
agaccagccc actgtagaga atcactctga ggctccaact tccttccttc cttcggggcc    3420
agtctcggcc gaagtctggt cacgctcaga cagagctgac cagaccagac cgtttgcctt    3480
ttcaagtttc ctagtcctgc tacaagatga gcttcttccg tggtttcctt ttggaaactc    3540
ctccttccaa caagcagtgg gatcccgggg cccagggcgg gccggtgttg gccgctgggg    3600
ctgttgtaag tcttgctgga tgttcccctg ttcctgagcc ttaacccctc gcacagccat    3660
ccccccccc gtcctgccat cccccccgc cgtcctgcct tccccacccc acccttaggt      3720
cccaggtagt tgctctgaag agtttcagta gagtggcccc agggtgatag ctcagggaac    3780
aacaaaaaag gaattccgtg aaaacatttt tttttctttg atgaattact cctgggtcac    3840
ttccaccact ggtaaagcca gaacttctcc aaaaagaacc ttgcaaaaag tccagtgaat    3900
cagtcgaatc attctgtgga tgccaaagaa tattttgacc ataatacagc acagcctgga    3960
cctgacaact tgtcatttgg actttttttt aaatggagtt ctttagcaac aaagtataga    4020
aacatgttca ttgcacacac ccaaggagaa gagctcaagc gcttggaaga ggatgctttg    4080
ctgctgctga agtgtacctg ggtgttagat ttcagatcct gggctgagcc cactgtgagc    4140
tttcctaaac tgtgagactc acagagggga aagatactga cggtgaaacc agcatggaaa    4200
acgtctttac catgtggttc cctcctcccc aaatacataa agcaaataag caggatgggg    4260
aacagcttga ccttcatcca cccctaactc caaaactatc aaggtacgac agtggcattg    4320
tcatcgacac tcaatttcat gtgaatttta gcaaaacagg aaacaaagat aatgactcag    4380
ttcagaggat cggacaaatg tgtctagtcc gggtggactc ggagggagtg gggtgggctt    4440
caaggattct gggcgttggg atggcatgag ctaccctgta gagtttagtc tgcctgcccg    4500
ccttggtagt agtgaccagt cagtgtcagc atcagtgtcc caaccccagt ctctgtttac    4560
tgcctttgaa cagaacttct tccttcccca tgctttgggt cacctcgggc tgcaaccctg    4620
tctgtgccag attgcccggt ctgaccctgc aggaagcaaa gaggtgagct taaagaacaa    4680
ccaaactctg ccaggggtcc cagaaagccc agggtccagc agtctcagca cttgcccct     4740
tgccccttca ccatcctg gggcaggggc tgggcctccc tggtggcagg ggtgggtgga     4800
gaattaggga gagggtgcaa cgagtctggc cccttgcctc gggctggctg tgttcttcc     4860
aagagcctct gctcacattg ttggcctctg gattctggcc cttcttcatt ggctgttgct    4920
ttggactgga ctgttgctga gcctgtgtcc tgcagaaccc agatgtctgt taggctggct    4980
ggctgctgcg aggggagggg ggtggccttt catttggggt gccctttcac tcccaggcca    5040
agccctggag caatcttctt caggcagctg tctccacctc caggatgtcc agcaggctgc    5100
aaggagaagg atgccagcca cccatcctcc cccagttccc agcctttccc ctgttggtca    5160
cagccgcttc tgtctttttc cggtctactg tccccagtgt agagggcttt gctgtccctg    5220
agactgagcc aggttccttt tccaggtcag aggtggaggt agatcttcct ctcaaccaca    5280
tctgcctcca cacacagctc ctccgcaggg aaggagaagc tgctctgtaa ctcattctgg    5340
ctatcgtccc ccttctcact gacctgaccg cccaccacct ccttccccct catcacatga    5400
caaaggataa tgtgcaagaa aagtattttt atgtatcata aatgtatttt gaaacaaatg    5460
agaagaagaa aggtagaagg gtttattttta ttaaatgagc ctgacttagt gacagtgtgt    5520
```

```
gagcatttgc aatgtaaggg cctcagcttc cttggagaag ccaccccagg tttccagaca    5580
tagatgttga attgtttgtg gggggtgtgc caggccacgt ctcgtgtgtc cgtatgcagg    5640
catgcctgtg tatactgtgt atgggcacac tgggactagc tgggacaatt cctagagatt    5700
caactgccca attctaacca acattggcag cggctgaact tggcatttcc ttgctaactg    5760
ccagatgtgg ccaacctttg tccatatgca aaccactgaa aaatgatctg gatttctata    5820
gcaaggccct tggggagggc actctcccat gcccttggcc tcgctggcca cattggccaa    5880
tgagccaggg ctggagtctg agacctttgg ttgttcttta aggcacctcc tgccactttc    5940
tccctcagag gcacaaacac tttgtgttcc acgtcagttt gaggggacgg tgggggatg     6000 atatgaatgt cacaggagga gacaccttct gtctttgttt caaagaaagt gatgtgccat    6060
ttgttaatat acaagagaaa tattgaaaat atattgaaaa gagcaatttt aaattatttt    6120
tggcttatgt tgcaatattt attttcttgt attagaaaag attcctttgt agagaaaaaa    6180 tgtattttc attaacgcaa agacctattt ctccttttg tacattgtcc atgtgcgcaa      6240
cccttaacga gcaatagaat gtatggtcac ctgggtgtgg ccagtgcccg ctgtgccctg    6300
catgattctg tgttgccgct gctgcatagt tcccagcccc atcctgtcct gctcactcat    6360
gggggcttcc agaccccggc cccaccaggg cttgtgtcat agggagccct ttgcactcct    6420
cgtgtgttgg caaacgcagt taataaagca gtgttttctg tgc                      6463

<210> SEQ ID NO 40
<211> LENGTH: 2828
<212> TYPE: DNA
<213> ORGANISM: Homo sapiens
<220> FEATURE:
<223> OTHER INFORMATION: BTN3A2 glucocorticoid receptor-responsive gene

<400> SEQUENCE: 40
catagatgaa aatggcaagt tccctggctt tccttctgct caactttcat gtctccctcc      60
tcttggtcca gctgctcact ccttgctcag ctcagttttc tgtgcttgga ccctctgggc     120
ccatcctggc catggtgggt gaagacgctg atctgccctg tcacctgttc ccgaccatga     180
gtgcagagac catggagctg aagtgggtaa gttccagcct aaggcaggtg gtgaacgtgt     240
atgcagatgg aaaggaagtg gaagacaggc agagtgcacc gtatcgaggg agaacttcga     300
ttctgcggga tggcatcact gcaggaagg ctgctctccg aatacacaac gtcacagcct      360
ctgacagtgg aaagtacttg tgttattcc aagatggtga cttctatgaa aaagccctgg      420
tggagctgaa ggttgcagca ctgggttcta atcttcacgt cgaagtgaag ggttatgagg     480
atggagggat ccatctggag tgcaggtcca ccggctggta ccccaaccc caaatacagt      540 ggagcaacgc caagggagag aacatcccag ctgtggaagc acctgtggtt gcagatggag     600
tgggcctata tgaagtagca gcatctgtga tcatgagagg cggctccggg gagggtgtat     660
cctgcatcat cagaaattcc ctcctcggcc tggaaaagac agccagcatt tccatcgcag     720
accccttctt caggagcgcc cagccctgga tcgcagccct ggcagggacc ctgcctatct     780
tgctgctgct tctcgccgga gccagttact tcttgtggag acaacagaag gaaataactg     840
ctctgtccag tgagatagaa agtgagcaag agatgaaaga aatgggatat gctgcaacag     900
agcgggaaat aagcctaaga gagagcctcc aggaggaact caagaggaaa aaaatccagt     960
acttgactcg tggagaggag tcttcgtccg ataccaataa gtcagcctga tgctctaatg    1020
gaaaaatggc cctcttcaag cctggaaaaa tggctgaccc catggacacc tcctcaaact    1080
```

| | |
|---|---|
| ctctgcagca gatgtaattc tgtatccaga catggcaaat gccatcctcc ttgtttctga | 1140 |
| ggaccagagg agtgtacagc gtgctgagga gccccatgac ctaccagaca accctgagag | 1200 |
| atttgaatgg cgttactgtg tgcttggctg tgaaagcttc atgtcagaga cacactactg | 1260 |
| ggaggtggaa gtgggggaca gaaaagagtg gcatattggg gtatgtagta agaacgtgga | 1320 |
| gaggaaaaaa gtttgggtca aaatgacacc ggagaacgga tactggacta tgggcctgac | 1380 |
| tgatgggaat aagtatcggg ctctcactga gcccagaacc aacctgaaac ttcctgagcc | 1440 |
| tcctaggaaa gtgggggtca tcctggacta tgagactgga catatctcgt tctacaatgc | 1500 |
| cacggatgga tctcatatct acacatttct gcacgcctct tcctctgagc tctgtatcc | 1560 |
| tgtattcaga attttgacct ggagcccac tgccctgacc gtttgcccaa taccaaaagt | 1620 |
| agagagttcc cccgatcccg acctagtgcc tgatcattcc ctggagatac cactgacccc | 1680 |
| aggcttagct aatgaaagtg gggagcctca ggctgaagta acatctctgc ttctccctgc | 1740 |
| ccagcctgga gctaagggtc tcaccctcca acagccag tcagaaccat aaagctacag | 1800 |
| gcacacactg aagcacttta ctgatattca ttcaattatt ccataggaca gttgtttgag | 1860 |
| tttggtgcca ccttattggc cccttatac agataaggaa actggggtgt agaaaagtgt | 1920 |
| attgacttta caaagcagac aggaatagtg aacaacagag ctgggatctg aacaacaatg | 1980 |
| actaacatta atggagaatt taaaacgttc tgagtgctgt gttatgagct ttggtgggtg | 2040 |
| tcactccttt aatcctcaca acaccctgtc aggtagtctc atttggcaag tatggaagca | 2100 |
| gaggcagggc aacattaagt agcttacata actcacacgg taatttgtgc agttgggaga | 2160 |
| tgttcagctt cagtccctgg ccaattgccc gttcttttcc agcctgattt ttcctgcatg | 2220 |
| ggaagagccc acatgtagcc ctgaggttcc cttcccagga cagctccagg atcgagatca | 2280 |
| ctgtgagtgg ttgtggagtt aagacccta tggactcctt cccagctgat tatcagagcc | 2340 |
| ttagacccag cactccttgg attggctctg cagagtgtct tggttgagag aataacgttg | 2400 |
| cagttcccac agggcatgtg actttgaaag agactagagg ccacactcag ttaataatgg | 2460 |
| ggcacagatg tgttcccacc caacaaatgt gataagtgat cgtgcagcca gagccagcct | 2520 |
| tccttcagtc aaggtttcca ggcagagcaa ataccctaga gattctctgt aatattggta | 2580 |
| atttggatga aggaagctag aagaattaca gggatgtttt taatcccact atggactcag | 2640 |
| tctcctggaa aaggatctgt ccactcctgg tcattggtgg atgttaaacc catattcctt | 2700 |
| tcaactgctg cctgctaggg aaaactgctc ctcattatca tcactattat tgctcaccac | 2760 |
| tgtatcccct ctactgggca agtgcttgtc aagttctagt tgttcaataa atttgttaat | 2820 |
| aatgctga | 2828 |

<210> SEQ ID NO 41
<211> LENGTH: 2698
<212> TYPE: DNA
<213> ORGANISM: Homo sapiens
<220> FEATURE:
<223> OTHER INFORMATION: SESN1 glucocorticoid receptor-responsive gene

<400> SEQUENCE: 41

| | |
|---|---|
| gccgtccgtg ctgactgagg cgctgcagcc aggagccgcg gccggctgcc cagcgctcgc | 60 |
| cgcctccgcg cgtccgcagc cgtccccgcg ccgacatgcg cttggccgcc gccgcgaacg | 120 |
| aggcgtacac ggccccctttg gcggtctcgg ggctgctggg ctgcaagcag tgcggcgggg | 180 |
| gccgcgacca ggacgaggaa cttggcatta gaattcctcg accactagga cagggaccaa | 240 |
| gcagattcat cccagaaaag gagatcctcc aagtggggag tgaagacgca cagatgcatg | 300 |

```
ctttatttgc agattctttt gctgctttgg gccgtttgga taacattacg ttagtgatgg    360
ttttccaccc acaatattta gaaagtttct taaaaactca gcactatcta ctgcaaatgg    420
atgggccgtt acccctacat tatcgtcact acattggaat aatggctgcg gcaagacatc    480
agtgctccta cttagtgaac ctgcatgtaa atgatttcct tcatgttggt ggggacccca    540
agtggctcaa tggtttagag aatgctcctc aaaaactaca gaatttagga gaacttaaca    600
aagtgttagc ccatagacct tggcttatta ccaaagaaca cattgaggga cttttaaaag    660
ctgaagagca cagctggtcc cttgcggaat tggtacatgc agtagtttta ctcacacact    720
atcattctct tgcctcattc acattcggct gtggaatcag tccagaaatt cattgtgatg    780
gtggccacac attcagacct ccttctgtta gcaactactg catctgtgac attacaaatg    840
gcaatcacag tgtggatgag atgccggtca actcagcaga aaatgtttct gtaagtgatt    900
cttctcttga ggttgaagcc ctcatggaaa agatgaggca gttacaggaa tgtcgagatg    960
aagaagaggc aagtcaggaa gagatggctt cacgttttga aatagaaaaa agagagagta   1020
tgtttgtctt ctcttcagat gatgaagaag ttacaccagc aagagctgta tctcgtcatt   1080
ttgaggatac tagttatggc tataaagatt tctctagaca tgggatgcat gttccaacat   1140 tcgtgtcca ggactattgc tgggaagatc atggttattc tttggtaaat cgcctttatc    1200
cagatgtggg acagttgatt gatgaaaaat tcacattgc ttacaatctt acttataata    1260
caatggcaat gcacaaagat gttgatacct caatgcttag acgggcaatt tggaactata   1320
ttcactgcat gtttggaata agatatgatg attatgacta tggtgaaatt aaccagctat   1380
tggatcgtag ctttaaagtt tatatcaaaa ctgttgtttg cactcctgaa aaggttacca   1440
aaagaatgta tgatagcttc tggaggcagt tcaagcactc tgagaaggtt catgttaatc   1500
tgcttcttat agaagctagg atgcaagcag aactccttta tgctctgaga gccattaccc   1560
gctatatgac ctgatgcctt tccttcatta aagatgattc tggaatgatc agcagatata   1620
gtctacaagg gggaaggtac taagcccag gaccaatggt agacaaaata attcagaaat   1680
ccattgtgcc atgattcctt tagtttctgc tattttctg tggaaaacca ctgctggcac    1740
aagcagtgac tgtttggcag cttcaagttt agagctgtga agacaggctg ccattcacag   1800
tattttgctt tttgacagta caagatgctg tgtaactgtt ttaatacagc aaatagtaac   1860
tctccaaatc ctgttgcttt tatgttaaat aagataacaa gaattggagc atgcaaagaa   1920
tgggacttgg ataatgactt aagctttata tgtaaagaat tttagaagat cttggtgctg   1980
ctattcctgc tggaggaatg aatagatggc tgtttcagtt aagctattag taataaaagt   2040
gaacattgct actatctgag cctacataca taacttgtgt gatttcaaat taaacttgca   2100
ttatgtgtta attttcttgc atctaaaaaa gcatagaatt cctactcaca cagctcagca   2160
acaaccattt tgatggtaac agttaatttc tttcattagt ttttttaaatt cagggttctg   2220 gatattaaat taaatggca ttcttaaaga ttttcttcaa aaagcaatcc taaatgaaag    2280
tgtgtaaatt ataagaagct ggcgatcttt tgatatgctg tttcacagga tcctgacact   2340
ggagggcagc tgtcttgtgc attacttgtg tttccagcac caaagttgtg ggacatgttg   2400
ctgtagactg ctgcgcagtc ctgggtgcat tcagtctctc tgcctctgcc tgcctcctgg   2460
tccccacttt aaaggctgtg cagctcctta ataataaag ctggaaaata ttttagtcg    2520 ggttatcaaa tttgatttac aaaaacgcta actttgtttg aaatgcaaac aggtttgaaa   2580
atatgtatta agtactttgt attctggaag cgtgaattgc ttttgaagtc tgtcagtatt   2640
``` actggtatt tttaaataaag aagaattttt ctccaattt aaaaaaaaaa aaaaaaaa 2698

<210> SEQ ID NO 42
<211> LENGTH: 5215
<212> TYPE: DNA
<213> ORGANISM: Homo sapiens
<220> FEATURE:
<223> OTHER INFORMATION: MAP3K5 glucocorticoid receptor-responsive gene

<400> SEQUENCE: 42

| | | | | | |
|---|---|---|---|---|---|
| cgagcgcggc | gcccttgagc | tgcaccgcgg | cgcaggtttg | cgagccgact | tgtcagccgg | 60 |
| ccaagaaaag | gaagctccgt | cccttcccgc | tcacccggct | tccccacccc | ttgtactcta | 120 |
| aactctgcag | agggcgagcg | gcgcggccac | ggaggcgccg | aggaggagcg | agccgccgcc | 180 |
| gggcagcggc | gtgccctcgg | gggagagggc | gccggagagg | aggcggcggc | gcggcggcga | 240 |
| gggcgcggcg | cgcgatggca | gctgcttagc | ccggcgggcg | cggagcagcc | ccgagctgtg | 300 |
| gctggccagg | cggtgcggct | gggcggggga | cgccgccgcc | gttgctgccc | ggcccggaga | 360 |
| gatgagcacg | gaggcggacg | agggcatcac | tttctctgtg | ccacccttcg | cccctcggg | 420 |
| cttctgcacc | atccccgagg | gcggcatctg | caggagggga | ggagcggcgg | cggtgggcga | 480 |
| gggcgaggag | caccagctgc | caccgccgcc | gccgggcagc | ttctggaacg | tggagagcgc | 540 |
| cgctgcccct | ggcatcggtt | gtccggcggc | cacctcctcg | agcagtgcca | cccgaggccg | 600 |
| gggcagctct | gttggcgggg | gcagccgacg | gaccacggtg | gcatatgtga | tcaacgaagc | 660 |
| gagccaaggg | caactggtgg | tggccgagag | cgaggccctg | cagagcttgc | gggaggcgtg | 720 |
| cgagacagtg | ggcgccaccc | tggaaaccct | gcattttggg | aaactcgact | ttggagaaac | 780 |
| caccgtgctg | gaccgctttt | acaatgcaga | tattgcggtg | gtggagatga | gcgatgcctt | 840 |
| ccggcagccg | tccttgtttt | accaccttgg | ggtgagagaa | agtttcagca | tggccaacaa | 900 |
| catcatcctc | tactgtgata | ctaactcgga | ctctctgcag | tcactgaagg | aaataatttg | 960 |
| ccagaagaat | actatgtgca | ctgggaacta | cacctttgtt | ccttacatga | taactccaca | 1020 |
| taacaaagtc | tactgctgtg | acagcagctt | catgaagggg | ttgacagagc | tcatgcaacc | 1080 |
| gaacttcgag | ctgcttcttg | gacccatctg | cttacctctt | gtggatcgtt | ttattcaact | 1140 |
| tttgaaggtg | gcacaagcaa | gttctagcca | gtacttccgg | gaatctatac | tcaatgacat | 1200 |
| caggaaagct | cgtaatttat | acactggtaa | agaattggca | gctgagttgg | caagaattcg | 1260 |
| gcagcgagta | gataatatcg | aagtcttgac | agcagatatt | gtcataaatc | tgttactttc | 1320 |
| ctacagagat | atccaggact | atgattctat | tgtgaagctg | gtagagactt | tagaaaaact | 1380 |
| gccaacctt | gatttggcct | cccatcacca | tgtgaagttt | cattatgcat | ttgcactgaa | 1440 |
| taggagaaat | ctccctggtg | acagagcaaa | agctcttgat | attatgattc | ccatggtgca | 1500 |
| aagcgaagga | caagttgctt | cagatatgta | ttgcctagtt | ggtcgaatct | acaaagatat | 1560 |
| gtttttggac | tctaatttca | cggacactga | aagcagagac | catggagctt | cttggttcaa | 1620 |
| aaaggcattt | gaatctgagc | caacactaca | gtcaggaatt | aattatgcgg | tcctcctcct | 1680 |
| ggcagctgga | caccagtttg | aatcttcctt | tgagctccgg | aaagttgggg | tgaagctaag | 1740 |
| tagtcttctt | ggtaaaaagg | gaaacttgga | aaaactccag | agctactggg | aagttggatt | 1800 |
| ttttctgggg | gccagcgtcc | tagccaatga | ccacatgaga | gtcattcaag | catctgaaaa | 1860 |
| gcttttaaa | ctgaagacac | cagcatggta | cctcaagtct | attgtagaga | caattttaat | 1920 |
| atataagcat | tttgtgaaac | tgaccacaga | acagcctgtg | gccaagcaag | aacttgtgga | 1980 |
| cttttggatg | gatttcctgg | tcgaggccac | aaagacagat | gttactgtgg | ttaggttcc | 2040 |

-continued

```
agtattaata ttagaaccaa ccaaaatcta tcaaccttct tatttgtcta tcaacaatga    2100
agttgaggaa aagacaatct ctatttggca cgtgcttcct gatgacaaga aaggtataca    2160
tgagtggaat tttagtgcct cttctgtcag gggagtgagt atttctaaat ttgaagaaag    2220
atgctgcttt ctttatgtgc ttcacaattc tgatgatttc caaatctatt tctgtacaga    2280
acttcattgt aaaaagtttt ttgagatggt gaacaccatt accgaagaga aggggagaag    2340
cacagaggaa ggagactgtg aaagtgactt gctggagtat gactatgaat atgatgaaaa    2400
tggtgacaga gtcgttttag gaaaaggcac ttatgggata gtctacgcag gtcgggactt    2460
gagcaaccaa gtcagaattg ctattaagga aatcccagag agagacagca gatactctca    2520 gccccctgcat gaagaaatag cattgcataa acacctgaag cacaaaaata ttgtccagta    2580
tctgggctct ttcagtgaga atggtttcat taaaatcttc atggagcagg tccctggagg    2640
aagtctttct gctctccttc gttccaaatg gggtccatta aaagacaatg agcaaacaat    2700
tggcttttat acaaagcaaa tactggaagg attaaaatat ctccatgaca atcagatagt    2760
tcaccgggac ataaagggtg acaatgtgtt gattaatacc tacagtggtg ttctcaagat    2820
ctctgacttc ggaacatcaa agaggcttgc tggcataaac ccctgtactg aaactttttac   2880 tggtaccctc cagtatatgg caccagaaat aatagataaa ggaccaagag gctacggaaa    2940
agcagcagac atctggtctc tgggctgtac aatcattgaa atggccacag gaaaaccccc    3000 atttttatgaa ctgggagaac cacaagcagc tatgttcaag gtgggaatgt ttaaagtcca    3060
ccctgagatc ccagagtcca tgtctgcaga ggccaaggca ttcatactga atgttttga    3120 accagatcct gacaagagag cctgtgctaa cgacttgctt gttgatgagt tttttaaaagt   3180 ttcaagcaaa aagaaaaaga cacaacctaa gctttcagct ctttcagctg gatcaaatga    3240
atatctcagg agtatatcct tgccggtacc tgtgctggtg gaggacacca gcagcagcag    3300
tgagtacggc tcagtttcac ccgacacgga gttgaaagtg gacccctct ctttcaaaac    3360 aagagccaag tcctgcggag aaagagatgt caagggaatt cggacactct ttttgggcat    3420
tccagatgag aattttgaag atcacagtgc tcctccttcc cctgaagaaa aagattctgg    3480
attcttcatg ctgaggaagg acagtgagag gcgagctacc cttcacagga tcctgacgga    3540
agaccaagac aaaattgtga gaaacctaat ggaatctta gctcagggg ctgaagaacc     3600 gaaactaaaa tgggaacaca tcacaaccct cattgcaagc ctcagagaat tgtgagatc    3660 cactgaccga aaaatcatag ccaccacact gtcaaagctg aaactggagc tggacttcga    3720
cagccatggc attagccaag tccaggtggt actctttggt tttcaagatg ctgtcaataa    3780
agttcttcgg aatcataaca tcaagccgca ctggatgttt gccttagaca gtatcattcg    3840
gaaggcggta cagacagcca ttaccatcct ggttccagaa ctaaggccac atttcagcct    3900
tgcatctgag agtgatactg ctgatcaaga agacttggat gtagaagatg accatgagga    3960
acagccttca aatcaaactg tccgaagacc tcaggctgtc attgaagatg ctgtggctac    4020
ctcaggcgtg agcacgctca gttctactgt gtctcatgat tcccagagtg ctcaccggtc    4080
actgaatgta cagcttggaa ggatgaaaat agaaaccaat agattactgg aagaattggt    4140
tcggaaagag aaagaattac aagcactcct tcatcgagct attgaagaaa aagaccaaga    4200
aattaaacac ctgaagctta agtcccaacc catagaaatt cctgaattgc ctgtatttca    4260
tctaaattct tctggcacaa atactgaaga ttctgaactt accgactggc tgagagtgaa    4320
tggagctgat gaagacacta taagccggtt tttggctgaa gattatacac tattggatgt    4380
```

```
tctctactat gttacacgtg atgacttaaa atgcttgaga ctaaggggag ggatgctgtg    4440
cacactgtgg aaggctatca ttgactttcg aaacaaacag acttgactgt tgctcaatct    4500
aatcttcgat ggaaattcta aaaattaata cagagctgat cttcttgggg gtgggaaaat    4560
cgaagggaga ggagaaaggc gctgcacttt aaatccagta tttgtttact catgttaaaa    4620
aaaaaaaaaa cagacaaaac acactgaaat ttcctaacta catctatttc tataattttt    4680
aaggactctt cataaggact cttaaaataa tcctgaacat tagaacccta atgttcagga    4740
agattttaat ctaagcattt ttatggaaat attttttaatg cagcagctat tgcacttcag    4800
ccaaatgttt atttcacaca aaacggatgt aacatttcat gtgatcgtgc accactggaa    4860
caaaaccaaa atgtgaccat aactgtttag gcttctgtgt gtttgtaata tgctctaata    4920
atctgagtag aaatgcgtaa tttcaattac tgtataaagt ttatgttttt ttaagtgtgc    4980
agaatctgag agcaatggtt tttacttctc tgtgttaatt gtaatattga ctctattttg    5040
taacttaagt ttctgacctg tcgtacattt gtttgagtcg tttatgtact actgaactgt    5100
accagttgca catgcttgaa ctgtagtaat gttagcttgt tctaaagcta tccattgtgt    5160
catatttact ctaaaaatta aagagactct caacaaaaaa aaaaaaaaaa aaaaa         5215

<210> SEQ ID NO 43
<211> LENGTH: 4655
<212> TYPE: DNA
<213> ORGANISM: Homo sapiens
<220> FEATURE:
<223> OTHER INFORMATION: DPYSL2 glucocorticoid receptor-responsive gene

<400> SEQUENCE: 43
tctgtgcacc ttgcggtggg cggcgaacgg cagccgcggc agcagctagg gggcttgtgc      60
acacagcgag ggagacttag ggactggcag acggacggac ggacggcgag gaccctaccc     120 gagccccga gccatggccg agagaaagca atccgggaag gcggcagagg acgaagaggt     180
ccctgctttt tttaaaaacc tgggctccgg cagccccaag ccccggcaga aattctgtgg     240
catgttctgc ccggtggaag ggtcctcgga gaacaagacc atcgacttcg actcgctgtc     300
ggtgggccgg ggctcgggcc aggtggtggc tcagcagcgg gacgtcgccc acttgggccc     360
ggacccgcag ccgccgtact cgcggcaggg ccggcgcgcc ggcggagagc catctgttga     420
atcgggccgc aaggtggaga tccggagggc ctcgggcaaa aagcccctgc agaacatcaa     480
cgaccagagc gatcgtcttc tgatcaaagg aggtaaaatt gttaatgatg accagtcgtt     540
ctatgcagac atatacatgg aagatgggtt gatcaagcaa ataggagaaa atctgattgt     600
gccaggagga gtgaagacca tcgaggccca ctcccggatg gtgatccccg gaggaattga     660
cgtccacact cgtttccaga tgcctgatca gggaatgacg tctgctgatg atttcttcca     720
aggaaccaag gcggccctgg ctgggggaac cactatgatc attgaccacg ttgttcctga     780
gcctgggaca agcctgctcg ctgcctttga ccagtggagg gaatgggccg acagcaagtc     840
ctgctgtgac tactctctgc atgtggacat cagcgagtgg cataagggca tccaggagga     900
gatggaagcg cttgtgaagg atcacggggt aaattccttc ctcgtgtaca tggctttcaa     960
agatcgcttc cagctaacgg attgccagat ttatgaagta ctgagtgtga tccgggatat    1020 tgcgccata gcccaagtcc acgcagaaaa tggcgacatc attgcagagg agcagcagag    1080
gatcctggat ctgggcatca cgggccccga gggacatgtg ctgagccgac ctgaggaggt    1140
cgaggccgaa gccgtgaatc gtgccatcac catcgccaac cagaccaact gcccgctgta    1200
tatcaccaag gtgatgagca aaagctctgc tgaggtcatc gcccaggcac ggaagaaggg    1260
```

```
aactgtggtg tatggcgagc ccatcactgc cagcttggga acggacggct cccattactg    1320
gagcaagaac tgggccaagg ctgctgcctt tgtcacctcc ccaccctgga gccctgatcc    1380
aaccactcca gactttctca actccttgct gtcctgtgga gacctccagg tcacgggcag    1440
tgcccattgc acgtttaaca ctgcccagaa ggctgtagga aaggacaact tcaccctgat    1500
tccggagggc accaatggca ctgaggagcg gatgtccgtc atctgggaca aggctgtggt    1560
cactgggaag atggatgaga accagtttgt ggctgtgacc agcaccaatg cagccaaagt    1620
cttcaacctt taccccggga aaggccgcat tgctgtggga tccgatgccg acctggtcat    1680
ctgggacccc gacagcgtta aaaccatctc tgccaagaca cacaacagct ctctcgagta    1740
caacatcttt gaaggcatgg agtgccgcgg ctccccactg gtggtcatca gccaggggaa    1800
gattgtcctg gaggacggca ccctgcatgt caccgaaggc tctggacgct acattccccg    1860
gaagcccttc cctgattttg tttacaagcg tatcaaggca aggagcaggc tggctgagct    1920
gagaggggtt cctcgtggcc tgtatgacgg acctgtgtgt gaagtgtctg tgacgcccaa    1980
gacagtcact ccagcctcct cggccaagac gtctcctgcc aagcagcagg ccccacctgt    2040
ccggaacctg caccagtctg gattcagttt gtctggtgct cagattgatg acaacattcc    2100
ccgccgcacc acccagcgta tcgtggcgcc ccccggtggc cgtgccaaca tcaccagcct    2160
gggctagagc tcctgggctg tgccgtccac tggggactgg ggatgggaca cctgaggaca    2220
ttctgagact tctttcttcc ttccttttt tttttttgtt ttttttttta agagcctgtg    2280
atagttactg tggagcagcc agttcatggg gtccccttg gggccccaca cccgtctct    2340 caccaagagt tactgatttt gctcatccac ttccctacac atctatgggt atcacaccca    2400
agactaccca ccaagctcat acagggaacc acacccaaca cttagacatg cgaacaagca    2460
gcccccagcg agggtctcct tcgccttcaa cctcctagtg tctgttagca tcttcctttt    2520
catgggggga gggaagataa agtgaattgc ccagagctgc cttttctttt tcttttaaa    2580 aattttaaga agttttcttt gtggggctgg ggaggggccg gggtcaggga gagtcttttt    2640
tttttttttt tttaaatact aaattggaac atttaattcc atattaatac aaggggtttg    2700
aactggacat cctaatgatg caattacgtc atcacccagc tgattccggg tggttggcaa    2760
actcatcgtg tctgtcctga gaggctccac aatgcccacc cgcatcgcca ttctgtagtc    2820
ttcagggtca gctgttgata aaggggcagg cttgcgttat tggcctagat tttgctgcag    2880
attaaatcct ttgaggattc tcttctcttt taccattttt ctgcgtgctc tcactctctc    2940
tttctctctc tagctttta attcatgaat attttcgtgt ctgtctctct ctctctctgt    3000
gtttcctcca gcccttgtct cggagacggt gttttcctcc cttgcccat tatcttttca    3060 cctcccaggt ctaccatttc atggtggtcg ttgggtccgc ctaaaggatt tgagcgtttg    3120
ccattgcaag catagtgctg tgtcatcctg gtccatgtag gactggtgct aaccacctgc    3180
catcatgagt atgtgtgcta gagtgtggga ccctggccaa gtgcaggaat gggccatgcc    3240
gtctcaccca cagtatcaca cgtggaaccg cagacagggc ccagaagctt tagaggtatg    3300
aggctgcaga accggagaga ttttcctctg tgcagtgctc tctggctaaa gtcacggtca    3360
aacctaaaca ccgagcctca ttaacccaag tgaaccaacc aaagtcacca gttcagaagt    3420
gctaagctaa taggagtctg acccgagggc ctgctgcttc ctggttaagt atcttttgag    3480
attctagaac acatgggagc ttttattttt cggggaaaaa ccgtattttt ttcttgtcca    3540
attatttcta aagacacact acatagaaag aggccctata aactcaaaaa gtcattggga    3600
```

```
aacttaaagt ctattctact ttgcaagagg agaaatgtgt tttatgaacg atagatcaca      3660
tcagaactcc tgtggggagg aaaccttata aattaaacac atggccccct tagagaccac      3720
aggtgatgtc tgtctccatc cttccctctc cttttctgtc acctttcccc ctagctggct      3780
cctttggacc taccctgtc cttgctgact tgtgttgcat tgtattccaa acgtgtttac       3840
aggttctctt aagcaatgtt gtatttgcag gcttttctga ataccaaatc tgctttttgt      3900
aaagcgtaaa aacatcacaa agtaggtcat tccatcacca cccttgtctc tctacacatt      3960
ttgcctttgg ggatctggtt gggttttgg gttttttgtt gttgttgttt atttgttatt       4020
ttaaaggtaa attgcacttt taaaaaaata attggttgac ttaatatatt tgcttttttt      4080
ctcacctgca cttagaggaa atttgaacaa gttggaaaaa acaattttt gtttcaattc       4140 taagaaacac ttgcagctct agtattcact tgagtcttcc tgttttcct gtaccgggtc       4200 atggtaattt ttggttgttt tggttgtttt cttaaaaaac aagttaaaac ctgacgattt      4260
ctgcaggctg tgtaagcatg tttacctgtt ggcttgcttt gtgtgtctgt taaatgaatg      4320
tcatatgtaa atgctaaaat aaatcgacag tgtctcagaa ctgaataact gcagtgactt      4380
gatgctctaa aacagtgtag gatttaagaa tagatggttt ttaatcctgg aaattgtgat      4440
tgtgacccat gagtggagga acttcagtt ctaaagctga taagtgtgt agccagaaga       4500 gtacttttt ttttgtaacc actgtcttga tggcaaaata attatggtaa aaaacaagtc      4560
tcgtgtttat tattccttaa gaactctgtg ttatattacc atggaacgcc taataaagca      4620
aaatgtggtt gtttcaggaa aaaaaaaaa aaaaa                                 4655

<210> SEQ ID NO 44
<211> LENGTH: 4417
<212> TYPE: DNA
<213> ORGANISM: Homo sapiens
<220> FEATURE:
<223> OTHER INFORMATION: SEMA4D glucocorticoid receptor-responsive gene

<400> SEQUENCE: 44
gctgtaacac tcaccgtgaa ggtctgcagc ttcactcccg agccagcgag accacgaacc      60
caccagaagg aagaaactct gaacacatct gaacatcaga agggacagac tccagacgcg     120
ccaccactct gctaacacca gatagtggaa agaaaccatg tgctgaaatg tttgacgaca     180
ctgatggttt gactctgcta actggaatgg cttattgtgc aagaaagtac acctggtcgg     240
gtcctggggc tcatctctag caccagcaaa gatttctgaa gacgtctttc tagaaatgac     300
tggaaagttt caagaggcat aagatacagc atttcttctg aggccctgaa gaagtatcaa     360
gtgggctttg acattgcggt ggtgagagcg acccctcctc acctggagaa ctgggaaatg     420
tggattctca gggaccgcgc tgttcacgag ctccaggctg tgctgctggc cctggtcctg     480
gggcgctgag ccgcatctgc aatagcacac ttgcccggcc acctgctgcc gtgagccttt     540
gctgctgaag cccctggggt cgcctctacc tgatgaggat gtgcaccccc attagggggc     600
tgctcatggc ccttgcagtg atgtttggga cagcgatggc atttgcaccc ataccccgga     660
tcacctggga gcacagagag gtgcacctgg tgcagtttca tgagccagac atctacaact     720
actcagcctt gctgctgagc gaggacaagg acaccttgta cataggtgcc cgggaggcgg     780
tcttcgctgt gaacgcactc aacatctccg agaagcagca tgaggtgtat tggaaggtct     840
cagaagacaa aaaagcaaaa tgtgcagaaa aggggaaatc aaaacagaca gagtgcctca     900
actacatccg ggtgctgcag ccactcagcg ccacttccct ttacgtgtgt gggaccaacg     960
cattccagcc ggcctgtgac cacctgaact taacatcctt taagtttctg gggaaaaatg    1020
```

-continued

```
aagatggcaa aggaagatgt cccttttgacc cagcacacag ctacacatcc gtcatggttg    1080
atggagaact ttattcgggg acgtcgtata atttttttggg aagtgaaccc atcatctccc    1140
gaaattcttc ccacagtcct ctgaggacag aatatgcaat cccttggctg aacgagccta    1200
gtttcgtgtt tgctgacgtg atccgaaaaa gcccagacag ccccgacggc gaggatgaca    1260
gggtctactt cttcttcacg gaggtgtctg tggagtatga gtttgtgttc agggtgctga    1320
tcccacggat agcaagagtg tgcaaggggg accaggcgg cctgaggacc ttgcagaaga     1380
aatggacctc cttcctgaaa gcccgactca tctgctcccg gccagacagc ggcttggtct    1440
tcaatgtgct gcgggatgtc ttcgtgctca ggtccccggg cctgaaggtg cctgtgttct    1500
atgcactctt caccccacag ctgaacaacg tggggctgtc ggcagtgtgc gcctacaacc    1560
tgtccacagc cgaggaggtc ttctcccacg ggaagtacat gcagagcacc acagtggagc    1620
agtcccacac caagtgggtg cgctataatg gcccggtacc caagccgcgg cctggagcgt    1680
gcatcgacag cgaggcacgg gccgccaact acaccagctc cttgaatttg ccagacaaga    1740
cgctgcagtt cgttaaagac cacccttttga tggatgactc ggtaacccca atagacaaca    1800
ggcccaggtt aatcaagaaa gatgtgaact acacccagat cgtggtggac cggacccagg    1860
ccctggatgg gactgtctat gatgtcatgt ttgtcagcac agaccgggga gctctgcaca    1920
aagccatcag cctcgagcac gctgttcaca tcatcgagga gacccagctc ttccaggact    1980
ttgagccagt ccagaccctg ctgctgtctt caaagaaggg caacaggtttt gtctatgctg    2040 gctctaactc gggcgtggtc caggccccgc tggccttctg tgggaagcac ggcacctgcg    2100
aggactgtgt gctggcgcgg gaccctact gcgcctggag cccgcccaca gcgacctgcg     2160
tggctctgca ccagaccgag agccccagca ggggtttgat tcaggagatg agcggcgatg    2220
cttctgtgtg cccggcctcg tctcctaagc ccctccctcc tctggctcc tcttccctgt     2280 cctgtctggg ccatgtgggg gacaggaggc tttcctctcc ctggaccccc tggccagcct    2340
cgggtgcggg gcccgacagc agctcgaggg tctccttgct gccgcccttc ctgagtgacc    2400
aggcacagca cgtgcacgcc ctggggaact tctacctctt ctgccaggcc acaggtcctg    2460
cagacattcg ctttgtctgg gagaagaatg ggcgagctct ggagacctgt gtccctgtgc    2520
agacccatgc actgcccgat ggcagggccc atgcactcag ctggctgcag gacgccatca    2580
gggaaagcgc tgagtatcgc tgctctgtcc tctcctcagc agggaacaag acttcgaagg    2640
tgcaggttgc tgtgatgaga cctgaagtga cccaccagga gaggtggacc agagagctct    2700
ctgcctggag ggctgtggct ggggagcacg accggatgat gcagagctgg aggaaggcgt    2760
gggaaagctg tagcaaggac accctgtagc caccaggaag gagtccctga caccgacctc    2820
aaccccaaca agaccctgct gccactgacc acagccaccc ccgagaagg cctggtcccc     2880 cacaactgtg aactgtcttg cccaagcctg ctctgaacac agccattggg ccaccacctg    2940
atgggcagag gcgggacagt ggagaagcct ggaacccaag tgggcctgtg acaggaacta    3000
agacttaaaa aattaggtgc ttacctggga cagtaagttc tgtctggcac aagcaggtaa    3060
ccaggatggc taacaggctt tgatagctgc tcgtgaacta aaacagcagg gtgtgtgcag    3120
gttcctcctc tacggtcagg cagcaggctc tgaaggctga tcctacaccg tcccagtgac    3180
tccccttgac agagtgcccc cacccccctaa tagccaacag ggttagcatg ccagcacag    3240 atcgctgctt ttattgatgc aaatcaagcc tgctgcttct cctccctgca gacttagcca    3300
aggaactcca agatgcatga ctgggacaag aaaaggtgag actccacatg gaaatgcctt    3360
```

```
gccctaaacc ttgaatgact gtgagatgcg atctgggagt gcatctgtca agtctttgtg    3420
ttttcttcac taacctcaga atactgggct ctattttatc aagcgctgca gtttatgcct    3480
ctgtcccgtc aatgctcagc ttctgcaaca ggacaccaaa cttgatgcag aaagccaaat    3540
aggtcaatta tgcaaatctc ctggtgccat attaaatttc ttgacgatgg aatgagtctc    3600
atgagtgttt tgttctacct gctttcaagt ctctaattat taaagctgta tctctgaaga    3660
ctgtgtcact gtgtgtgtga acttgtccta aagctactca gcctttaatc ttacacacac    3720
gtctcttctt gtctgttgaa tgacagtttt catgtctatc ataaaaccaa agcctctgtt    3780
aaaagtcaag ccgcaccoct ctggtgatcc tagcaaatac tgagtgtctt cccagcagtg    3840
tgacaatgac ctgttttgca tccoctcttt ctggagctgg acaaattctc taccagcctt    3900
tgtgtgggat cagcatacat cgcctgctaa ttccttcagg atccatcaca acaggtgtcc    3960
tgaagatgct ggagacaccc tggttgtctc cacacgttcc cootccgcac cccaagtcga    4020 gaggcccagc tgcctgtgag gtgtgtgctt gcccatccag ccaaggatgc cagtcttgct    4080
cacggaacca tcacatactc ataacctgaa gttttcctgt aaaatatcca tcagctcact    4140
gtggttcttg ctttgggtgt ggcttcaacc actacaaact gatgagtgaa atgctatggg    4200
ctttaggctt atattcttgg tgctgttttc tgtctcttct cctgaagtct ggatttcaag    4260
cactttcaca cttaacaaaa taattacata cttgaagttt tcgtaatgtg gagtgttcta    4320
ctgggaaatg gagttatgag gatgaatttc tgagtctttc tttgctctgc tggaaaaaat    4380
aaaaatagag ttgtacattg aaaaaaaaaa aaaaaa                              4417

<210> SEQ ID NO 45
<211> LENGTH: 3108
<212> TYPE: DNA
<213> ORGANISM: Homo sapiens
<220> FEATURE:
<223> OTHER INFORMATION: STOM glucocorticoid receptor-responsive gene

<400> SEQUENCE: 45
gcctctggct cctcagggca ttcccggcgg ctccgggttt ggcaacgagg acggggagt      60 gcgactgcgt ctcgggcagc atggccgaga agcggcacac acgggactcc gaagcccagc    120
ggctccccga ctccttcaag gacagcccca gtaagggcct tggaccttgc ggatggattt    180
tggtggcgtt ctcattctta ttcaccgtta aactttccc aatctcaata tggatgtgca    240
taaagattat aaaagagtat gaaagagcca tcatctttag attgggtcgc attttacaag    300
gaggagccaa aggacctggt ttgtttttta ttctgccatg cactgacagc ttcatcaaag    360
tggacatgag aactatttca tttgatattc ctcctcagga gatcctcaca aaggattcag    420
tgacaattag cgtggatggt gtggtctatt accgcgttca gaatgcaacc ctggctgtgg    480
caaatatcac caacgctgac tcagcaaccc gtcttttggc acaaactact ctgaggaatg    540
ttctgggcac caagaatctt tctcagatcc tctctgacag agaagaaatt gcacacaaca    600
tgcagtctac tctggatgat gccactgatg cctggggaat aaaggtggag cgtgtggaaa    660
ttaaggatgt gaaactacct gtgcagctcc agagagctat ggctgcagaa gcagaagcgt    720
cccgcgaggc ccgcgccaag gttattgcag ccgaaggaga aatgaatgca tccagggctc    780
tgaaagaagc ctccatggtc atcactgaat ctcctgcagc ccttcagctc cgatacctgc    840
agacactgac caccattgct gctgagaaaa actcaacaat tgtcttccct ctgcccatag    900
atatgctgca aggaatcata ggggcaaaac acagccatct aggctagtgt agagatgagc    960
gctagccttc caagcatgaa gtcggggacc aaattagcct ttaactcata aagagagggt   1020
```

```
agggcttttc ttttttccata tgtcaattgt ggtgttccca gaatgtatag cagttataaa    1080
aataggtgaa agaattgtta gcttgtaaat actgagagat tggtgattta tataaggtaa    1140
tctgttagtc ttaaaatagt taaaagtttg tatttttaga ttattatgta gtaggttaga    1200
tccctcttgt tttgacttcc actgactcat tctgaacccc ctaagcaccc aggccagagg    1260
caagaacctg ggctgtaact gccacctgac accgctgact ggctaaatgc tttgcagaaa    1320
gtgatgacct tacaccacaa ccagcttctc caggtcatat gtgccttacc tccagagagt    1380
cttttttttt tttttttctga gatggagttt cactcttgtt gcccaggctg gagtgcaata    1440
gcatgatctc ggctcactgc aacctccgcc tcctgggttc aagagattct cctgcctcag    1500
cctcccccagt agctgggatt acaggctcat gccaccatgc ccagctaatt tttgtattat    1560
tattattgtt tttagtaga cggggtttt caccatgttg gccaggctag tcacgaactc    1620
ctaacctcag gtgatccacc cacctctgcc tcccaaagtg ctgggattac aggcatgagc    1680
taccacacct ggtttggaga gtcttaatta aggaaatttc cctaatgttc atttatttc     1740
taaatccaga ccgtgtttca gaataatcct tacttgagag tagccatttt cttgcctgta    1800
cttgtcagaa ctagaggaaa tagccaagac taatgaaaaa gattactcta acccttaaaa    1860
gacttttaaa ttcactacta gagtggtcat tttaaaaata catccatgtt ttaacttatt    1920
tgagccttct ttatgagtaa atgattcctc cttgttctgt ctttcaaacc agctaaatat    1980
ttgtcacaaa agtgcttttt tctcactgtt gcctatttc atatatcagg ttttaaatag    2040
ttttaatttt ttaataaaat tttctctacg ttctatatgc aattgttata tatctatttg    2100
aatagctgaa ggactaaaat actttttaa gagataactt caggaaacca ttatatttta    2160
ctatctgcat gctgttaact gtggtacact gtgaaatatg ttgattacaa acccattcat    2220
tacatagtat aaggaattca cagtatattg actatatagt gtctaatgat cttgggcaga    2280
tactgtcaaa cttacaatat ctatatagat gtaggtcttt ttaaatttac ctagtcattc    2340
ttctatcatg tatattgatg ctgaaagagg aactggtcag ctcctctgga caacaaattc    2400
ttagtctata atattaggag acatcttctg ttttgcaaat gtctgtgaat ctgagcaacc    2460
tggcattctg cttactggcc agaaagctgg cgggtgacat ttgtaacatt tcctctttga    2520
gactctgagt tcacctagag aagtctaagc ataacagctt tctttcccag cacgagcctt    2580
tatagctctc tttagctcaa ccactctgtc catccagcca atggatgtcc cttcccctgt    2640
accccaattt caagcttatt ttaggaagcc ttgaactacc atgtatcctg gctcctagct    2700
gagtttatta gaggtatgga gcagtgcaac ttaaactcaa gttgcactta cattttgaat    2760
tttaaaatga tggttttatc tgttgtgtga agtggttcac ccttgaggac caggagcctc    2820
catatcctga ctgaaaacct tttctgagac ttagagtaac agtgcttttg gttccttgag    2880
ttctcctgtc tccagatacc aaatgacctt gacttttctg ccttgtgaat tcgtagtcca    2940
atcagctgaa attaaatcac ttgggaggga cgcatagaag gagctctagg aacacagtgc    3000
cagtgcagaa gtttctccag gtggcctccc tttccaacaa tgtacataat aaagtgtatg    3060
cactttcact aataaaaaaa aaaaaaaaaa aaaaaaaaa aaaaaaaa                  3108
```

<210> SEQ ID NO 46
<211> LENGTH: 4090
<212> TYPE: DNA
<213> ORGANISM: Homo sapiens
<220> FEATURE:
<223> OTHER INFORMATION: MAOA glucocorticoid receptor-responsive gene

```
<400> SEQUENCE: 46
gggcgctccc ggagtatcag caaaagggtt cgccccgccc acagtgcccg gctcccccg      60
ggtatcaaaa gaaggatcgg ctccgccccc gggctccccg ggggagttga tagaagggtc    120
cttcccaccc tttgccgtcc ccactcctgt gcctacgacc caggagcgtg tcagccaaag    180
catggagaat caagagaagg cgagtatcgc gggccacatg ttcgacgtag tcgtgatcgg    240
aggtggcatt tcaggactat ctgctgccaa actcttgact gaatatggcg ttagtgtttt    300
ggttttagaa gctcgggaca gggttggagg aagaacatat actataagga atgagcatgt    360
tgattacgta gatgttggtg gagcttatgt gggaccaacc caaaacagaa tcttacgctt    420
gtctaaggag ctgggcatag agacttacaa agtgaatgtc agtgagcgtc tcgttcaata    480
tgtcaagggg aaaacatatc catttcgggg cgcctttcca ccagtatgga atcccattgc    540
atatttggat tacaataatc tgtggaggac aatagataac atggggaagg agattccaac    600
tgatgcaccc tgggaggctc aacatgctga caaatgggac aaaatgacca tgaaagagct    660
cattgacaaa atctgctgga caaagactgc taggcggttt gcttatcttt ttgtgaatat    720
caatgtgacc tctgagcctc acgaagtgtc tgccctgtgg ttcttgtggt atgtgaagca    780
gtgcggggc accactcgga tattctctgt caccaatggt ggccaggaac ggaagtttgt    840
aggtggatct ggtcaagtga gcgaacggat aatggacctc ctcggagacc aagtgaagct    900
gaaccatcct gtcactcacg ttgaccagtc aagtgacaac atcatcatag agacgctgaa    960
ccatgaacat tatgagtgca atacgtaat taatgcgatc cctccgacct tgactgccaa   1020
gattcacttc agaccagagc ttccagcaga gagaaaccag ttaattcagc ggcttccaat   1080
gggagctgtc attaagtgca tgatgtatta caaggaggcc ttctggaaga agaaggatta   1140
ctgtggctgc atgatcattg aagatgaaga tgctccaatt tcaataacct tggatgacac   1200
caagccagat gggtcactgc ctgccatcat gggcttcatt cttgcccgga agctgatcg   1260
acttgctaag ctacataagg aaataaggaa gaagaaaatc tgtgagctct atgccaaagt   1320
gctgggatcc caagaagctt tacatccagt gcattatgaa gagaagaact ggtgtgagga   1380
gcagtactct gggggctgct acacggccta cttcccctcct gggatcatga ctcaatatgg   1440
aagggtgatt cgtcaacccg tgggcaggat tttctttgcg ggcacagaga ctgccacaaa   1500
gtggagcggc tacatggaag gggcagttga ggctggagaa cgagcagcta gggaggtctt   1560
aaatggtctc gggaaggtga ccgagaaaga tatctgggta caagaacctg aatcaaagga   1620
cgttccagcg gtagaaatca cccacacctt ctgggaaagg aacctgccct ctgtttctgg   1680
cctgctgaag atcattggat tttccacatc agtaactgcc ctggggtttg tgctgtacaa   1740
atacaagctc ctgccacggt cttgaagttc tgttcttatg ctctctgctc actggttttc   1800
aataccacca agaggaaaat attgacaagt ttaaaggctg tgtcattggg ccatgtttaa   1860
gtgtactgga tttaactacc tttggcttaa ttccaatcat tgttaaagta aaacaattc    1920
aaagaatcac ctaattaatt tcagtaagat caagctccat cttatttgtc agtgtagatc   1980
aactcatgtt aattgataga ataaagcctt gtgatcactt tctgaaattc acaaagttaa   2040
acgtgatgtc tcatcagaa acaatttctg tgtcctgttt ttattccctt caatgcaaaa    2100
tacatgatga tttcagaaac aaagcatttg actttctgtc tgtggaggtg gagtaggtga   2160
aggcccagcc tgtaactgtc ctttttcttc ccttaggcaa tggtgaactg tcattacaga   2220
gcctagaggc tcacagcctc ctggaggaag cagcctccac tttggatcag gaaatagtaa   2280
aggaaagcag tgttgggggt agcggcatgc agaccctcag accagaatgg ggacatcttg   2340
```

```
tggtctgctg cctcaggaat ctcctgacca cttgtagtcc ctccgacttc tctagacatc    2400
tagtctcagt gctagcttat ttgtattttt cctctttcac ttcttatgga ggagagtgtt    2460
taactgagtt agaatgttga aactgacttg ctgtgactta tgtgcagctt tccagttgag    2520
cagaggaaaa tagtggcagg actgtccccc aggaggactc cctgcttagc tctgtgggag    2580
accaactacg actggcatct tctcttcccc ctggaaggca gctagacacc aatggatcct    2640
tgtcagttgt aacattctat ttcaacttca ggaaagcagc agttttcttt taattttcc    2700 tatgaccata aaattagaca tacctctcaa cttacatatg tcttcaacat ggttacctct    2760
gcataaatat tagcaaagca tgccaatttc tcttaagtac tgaaatacat atgataaatt    2820
tgactgttat ttgttgagac tatcaaacag aaaagaaatt agggctctaa tttccttaaa    2880
gcaagctcac ttgctttagt tgttaagttt tataaaagac atgaaattga gtcattttat    2940
atatgaaaac taagttctct atcttaggag taatgtcggc ccacaagggt gcccacctct    3000
tgttttcccc ttttaaaaac tcagattttt aaaagccctt tccaaaggtt tcaactgtaa    3060
aatacttctt tttacaatgt atcaacatat tttattttaa ggggaattaa caattgccag    3120
ggaaaccagc caacccaagt ttattatatc attaaccta tcataaattc aaacctaagt    3180
tgctggaccc tggtgtgagg acataaatct tccaaagttt tgcctatcct aagagctgca    3240 ttttctact gctctttacc ttgcatttta gctaatttag gagttttgag aatgtattgg    3300
atacgctcca gtacataagg agttgccgca tattatatca gactgctttg agaaatctca    3360
tccctagtct attgcagttg tttctattag cttactgatt aactcagtcc tgacacacct    3420
tttgggaaat gctgatttaa acttcttaac tggcaacagt tggaacagta atcagtttgc    3480
taacatattt aaagtcttga atgttgaaga actcatgtga tttaccctt tcaacttttt    3540 ggaaaacgat ttaatttatt ctaattagat taaccctatt aatctatgga ttgggtatca    3600
aaatgaatgc cagtccagat gtgcctagac acgaaattgg agctgaggac tctcacgata    3660
tgcaagttca tccaacgtga agataccata agcttttct ctgaaccaga gaaatgaaag    3720
tcagtttaag aggctgatag atcttggccc tgttaaggca tccacttcac agttctgaag    3780
gctgagtcag ccccactcca cagttaggcc aagaattaga ttttaaaact tcatctgtct    3840
gtcccagtta actgttaaat aaggcctcat cctccactga agagtatgga ttgaaggatt    3900
gtgaactatg tttagtgtga ttgtgaactt ggtgcctaat gttccatgtc tgaagtttgc    3960
cccagtgcta cacgttggag tatacctatg tgtgtgcttt gccactgaag taagattttg    4020
cctgtatggt actgttttgt ttgttaataa agtgcactgc cacccccaat gcaaaaaaaa    4080
aaaaaaaaa                                                           4090

<210> SEQ ID NO 47
<211> LENGTH: 6784
<212> TYPE: DNA
<213> ORGANISM: Homo sapiens
<220> FEATURE:
<223> OTHER INFORMATION: glucocorticoid receptor (GR) alpha

<400> SEQUENCE: 47
ggcgccgcct ccacccgctc cccgctcggt cccgctcgct cgcccaggcc gggctgccct      60
ttcgcgtgtc cgcgctctct tccctccgcc gccgcctcct ccatttgcg agctcgtgtc     120 tgtgacggga gcccgagtca ccgcctgccc gtcggggacg gattctgtgg gtggaaggag     180
acgccgcagc cggagcggcc gaagcagctg ggaccgggac ggggcacgcg cgcccggaac     240
```

```
ctcgacccgc ggagcccggc gcggggcgga gggctggctt gtcagctggg caatgggaga    300 cttttcttaaa tagggctct ccccccaccc atggagaaag gggcggctgt ttacttcctt    360
tttttagaaa aaaaaatat atttccctcc tgctccttct gcgttcacaa gctaagttgt    420
ttatctcggc tgcggcggga actgcggacg gtggcgggcg agcggctcct ctgccagagt    480
tgatattcac tgatggactc caaagaatca ttaactcctg gtagagaaga aaaccccagc    540
agtgtgcttg ctcaggagag gggagatgtg atggacttct ataaaaccct aagaggagga    600
gctactgtga aggtttctgc gtcttcaccc tcactggctg tcgcttctca atcagactcc    660
aagcagcgaa acttttggt tgattttcca aaaggctcag taagcaatgc gcagcagcca    720
gatctgtcca aagcagtttc actctcaatg ggactgtata tgggagagac agaaacaaaa    780
gtgatgggaa atgacctggg attcccacag cagggccaaa tcagcctttc ctcgggggaa    840
acagacttaa agcttttgga agaaagcatt gcaaacctca ataggtcgac cagtgttcca    900 gagaaccccca agagttcagc atccactgct gtgtctgctg cccccacaga gaaggagttt    960
ccaaaaactc actctgatgt atcttcagaa cagcaacatt tgaagggcca gactggcacc    1020
aacggtggca atgtgaaatt gtataccaca gaccaaagca cctttgacat tttgcaggat    1080
ttggagtttt cttctgggtc cccaggtaaa gagacgaatg agagtccttg gagatcagac    1140
ctgttgatag atgaaaactg tttgctttct cctctggcgg gagaagacga ttcattcctt    1200
ttggaaggaa actcgaatga ggactgcaag cctctcattt taccggacac taaacccaaa    1260
attaaggata tggagatctg gttttgtca agccccagta atgtaacact gccccaagtg    1320
aaaacagaaa aagaagattt catcgaactc tgcacccctg gggtaattaa gcaagagaaa    1380
ctgggcacag tttactgtca ggcaagcttt cctggagcaa atataattgg taataaaatg    1440
tctgccattt ctgttcatgg tgtgagtacc tctggaggac agatgtacca ctatgacatg    1500
aatacagcat ccctttctca acagcaggat cagaagccta ttttaatgt cattccacca    1560 attcccgttg gttccgaaaa ttggaatagg tgccaaggat ctggagatga caacttgact    1620
tctctgggga ctctgaactt ccctggtcga acagttttt ctaatggcta ttcaagcccc    1680
agcatgagac cagatgtaag ctctcctcca tccagctcct caacagcaac aacaggacca    1740
cctcccaaac tctgcctggt gtgctctgat gaagcttcag gatgtcatta tggagtctta    1800
acttgtggaa gctgtaaagt tttcttcaaa agagcagtgg aaggacagca caattaccta    1860
tgtgctggaa ggaatgattg catcatcgat aaaattcgaa gaaaaaactg cccagcatgc    1920
cgctatcgaa aatgtcttca ggctggaatg aaccctggaag ctcgaaaaac aaagaaaaaa    1980
ataaaaggaa ttcagcaggc cactacagga gtctcacaag aaacctctga aaatcctggt    2040
aacaaaacaa tagttcctgc aacgttacca caactcacccc ctaccctggt gtcactgttg    2100
gaggttattg aacctgaagt gttatatgca ggatatgata gctctgttcc agactcaact    2160
tggaggatca tgactacgct caacatgtta ggagggcggc aagtgattgc agcagtgaaa    2220
tgggcaaagg caataccagg tttcaggaac ttacacctgg atgaccaaat gaccctactg    2280
cagtactcct ggatgtttct tatggcattt gctctggggt ggagatcata tagacaatca    2340
agtgcaaacc tgctgtgttt tgctcctgat ctgattatta tgagcagag aatgactcta    2400 ccctgcatgt acgaccaatg taaacacatg ctgtatgttt cctctgagtt acacaggctt    2460
caggtatctt atgaagagta tctctgtatg aaaaccttac tgcttctctc ttcagttcct    2520
aaggacggtc tgaagagcca agagctattt gatgaaatta gaatgaccta catcaaagag    2580
ctaggaaaag ccattgtcaa gagggaagga aactccagcc agaactggca gcggtttttat    2640
```

```
caactgacaa aactcttgga ttctatgcat gaagtggttg aaaatctcct taactattgc    2700
ttccaaacat ttttggataa gaccatgagt attgaattcc ccgagatgtt agctgaaatc    2760
atcaccaatc agataccaaa atattcaaat ggaaatatca aaaaacttct gtttcatcaa    2820
aagtgactgc cttaataaga atggttgcct taaagaaagt cgaattaata gcttttattg    2880
tataaactat cagtttgtcc tgtagaggtt ttgttgtttt attttttatt gttttcatct    2940
gttgttttgt tttaaatacg cactacatgt ggtttataga gggccaagac ttggcaacag    3000
aagcagttga gtcgtcatca cttttcagtg atgggagagt agatggtgaa atttattagt    3060
taatatatcc cagaaattag aaaccttaat atgtggacgt aatctccaca gtcaaagaag    3120
gatggcacct aaaccaccag tgcccaaagt ctgtgtgatg aactttctct tcatactttt    3180
tttcacagtt ggctggatga aattttctag actttctgtt ggtgtatccc ccccctgtat    3240
agttaggata gcatttttga tttatgcatg gaaacctgaa aaaaagttta caagtgtata    3300
tcagaaaagg gaagttgtgc cttttatagc tattactgtc tggttttaac aatttccttt    3360
atatttagtg aactacgctt gctcattttt tcttacataa ttttttattc aagttattgt    3420
acagctgttt aagatgggca gctagttcgt agctttccca aataaactct aaacattaat    3480
caatcatctg tgtgaaaatg ggttggtgct tctaacctga tggcacttag ctatcagaag    3540
accacaaaaa ttgactcaaa tctccagtat tcttgtcaaa aaaaaaaaaa aaaaagctca    3600
tattttgtat atatctgctt cagtggagaa ttatataggt tgtgcaaatt aacagtccta    3660
actggtatag agcacctagt ccagtgacct gctgggtaaa ctgtggatga tggttgcaaa    3720
agactaattt aaaaaataac taccaagagg ccctgtctgt acctaacgcc ctatttttgc    3780
aatggctata tggcaagaaa gctggtaaac tatttgtctt tcaggacctt ttgaagtagt    3840
ttgtataact tcttaaaagt tgtgattcca gataaccagc tgtaacacag ctgagagact    3900
tttaatcaga caaagtaatt cctctcacta aactttaccc aaaaactaaa tctctaatat    3960
ggcaaaaatg gctagacacc catttttcaca ttcccatctg tcaccaattg gttaatcttt    4020
cctgatggta caggaaagct cagctactga ttttttgtgat ttagaactgt atgtcagaca    4080
tccatgtttg taaaactaca catccctaat gtgtgccata gagtttaaca caagtcctgt    4140
gaatttcttc actgttgaaa attatttttaa acaaaataga agctgtagta gcccttctg    4200 tgtgcacctt accaacttttc tgtaaactca aaacttaaca tatttactaa gccacaagaa    4260
atttgatttc tattcaaggt ggccaaatta tttgtgtaat agaaaactga aaatctaata    4320
ttaaaaatat ggaacttcta atatattttt atatttagtt atagtttcag atatatatca    4380
tattggtatt cactaatctg ggaagggaag ggctactgca gctttacatg caatttatta    4440
aaatgattgt aaaatagctt gtatagtgta aaataagaat gatttttaga tgagattgtt    4500
ttatcatgac atgttatata ttttttgtag gggtcaaaga aatgctgatg gataacctat    4560
atgatttata gtttgtacat gcattcatac aggcagcgat ggtctcagaa accaaacagt    4620
ttgctctagg ggaagaggga gatggagact ggtcctgtgt gcagtgaagg ttgctgaggc    4680
tctgacccag tgagattaca gaggaagtta tcctctgcct cccattctga ccacccttct    4740
cattccaaca gtgagtctgt cagcgcaggt ttagtttact caatctcccc ttgcactaaa    4800
gtatgtaaag tatgtaaaca ggagacagga aggtggtgct tacatcctta aaggcaccat    4860
ctaatagcgg gttactttca catacagccc tcccccagca gttgaatgac aacagaaagct    4920 tcagaagttt ggcaatagtt tgcatagagg taccagcaat atgtaaatag tgcagaatct    4980
```

| | |
|---|---|
| cataggttgc caataataca ctaattcctt tctatcctac aacaagagtt tatttccaaa | 5040 |
| taaaatgagg acatgttttt gttttctttg aatgctttt gaatgttatt tgttattttc | 5100 |
| agtattttgg agaaattatt taataaaaaa acaatcattt gctttttgaa tgctctctaa | 5160 |
| aagggaatgt aatattttaa gatggtgtgt aacccggctg gataaatttt tggtgcctaa | 5220 |
| gaaaactgct tgaatattct tatcaatgac agtgttaagt ttcaaaaaga gcttctaaaa | 5280 |
| cgtagattat cattccttta tagaatgtta tgtggttaaa accagaaagc acatctcaca | 5340 |
| cattaatctg attttcatcc caacaatctt ggcgctcaaa aaatagaact caatgagaaa | 5400 |
| aagaagatta tgtgcacttc gttgtcaata ataagtcaac tgatgctcat cgacaactat | 5460 |
| aggaggcttt tcattaaatg ggaaagaag ctgtgcccct ttaggatacg tggggggaaaa | 5520 |
| gaaagtcatc ttaattatgt ttaattgtgg atttaagtgc tatatggtgg tgctgtttga | 5580 |
| aagcagattt atttcctatg tatgtgttat ctggccatcc caacccaaac tgttgaagtt | 5640 |
| tgtagtaact tcagtgagag ttggttactc acaacaaatc ctgaaaagta ttttagtgt | 5700 |
| ttgtaggtat tctgtgggat actatacaag cagaactgag gcacttagga cataacactt | 5760 |
| ttggggtata tatatccaaa tgcctaaaac tatgggagga aaccttggcc accccaaaag | 5820 |
| gaaaactaac atgatttgtg tctatgaagt gctggataat tagcatggga tgagctctgg | 5880 |
| gcatgccatg aaggaaagcc acgctcccctt cagaattcag aggcagggag caattccagt | 5940 |
| ttcacctaag tctcataatt ttagttccct tttaaaaacc ctgaaaacta catcaccatg | 6000 |
| gaatgaaaaa tattgttata caatacattg atctgtcaaa cttccagaac catggtagcc | 6060 |
| ttcagtgaga tttccatctt ggctggtcac tccctgactg tagctgtagg tgaatgtgtt | 6120 |
| tttgtgtgtg tgtgtctggt tttagtgtca gaagggaaat aaaagtgtaa ggaggacact | 6180 |
| ttaaacccctt tgggtggagt ttcgtaattt cccagactat tttcaagcaa cctggtccac | 6240 |
| ccaggattag tgaccaggtt ttcaggaaag gatttgcttc tctctagaaa atgtctgaaa | 6300 |
| ggattttatt ttctgatgaa aggctgtatg aaaataccct cctcaaataa cttgcttaac | 6360 |
| tacatataga ttcaagtgtg tcaatattct attttgtata ttaaatgcta tataatgggg | 6420 |
| acaaatctat attatactgt gtatggcatt attaagaagc ttttcatta ttttttatca | 6480 |
| cagtaatttt aaaatgtgta aaaattaaaa ccagtgactc ctgtttaaaa ataaaagttg | 6540 |
| tagtttttta ttcatgctga ataataatct gtagttaaaa aaaagtgtc ttttttaccta | 6600 |
| cgcagtgaaa tgtcagactg taaaaccttg tgtggaaatg tttaactttt attttttcat | 6660 |
| ttaaatttgc tgttctggta ttaccaaacc acacatttgt accgaattgg cagtaaatgt | 6720 |
| tagccattta cagcaatgcc aaatatggag aaacatcata ataaaaaaat ctgcttttc | 6780 |
| atta | 6784 |

<210> SEQ ID NO 48
<211> LENGTH: 4154
<212> TYPE: DNA
<213> ORGANISM: Homo sapiens
<220> FEATURE:
<223> OTHER INFORMATION: glucocorticoid receptor (GR) beta

<400> SEQUENCE: 48

| | |
|---|---|
| ggcgccgcct ccacccgctc cccgctcggt cccgctcgct cgcccaggcc gggctgccct | 60 |
| ttcgcgtgtc cgcgctctct tccctccgcc gccgcctcct ccattttgcg agctcgtgtc | 120 |
| tgtgacggga gcccgagtca ccgcctgccc gtcggggacg gattctgtgg gtggaaggag | 180 |
| acgccgcagc cggagcggcc gaagcagctg ggaccgggac ggggcacgcg cgcccggaac | 240 |

```
ctcgacccgc ggagcccggc gcggggcgga gggctggctt gtcagctggg caatgggaga      300 cttcttaaa  taggggctct ccccccaccc atggagaaag gggcggctgt ttacttcctt      360
tttttagaaa aaaaaaatat atttccctcc tgctccttct gcgttcacaa gctaagttgt      420
ttatctcggc tgcggcggga actgcggacg gtggcgggcg agcggctcct ctgccagagt      480
tgatattcac tgatggactc caaagaatca ttaactcctg gtagagaaga aaaccccagc      540
agtgtgcttg ctcaggagag gggagatgtg atggacttct ataaaccct  aagaggagga      600 gctactgtga aggtttctgc gtcttcaccc tcactggctg tcgcttctca atcagactcc      660
aagcagcgaa gacttttggt tgattttcca aaaggctcag taagcaatgc gcagcagcca      720
gatctgtcca aagcagtttc actctcaatg ggactgtata tgggagagac agaaacaaaa      780
gtgatgggaa atgacctggg attcccacag cagggccaaa tcagcctttc ctcgggggaa      840
acagacttaa agcttttgga agaaagcatt gcaaacctca ataggtcgac cagtgttcca      900
gagaacccca agagttcagc atccactgct gtgtctgctg cccccacaga gaaggagttt      960
ccaaaaactc actctgatgt atcttcagaa cagcaacatt tgaagggcca gactggcacc     1020
aacggtggca atgtgaaatt gtataccaca gaccaaagca cctttgacat tttgcaggat     1080
ttggagtttt cttctgggtc cccaggtaaa gagacgaatg agagtccttg gagatcagac     1140
ctgttgatag atgaaaactg tttgctttct cctctggcgg gagaagacga ttcattcctt     1200
ttggaaggaa actcgaatga ggactgcaag cctctcattt taccggacac taaacccaaa     1260
attaaggata tggagatct  ggttttgtca agccccagta atgtaacact gccccaagtg     1320
aaaacagaaa agaagatttt catcgaactc tgcaccctg  gggtaattaa gcaagagaaa     1380
ctgggcacag tttactgtca ggcaagcttt cctggagcaa atataattgg taataaaatg     1440
tctgccattt ctgttcatgg tgtgagtacc tctggaggac agatgtacca ctatgacatg     1500
aatacagcat ccctttctca acagcaggat cagaagccta ttttaatgt  cattccacca     1560 attcccgttg gttccgaaaa ttggaatagg tgccaaggat ctggagatga aacttgact      1620 tctctgggga ctctgaactt ccctggtcga acagttttt  ctaatggcta ttcaagcccc     1680
agcatgagac cagatgtaag ctctcctcca tccagctcct caacagcaac aacaggacca     1740
cctcccaaac tctgcctggt gtgctctgat gaagcttcag gatgtcatta tggagtctta     1800
acttgtggaa gctgtaaagt tttcttcaaa agagcagtgg aaggacagca caattaccta     1860
tgtgctggaa ggaatgattg catcatcgat aaaattcgaa gaaaaactg  cccagcatgc     1920 cgctatcgaa aatgtcttca ggctggaatg aacctggaag ctcgaaaaac aaagaaaaaa     1980 ataaaggaa  ttcagcaggc cactacagga gtctcacaag aaacctctga aaatcctggt     2040
aacaaaacaa tagttcctgc aacgttacca caactcaccc ctaccctggt gtcactgttg     2100
gaggttattg aacctgaagt gttatatgca ggatatgata gctctgttcc agactcaact     2160
tggaggatca tgactacgct caacatgtta ggagggcggc aagtgattgc agcagtgaaa     2220
tgggcaaagg caataccagg tttcaggaac ttacacctgg atgaccaaat gaccctactg     2280
cagtactcct ggatgtttct tatggcattt gctctggggt ggagatcata tagacaatca     2340
agtgcaaacc tgctgtgttt tgctcctgat ctgattatta tgagcagag  aatgactcta     2400 ccctgcatgt acgaccaatg taaacacatg ctgtatgttt cctctgagtt acacaggctt     2460
caggtatctt atgaagagta tctctgtatg aaaaccttac tgcttctctc ttcagttcct     2520
aaggacggtc tgaagagcca agagctattt gatgaaatta gaatgaccta catcaaagag     2580
```

| | |
|---|---|
| ctaggaaaag ccattgtcaa gagggaagga aactccagcc agaactggca gcggttttat | 2640 |
| caactgacaa aactcttgga ttctatgcat gaaaatgtta tgtggttaaa accagaaagc | 2700 |
| acatctcaca cattaatctg attttcatcc caacaatctt ggcgctcaaa aaatagaact | 2760 |
| caatgagaaa aagaagatta tgtgcacttc gttgtcaata ataagtcaac tgatgctcat | 2820 |
| cgacaactat aggaggcttt tcattaaatg ggaaagaag ctgtgcctt ttaggatacg | 2880 |
| tgggggaaaa gaaagtcatc ttaattatgt ttaattgtgg atttaagtgc tatatggtgg | 2940 |
| tgctgtttga aagcagattt atttcctatg tatgtgttat ctggccatcc caacccaaac | 3000 |
| tgttgaagtt tgtagtaact tcagtgagag ttggttactc acaacaaatc ctgaaaagta | 3060 |
| tttttagtgt ttgtaggtat tctgtgggat actatacaag cagaactgag gcacttagga | 3120 |
| cataacactt tgggtata tatatccaaa tgcctaaaac tatgggagga aaccttggcc | 3180 |
| acccaaaag gaaaactaac atgatttgtg tctatgaagt gctggataat tagcatggga | 3240 |
| tgagctctgg gcatgccatg aaggaaagcc acgctccctt cagaattcag aggcagggag | 3300 |
| caattccagt ttcacctaag tctcataatt ttagttccct tttaaaaacc ctgaaaacta | 3360 |
| catcaccatg gaatgaaaaa tattgttata caatacattg atctgtcaaa cttccagaac | 3420 |
| catggtagcc ttcagtgaga tttccatctt ggctggtcac tccctgactg tagctgtagg | 3480 |
| tgaatgtgtt tttgtgtgtg tgtgtctggt tttagtgtca gaagggaaat aaaagtgtaa | 3540 |
| ggaggacact ttaaacccctt tgggtggagt ttcgtaattt cccagactat tttcaagcaa | 3600 |
| cctggtccac ccaggattag tgaccaggtt ttcaggaaag gatttgcttc tctctagaaa | 3660 |
| atgtctgaaa ggatttttatt ttctgatgaa aggctgtatg aaaatacccct cctcaaataa | 3720 |
| cttgcttaac tacatataga ttcaagtgtg tcaatattct atttttgtata ttaaatgcta | 3780 |
| tataatgggg acaaatctat attatactgt gtatggcatt attaagaagc ttttcatta | 3840 |
| tttttatca cagtaatttt aaaatgtgta aaaattaaaa ccagtgactc ctgtttaaaa | 3900 |
| ataaagttg tagttttta ttcatgctga ataataatct gtagttaaaa aaaaagtgtc | 3960 |
| ttttaccta cgcagtgaaa tgtcagactg taaaaccttg tgtggaaatg tttaactttt | 4020 |
| attttttcat ttaaatttgc tgttctggta ttaccaaacc acacatttgt accgaattgg | 4080 |
| cagtaaatgt tagccattta cagcaatgcc aaatatggag aaacatcata ataaaaaaat | 4140 |
| ctgcttttc atta | 4154 |

<210> SEQ ID NO 49
<211> LENGTH: 6330
<212> TYPE: DNA
<213> ORGANISM: Homo sapiens
<220> FEATURE:
<223> OTHER INFORMATION: nuclear receptor subfamily 3, group A, member
1, transcript variant 4 (NR3A1), estrogen receptor
(ESR1, ER, ESR, ESRA, ESTRR) cDNA (complete)

<400> SEQUENCE: 49

| | |
|---|---|
| aggagctggc ggagggcgtt cgtcctggga ctgcacttgc tcccgtcggg tcgcccggct | 60 |
| tcaccggacc cgcaggctcc cggggcaggg ccggggccag agctcgcgtg tcggcgggac | 120 |
| atgcgctgcg tcgcctctaa cctcgggctg tgctcttttt ccaggtggcc cgccggtttc | 180 |
| tgagccttct gccctgcggg gacacggtct gcaccctgcc cgcggccacg gaccatgacc | 240 |
| atgaccctcc acaccaaagc atctgggatg ccctactgc atcagatcca agggaacgag | 300 |
| ctggagcccc tgaaccgtcc gcagctcaag atccccctgg agcggcccct gggcgaggtg | 360 |
| tacctggaca gcagcaagcc cgccgtgtac aactacccg agggcgccgc ctacgagttc | 420 |

-continued

| | |
|---|---|
| aacgccgcgg ccgccgccaa cgcgcaggtc tacggtcaga ccggcctccc ctacggcccc | 480 |
| gggtctgagg ctgcggcgtt cggctccaac ggcctggggg gtttcccccc actcaacagc | 540 |
| gtgtctccga gcccgctgat gctactgcac ccgccgccgc agctgtcgcc tttcctgcag | 600 |
| ccccacggcc agcaggtgcc ctactacctg gagaacgagc ccagcggcta cacggtgcgc | 660 |
| gaggccggcc cgccggcatt ctacaggcca aattcagata tcgacgcca gggtggcaga | 720 |
| gaaagattgg ccagtaccaa tgacaaggga agtatgcta tggaatctgc caaggagact | 780 |
| cgctactgtg cagtgtgcaa tgactatgct tcaggctacc attatggagt ctggtcctgt | 840 |
| gagggctgca aggccttctt caagagaagt attcaaggac ataacgacta tatgtgtcca | 900 |
| gccaccaacc agtgcaccat tgataaaaac aggaggaaga gctgccaggc ctgccggctc | 960 |
| cgcaaatgct acgaagtggg aatgatgaaa ggtgggatac gaaaagaccg aagaggaggg | 1020 |
| agaatgttga acacaagcg ccagagagat gatggggagg cagggggtga agtggggtct | 1080 |
| gctggagaca tgagagctgc caaccttttgg ccaagcccgc tcatgatcaa acgctctaag | 1140 |
| aagaacagcc tggccttgtc cctgacggcc gaccagatgg tcagtgcctt gttggatgct | 1200 |
| gagcccccca tactctattc cgagtatgat cctaccagac ccttcagtga agcttcgatg | 1260 |
| atgggcttac tgaccaacct ggcagacagg gagctggttc acatgatcaa ctgggcgaag | 1320 |
| agggtgccag gctttgtgga tttgacccctc catgatcagg tccaccttct agaatgtgcc | 1380 |
| tggctagaga tcctgatgat tggtctcgtc tggcgctcca tggagcaccc agggaagcta | 1440 |
| ctgtttgctc ctaacttgct cttggacagg aaccagggaa aatgtgtaga gggcatggtg | 1500 |
| gagatcttcg acatgctgct ggctacatca tctcggttcc gcatgatgaa tctgcaggga | 1560 |
| gaggagtttg tgtgcctcaa atctattatt ttgcttaatt ctggagtgta cacatttctg | 1620 |
| tccagcaccc tgaagtctct ggaagagaag gaccatatcc accgagtcct ggacaagatc | 1680 |
| acagacactt tgatccacct gatggccaag gcaggcctga ccctgcagca gcagcaccag | 1740 |
| cggctggccc agctcctcct catcctctcc cacatcaggc acatgagtaa caaaggcatg | 1800 |
| gagcatctgt acagcatgaa gtgcaagaac gtggtgcccc tctatgacct gctgctggag | 1860 |
| atgctggacg cccaccgcct acatgcgccc actagccgtg gaggggcatc cgtggaggag | 1920 |
| acggaccaaa gccacttggc cactgcgggc tctacttcat cgcattcctt gcaaaagtat | 1980 |
| tacatcacgg gggaggcaga gggtttccct gccacggtct gagagctccc tggctcccac | 2040 |
| acggttcaga taatccctgc tgcatttac cctcatcatg caccacttta gccaaattct | 2100 |
| gtctcctgca tacactccgg catgcatcca acaccaatgg ctttctagat gagtggccat | 2160 |
| tcatttgctt gctcagttct tagtggcaca tcttctgtct tctgttggga acagccaaag | 2220 |
| ggattccaag gctaaatctt tgtaacagct ctctttcccc cttgctatgt tactaagcgt | 2280 |
| gaggattccc gtagctcttc acagctgaac tcagtctatg ggttggggct cagataactc | 2340 |
| tgtgcattta agctacttgt agagacccag gcctggagag tagacatttt gcctctgata | 2400 |
| agcactttt aaatggctct aagaataagc cacagcaaag aatttaaagt ggctccttta | 2460 |
| attggtgact tggagaaagc taggtcaagg gtttattata gcaccctctt gtattcctat | 2520 |
| ggcaatgcat cctttatga aagtggtaca ccttaaagct tttatatgac tgtagcagag | 2580 |
| tatctggtga ttgtcaattc attcccccta taggaataca aggggcacac agggaaggca | 2640 |
| gatcccctag ttggcaagac tatttttaact tgatacactg cagattcaga gtgtgctgaaa | 2700 |
| gctctgcctc tggctttccg gtcatggggtt ccagttaatt catgcctccc atggacctat | 2760 |

```
ggagagcagc aagttgatct tagttaagtc tccctatatg agggataagt tcctgatttt    2820
tgttttattt tttgtgttac aaaagaaagc cctccctccc tgaacttgca gtaaggtcag    2880
cttcaggacc tgttccagtg ggcactgtac ttggatcttc ccggcgtgtg tgtgccttac    2940 acagggtga  actgttcact gtggtgatgc atgatgaggg taaatggtag ttgaaaggag    3000
caggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttggggtg  ccctgggatc cctggggtag tccagctctt    3240
cttcatttcc cagcgtggcc ctggttggaa gaagcagctg tcacagctgc tgtagacagc    3300
tgtgttccta caattggccc agcaccctgg ggcacgggag aagggtgggg accgttgctg    3360
tcactactca ggctgactgg ggcctggtca gattacgtat gcccttggtg gtttagagat    3420
aatccaaaat cagggtttgg tttggggaag aaaatcctcc cccttcctcc cccgccccgt    3480
tccctaccgc ctccactcct gccagctcat ttccttcaat ttcctttgac ctataggcta    3540
aaaaagaaag gctcattcca gccacagggc agccttccct gggcctttgc ttctctagca    3600
caattatggg ttacttcctt tttcttaaca aaaaagaatg tttgatttcc tctgggtgac    3660
cttattgtct gtaattgaaa ccctattgag aggtgatgtc tgtgttagcc aatgacccag    3720
gtgagctgct cgggcttctc ttggtatgtc ttgtttggaa aagtggattt cattcatttc    3780
tgattgtcca gttaagtgat caccaaagga ctgagaatct gggagggcaa aaaaaaaaa    3840 aaagttttta tgtgcactta aatttgggga caatttatg  tatctgtgtt aaggatatgt    3900
ttaagaacat aattcttttg ttgctgtttg tttaagaagc accttagttt gtttaagaag    3960
caccttatat agtataatat atattttttt gaaattacat tgcttgttta tcagacaatt    4020
gaatgtagta attctgttct ggatttaatt tgactgggtt aacatgcaaa aaccaaggaa    4080
aaatatttag tttttttttt ttttttttgta tacttttcaa gctaccttgt catgtataca    4140
gtcatttatg cctaaagcct ggtgattatt catttaaatg aagatcacat ttcatatcaa    4200
cttttgtatc cacagtagac aaaatagcac taatccagat gcctattgtt ggatactgaa    4260
tgacagacaa tcttatgtag caaagattat gcctgaaaag gaaaattatt cagggcagct    4320
aattttgctt ttaccaaaat atcagtagta atatttttgg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtggggaag    4800
tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttcttttcg    5040
ccattgccta gcttgccgta atgattctat aatgccatca tgcagcaatt atgagaggct    5100
aggtcatcca aagagaagac cctatcaatg taggttgcaa aatctaaccc ctaaggaagt    5160
```

-continued

```
gcagtctttg atttgatttc cctagtaacc ttgcagatat gtttaaccaa gccatagccc    5220
atgccttttg agggctgaac aaataaggga cttactgata atttactttt gatcacatta    5280
aggtgttctc accttgaaat cttatacact gaaatggcca ttgatttagg ccactggctt    5340
agagtactcc ttcccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctctttggtg caggtcttgg gagcgtgatc tagattacac    5580
tgcaccattc ccaagttaat cccctgaaaa cttactctca actggagcaa atgaactttg    5640
gtcccaaata tccatctttt cagtagcgtt aattatgctc tgtttccaac tgcatttcct    5700
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820
tattcttttt tttgcatcca attgtgcctg aactttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agtttctgtt ctctcacagg tgataaacaa    6060 tgcttttgt gcactacata ctcttcagtg tagagctctt gttttatggg aaaaggctca    6120
aatgccaaat tgtgtttgat ggattaatat gcccttttgc cgatgcatac tattactgat    6180
gtgactcggt tttgtcgcag ctttgctttg tttaatgaaa cacacttgta aacctctttt    6240
gcactttgaa aaagaatcca gcgggatgct cgagcacctg taaacaattt tctcaaccta    6300
tttgatgttc aaataaagaa ttaaactaaa                                     6330
```